US009822111B2

(12) United States Patent
Barlaam et al.

(10) Patent No.: US 9,822,111 B2
(45) Date of Patent: *Nov. 21, 2017

(54) IMIDAZO[4,5-C]QUINOLIN-2-ONE COMPOUNDS AND THEIR USE IN TREATING CANCER

(71) Applicant: AstraZeneca AB, Södertälje (SE)

(72) Inventors: Bernard Christophe Barlaam, Cheshire (GB); Kurt Gordon Pike, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/217,079

(22) Filed: Jul. 22, 2016

(65) Prior Publication Data
US 2016/0368920 A1 Dec. 22, 2016

Related U.S. Application Data

(63) Continuation of application No. 14/704,031, filed on May 5, 2015, now Pat. No. 9,428,503.

(60) Provisional application No. 61/990,232, filed on May 8, 2014.

(51) Int. Cl.
| C07D 471/04 | (2006.01) |
|---|---|
| A61K 31/444 | (2006.01) |
| A61K 45/06 | (2006.01) |
| A61K 31/4545 | (2006.01) |
| A61K 31/4745 | (2006.01) |
| A61K 31/502 | (2006.01) |

(52) U.S. Cl.
CPC .......... *C07D 471/04* (2013.01); *A61K 31/444* (2013.01); *A61K 31/4545* (2013.01); *A61K 31/4745* (2013.01); *A61K 31/502* (2013.01); *A61K 45/06* (2013.01)

(58) Field of Classification Search
CPC .......................... C07D 471/04; A61K 31/4353
USPC .......................................................... 546/82
See application file for complete search history.

(56) References Cited

U.S. PATENT DOCUMENTS

| 7,667,039 B2 * | 2/2010 | Garcia-Echeverria | C07D 471/04 544/295 |
| 8,557,984 B2 * | 10/2013 | Bouillot | C07D 471/04 544/126 |

FOREIGN PATENT DOCUMENTS

| CN | 102199152 A | 3/2010 |
| CN | 102372711 A | 3/2012 |
| CN | 102399218 A | 4/2012 |
| WO | WO2005054237 | 6/2005 |
| WO | WO 2006/122806 A2 | 11/2006 |
| WO | WO 2010/038165 A1 | 4/2010 |
| WO | 2010139747 | * 12/2010 |
| WO | WO 2010/139747 A1 | 12/2010 |
| WO | WO 2012/028233 A1 | 3/2012 |
| WO | WO 2012/138789 A3 | 10/2012 |

OTHER PUBLICATIONS

Calabresi and Chabner, Section IX "Chemotherapy of Neoplastic Diseases—Introduction," Goodman & Gilman's The Pharmacological Basis of Therapeutics 10th ed., 2001, Table IX-1.*
Bakkenist et al., 'DNA damage activates ATM through intermolecular autophosphorylation and dimer dissociation', Nature (2003); vol. 421; pp. 499-506.
Cheng et al., 'Discovery of the highly potent PI3/mTOR Dual Inhibitor PF-04979064 through structure-based drug design', ACS Medicinal Chemistry Letters (2013); vol. 4; pp. 91-97.
Cremona et al., 'ATM signalling and cancer', Oncogene (2014); vol. 33; pp. 3351-3360.
International Search Report for PCT/GB2015/051312; dated Jul. 24, 2015.

(Continued)

*Primary Examiner* — Rita Desai

(57) ABSTRACT

The specification generally relates to compounds of Formula (I):

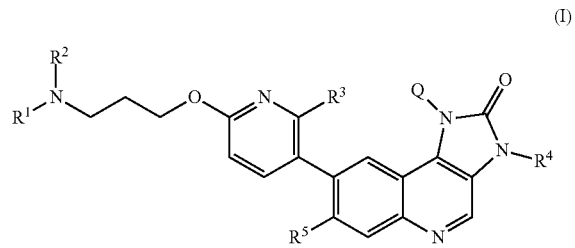

and pharmaceutically acceptable salts thereof, where Q, $R^1$, $R^2$, $R^3$, $R^4$ and $R^5$ have any of the meanings defined herein. The specification also relates to the use of such compounds and salts thereof to treat or prevent ATM kinase mediated disease, including cancer. The specification further relates to crystalline forms of compounds of imidazo[4,5-c]quinolin-2-one compounds and pharmaceutically acceptable salts thereof; pharmaceutical compositions comprising such compounds and salts; kits comprising such compounds and salts; methods of manufacture of such compounds and salts; intermediates useful in the manufacture of such compounds and salts; and to methods of treating ATM kinase mediated disease, including cancer, using such compounds and salts.

2 Claims, 5 Drawing Sheets

(56) References Cited

OTHER PUBLICATIONS

Kurz et al., 'DNA damage-inducted activation of ATM and ATM-dependent signaling pathways', DNA Repair (2004); vol. 3; pp. 889-900.
Lavin, 'Ataxi-telangiectasia: from a rare disorder to a paradigm for cell signalling and cancer', Nature Reviews Molecular Cell Biology (2008); vol. 9; pp. 759-769.
Matsuoka et al., 'ATM and ATR Substrate Analysis Reveals Extensive Protein Networks Responsive to DNA Damage', Science (2007); vol. 316; pp. 1160-1166.
Written Opinion for PCT/GB2015/051312; dated Jul. 24, 2015.

* cited by examiner

IMIDAZO[4,5-C]QUINOLIN-2-ONE COMPOUNDS AND THEIR USE IN TREATING CANCER

FIELD OF INVENTION

The specification generally relates to substituted imidazo[4,5-c]quinolin-2-one compounds and pharmaceutically acceptable salts thereof. These compounds and their pharmaceutically acceptable salts selectively modulate ataxia telangiectasia mutated ("ATM") kinase, and the specification therefore also relates to the use of such compounds and salts thereof to treat or prevent ATM kinase mediated disease, including cancer. The specification further relates to crystalline forms of compounds of substituted imidazo[4,5-c]quinolin-2-one compounds and pharmaceutically acceptable salts thereof: pharmaceutical compositions comprising such compounds and salts; kits comprising such compounds and salts; methods of manufacture of such compounds and salts, intermediates useful in the manufacture of such compounds and salts; and to methods of treating ATM kinase mediated disease, including cancer, using such compounds and salts.

BACKGROUND

ATM kinase is a serine threonine kinase originally identified as the product of the gene mutated in ataxia telangiectasia. Ataxia telangiectasia is located on human chromosome 11q22-23 and codes for a large protein of about 350 kDa, which is characterized by the presence of a phosphatidylinositol ("PI") 3-kinase-like serine/threonine kinase domain flanked by FRAP-ATM-TRRAP and FATC domains which modulate ATM kinase activity and function. ATM kinase has been identified as a major player of the DNA damage response elicited by double strand breaks. It primarily functions in S/G2/M cell cycle transitions and at collapsed replication forks to initiate cell cycle checkpoints, chromatin modification, HR repair and pro-survival signalling cascades in order to maintain cell integrity after DNA damage (Lavin, 2008).

ATM kinase signalling can be broadly divided into two categories: a canonical pathway, which signals together with the Mre11-Rad50-NBS1 complex from double strand breaks and activates the DNA damage checkpoint, and several non-canonical modes of activation, which are activated by other forms of cellular stress (Cremona et al., 2013).

ATM kinase is rapidly and robustly activated in response to double strand breaks and is reportedly able to phosphorylate in excess of 800 substrates (Matsuoka et al., 2007), coordinating multiple stress response pathways (Kurz and Lees Miller, 2004). ATM kinase is present predominantly in the nucleus of the cell in an inactive homodimeric form but autophosphorylates itself on Ser1981 upon sensing a DNA double strand break (canonical pathway), leading to dissociation to a monomer with full kinase activity (Bakkenist et al., 2003). This is a critical activation event, and ATM phospho-Ser1981 is therefore both a direct pharmacodynamic and patient selection biomarker for tumour pathway dependency.

ATM kinase responds to direct double strand breaks caused by common anti-cancer treatments such as ionising radiation and topoisomerase-II inhibitors (doxorubicin, etoposide) but also to topoisomerase-1 inhibitors (for example irinotecan and topotecan) via single strand break to double strand break conversion during replication. ATM kinase inhibition can potentiate the activity of any these agents, and as a result ATM kinase inhibitors are expected to be of use in the treatment of cancer, for example as rational combination partners for existing therapies.

CN102372711A reports certain imidazo[4,5-c]quinolin-2-one compounds which are mentioned to be dual inhibitors of PI 3-kinase α and mammalian target of rapamycin ("mTOR") kinase. Among the compounds reported in CN102372711A are the following:

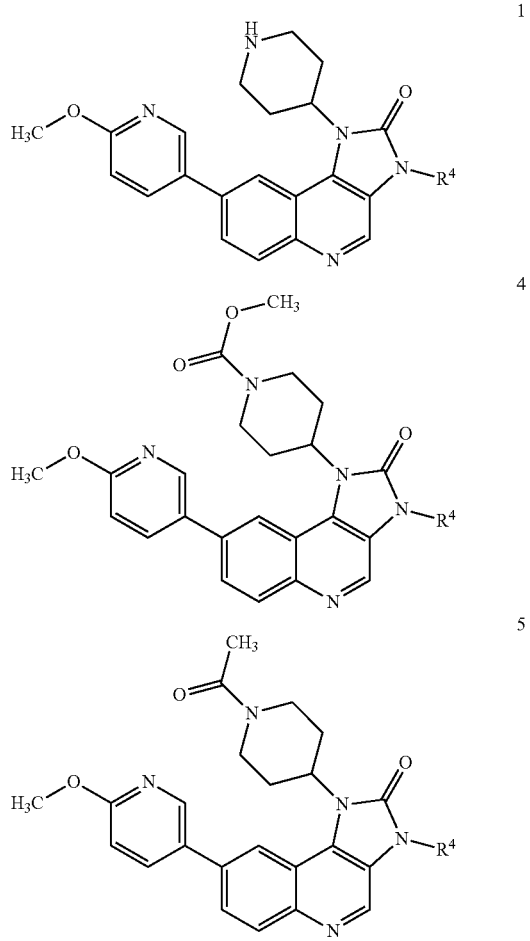

Certain Compounds Reported in CN102372711A

CN102399218A reports certain imidazo[4,5-c]quinolin-2-one compounds which are mentioned to be PI 3-kinase α inhibitors. Among the compounds reported in CN102399218A are the following:

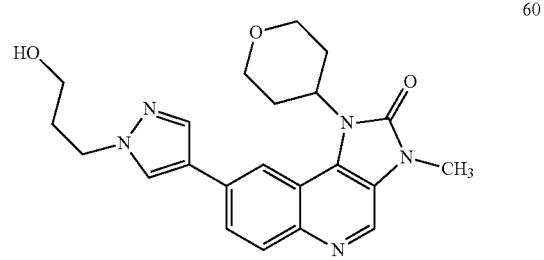

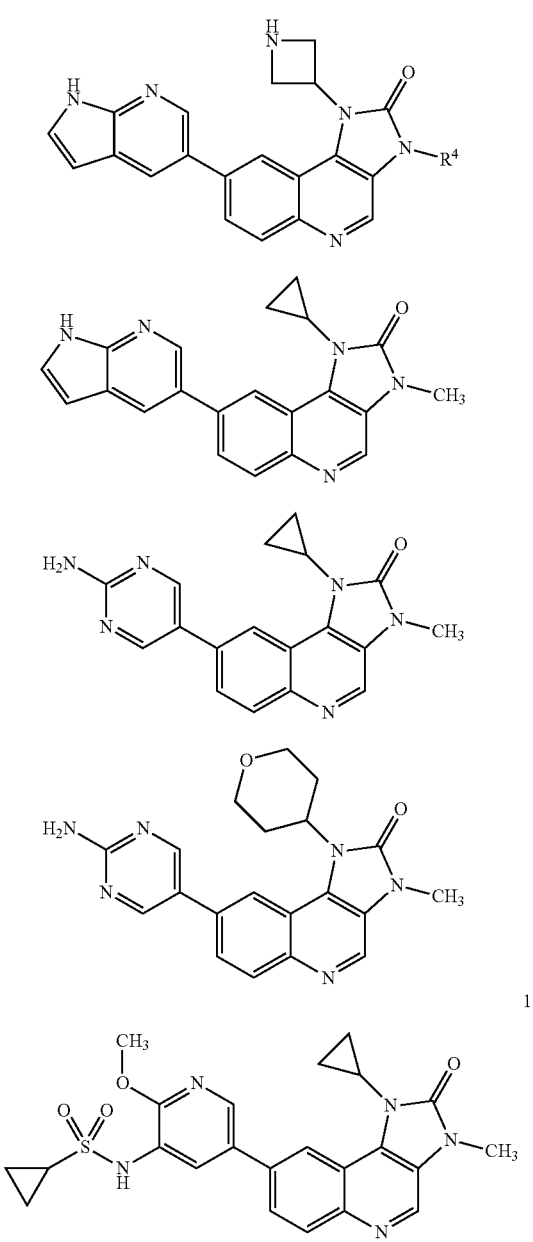

Certain Compounds Reported in CN10239928A

While the compounds or CN102372711A and CN102399218A are reported to possess activity against PI 3-kinase α and in some cases mTOR kinase, there remains a need to develop new compounds that are more effective against different kinase enzymes, such as ATM kinase. There further exists a need for new compounds which act against certain kinase enzymes, like ATM kinase, in a highly selective fashion (i.e. by modulating ATM more effectively than other biological targets).

As demonstrated elsewhere in the specification (for example in the cell based assays described in the experimental section), the compounds of the present specification generally possess very potent ATM kinase inhibitory activity, but much less potent activity against other tyrosine kinase enzymes, such as PI 3-kinase α, mTOR kinase and ataxia telangiectasia and Rad3-related protein ("ATR") kinase. As such, the compounds of the present specification not only inhibit ATM kinase, but can be considered to be highly selective inhibitors of ATM kinase.

As a result of their highly selective nature, the compounds of the present specification are expected to be particularly useful in the treatment of diseases in which ATM kinase is implicated (for example, in the treatment of cancer), but where it is desirable to minimise off-target effects or toxicity that might arise due to the inhibition of other tyrosine kinase enzymes, such as class PI 3-kinase α, mTOR kinase and ATR kinase.

SUMMARY OF INVENTION

Briefly, this specification describes, in part, a compound of Formula (I):

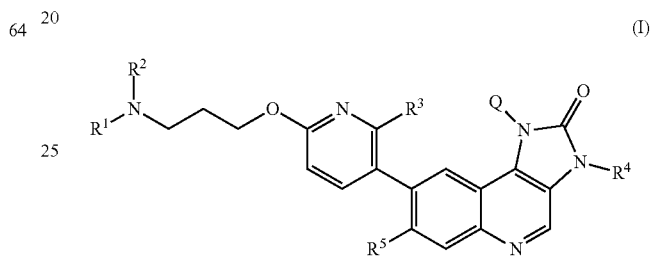

(I)

or a pharmaceutically acceptable salt thereof, where:

Q is a cyclobutyl or cyclopentyl ring, each of which is optionally substituted by one hydroxy or methoxy group, or Q is an oxetanyl, tetrahydrofuranyl or oxanyl ring, each of which is optionally substituted by one methyl group;

$R^1$ is methyl;

$R^2$ is hydrogen or methyl; or $R^1$ and $R^2$ together form an azetidinyl, pyrrolidinyl or piperidinyl ring;

$R^3$ is hydrogen or fluoro;

$R^4$ is hydrogen or methyl; and $R^5$ is hydrogen or fluoro.

This specification also describes, in part, a pharmaceutical composition which comprises a compound of Formula (I), or a pharmaceutically acceptable salt thereof, and at least one pharmaceutically acceptable diluent or carrier.

This specification also describes, in part, a compound of formula (I), or a pharmaceutically acceptable salt thereof, for use in therapy.

This specification also describes, in part, a compound of formula (I), or a pharmaceutically acceptable salt thereof, for use in the treatment of cancer.

This specification also describes, in part, a compound of formula (I), or a pharmaceutically acceptable salt thereof, for the manufacture of a medicament for the treatment of cancer.

This specification also describes, in part, a method for treating cancer in a warm blooded animal in need of such treatment, which comprises administering to said warm-blooded animal a therapeutically effective amount of a compound of Formula (I), or a pharmaceutically acceptable salt thereof.

DESCRIPTION OF ILLUSTRATIVE EMBODIMENTS

Figure 1:
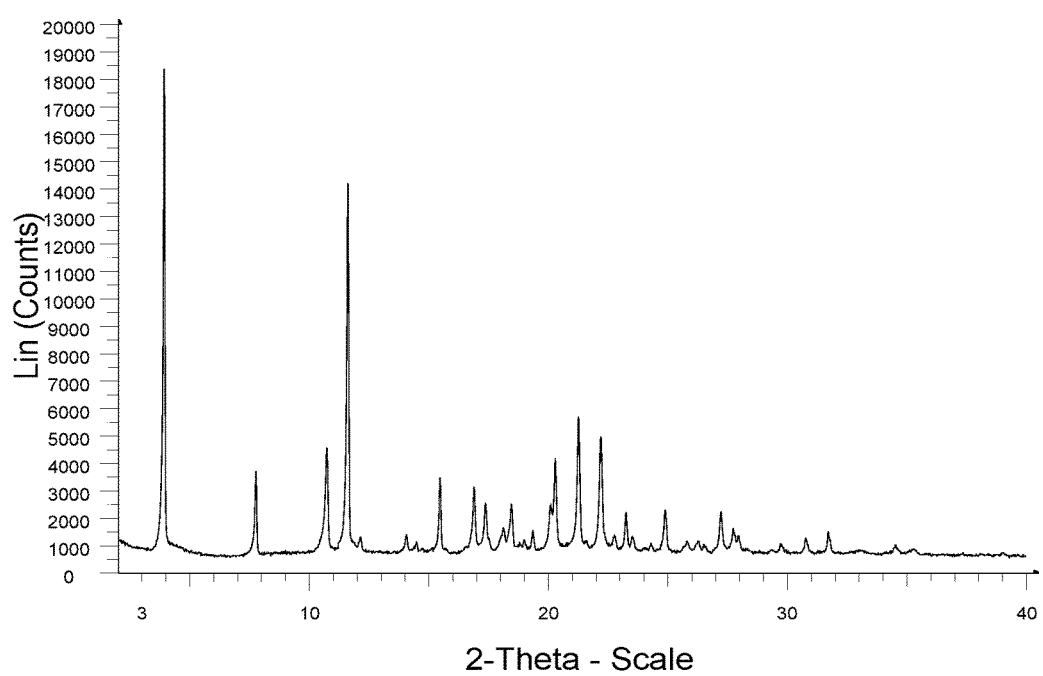
FIG. 1: X-Ray Powder Diffraction Pattern of Form A of 8-[6-(3-Dimethylaminopropoxy)pyridin-3-yl]-3-methyl-1-(oxan-4-yl)imidazo[5,4-c]quinolin-2-one.

Many embodiments of the invention are detailed throughout the specification and will be apparent to a reader skilled in the art. The invention is not to be interpreted as being limited to any particular embodiment(s) thereof.

In the first embodiment there is provided a compound of Formula (I):

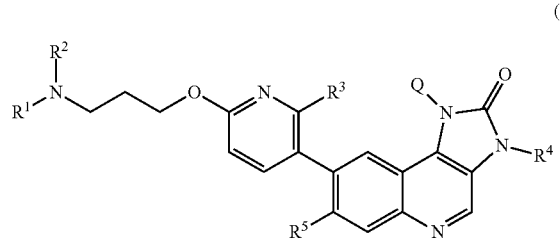

(I)

or a pharmaceutically acceptable salt thereof, where:

Q is a cyclobutyl or cyclopentyl ring, each of which is optionally substituted by one hydroxy or methoxy group, or Q is an oxetanyl, tetrahydrofuranyl or oxanyl ring, each of which is optionally substituted by one methyl group;

$R^1$ is methyl;

$R^2$ is hydrogen or methyl; or $R^1$ and $R^2$ together form an azetidinyl, pyrrolidinyl or piperidinyl ring;

$R^3$ is hydrogen or fluoro;

$R^4$ is hydrogen or methyl; and $R^5$ is hydrogen or fluoro.

The terms "cyclobutyl ring" and "cyclopentyl ring" refer to carbocyclic rings containing no heteroatoms. 1-methoxycyclobut-3-yl groups and 3-methoxycyclobut-1-yl groups have the same structure, as shown below.

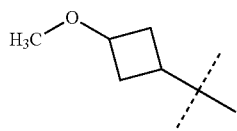

1-methoxycyclobut-3-yl/3-methoxycyclobut-1-yl

A cis-1-methoxy-cyclobut-3-yl group is equivalent to a cis-3-methoxy-cyclobut-1-yl and has the following structure:

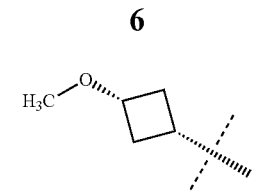

cis-1-methoxycyclobut-3-yl/cis-3-methoxycyclobut-1-yl

The same conventions apply to other cyclobutyl groups, for example 1-hydroxycyclobut-3-yl groups and 3-hydroxycyclobut-1-yl groups.

In a similar fashion, 1-methoxycyclopent-3-yl groups and 3-methoxycyclopent-1-yl groups have the same structure, as shown below.

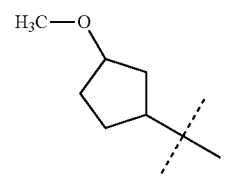

1-methoxycyclobut-3-yl/3-methoxycyclobut-1-yl

The term "oxetanyl ring" includes oxetan-2-yl and oxetan-3-yl groups, the structures of which are shown below.

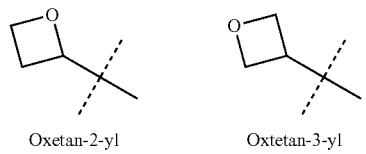

Oxetan-2-yl    Oxtetan-3-yl

The term "tetrahydrofuranyl ring" includes tetrahydrofuran-2-yl and tetrahydrofuran-3-yl groups, the structures of which are shown below.

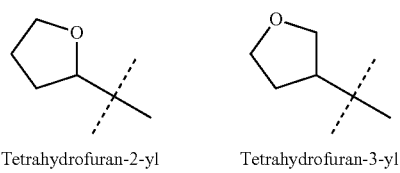

Tetrahydrofuran-2-yl    Tetrahydrofuran-3-yl

The term "oxanyl ring" includes oxan-2-yl, oxan-3-yl, and oxan-4-yl groups, the structures of which are shown below.

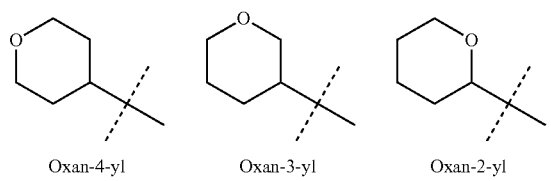

Oxan-4-yl    Oxan-3-yl    Oxan-2-yl

In the above structures the dashed line indicates the bonding position of the relevant group.

An oxanyl ring may also be referred to as a tetrahydropyranyl ring. Similarly, an oxan-4-yl ring may be referred to as as a tetrahydropyran-4-yl ring; an oxan-3-yl ring may be referred to as a tetrahydropyran-3-yl ring, and an oxan-2-yl ring may be referred to as a tetrahydropyran-2-yl ring.

Where it is mentioned that "$R^1$ and $R^2$ together form an azetidinyl, pyrrolidinyl or piperidinyl ring", this means the $R^1$ and $R^2$ groups are joined via a carbon-carbon covalent bond to form an unsubstituted alkylene chain of the appropriate length for the corresponding ring. For example, when $R^1$ and $R^2$ together form a pyrrolidinyl ring, $R^1$ and $R^2$ together represent an unsubstituted butylene chain which is attached to the relevant nitrogen atom in Formula (I) at both terminal carbons.

Where the term "optionally" is used, it is intended that the subsequent feature may or may not occur. As such, use of the term "optionally" includes instances where the feature is present, and also instances where the feature is not present. For example, a group "optionally substituted by one methoxy group" includes groups with and without a methoxy substituent.

The term "substituted" means that one or more hydrogens (for example 1 or 2 hydrogens, or alternatively 1 hydrogen) on the designated group is replaced by the indicated substituent(s) (for example 1 or 2 substituents, or alternatively 1 substituent), provided that any atom(s) bearing a substituent maintains a permitted valency. Substituent combinations encompass only stable compounds and stable synthetic intermediates. "Stable" means that the relevant compound or intermediate is sufficiently robust to be isolated and have utility either as a synthetic intermediate or as an agent having potential therapeutic utility. If a group is not described as "substituted", or "optionally substituted", it is to be regarded as unsubstituted (i.e. that none of the hydrogens on the designated group have been replaced).

The term "pharmaceutically acceptable" is used to specify that an object (for example a salt, dosage form, diluent or carrier) is suitable for use in patients. An example list of pharmaceutically acceptable salts can be found in the *Handbook of Pharmaceutical Salts: Properties, Selection and Use*, P. H. Stahl and C. G. Wermuth, editors, Weinheim/Zürich:Wiley-VCH\VHCA, 2002. A suitable pharmaceutically acceptable salt of a compound of Formula (I) is, for example, an acid-addition salt. An acid addition salt of a compound of Formula (I) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (I) or a pharmaceutically acceptable salt thereof, where the pharmaceutically acceptable salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt. In one embodiment there is provided a compound of Formula (I) or a pharmaceutically acceptable salt thereof, where the pharmaceutically acceptable salt is a trifluoroacetic acid, formic acid or methanesulfonic acid salt. In one embodiment there is provided a compound of Formula (I) or a pharmaceutically acceptable salt thereof, where the pharmaceutically acceptable salt is a trifluoroacetic acid or methanesulfonic acid salt. In one embodiment there is provided a compound of Formula (I) or a pharmaceutically acceptable salt thereof, where the pharmaceutically acceptable salt is a methanesulfonic acid salt. In one embodiment there is provided a compound of Formula (I) or a pharmaceutically acceptable salt thereof, where the pharmaceutically acceptable salt is a mono-methanesulfonic acid salt, i.e. the stoichiometry of the compound of the compound of Formula (I) to methanesulfonic acid is 1:1.

A further embodiment provides any of the embodiments defined herein (for example the embodiment of claim 1) with the proviso that one or more specific Examples (for instance one, two or three specific Examples) selected from the group consisting of Examples 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70 and 71 is individually disclaimed.

Some values of variable groups in Formula (I) are as follows. Such values may be used in combination with any of the definitions, claims (for example claim 1), or embodiments defined herein to provide further embodiments.

a) Q is a cyclobutyl or cyclopentyl ring, each of which is substituted by one hydroxy or methoxy group, or Q is an oxetanyl, tetrahydrofuranyl or oxanyl ring, each of which is optionally substituted by one methyl group.

b) Q is a cyclobutyl ring substituted by one hydroxy or methoxy group, or Q is an oxetanyl or oxanyl ring, each of which is optionally substituted by one methyl group.

c) Q is a cyclobutyl ring substituted by one hydroxy or methoxy group, or Q is an oxetanyl or oxanyl ring.

d) Q is cyclobutyl, 1-methoxy-cyclobut-3-yl, 1-hydroxy-cyclobut-3-yl, 3-methoxycyclopent-1-yl, oxetan-3-yl, tetrahydrofuran-3-yl, oxan-3-yl, oxan-4-yl or 4-methyloxan-4-yl.

e) Q is 1-methoxy-cyclobut-3-yl, 1-hydroxy-cyclobut-3-yl, 3-methoxycyclopent-1-yl, oxetan-3-yl, oxan-3-yl, oxan-4-yl or 4-methyloxan-4-yl.

f) Q is L-methoxy-cyclobut-3-yl, 1-hydroxy-cyclobut-3-yl or oxan-4-yl.

g) Q is cis-1-methoxy-cyclobut-3-yl or oxan-4-yl.

h) Q is a cyclobutyl or cyclopentyl ring, each of which is optionally substituted by one hydroxy or methoxy group.

i) Q is a cyclobutyl or cyclopentyl ring, each of which is optionally substituted by one methoxy group.

j) Q is a cyclobutyl ring substituted by one hydroxy or methoxy group.

k) Q is cyclobutyl, 1-hydroxy-cyclobut-3-yl or 1-methoxy-cyclobut-3-yl.

l) Q is cyclobutyl.

m) Q is a cyclopentyl ring substituted by one hydroxy or methoxy group.

n) Q is a cyclopentyl ring substituted by one methoxy group.

o) Q is 3-methoxycyclopent-1-yl.

p) Q is 1-hydroxy-cyclobut-3-yl or 1-methoxy-cyclobut-3-yl.

q) Q is cis-1-hydroxy-cyclobut-3-yl or cis-1-methoxy-cyclobut-3-yl.

r) Q is cis-1-methoxy-cyclobut-3-yl.

s) Q is an oxetanyl, tetrahydrofuranyl or oxanyl ring, each of which is optionally substituted by one methyl group.

t) Q is an oxetanyl or oxanyl ring, each of which is optionally substituted by one methyl group.
u) Q is an oxetanyl or tetrahydrofuranyl ring.
v) Q is an oxetanyl ring.
w) Q is oxetan-3-yl.
x) Q is a tetrahydrofuranyl ring.
y) Q is tetrahydrofuran-3-yl.
z) Q is an oxanyl ring optionally substituted by one methyl group.
aa) Q is an oxanyl ring.
bb) Q is oxan-4-yl.
cc) $R^1$ is methyl.
dd) $R^2$ is methyl.
ee) $R^2$ is hydrogen.
ff) $R^1$ is methyl and $R^2$ is hydrogen or methyl.
gg) $R^1$ and $R^2$ are both methyl; or $R^1$ and $R^2$ together form a pyrrolidinyl ring.
hh) $R^1$ and $R^2$ are both methyl.
ii) $R^1$ and $R^2$ together form an azetidinyl, pyrrolidinyl or piperidinyl ring.
jj) $R^1$ and $R^2$ together form an azetidinyl ring.
kk) $R^1$ and $R^2$ together form a pyrrolidinyl ring.
ll) $R^1$ and $R^2$ together form a piperidinyl ring.
mm) $R^3$ and $R^5$ are both hydrogen.
nn) $R^3$ is hydrogen.
oo) $R^3$ is fluoro.
pp) $R^4$ is hydrogen.
qq) $R^4$ is methyl.
rr) $R^5$ is hydrogen.
ss) $R^5$ is fluoro.

In one embodiment there is provided a compound of Formula (I), or a pharmaceutically acceptable salt thereof, where:
Q is cyclobutyl, 1-methoxy-cyclobut-3-yl, 1-hydroxy-cyclobut-3-yl, 3-methoxycyclopent-1-yl, oxetan-3-yl, tetrahydrofuran-3-yl, oxan-3-yl, oxan-4-yl or 4-methyloxan-4-yl;
$R^1$ is methyl;
$R^2$ is hydrogen or methyl; or $R^1$ and $R^2$ together form an azetidinyl, pyrrolidinyl or piperidinyl ring;
$R^3$ is hydrogen or fluoro;
$R^4$ is hydrogen or methyl; and
$R^5$ is hydrogen or fluoro.

In one embodiment there is provided a compound of Formula (I), or a pharmaceutically acceptable salt thereof, where:
Q is 1-methoxy-cyclobut-3-yl, 1-hydroxy-cyclobut-3-yl, 3-methoxycyclopent-1-yl, oxetan-3-yl, oxan-3-yl, oxan-4-yl or 4-methyloxan-4-yl;
$R^1$ is methyl;
$R^2$ is hydrogen or methyl; or $R^1$ and $R^2$ together form an azetidinyl, pyrrolidinyl or piperidinyl ring;
$R^3$ is hydrogen or fluoro;
$R^4$ is hydrogen or methyl; and
$R^5$ is hydrogen or fluoro.

In one embodiment there is provided a compound of Formula (I), where:
Q is 1-methoxy-cyclobut-3-yl, 1-hydroxy-cyclobut-3-yl or 3-methoxycyclopent-1-yl;
$R^1$ is methyl;
$R^2$ is hydrogen or methyl; or $R^1$ and $R^2$ together form an azetidinyl, pyrrolidinyl or piperidinyl ring;
$R^3$ is hydrogen or fluoro;
$R^4$ is hydrogen or methyl; and
$R^5$ is hydrogen or fluoro.

In one embodiment there is provided a compound of Formula (I), or a pharmaceutically acceptable salt thereof, where:
Q is oxetan-3-yl, oxan-3-yl, oxan-4-yl or 4-methyloxan-4-yl;
$R^1$ is methyl;
s $R^2$ is hydrogen or methyl; or $R^1$ and $R^2$ together form an azetidinyl, pyrrolidinyl or piperidinyl ring;
$R^3$ is hydrogen or fluoro:
$R^4$ is hydrogen or methyl; and
$R^5$ is hydrogen or fluoro.

In one embodiment there is provided a compound of Formula (I), or a pharmaceutically acceptable salt thereof, where:
Q is cis-1-methoxy-cyclobut-3-yl or oxan-4-yl;
$R^1$ is methyl;
$R^2$ is methyl or hydrogen;
$R^3$ is hydrogen;
$R^4$ is methyl or hydrogen; and
$R^5$ is hydrogen.

In one embodiment there is provided a compound of Formula (I), or a pharmaceutically acceptable salt thereof, wherein the compound is selected from the group consisting of:
8-[6-(3-Dimethylaminopropoxy)pyridin-3-yl]-3-methyl-1-(oxan-4-yl)imidazo[5,4-c]quinolin-2-one;
8-[6-(3-Dimethylaminopropoxy)pyridin-3-yl]-1-(cis-3-methoxycyclobutyl)-3-methylimidazo[4,5-c]quinolin-2-one;
8-[6-(3-Dimethylaminopropoxy)pyridin-3-yl]-7-fluoro-3-methyl-1-(4-methyloxan-4-yl)imidazo[5,4-c]quinolin-2-one;
8-[6-(3-Dimethylaminopropoxy)pyridin-3-yl]-3-methyl-1-(oxetan-3-yl)imidazo[5,4-c]quinolin-2-one;
8-[6-(3-Dimethylaminopropoxy)pyridin-3-yl]-1-(cis-3-hydroxycyclobutyl)-3-methylimidazo[4,5-c]quinolin-2-one;
8-[6-(3-Dimethylaminopropoxy)pyridin-3-yl]-7-fluoro-1-(cis-3-methoxycyclobutyl)-3-methylimidazo[4,5-c]quinolin-2-one;
8-[6-(3-Dimethylaminopropoxy)pyridin-3-yl]-3-methyl-1-(4-methyloxan-4-yl)imidazo[5,4-c]quinolin-2-one;
8-[6-(3-Dimethylaminopropoxy)pyridin-3-yl]-7-fluoro-3-methyl-1-(oxan-4-yl)imidazo[5,4-c]quinolin-2-one;
8-[6-(3-Dimethylaminopropoxy)pyridin-3-yl]-7-fluoro-3-methyl-1-(oxetan-3-yl)imidazo[5,4-c]quinolin-2-one;
8-[6-(3-Dimethylaminopropoxy)pyridin-3-yl]-7-fluoro-3-methyl-1-[(3R)-oxan-3-yl]imidazo[5,4-c]quinolin-2-one;
8-[6-(3-Dimethylaminopropoxy)pyridin-3-yl]-7-fluoro-3-methyl-1-[(3S)-oxan-3-yl]imidazo[5,4-c]quinolin-2-one;
8-[6-(3-Dimethylaminopropoxy)pyridin-3-yl]-1-(cis-3-methoxycyclobutyl)-3H-imidazo[4,5-c]quinolin-2-one;
8-[6-(3-Dimethylaminopropoxy)pyridin-3-yl]-1-(oxan-4-yl)-3H-imidazo[4,5-c]quinolin-2-one;
8-[6-[3-(Azetidin-1-yl)propoxy]pyridin-3-yl]-1-(cis-3-hydroxycyclobutyl)-3-methylimidazo[4,5-c]quinolin-2-one;
1-(3-cis-Hydroxycyclobutyl)-3-methyl-8-[6-(3-pyrrolidin-1-ylpropoxy)pyridin-3-yl]imidazo[4,5-c]quinolin-2-one;
8-[6-(3-Dimethylaminopropoxy)pyridin-3-yl]-3-methyl-1-[(3R)-oxan-3-yl]imidazo[5,4-c]quinolin-2-one;
8-[6-(3-Dimethylaminopropoxy)pyridin-3-yl]-3-methyl-1-[(3S)-oxan-3-yl]imidazo[5,4-c]quinolin-2-one;
8-[6-(3-Dimethylaminopropoxy)-2-fluoropyridin-3-yl]-1-(cis-3-methoxycyclobutyl)-3-methylimidazo[4,5-c]quinolin-2-one;
8-[6-(3-Dimethylaminopropoxy)-2-fluoropyridin-3-yl]-7-fluoro-1-(cis-3-methoxycyclobutyl)-3-methylimidazo[4,5-c]quinolin-2-one 8-[6-(3-Dimethylaminopropoxy)-2-fluoropyridin-3-yl]-3-methyl-1-[(3S)-oxan-3-yl]imidazo[5,4-c]quinolin-2-one;
8-[6-(3-Dimethylaminopropoxy)-2-fluoropyridin-3-yl]-3-methyl-1-(oxan-4-yl)imidazo[5,4-c]quinolin-2-one;
8-[6-(3-Dimethylaminopropoxy)-2-fluoropyridin-3-yl]-3-methyl-1-[(3R)-oxan-3-yl]imidazo[5,4-c]quinolin-2-one;
7-Fluoro-3-methyl-8-[6-(3-pyrrolidin-1-ylpropoxy)-3-pyridyl]-1-[(3S)-tetrahydropyran-3-yl]imidazo[4,5-c]quinolin-2-one;
7-Fluoro-3-methyl-8-[6-(3-pyrrolidin-1-ylpropoxy)-3-pyridyl]-1-[(3S)-tetrahydropyran-3-yl]imidazo[4,5-c]quinolin-2-one;
8-[6-(3-Dimethylaminopropoxy)pyridin-3-yl]-1-[(1R,3R)-3-methoxycyclopentyl]-3-methylimidazo[4,5-c]quinolin-2-one;
8-[6-(3-Dimethylaminopropoxy)pyridin-3-yl]-1-[(1S,3S)-3-methoxycyclopentyl]-3-methylimidazo[4,5-c]quinolin-2-one;
7-Fluoro-1-(cis-3-methoxycyclobutyl)-3-methyl-8-[6-(3-pyrrolidin-1-ylpropoxy)pyridin-3-yl]imidazo[4,5-c]quinolin-2-one;
1-(cis-3-Methoxycyclobutyl)-3-methyl-8-[6-(3-pyrrolidin-1-ylpropoxy)pyridin-3-yl]imidazo[4,5-c]quinolin-2-one;
3-Methyl-1-[(3S)-oxan-3-yl]-8-[6-(3-pyrrolidin-1-ylpropoxy)pyridin-3-yl]imidazo[5,4-c]quinolin-2-one;
3-Methyl-1-(oxan-4-yl)-8-[6-(3-pyrrolidin-1-ylpropoxy)pyridin-3-yl]imidazo[5,4-c]quinolin-2-one;
3-Methyl-1-[(3S)-oxan-3-yl]-8-[6-(3-piperidin-1-ylpropoxy)pyridin-3-yl]imidazo[5,4-c]quinolin-2-one;
3-Methyl-1-[(3R)-oxan-3-yl]-8-[6-(3-piperidin-1-ylpropoxy)pyridin-3-yl]imidazo[5,4-c]quinolin-2-one;
1-(cis-3-Methoxycyclobutyl)-3-methyl-8-[6-(3-piperidin-1-ylpropoxy)pyridin-3-yl]imidazo[4,5-c]quinolin-2-one;
8-[6-[3-(Azetidin-1-yl)propoxy]pyridin-3-yl]-3-methyl-1-[(3R)-oxan-3-yl]imidazo[5,4-c]quinolin-2-one;
1-(cis-3-Methoxycyclobutyl)-8-[6-(3-pyrrolidin-1-ylpropoxy)pyridin-3-yl]-3H-imidazo[4,5-c]quinolin-2-one;
1-(Oxan-4-yl)-8-[6-(3-piperidin-1-ylpropoxy)pyridin-3-yl]-3H-imidazo[4,5-c]quinolin-2-one;
3-Methyl-1-(oxan-4-yl)-8-[6-(3-piperidin-1-ylpropoxy)pyridin-3-yl]imidazo[5,4-c]quinolin-2-one;
8-[6-[3-(Azetidin-1-yl)propoxy]pyridin-3-yl]-1-(cis-3-methoxycyclobutyl)-3-methylimidazo[4,5-c]quinolin-2-one;
8-[6-[3-(Azetidin-1-yl)propoxy]pyridin-3-yl]-3-methyl-1-(oxan-4-yl)imidazo[5,4-c]quinolin-2-one;
3-Methyl-8-[6-(3-methylaminopropoxy)pyridin-3-yl]-1-(oxan-4-yl)imidazo[5,4-c]quinolin-2-one;
3-Methyl-8-[6-(3-methylaminopropoxy)pyridin-3-yl]-1-[(3S)-oxan-3-yl]imidazo[5,4-c]quinolin-2-one; and
1-(cis-3-Methoxycyclobutyl)-3-methyl-8-[6-(3-methylaminopropoxy)pyridin-3-yl]imidazo[4,5-c]quinolin-2-one;
3-Methyl-8-[6-[3-(methylamino)propoxy]-3-pyridyl]-1-[(3R)-tetrahydropyran-3-yl]imidazo[4,5-c]quinolin-2-one;
8-[6-[3-(Dimethylamino)propoxy]-3-pyridyl]-3-methyl-1-[(3R)-tetrahydrofuran-3-yl]imidazo[4,5-c]quinolin-2-one;
8-[6-[3-(Dimethylamino)propoxy]-3-pyridyl]-3-methyl-1-[(3S)-tetrahydrofuran-3-yl]imidazo[4,5-c]quinolin-2-one;
1-Cyclobutyl-8-[6-[3-(dimethylamino)propoxy]-3-pyridyl]-3-methyl-imidazo[4,5-c]quinolin-2-one;
7-Fluoro-3-methyl-8-[6-[3-(1-piperidyl)propoxy]-3-pyridyl]-1-[(3S)-tetrahydropyran-3-yl]imidazo[4,5-c]quinolin-2-one;

8-[6-[3-(Dimethylamino)propoxy]-2-fluoro-3-pyridyl]-7-fluoro-3-methyl-1-[(3S)-tetrahydropyran-3-yl]imidazo[4,5-c]quinolin-2-one;
8-[6-[3-(Dimethylamino)propoxy]-2-fluoro-3-pyridyl]-3-methyl-1-[(3S)-tetrahydrofuran-3-yl]imidazo[4,5-c]quinolin-2-one;
8-[6-[3-(Dimethylamino)propoxy]-2-fluoro-3-pyridyl]-3-methyl-1-[(3R)-tetrahydrofuran-3-yl]imidazo[4,5-c]quinolin-2-one;
1-Cyclobutyl-8-[6-[3-(dimethylamino)propoxy]-2-fluoro-3-pyridyl]-3-methyl-imidazo[4,5-c]quinolin-2-one;
8-[6-[3-(Dimethylamino)propoxy]-2-fluoro-3-pyridyl]-3-methyl-1-(oxetan-3-yl)imidazo[4,5-c]quinolin-2-one;
7-Fluoro-3-methyl-8-[6-[3-(1-piperidyl)propoxy]-3-pyridyl]-1-tetrahydropyran-4-yl-imidazo[4,5-c]quinolin-2-one
3-Methyl-8-[6-[3-(1-piperidyl)propoxy]-3-pyridyl]-1-[(3R)-tetrahydrofuran-3-yl]imidazo[4,5-c]quinolin-2-one;
3-Methyl-8-[6-[3-(1-piperidyl)propoxy]-3-pyridyl]-1-[(3S)-tetrahydrofuran-3-yl]imidazo[4,5-c]quinolin-2-one;
3-Methyl-1-(oxetan-3-yl)-8-[6-[3-(1-piperidyl)propoxy]-3-pyridyl]imidazo[4,5-c]quinolin-2-one;
1-Cyclobutyl-3-methyl-8-[6-[3-(1-piperidyl)propoxy]-3-pyridyl]imidazo[4,5-c]quinolin-2-one;
1-Cyclobutyl-3-methyl-8-[6-(3-pyrrolidin-1-ylpropoxy)-3-pyridyl]imidazo[4,5-c]quinolin-2-one;
3-Methyl-8-[6-(3-pyrrolidin-1-ylpropoxy)-3-pyridyl]-1-[(3R)-tetrahydropyran-3-yl]imidazo[4,5-c]quinolin-2-one;
8-[6-[3-(Azetidin-1-yl)propoxy]-3-pyridyl]-3-methyl-1-[(3S)-tetrahydropyran-3-yl]imidazo[4,5-c]quinolin-2-one;
8-[2-Fluoro-6-(3-pyrrolidin-1-ylpropoxy)-3-pyridyl]-3-methyl-1-[(3S)-tetrahydropyran-3-yl]imidazo[4,5-c]quinolin-2-one;
8-[6-[3-(Dimethylamino)propoxy]-3-pyridyl]-7-fluoro-1-[(1R,3R)-3-methoxycyclopentyl]-3-methyl-imidazo[4,5-c]quinolin-2-one;
8-[6-[3-(Dimethylamino)propoxy]-3-pyridyl]-7-fluoro-1-[(1S,3S)-3-methoxycyclopentyl]-3-methyl-imidazo[4,5-c]quinolin 2-one;
1-[(1R,3R)-3-Methoxycyclopentyl]-3-methyl-8-[6-[3-(1-piperidyl)propoxy]-3-pyridyl]imidazo[4,5-c]quinolin-2-one;
1-[(1S,3S)-3-Methoxycyclopentyl]-3-methyl-8-[6-[3-(1-piperidyl)propoxy]-3-pyridyl]imidazo[4,5-c]quinolin-2-one;
1-[(1S,3S)-3-Methoxycyclopentyl]-3-methyl-8-[6-(3-pyrrolidin-1-ylpropoxy)-3-pyridyl]imidazo[4,5-c]quinolin-2-one;
1-[(1R,3R)-3-Methoxycyclopentyl]-3-methyl-8-[6-(3-pyrrolidin-1-ylpropoxy)-3-pyridyl]imidazo[4,5-c]quinolin-2-one;
8-[6-[3-(Dimethylamino)propoxy]-2-fluoro-3-pyridyl]-1-[(1R,3R)-3-methoxycyclopentyl]-3-methyl-imidazo[4,5-c]quinolin-2-one;
8-[6-[3-(Dimethylamino)propoxy]-2-fluoro-3-pyridyl]-1-[(1S,3S)-3-methoxycyclopentyl]-3-methyl-imidazo[4,5-c]quinolin-2-one;
8-[6-[3-(Dimethylamino)propoxy]-3-pyridyl]-7-fluoro-1-[(1R,3S)-3-methoxycyclopentyl]-3-methyl-imidazo[4,5-c]quinolin-2-one; and
8-[6-[3-(Dimethylamino)propoxy]-3-pyridyl]-7-fluoro-1-[(1S,3R)-3-methoxycyclopentyl]-3-methyl-imidazo[4,5-c]quinolin-2-one.

In one embodiment there is provided a compound of Formula (I), or a pharmaceutically acceptable salt thereof, wherein the compound is selected from the group consisting of:

8-[6-(3-Dimethylaminopropoxy)pyridin-3-yl]-3-methyl-1-(oxan-4-yl)imidazo[5,4-c]quinolin-2-one;
8-[6-(3-Dimethylaminopropoxy)pyridin-3-yl]-1-(cis-3-methoxycyclobutyl)-3-methylimidazo[4,5-c]quinolin-2-one;
8-[6-(3-Dimethylaminopropoxy)pyridin-3-yl]-7-fluoro-3-methyl-1-(4-methyloxan-4-yl)imidazo[5,4-c]quinolin-2-one;
8-[6-(3-Dimethylaminopropoxy)pyridin-3-yl]-3-methyl-1-(oxetan-3-yl)imidazo[5,4-c]quinolin-2-one;
8-[6-(3-Dimethylaminopropoxy)pyridin-3-yl]-1-(cis-3-hydroxycyclobutyl)-3-methylimidazo[4,5-c]quinolin-2-one;
8-[6-(3-Dimethylaminopropoxy)pyridin-3-yl]-7-fluoro-1-(cis-3-methoxycyclobutyl)-3-methylimidazo[4,5-c]quinolin-2-one;
8-[6-(3-Dimethylaminopropoxy)pyridin-3-yl]-3-methyl-1-(4-methyloxan-4-yl)imidazo[5,4-c]quinolin-2-one;
8-[6-(3-Dimethylaminopropoxy)pyridin-3-yl]-7-fluoro-3-methyl-1-(oxan-4-yl)imidazo[5,4-c]quinolin-2-one;
8-[6-(3-Dimethylaminopropoxy)pyridin-3-yl]-7-fluoro-3-methyl-1-(oxetan-3-yl)imidazo[5,4-c]quinolin-2-one;
8-[6-(3-Dimethylaminopropoxy)pyridin-3-yl]-7-fluoro-3-methyl-1-[(3R)-oxan-3-yl]imidazo[5,4-c]quinolin-2-one;
8-[6-(3-Dimethylaminopropoxy)pyridin-3-yl]-7-fluoro-3-methyl-1-[(3S)-oxan-3-yl]imidazo[5,4-c]quinolin-2-one;
8-[6-(3-Dimethylaminopropoxy)pyridin-3-yl]-1-(cis-3-methoxycyclobutyl)-3H-imidazo[4,5-c]quinolin-2-one;
8-[6-(3-Dimethylaminopropoxy)pyridin-3-yl]-1-(oxan-4-yl)-3H-imidazo[4,5-c]quinolin-2-one;
8-[6-[3-(Azetidin-1-yl)propoxy]pyridin-3-yl]-1-(cis-3-hydroxycyclobutyl)-3-methylimidazo[4,5-c]quinolin-2-one;
1-(3-cis-Hydroxycyclobutyl)-3-methyl-8-[6-(3-pyrrolidin-1-ylpropoxy)pyridin-3-yl]imidazo[4,5-c]quinolin-2-one;
8-[6-(3-Dimethylaminopropoxy)pyridin-3-yl]-3-methyl-1-[(3R)-oxan-3-yl]imidazo[5,4-c]quinolin-2-one;
8-[6-(3-Dimethylaminopropoxy)pyridin-3-yl]-3-methyl-1-[(3S)-oxan-3-yl]imidazo[5,4-c]quinolin-2-one;
8-[6-(3-Dimethylaminopropoxy)-2-fluoropyridin-3-yl]-1-cis-3-methoxycyclobutyl)-3-methylimidazo[4,5-c]quinolin-2-one;
8-[6-(3-Dimethylaminopropoxy)-2-fluoropyridin-3-yl]-7-fluoro-1-(cis-3-methoxycyclobutyl)-3-methylimidazo[4,5-c]quinolin-2-one;
8-[6-(3-Dimethylaminopropoxy)-2-fluoropyridin-3-yl]-3-methyl-1-[(3R)-oxan-3-yl]imidazo[5,4-c]quinolin-2-one;
8-[6-(3-Dimethylaminopropoxy)-2-fluoropyridin-3-yl]-3-methyl-1-(oxan-4-yl)imidazo[5,4-c]quinolin-2-one;
8-[6-(3-Dimethylaminopropoxy)-2-fluoropyridin-3-yl]-3-methyl-1-[(3R)-oxan-3-yl]imidazo[5,4-c]quinolin-2-one;
3-Methyl-1-[(3R)-oxan-3-yl]-8-[6-(3-pyrrolidin-1-ylpropoxy)pyridin-3-yl]imidazo[5,4-c]quinolin-2-one;
8-[6-(3-Dimethylaminopropoxy)pyridin-3-yl]-1-[(1R,3R)-3-methoxycyclopentyl]-3-methylimidazo[4,5-c]quinolin-2-one;
8-[6-(3-Dimethylaminopropoxy)pyridin-3-yl]-1-[(1S,3S)-3-methoxycyclopentyl]-3-methylimidazo[4,5-c]quinolin-2-one;
7-Fluoro-1-(cis-3-methoxycyclobutyl)-3-methyl-8-[6-(3-pyrrolidin-1-ylpropoxy)pyridin-3-yl]imidazo[4,5-c]quinolin-2-one;
1-(cis-3-Methoxycyclobutyl)-3-methyl-8-[6-(3-pyrrolidin-1-ylpropoxy)pyridin-3-yl]imidazo[4,5-c]quinolin-2-one;
3-Methyl-1-[(3S)-oxan-3-yl]-8-[6-(3-pyrolidin-1-ylpropoxy)pyridin-3-yl]imidazo[5,4-c]quinolin-2-one;
3-Methyl-1-(oxan-4-yl)-8-[6-(3-pyrrolidin-1-ylpropoxy)pyridin-3-yl]imidazo[5,4-c]quinolin-2-one;
3-Methyl-1-[(3S)-oxan-3-yl]-8-[6-(3-piperidin-1-ylpropoxy)pyridin-3-yl]imidazo[5,4-c]quinolin-2-one;
3-Methyl-1-[(3R)-oxan-3-yl]-8-[6-(3-piperidin-1-ylpropoxy)pyridin-3-yl]imidazo[5,4-c]quinolin-2-one;
1-(cis-3-Methoxycyclobutyl)-3-methyl-8-[6-(3-piperidin-1-ylpropoxy)pyridin-3-yl]imidazo[4,5-c]quinolin-2-one;
8-[6-[3-(Azetidin-1-yl)propoxy]pyridin-3-yl]-3-methyl-1-[(3R)-oxan-3-yl]imidazo[5,4-c]quinolin-2-one;
1-(cis-3-Methoxycyclobutyl)-8-[6-(3-pyrrolidin-1-ylpropoxy)pyridin-3-yl]-3H-imidazo[4,5-c]quinolin-2-one;
1-(Oxan-4-yl)-8-[6-(3-piperidin-1-ylpropoxy)pyridin-3-yl]-3H-imidazo[4,5-c]quinolin-2-one;
3-Methyl-1-(oxan-4-yl)-8-[6-(3-piperidin-1-ylpropoxy)pyridin-3-yl]imidazo[5,4-c]quinolin-2-one;
8-[6-[3-(Azetidin-1-yl)propoxy]pyridin-3-yl]-1-(cis-3-methoxycyclobutyl)-3-methylimidazo[4,5-c]quinolin-2-one;
8-[6-[3-(Azetidin-1-yl)propoxy]pyridin-3-yl]-3-methyl-1-(oxan-4-yl) imidazo[5,4-c]quinolin-2-one;
3-Methyl-8-[6-(3-methyl aminopropoxy)pyridin-3-yl]-1-(oxan-4-yl)imidazo[5,4-c]quinolin-2-one;
3-Methyl-8-[6-(3-methylaminopropoxy)pyridin-3-yl]-1-[(3S)-oxan-3-yl]imidazo[5,4-c]quinolin-2-one; and
1-(cis-3-Methoxycyclobutyl)-3-methyl-8-[6-(3-methylaminopropoxy)pyridin-3-yl]imidazo[4,5-c]quinolin-2-one.

In one embodiment there is provided a compound of Formula (I), or a pharmaceutically acceptable salt thereof, wherein the compound is selected from the group consisting of:

8-[6-(3-Dimethylaminopropoxy)pyridin-3-yl]-3-methyl-1-(oxan-4-yl)imidazo[5,4-c]quinolin-2-one;
8-[6-(3-Dimethylaminopropoxy)pyridin-3-yl]-1-(cis-3-methoxycyclobutyl)-3-methylimidazo[4,5-c]quinolin-2-one;
8-[6-(3-Dimethylaminopropoxy)pyridin-3-yl]-7-fluoro-3-methyl-1-(4-methyloxan-4-yl)imidazo[5,4-c]quinolin-2-one;
8-[6-(3-Dimethylaminopropoxy)pyridin-3-yl]-3-methyl-1-(oxetan-3-yl)imidazo[5,4-c]quinolin-2-one;
8-[6-(3-Dimethylaminopropoxy)pyridin-3-yl]-1-(cis-3-hydroxycyclobutyl)-3-methylimidazo[4,5-c]quinolin-2-one;
8-[6-(3-Dimethylaminopropoxy)pyridin-3-yl]-7-fluoro-1-(cis-3-methoxycyclobutyl)-3-methylimidazo[4,5-c]quinolin-2-one;
8-[6-(3-Dimethylaminopropoxy)pyridin-3-yl]-3-methyl-1-(4-methyloxan-4-yl)imidazo[5,4-c]quinolin-2-one;
8-[6-(3-Dimethylaminopropoxy)pyridin-3-yl]-7-fluoro-3-methyl-1-(oxan-4-yl)imidazo[5,4-c]quinolin-2-one;
8-[6-(3-Dimethylaminopropoxy)pyridin-3-yl]-7-fluoro-3-methyl-1-(oxetan-3-yl)imidazo[5,4-c]quinolin-2-one;
8-[6-(3-Dimethylaminopropoxy)pyridin-3-yl]-7-fluoro-3-methyl-1-[(3R)-oxan-3-yl]imidazo[5,4-c]quinolin-2-one;
8-[6-(3-Dimethylaminopropoxy)pyridin-3-yl]-7-fluoro-3-methyl-1-[(3S)-oxan-3-yl]imidazo[5,4-c]quinolin-2-one;
8-[6-(3-Dimethylaminopropoxy)pyridin-3-yl]-1-(cis-3-methoxycyclobutyl)-3H-imidazo[4,5-c]quinolin-2-one;
8-[6-(3-Dimethylaminopropoxy)pyridin-3-yl]-1-(oxan-4-yl)-3H-imidazo[4,5-c]quinolin-2-one;
8-[6-[3-(Azetidin-1-yl)propoxy]pyridin-3-yl]-1-(cis-3-hydroxycyclobutyl)-3-methylimidazo[4,5-c]quinolin-2-one;
1-(3-cis-Hydroxycyclobutyl)-3-methyl-8-[6-(3-pyrrolidin-1-ylpropoxy)pyridin-3-yl]imidazo[4,5-c]quinolin-2-one, 8-[6-(3-Dimethylaminopropoxy)pyridin-3-yl]-3-methyl-1-[(3R)-oxan-3-yl]imidazo[5,4-c]quinolin-2-one;

8-[6-(3-Dimethylaminopropoxy)pyridin-3-yl]-3-methyl-1-[(3S)-oxan-3-yl]imidazo[5,4-c]quinolin-2-one;

8-[6-(3-Dimethylaminopropoxy)-2-fluoropyridin-3-yl]-1-(cis-3-methoxycyclobutyl)-3-methylimidazo[4,5-c]quinolin-2-one;

8-[6-(3-Dimethylaminopropoxy)-2-fluoropyridin-3-yl]-7-fluoro-1-(cis-3-methoxycyclobutyl)-3-methylimidazo[4,5-c]quinolin-2-one;

8-[6-(3-Dimethylaminopropoxy)-2-fluoropyridin-3-yl]-3-methyl-1-[(3S)-oxan-3-yl]imidazo[5,4-c]quinolin-2-one;

8-[6-(3-Dimethylaminopropoxy)-2-fluoropyridin-3-yl]-3-methyl-1-(oxan-4-yl)imidazo[5,4-c]quinolin-2-one;

8-[6-(3-Dimethylaminopropoxy)-2-fluoropyridin-3-yl]-3-methyl-1-[(3R)-oxan-3-yl]imidazo[5,4-c]quinolin-2-one;

3-Methyl-1-[(3R)-oxan-3-yl]-8-[6-(3-pyrrolidin-1-ylpropoxy)pyridin-3-yl]imidazo[5,4-c]quinolin-2-one;

7-Fluoro-1-(cis-3-methoxycyclobutyl)-3-methyl-8-[6-(3-pyrrolidin-1-ylpropoxy)pyridin-3-yl]imidazo[4,5-c]quinolin-2-one;

1-(cis-3-Methoxycyclobutyl)-3-methyl-8-[6-(3-pyrrolidin-1-ylpropoxy)pyridin-3-yl]imidazo[4,5-c]quinolin-2-one;

3-Methyl-1-[(3S)-oxan-3-yl]-8-[6-(3-pyrrolidin-1 ylpropoxy)pyridin-3-yl]imidazo[5,4-c]quinolin-2-one;

3-Methyl-1-(oxan-4-yl)-8-[6-(3-pyrrolidin-1-ylpropoxy)pyridin-3-yl]imidazo[5,4-c]quinolin-2-one;

3-Methyl-1-[(3S)-oxan-3-yl]-8-[6-(3-piperidin-1-ylpropoxy)pyridin-3-yl]imidazo[5,4-c]quinolin-2-one;

3-Methyl-1-[(3R)-oxan-3-yl]-8-[6-(3-piperidin-1-ylpropoxy)pyridin-3-yl]imidazo[5,4-c]quinolin-2-one;

1-(cis-3-Methoxycyclobutyl)-3-methyl-8-[6-(3-piperidin-1-ylpropoxy)pyridin-3-yl]imidazo[4,5-c]quinolin-2-one;

8-[6-[3-(Azetidin-1-yl)propoxy]pyridin-3-yl]-3-methyl-1-[(3R)-oxan-3-yl]imidazo[5,4-c]quinolin-2-one;

1-(cis-3-Methoxycyclobutyl)-8-[6-(3-pyrrolidin-1-ylpropoxy)pyridin-3-yl]-3H-imidazo[4,5-c]quinolin-2-one;

1-(Oxan-4-yl)-8-[6-(3-piperidin-1 ylpropoxy)pyridin-3-yl]-3H-imidazo[4,5-c]quinolin-2-one;

3-Methyl-1-(oxan-4-yl)-8-[6-(3-piperidin-1-ylpropoxy)pyridin-3-yl]imidazo[5,4-c]quinolin-2-one;

8-[6-[3-(Azetidin-1-yl)propoxy]pyridin-3-yl]-1-(cis-3-methoxycyclobutyl)-3-methylimidazo[4,5-c]quinolin-2-one;

8-[6-[3-(Azetidin-1-yl)propoxy]pyridin-3-yl]-3-methyl-1-(oxan-4-yl)imidazo[5,4-c]quinolin-2-one;

3-Methyl-8-[6-(3-methylaminopropoxy)pyridin-3-yl]-1-(oxan-4-yl)imidazo[5,4-c]quinolin-2-one;

3-Methyl-8-[6-(3-methylaminopropoxy)pyridin-3-yl]-1-[(3S)-oxan-3-yl]imidazo[5,4-c]quinolin-2-one; and 1-(cis-3-Methoxycyclobutyl)-3-methyl-8-[6-(3-methylaminopropoxy)pyridin-3-yl]imidazo[4,5-c]quinolin-2-one.

In one embodiment, there is provided a compound of Formula (I), or a pharmaceutically acceptable salt thereof, wherein the compound is selected from the group consisting of:

7-Fluoro-3-methyl-8-[6-(3-pyrrolidin-1-ylpropoxy)-3-pyridyl]-1-[(3S)-tetrahydropyran-3-yl]imidazo[4,5-c]quinolin-2-one;

7-Fluoro-3-methyl-8-[6-(3-pyrrolidin-1-ylpropoxy)-3-pyridyl]-1-[(3R)-tetrahydropyran-3-yl]imidazo[4,5-c]quinolin-2-one;

3-Methyl-8-[6-[3-(methylamino)propoxy]-3-pyridyl]-1-[(3R)-tetrahydropyran-3-yl]imidazo[4,5-c]quinolin-2-one;

8-[6-[3-(Dimethylamino)propoxy]-3-pyridyl]-3-methyl-1-[(3R)-tetrahydrofuran-3-yl]imidazo[4,5-c]quinolin-2-one;

8-[6-[3-(Dimethylamino)propoxy]-3-pyridyl]-3-methyl-1-[(3S)-tetrahydrofuran-3-yl]imidazo[4,5-c]quinolin-2-one;

1-Cyclobutyl-8-[6-[3-(dimethylamino)propoxy]-3-pyridyl]-3-methyl-imidazo[4,5-c]quinolin-2-one;

7-Fluoro-3-methyl-8-[6-[3-(1-piperidyl)propoxy]-3-pyridyl]-1-[(3S)-tetrahydropyran-3-yl]imidazo[4,5-c]quinolin-2-one;

8-[6-[3-(Dimethylamino)propoxy]-2-fluoro-3-pyridyl]-7-fluoro-3-methyl-1-[(3S)-tetrahydropyran-3-yl]imidazo[4,5-c]quinolin-2-one;

8-[6-[3-(Dimethylamino)propoxy]-2-fluoro-3-pyridyl]-3-methyl-1-[(3S)-tetrahydrofuran-3-yl]imidazo[4,5-c]quinolin-2-one;

8-[6-[3-(Dimethylamino)propoxy]-2-fluoro-3-pyridyl]-3-methyl-1-[(3R)-tetrahydrofuran-3-yl]imidazo[4,5-c]quinolin-2-one;

1-Cyclobutyl-8-[6-[3-(dimethylamino)propoxy]-2-fluoro-3-pyridyl]-3-methyl-imidazo[4,5-c]quinolin-2-one;

8-[6-[3-(Dimethylamino)propoxy]-2-fluoro-3-pyridyl]-3-methyl-1-(oxetan-3-yl)imidazo[4,5-c]quinolin-2-one;

7-Fluoro-3-methyl-8-[6-[3-(1-piperidyl)propoxy]-3-pyridyl]-1-tetrahydropyran-4-yl-imidazo[4,5-c]quinolin-2-one;

13-Methyl-8-[6-[3-(1-piperidyl)propoxy]-3-pyridyl]-1-[(3R)-tetrahydrofuran-3-yl]imidazo[4,5-c]quinolin-2-one;

3-Methyl-8-[6-[3-(1-piperidyl)propoxy]-3-pyridyl]-1-[(3S)-tetrahydrofuran-3-yl]imidazo[4,5-c]quinolin-2-one;

3-Methyl-1-(oxetan-3-yl)-8-[6-[3-(1-piperidyl)propoxy]-3-pyridyl]imidazo[4,5-c]quinolin-2-one;

1-Cyclobutyl-3-methy-8-[6-[3-(1-piperidyl)propoxy]-3-pyridyl]imidazo[4,5-c]quinolin-2-one;

1-Cyclobutyl-3-methyl-8-[6-(3-pyrrolidin-1-ylpropoxy)-3-pyridyl]imidazo[4,5-c]quinolin-2-one;

3-Methyl-8-[6-(3-pyrrolidin-1-ylpropoxy)-3-pyridyl]-1-[(3R)-tetrahydropyran-3-yl]imidazo[4,5-c]quinolin-2-one;

8-[6-[3-(Azetidin-1-yl)propoxy]-3-pyridyl]-3-methyl-1-[(3S)-tetrahydropyran-3-yl]imidazo[4,5-c]quinolin-2-one;

8-[2-Fluoro-6-(3-pyrrolidin-1-ylpropoxy)-3-pyridyl]-3-methyl-1-[(3S)-tetrahydropyran-3-yl]imidazo[4,5-c]quinolin-2-one;

8-[6-[3-(Dimethylamino)propoxy]-3-pyridyl]-7-fluoro-1-[(1R,3R)-3-methoxycyclopentyl]-3-methyl-imidazo[4,5-c]quinolin-2-one;

8-[6-[3-(Dimethylamino)propoxy]-3-pyridyl]-7-fluoro-1-[(1S,3S)-3-methoxycyclopentyl]-3-methyl-imidazo[4,5-c]quinolin-2-one;

1-[(1R,3R)-3-Methoxycyclopentyl]-3-methyl-8-[6-[3-(1-piperidyl)propoxy]-3-pyridyl]imidazo[4,5-c]quinolin-2-one;

1-[(1S,3 S)-3-Methoxycyclopentyl]-3-methyl-8-[6-[3-(1-piperidyl)propoxy]-3-pyridyl]imidazo[4,5-c]quinolin-2-one;

1-[(1S,3S)-3-Methoxycyclopentyl]-3-methyl-8-[6-(3-pyrrolidin-1-ylpropoxy)-3-pyridyl]imidazo[4,5-c]quinolin-2-one;

1-[(1R,3R)-3-Methoxycyclopentyl]-3-methyl-8-[6-(3-pyrrolidin-1-ylpropoxy)-3-pyridyl]imidazo[4,5-c]quinolin-2-one;

8-[6-[3-(Dimethylamino)propoxy]-2-fluoro-3-pyridyl]-1-[(1R,3R)-3-methoxycyclopentyl]-3-methyl-imidazo[4,5-c]quinolin-2-one;

8-[6-[3-(Dimethylamino)propoxy]-2-fluoro-3-pyridyl]-1-[(1S,3S)-3-methoxycyclopentyl]-3-methyl-imidazo[4,5-c]quinolin-2-one;

8-[6-[3-(Dimethylamino)propoxy]-3-pyridyl]-7-fluoro-1-[(1R,3R)-3-methoxycyclopentyl]-3-methyl-imidazo[4,5-c]quinolin-2-one; and 8-[6-[3-(Dimethylamino)propoxy]-3-pyridyl]-7-fluoro-1-[(1S,3R)-3-methoxycyclopentyl]-3-methyl-imidazo[4,5-c]quinolin-2-one.

In one embodiment there is provided a compound of Formula (I), or a pharmaceutically acceptable salt thereof, wherein the compound is selected from the group consisting of:

8-[6-(3-Dimethylaminopropoxy)pyridin-3-yl]-1-[(1R,3R)-3-methoxycyclopentyl]-3-methylimidazo[4,5-c]quinolin-2-one; and 8-[6-(3-Dimethylaminopropoxy)pyridin-3-yl]-1-[(1S,3S)-3-methoxycyclopentyl]-3-methylimidazo[4,5-c]quinolin-2-one.

In one embodiment there is provided 8-[6-(3-dimethylaminopropoxy)pyridin-3-yl]-1-(cis-3-methoxycyclobutyl)-3-methylimidazo[4,5-c]quinolin-2-one, or a pharmaceutically acceptable salt thereof.

In one embodiment there is provided 8-[6-(3-dimethylaminopropoxy)pyridin-3-yl]-1-(cis-3-methoxycyclobutyl)-3-methylimidazo[4,5-c]quinolin-2-one.

In one embodiment there is provided a pharmaceutically acceptable salt of 8-[6-(3-dimethylaminopropoxy)pyridin-3-yl]-1-(cis-3-methoxycyclobutyl)-3-methylimidazo[4,5-c]quinolin-2-one.

In one embodiment there is provided 8-[6-(3-dimethylaminopropoxy)pyridin-3-yl]-3-methyl-1-(oxan-4-yl)imidazo[5,4-c]quinolin-2-one, or a pharmaceutically acceptable salt thereof.

In one embodiment there is provided 8-[6-(3-dimethylaminopropoxy)pyridin-3-yl]-3-methyl-1-(oxan-4-yl)imidazo[5,4-c]quinolin-2-one.

In one embodiment there is provided a pharmaceutically acceptable salt of 8-[6-(3-dimethylaminopropoxy)pyridin-3-yl]-3-methyl-1-(oxan-4-yl)imidazo[5,4-c]quinolin-2-one.

In one embodiment there is provided 1-(cis-3-methoxycyclobutyl)-3-methyl-8-{6-[3-(pyrrolidin-1-yl)propoxy]pyridin-3-yl}-1,3-dihydro-2H-imidazo[4,5-c]quinolin-2-one, or a pharmaceutically acceptable salt thereof.

In one embodiment there is provided 1-(cis-3-methoxycyclobutyl)-3-methyl-8-{6-[3-(pyrrolidin-1-yl)propoxy]pyridin-3-yl}-1,3-dihydro-2H-imidazo[4,5-c]quinolin-2-one.

In one embodiment there is provided a pharmaceutically acceptable salt of 1-(cis-3-methoxycyclobutyl)-3-methyl-8-{6-[3-(pyrrolidin-1-yl)propoxy]pyridin-3-yl}-1,3-dihydro-2H-imidazo[4,5-c]quinolin-2-one.

Compounds and salts described in this specification may exist in solvated forms and unsolvated forms. For example, a solvated form may be a hydrated form, such as a hemi-hydrate, a mono-hydrate, a di-hydrate, a tri-hydrate or an alternative quantity thereof. The invention encompasses all such solvated and unsolvated forms of compounds of Formula (I), particularly to the extent that such forms possess ATM kinase inhibitory activity, as for example measured using the tests described herein.

Atoms of the compounds and salts described in this specification may exist as their isotopes. The invention encompasses all compounds of Formula (I) where an atom is 2 replaced by one or more of its isotopes (for example a compound of Formula (I) where one or more carbon atom is an $^{11}C$ or $^{13}C$ carbon isotope, or where one or more hydrogen atoms is a $^{2}H$ or $^{3}H$ isotope, or where one of more fluorine atoms is an $^{18}F$ isotope).

Compounds and salts described in this specification may exist as a mixture of tautomers. "Tautomers" are structural isomers that exist in equilibrium resulting from the migration of a hydrogen atom. The invention includes all tautomers of compounds of Formula (I) particularly to the extent that such tautomers possess ATM kinase inhibitory activity.

Compounds and salts described in this specification may exist in optically active or racemic forms by virtue of one or more asymmetric carbon atoms. The invention includes any optically active or racemic form of a compound of Formula (I) which possesses ATM kinase inhibitory activity, as for example measured using the tests described herein. The synthesis of optically active forms may be carried out by standard techniques of organic chemistry well known in the art, for example by synthesis using optically active materials or by resolution of a racemic form.

Therefore, in one embodiment there is provided a compound of Formula (I), or a pharmaceutically acceptable salt thereof, which is a single optical isomer being in an enantiomeric excess (% ee) of ≥95%, ≥98% or ≥99%. In one embodiment, the single optical isomer is present in an enantiomeric excess (% ee) of ≥99%.

Compounds and salts described in this specification may be crystalline, and may exhibit one or more crystalline forms. The invention encompasses any crystalline or amorphous form of a compound of Formula (I), or mixture of such forms, which possesses ATM kinase inhibitory activity.

It is generally known that crystalline materials may be characterised using conventional techniques such as X-Ray Powder Diffraction (XRPD), Differential Scanning Calorimetry (DSC). Thermal Gravimetric Analysis (TGA), Diffuse Reflectance Infrared Fourier Transform (DRIFT) spectroscopy, Near Infrared (NIR) spectroscopy, solution and/or solid state nuclear magnetic resonance spectroscopy. The water content of such crystalline materials may be determined by Karl Fischer analysis.

The specific solid forms described herein provide XRPD patterns substantially the same as the XRPD patterns shown in the Figures, and have the various 2-theta values as shown in the Tables included herein. One skilled in the art will understand that an XRPD pattern or diffractogram may be obtained which has one or more measurement errors depending on the recording conditions, such as the equipment or machine used. Similarly, it is generally known that intensities in an XRPD pattern may fluctuate depending on measurement conditions or sample preparation as a result of preferred orientation. Persons skilled in the art of XRPD will further realise that the relative intensity of peaks can also be affected by, for example, grains above 30 μm in size and non-unitary aspect ratios. The skilled person understands that the position of reflections can be affected by the precise height at which the sample sits in the diffractometer, and also the zero calibration of the diffractometer. The surface planarity of the sample may also have a small effect.

As a result of these considerations, the diffraction pattern data presented are not to be taken as absolute values (Jenkins, R & Snyder, R. L. 'Introduction to X-Ray Powder Diffractometry' John Wiley & Sons 1996; Bunn, C. W. (1948). 'Chemical Crystallography', Clarendon Press, London; Klug, H. P. & Alexander, L. E. (1974), 'X-Ray Diffraction Procedure'). It should correspondingly be understood that the solid forms are not limited to the crystals that provide XRPD patterns that are identical to the XRPD pattern shown in the Figures, and any crystals providing XRPD patterns substantially the same as those shown in the Figures fall within the scope of the invention. A person skilled in the art of XRPD is able to judge the substantial identity of XRPD patterns. Generally, a measurement error of a diffraction angle in an XRPD is approximately plus or minus 0.2° 2-theta, and such degree of a measurement error should be taken into account when considering the X-ray powder diffraction pattern in the Figures and when reading data contained in the Tables included herein.

The compound of Example 1 exhibits crystalline properties, and one crystalline form has been characterised.

Therefore, in one embodiment there is provided Form A of 8-[6-(3-dimethylaminopropoxy)pyridin-3-yl]-3-methyl-1-(oxan-4-yl)imidazo[5,4-c]quinolin-2-one.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with at least one specific peak at about 2-theta=3.9°.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with at least one specific peak at about 2-theta=11.6°.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with at least two specific peaks at about 2-theta=3.9 and 11.6°.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with specific peaks at about 2-theta=3.9, 7.7, 10.7, 11.6, 15.4, 16.9, 17.4, 18.4, 21.3 and 22.2°.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one which has an X-ray powder diffraction pattern substantially the same as the X-ray powder diffraction pattern shown in FIG. 1.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with at least one specific peak at 2-theta=3.9° plus or minus 0.2° 2-theta.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with at least one specific peak at 2-theta=11.6° plus or minus 0.2° 2-theta.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with at least two specific peaks at 2-theta=3.9 and 11.6° plus or minus 0.2° 2-theta.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one, which has an X-ray powder diffraction pattern with specific peaks at 2-theta=3.9, 7.7, 10.7, 11.6, 15.4, 16.9, 17.4, 18.4, 21.3 and 22.20 plus or minus 0.2° 2-theta.

Figure 2:
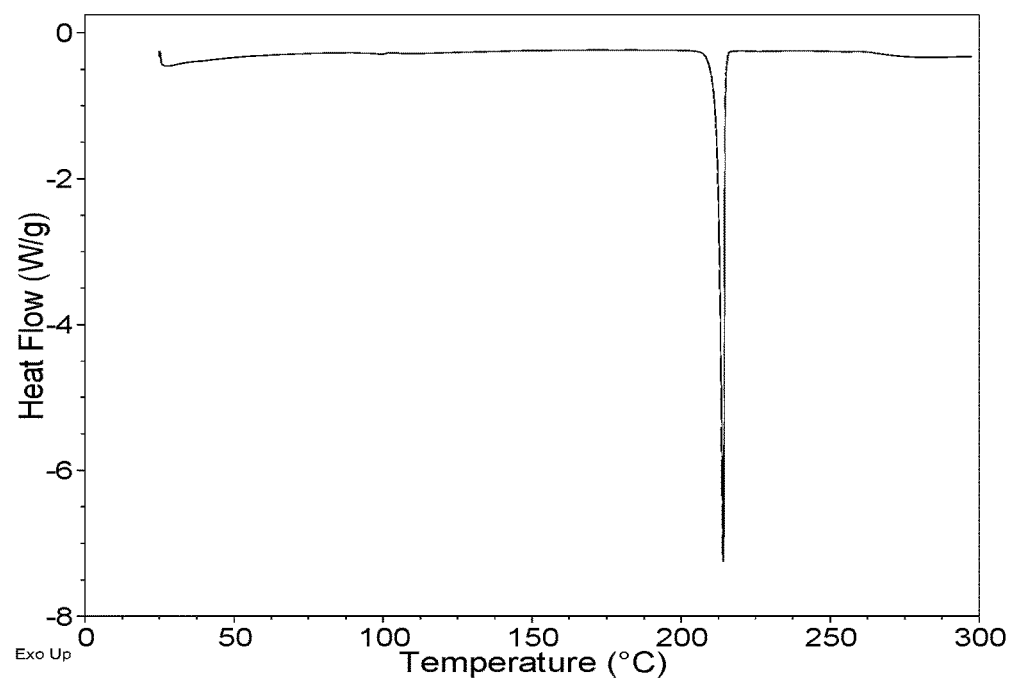
FIG. 2: DSC Thermogram of Form A of 8-[6-(3-Dimethylaminopropoxy)pyridin-3-yl]-3-methyl-1-(oxan-4-yl)imidazo[5,4-c]quinolin-2-one.

DSC analysis of Form A of 8-[6-(3-dimethylaminopropoxy)pyridin-3-yl]-3-methyl-1-(oxan-4-yl)imidazo[5,4-c]quinolin-2-one shows a melting endotherm with an onset of 212.3° C. and a peak at 214.1° C. (FIG. 2).

A person skilled in the art understands that the value or range of values observed in a particular compound's DSC Thermogram will show variation between batches of different purities. Therefore, whilst for one compound the range may be small, for others the range may be quite large. Generally, a measurement error of a diffraction angle in DSC thermal events is approximately plus or minus 5° C., and such degree of a measurement error should be taken into account when considering the DSC data included herein.

Therefore, in one embodiment there is provided a crystalline form, Form A of 8-[6-(3-dimethylaminopropoxy)pyridin-3-yl]-3-methyl-1-(oxan-4-yl)imidazo[5,4-c]quinolin-2-one which has a DSC endotherm with an onset of melting at about 212.3° C. and a peak at about 214.1° C.

Therefore, in one embodiment there is provided a crystalline form, Form A of 8-[6-(3-dimethylaminopropoxy)pyridin-3-yl]-3-methyl-1-(oxan-4-yl)imidazo[5,4-c]quinolin-2-one which has a DSC endotherm with an onset of melting at 212.3° C. plus or minus 5° C. and a peak at 214.1° C. plus or minus 5° C.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one which has a DSC endotherm with an onset of melting at 212.3° C. and a peak at 214.1° C.

In one embodiment there is provided a crystalline form, Form A of 8-[6-(3-dimethylaminopropoxy)pyridin-3-yl]-3-methyl-1-(oxan-4-yl)imidazo[5,4-c]quinolin-2-one which has a DSC thermogram substantially as shown in FIG. 2.

When it is stated that an embodiment relates to a crystalline form, the degree of crystallinity may be greater than about 60%. In some embodiments the degree of crystallinity is greater than about 80%. In some embodiments the degree of crystallinity is greater than about 90%. In some embodiments the degree of crystallinity is greater than about 95%. In some embodiments the degree of crystallinity is greater than about 98%.

Compounds of Formula (I) may for example be prepared by the reaction of a compound of Formula (II):

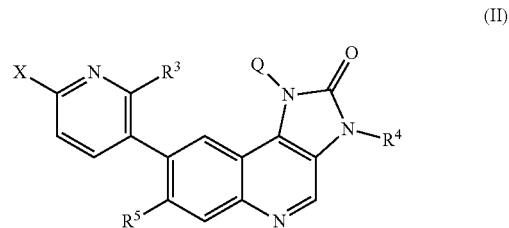

Or a salt thereof, where Q, $R^3$, $R^4$ and $R^5$ are as defined in any of the embodiments herein and X is a leaving group (for example a halogen atom, or alternatively a fluorine atom) with a compound of formula (III):

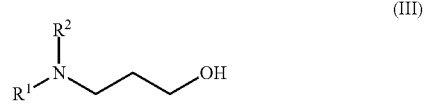

Or a salt thereof, where $R^1$ and $R^2$ are as defined in any of the embodiments herein. The reaction is conveniently performed in a suitable solvent (for example DMF, DMA or THF) and in the presence of a base (for example sodium hydride) at a suitable temperature (for example a temperature in the range of about 20-50° C.).

Compounds of Formula (II), and salts thereof, are therefore useful as intermediates in the preparation of the compounds of Formula (I) and provide a further embodiment.

In one embodiment there is provided a compound of Formula (II), or a salt thereof, where:

Q is a cyclobutyl or cyclopentyl ring, each of which is optionally substituted by one hydroxy or methoxy group, or Q is an oxetanyl, tetrahydrofuranyl or oxanyl ring, each of which is optionally substituted by one methyl group;

$R^3$ is hydrogen or fluoro;

$R^4$ is hydrogen or methyl:

$R^5$ is hydrogen or fluoro; and

X is a leaving group. In one embodiment X is a halogen atom or a triflate group. In one embodiment X is a fluorine atom.

In one embodiment there is provided a compound of Formula (I), or a salt thereof, where:

Q is cyclobutyl, 1-methoxy-cyclobut-3-yl, 1-hydroxy-cyclobut-3-yl, 3-methoxycyclopent-1-yl, oxetan-3-yl, tetrahydrofuran-3-yl, oxan-3-yl, oxan-4-yl or 4-methyloxan-4-yl;

$R^3$ is hydrogen or fluoro;

$R^4$ is hydrogen or methyl:

$R^5$ is hydrogen or fluoro; and

X is a leaving group. In one embodiment X is a halogen atom or a triflate group. In one embodiment X is a fluorine atom.

In one embodiment there is provided a compound of Formula (II), or a salt thereof, where:

Q is 1-methoxy-cyclobut-3-yl, 1-hydroxy-cyclobut-3-yl, 3-methoxycyclopent-1-yl, oxetan-3-yl, oxan-3-yl, oxan-4-yl or 4-methyloxan-4-yl.

$R^3$ is hydrogen or fluoro;

$R^4$ is hydrogen or methyl;

$R^5$ is hydrogen or fluoro; and

X is a leaving group. In one embodiment X is a halogen atom or a triflate group. In one embodiment X is a fluorine atom.

In one embodiment there is provided 8-(6-fluoropyridin-3-yl)-3-methyl-1-(oxan-4-yl)imidazo[5,4-c]quinolin-2-one, or a salt thereof.

In one embodiment there is provided 8-(6-fluoropyridin-3-yl)-1-(cis-3-methoxycyclobutyl)-3-methylimidazo[4,5-c]quinolin-2-one or a salt thereof.

In any of the embodiments where a compound of Formula (II) or a salt thereof is mentioned it is to be understood that such salts do not need to be pharmaceutically acceptable salts. A suitable salt of a compound of Formula (II) is, for example, an acid-addition salt. An acid addition salt of a compound of Formula (II) may be formed by bringing the compound into contact with a suitable inorganic or organic acid under conditions known to the skilled person. An acid addition salt may for example be formed using an inorganic acid selected from the group consisting of hydrochloric acid, hydrobromic acid, sulphuric acid and phosphoric acid. An acid addition salt may also be formed using an organic acid selected from the group consisting of trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid and para-toluenesulfonic acid.

Therefore, in one embodiment there is provided a compound of Formula (II) or a salt thereof, where the salt is a hydrochloric acid, hydrobromic acid, sulphuric acid, phosphoric acid, trifluoroacetic acid, citric acid, maleic acid, oxalic acid, acetic acid, formic acid, benzoic acid, fumaric acid, succinic acid, tartaric acid, lactic acid, pyruvic acid, methanesulfonic acid, benzenesulfonic acid or para-toluenesulfonic acid salt.

The compounds of Formula (II) may for example be prepared by the reaction of a compound of Formula (IV):

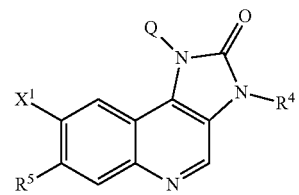

(IV)

Where Q, $R^4$ and $R^5$ are as defined in any of the embodiments herein and $X^1$ is a leaving group (for example an iodine, bromine, or chlorine atom or a triflate group, or alternatively a bromine atom) with a compound of formula (V):

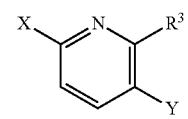

(V)

Or a salt thereof, where $R^3$ and X are as defined in any of the embodiments herein and Y is a boronic acid, boronic ester or potassium trifluoroborate group (for example boronic acid, boronic acid pinacol ester, or potassium trifluoroborate). The reaction may be performed under standard conditions well known to those skilled in the art, for example in the presence of a palladium source (for example tetrakis triphenylphosphine palladium or palladium(II) acetate), optionally a phosphine ligand (for example Xantphos or S-phos), and a suitable base (for example cesium carbonate or triethylamine).

Compounds of Formula (IV) are therefore useful as intermediates in the preparation of the compounds of Formula (I) and provide a further embodiment.

In one embodiment there is provided a compound of Formula (IV), or a salt thereof, where:

Q is a cyclobutyl or cyclopentyl ring, each of which is optionally substituted by one hydroxy or methoxy group, or Q is an oxetanyl, tetrahydrofuranyl or oxanyl ring, each of which is optionally substituted by one methyl group;

$R^4$ is hydrogen or methyl;

$R^5$ is hydrogen or fluoro; and $X^1$ is a leaving group. In one embodiment $X^1$ is an iodine, bromine, or chlorine atom or a triflate group. In one embodiment $X^1$ is a bromine atom.

In one embodiment there is provided a compound of Formula (IV), or a salt thereof, where:

Q is cyclobutyl, 1-methoxy-cyclobut-3-yl, 1-hydroxy-cyclobut-3-yl, 3-methoxycyclopent-1-yl, oxetan-3-yl, tetrahydrofuran-3-yl, oxan-3-yl, oxan-4-yl or 4-methyloxan-4-yl;

$R^4$ is hydrogen or methyl;

$R^5$ is hydrogen or fluoro; and $X^1$ is a leaving group. In one embodiment $X^1$ is an iodine, bromine, or chlorine atom or a triflate group. In one embodiment $X^1$ is a bromine atom.

In one embodiment there is provided a compound of Formula (IV), or a salt thereof, where:

Q is 1-methoxy-cyclobut-3-yl, 1-hydroxy-cyclobut-3-yl, 3-methoxycyclopent-1-yl, oxetan-3-yl, oxan-3-yl, oxan-4-yl or 4-methyloxan-4-yl;

$R^4$ is hydrogen or methyl;

$R^5$ is hydrogen or fluoro; and $X^1$ is a leaving group. In one embodiment $X^1$ is an iodine, bromine, or chlorine atom or a triflate group. In one embodiment $X^1$ is a bromine atom.

In one embodiment there is provided 8-bromo-3-methyl-1-(oxan-4-yl)imidazo[5,4-c]quinolin-2-one.

In one embodiment there is provided 8-bromo-1-(cis-3-methoxycyclobutyl)-3-methylimidazo[4,5-c]quinolin-2-one.

Compounds of formula (IV) can be prepared by methods similar to those shown in the Examples section.

Compounds of Formula (I) may also be prepared by the reaction of a compound of Formula (IV) as described above with a compound of formula (VI):

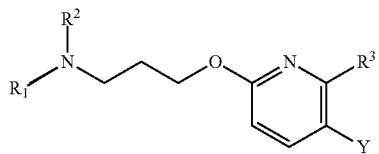

Where $R^1$, $R^2$ and $R^3$ are as defined in any of the embodiments herein and Y is a boronic acid, boronic ester or potassium trifluoroborate group (for example boronic acid, boronic acid pinacol ester, or potassium trifluoroborate). The reaction may be performed under standard conditions well known to those skilled in the art, for example in the presence of a palladium source (for example tetrakis triphenylphosphine palladium or palladium(II) acetate), optionally a phosphine ligand (for example Xantphos or S-phos), and a suitable base (for example cesium carbonate or triethylamine).

Compounds of formula (VI) can be prepared by methods similar to those shown in the Examples section.

As a result of their ATM kinase inhibitory activity, the compounds of Formula (I), and pharmaceutically acceptable salts thereof are expected to be useful in therapy, for example in the treatment of diseases or medical conditions mediated at least in part by ATM kinase, including cancer.

Where "cancer" is mentioned, this includes both non-metastatic cancer and also metastatic cancer, such that treating cancer involves treatment of both primary tumours and also tumour metastases.

"ATM kinase inhibitory activity" refers to a decrease in the activity of ATM kinase as a direct or indirect response to the presence of a compound of Formula (I), or pharmaceutically acceptable salt thereof, relative to the activity of ATM kinase in the absence of compound of Formula (I), or pharmaceutically acceptable salt thereof. Such a decrease in activity may be due to the direct interaction of the compound of Formula (I), or pharmaceutically acceptable salt thereof with ATM kinase, or due to the interaction of the compound of Formula (I), or pharmaceutically acceptable salt thereof with one or more other factors that in turn affect ATM kinase activity. For example, the compound of Formula (I), or pharmaceutically acceptable salt thereof may decrease ATM kinase by directly binding to the ATM kinase, by causing (directly or indirectly) another factor to decrease ATM kinase activity, or by (directly or indirectly) decreasing the amount of ATM kinase present in the cell or organism.

The term "therapy" is intended to have its normal meaning of dealing with a disease in order to entirely or partially relieve one, some or all of its symptoms, or to correct or compensate for the underlying pathology. The term "therapy" also includes "prophylaxis" unless there are specific indications to the contrary. The terms "therapeutic" and "therapeutically" should be interpreted in a corresponding manner.

The term "prophylaxis" is intended to have its normal meaning and includes primary prophylaxis to prevent the development of the disease and secondary prophylaxis whereby the disease has already developed and the patient is temporarily or permanently protected against exacerbation or worsening of the disease or the development of new symptoms associated with the disease.

The term "treatment" is used synonymously with "therapy". Similarly the term "treat" can be regarded as "applying therapy" where "therapy" is as defined herein.

In one embodiment there is provided a compound of Formula (I), or a pharmaceutically acceptable salt thereof, for use in therapy.

In one embodiment there is provided the use of the compound of Formula (I), or a pharmaceutically acceptable salt thereof, for the manufacture of a medicament.

In one embodiment there is provided a compound of Formula (I), or a pharmaceutically acceptable salt thereof, for use in the treatment of a disease mediated by ATM kinase. In one embodiment, said disease mediated by ATM kinase is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, ghloblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In one embodiment there is provided a compound of Formula (I), or a pharmaceutically acceptable salt thereof, for use in the treatment of cancer.

In one embodiment there is provided a compound of Formula (I), or a pharmaceutically acceptable salt thereof, for use in the treatment of Huntingdon's disease.

In one embodiment there is provided the use of the compound of Formula (I), or a pharmaceutically acceptable salt thereof, for the manufacture of a medicament for the treatment of a disease mediated by ATM kinase. In one embodiment, said disease mediated by ATM kinase is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In one embodiment there is provided the use of the compound of Formula (I), or a pharmaceutically acceptable salt thereof, for the manufacture of a medicament for the treatment of cancer.

In one embodiment there is provided a method for treating a disease in which inhibition of ATM kinase is beneficial in a warm-blooded animal in need of such treatment, which comprises administering to said warm-blooded animal a therapeutically effective amount of a compound of Formula (I), or a pharmaceutically acceptable salt thereof. In one embodiment, said disease is cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

The term "therapeutically effective amount" refers to an amount of a compound of Formula (I) as described in any of the embodiments herein which is effective to provide "therapy" in a subject, or to "treat" a disease or disorder in a subject. In the case of cancer, the therapeutically effective amount may cause any of the changes observable or measurable in a subject as described in the definition of "therapy". "treatment" and "prophylaxis" above. For example, the effective amount can reduce the number of cancer or tumour cells; reduce the overall tumour size; inhibit or stop tumour cell infiltration into peripheral organs including, for example, the soft tissue and bone; inhibit and stop tumour metastasis; inhibit and stop tumour growth; relieve to some extent one or more of the symptoms associated with the cancer; reduce morbidity and mortality; improve quality of life; or a combination of such effects. An effective amount may be an amount sufficient to decrease the symptoms of a disease responsive to inhibition of ATM kinase activity. For cancer therapy, efficacy in-vivo can, for example, be measured by assessing the duration of survival, time to disease progression (TTP), the response rates (RR), duration of response, and/or quality of life. As recognized by those skilled in the art, effective amounts may vary depending on route of administration, excipient usage, and co-usage with other agents. For example, where a combination therapy is used, the amount of the compound of formula (I) or pharmaceutically acceptable salt described in this specification and the amount of the other pharmaceutically active agent(s) are, when combined, jointly effective to treat a targeted disorder in the animal patient. In this context, the combined amounts are in a "therapeutically effective amount" if they are, when combined, sufficient to decrease the symptoms of a disease responsive to inhibition of ATM activity as described above. Typically, such amounts may be determined by one skilled in the art by, for example, starting with the dosage range described in this specification for the compound of formula (I) or pharmaceutically acceptable salt thereof and an approved or otherwise published dosage range(s) of the other pharmaceutically active compound(s).

"Warm-blooded animals" include, for example, humans.

In one embodiment there is provided a method for treating cancer in a warm-blooded animal in need of such treatment, which comprises administering to said warm-blooded animal a therapeutically effective amount of a compound of Formula (I), or a pharmaceutically acceptable salt thereof. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

In any embodiment where cancer is mentioned in a general sense, said cancer may be selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. Said cancer may also be selected from the group consisting of colorectal cancer, glioblastoma, gastric cancer, ovarian cancer, diffuse large B-cell lymphoma, chronic lymphocytic leukaemia, and head and neck squamous cell carcinoma and lung cancer.

In any embodiment where cancer is mentioned in a general sense the following embodiments may apply:

In one embodiment the cancer is colorectal cancer.

In one embodiment the cancer is glioblastoma.

In one embodiment the cancer is gastric cancer.

In one embodiment the cancer is oesophageal cancer.

In one embodiment the cancer is ovarian cancer.

In one embodiment the cancer is endometrial cancer.

In one embodiment the cancer is cervical cancer.

In one embodiment the cancer is diffuse large B-cell lymphoma.

In one embodiment the cancer is chronic lymphocytic leukaemia.

In one embodiment the cancer is acute myeloid leukaemia.

In one embodiment the cancer is head and neck squamous cell carcinoma.

In one embodiment the cancer is breast cancer. In one embodiment the cancer is triple negative breast cancer.

"Triple negative breast cancer" is any breast cancer that does not express the genes for the oestrogen receptor, progesterone receptor and Her2/neu.

In one embodiment the cancer is hepatocellular carcinoma.

In one embodiment the cancer is lung cancer. In one embodiment the lung cancer is small cell lung cancer. In one embodiment the lung cancer is non-small cell lung cancer.

In one embodiment the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

"Leptomeningeal metastases" occur when cancer spreads to the meninges, the layers of tissue that cover the brain and the spinal cord. Metastases can spread to the meninges through the blood or they can travel from brain metastases, carried by the cerebrospinal fluid (CSF) that flows through the meninges. In one embodiment the cancer is non-metastatic cancer. The anti-cancer treatment described in this specification may be useful as a sole therapy, or may involve, in addition to administration of the compound of Formula (I), conventional surgery, radiotherapy or chemotherapy, or a combination of such additional therapies. Such conventional surgery, radiotherapy or chemotherapy may be administered simultaneously, sequentially or separately to treatment with the compound of Formula (I).

Radiotherapy may include one or more of the following categories of therapy:
  i. External radiation therapy using electromagnetic radiation, and intraoperative radiation therapy using electromagnetic radiation;
  ii. Internal radiation therapy or brachytherapy; including interstitial radiation therapy or intraluminal radiation therapy; or
  iii. Systemic radiation therapy, including but not limited to iodine 131 and strontium 89.

Therefore, in one embodiment there is provided a compound of Formula (I), or a pharmaceutically acceptable salt thereof, and radiotherapy, for use in the treatment of cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with radiotherapy. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, and radiotherapy, for use in the simultaneous, separate or sequential treatment of cancer. In one embodiment the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with radiotherapy. In one embodiment the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a method of treating cancer in a warm-blooded animal who is in need of such treatment, which comprises administering to said warm-blooded animal a compound of Formula (I), or a pharmaceutically acceptable salt thereof and radiotherapy, wherein the compound of Formula (I), or a pharmaceutically acceptable salt thereof, and radiotherapy are jointly effective in producing an anti-cancer effect. In one embodiment the cancer is selected from glioblastoma, lung cancer (for example small cell lung cancer or non-small cell lung cancer), breast cancer (for example triple negative breast cancer), head and neck squamous cell carcinoma, oesophageal cancer, cervical cancer and endometrial cancer. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In one embodiment there is provided a method of treating cancer in a warm-blooded animal who is in need of such treatment, which comprises administering to said warm-blooded animal a compound of Formula (I), or a pharmaceutically acceptable salt thereof and simultaneously, separately or sequentially administering radiotherapy, wherein the compound of Formula (I), or a pharmaceutically acceptable salt thereof, and radiotherapy are jointly effective in producing an anti-cancer effect. In one embodiment the cancer is glioblastoma. In one embodiment, the cancer is metastatic cancer. In one embodiment the metastatic cancer comprises metastases of the central nervous system. In one embodiment the metastases of the central nervous system comprise brain metastases. In one embodiment the metastases of the central nervous system comprise leptomeningeal metastases.

In any embodiment the radiotherapy is selected from the group consisting of one or more of the categories of radiotherapy listed under points (i)-(iii) above.

Chemotherapy may include one or more of the following categories of anti-tumour substance:
  i. Antineoplastic agents and combinations thereof, such as DNA alkylating agents (for example cisplatin, oxaliplatin, carboplatin, cyclophosphamide, nitrogen mustards like ifosfamide, bendamustine, melphalan, chlorambucil, busulphan, temozolamide and nitrosoureas like carmustine); antimetabolites (for example gemcitabine and antifolates such as fluoropyrimidines like 5-fluorouracil and tegafur, raltitrexed, methotrexate, cytosine arabinoside, and hydroxyurea); anti-tumour antibiotics (for example anthracyclines like adriamycin, bleomycin, doxorubicin, liposomal doxorubicin, pirarubicin, daunomycin, valrubicin, epirubicin, idarubicin, mitomycin-C, dactinomycin, amrubicin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, irinotecan, topotecan and camptothecin); inhibitors of DNA repair mechanisms such as CHK kinase; DNA-dependent protein kinase inhibitors; inhibitors of poly (ADP-ribose) polymerase (PARP inhibitors, including olaparib); and Hsp90 inhibitors such as tanespimycin and retaspimycin, inhibitors of ATR kinase (such as AZD6738); and inhibitors of WEE1 kinase (such as AZD1775/MK-1775);

ii. Antiangiogenic agents such as those that inhibit the effects of vascular endothelial growth factor, for example the anti-vascular endothelial cell growth factor antibody bevacizumab and for example, a VEGF receptor tyrosine kinase inhibitor such as vandetanib (ZD6474), somfenib, vatalanib (PTK787), sunitinib (SU11248), axitinib (AG-013736), pazopanib (GW 786034) and cediranib (AZD2171); compounds such as those disclosed in International Patent Applications WO97/22596, WO 97/30035, WO 97/32856 and WO 98/13354; and compounds that work by other mechanisms (for example linomide, inhibitors of integrin $\alpha v \beta 3$ function and angiostatin), or inhibitors of angiopoietins and their receptors (Tie-1 and Tie-2), inhibitors of PLGF, inhibitors of delta-like ligand (DLL-4);

iii. Immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor; approaches to decrease T-cell anergy or regulatory T-cell function; approaches that enhance T-cell responses to tumours, such as blocking antibodies to CTLA4 (for example ipilimumab and tremelimumab), B7H1, PD-1 (for example BMS-936558 or AMP-S 14), PD-L1 (for example MEDI4736) and agonist antibodies to CD137; approaches using transfected immune cells such as cytokine-transfected dendritic cells; approaches using cytokine-transfected tumour cell lines, approaches using antibodies to tumour associated antigens, and antibodies that deplete target cell types (e.g., unconjugated anti-CD20 antibodies such as Rituximab, radiolabeled anti-CD20 antibodies Bexxar and Zevalin, and anti-CD54 antibody Campath); approaches using anti-idiotypic antibodies; approaches that enhance Natural Killer cell function; and approaches that utilize antibody-toxin conjugates (e.g. anti-CD33 antibody Mylotarg); immunotoxins such as moxetumumab pasudotox; agonists of toll-like receptor 7 or toll-like receptor 9;

iv. Efficacy enhancers, such as leucovorin.

Therefore, in one embodiment there is provided a compound of Formula (I), or a pharmaceutically acceptable salt thereof, and at least one additional anti-tumour substance, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof is administered in combination with an additional anti-tumour substance. In one embodiment there is one additional anti-tumour substance. In one embodiment there are two additional anti-tumour substances. In one embodiment there are three or more additional anti-tumour substances.

In one embodiment there is provided a compound of Formula (I), or a pharmaceutically acceptable salt thereof, and at least one additional anti-tumour substance for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with an additional anti-tumour substance.

In one embodiment there is provided a method of treating cancer in a warm-blooded animal who is in need of such treatment, which comprises administering to said warm-blooded animal a compound of Formula (I), or a pharmaceutically acceptable salt thereof and at least one additional anti-tumour substance, wherein the amounts of the compound of Formula (I), or a pharmaceutically acceptable salt thereof, and the additional anti-tumour substance are jointly effective in producing an anti-cancer effect.

In one embodiment there is provided a method of treating cancer in a warm-blooded animal who is in need of such treatment, which comprises administering to said warm-blooded animal a compound of Formula (I), or a pharmaceutically acceptable salt thereof, and simultaneously, separately or sequentially administering at least one additional anti-tumour substance to said warm-blooded animal, wherein the amounts of the compound of Formula (I), or pharmaceutically acceptable salt thereof, and the additional anti-tumour substance are jointly effective in producing an anti-cancer effect.

In any embodiment the additional anti-tumour substance is selected from the group consisting of one or more of the anti-tumour substances listed under points (i)-(iv) above.

In one embodiment there is provided a compound of Formula (I), or a pharmaceutically acceptable salt thereof, and at least one anti-neoplastic agent for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one anti-neoplastic agent. In one embodiment the anti-neoplastic agent is selected from the list of antineoplastic agents in point (i) above.

In one embodiment there is provided a compound of Formula (I), or a pharmaceutically acceptable salt thereof, and at least one anti-neoplastic agent for use in the simultaneous, separate or sequential treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered simultaneously, separately or sequentially with at least one anti-neoplastic agent. In one embodiment the antineoplastic agent is selected from the list of antineoplastic agents in point (i) above.

In one embodiment there is provided a compound of Formula (I), or a pharmaceutically acceptable salt thereof, and at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736, AZD1775 and AZD6738, for use in the treatment of cancer.

In one embodiment there is provided a compound of Formula (I), or a pharmaceutically acceptable salt thereof, and at least one additional anti-tumour substance selected from the group consisting of cisplatin, oxaliplatin, carboplatin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, AZD1775 and AZD6738, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of cisplatin, oxaliplatin, carboplatin, valrubicin, idarubicin, doxorubicin, pirarubicin, irinotecan, topotecan, amrubicin, epirubicin, etoposide, mitomycin, bendamustine, chlorambucil, cyclophosphamide, ifosfamide, carmustine, melphalan, bleomycin, olaparib, MEDI4736, AZD1775 and AZD6738.

In one embodiment there is provided a compound of Formula (I), or a pharmaceutically acceptable salt thereof, and at least one additional anti-tumour substance selected from the group consisting of doxorubicin, irinotecan, topotecan, etoposide, mitomycin, bendamustine, chlorambucil, cyclophosphamide, ifosfamide, carmustine, melphalan, bleomycin and olaparib for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, irinotecan, topotecan, etoposide, mitomycin, bendamustine, chlorambucil, cyclophosphamide, ifosfamide, carmustine, melphalan, bleomycin and olaparib.

In one embodiment there is provided a compound of Formula (I), or a pharmaceutically acceptable salt thereof, and at least one additional anti-tumour substance selected from the group consisting of doxorubicin, irinotecan, topotecan, etoposide, mitomycin, bendamustine, chlorambucil, cyclophosphamide, ifosfamide, carmustine, melphalan and bleomycin, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, irinotecan, topotecan, etoposide, mitomycin, bendamustine, chlorambucil, cyclophosphamide, ifosfamide, carmustine, melphalan and bleomycin.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with at least one additional anti-tumour substance selected from the group consisting of doxorubicin, pirarubicin, amrubicin and epirubicin. In one embodiment the cancer is acute myeloid leukaemia. In one embodiment the cancer is breast cancer (for example triple negative breast cancer). In one embodiment the cancer is hepatocellular carcinoma.

In one embodiment there is provided a compound of Formula (I), or a pharmaceutically acceptable salt thereof, and irinotecan, for use in the treatment of cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with irinotecan. In one embodiment the cancer is colorectal cancer.

In one embodiment there is provided a compound of Formula (I), or a pharmaceutically acceptable salt thereof, and FOLFIRI, for use in the treatment of cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with FOLFIRI. In one embodiment the cancer is colorectal cancer.

FOLFIRI is a dosage regime involving a combination of leucovorin, 5-fluorouracil and irinotecan.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with olaparib. In one embodiment the cancer is gastric cancer.

In one embodiment there is provided a compound of Formula (I), or a pharmaceutically acceptable salt thereof, for use in the treatment of cancer, where the compound of Formula (I), or a pharmaceutically acceptable salt thereof, is administered in combination with topotecan. In one embodiment the cancer is small cell lung cancer. In one embodiment there is provided a compound of Formula (I), or a pharmaceutically acceptable salt thereof, for use in the treatment of cancer, where the compound of Formula (I), or a pharmaceutically acceptable salt thereof, is administered in combination with immunotherapy. In one embodiment the immunotherapy is one or more of the agents listed under point (iii) above. In one embodiment the immunotherapy is an anti-PD-L1 antibody (for example MEDI4736).

In one embodiment there is provided a pharmaceutical composition comprising a compound of Formula (I) and at least one additional anti-tumour substance. In one embodiment the pharmaceutical composition also comprises at least one pharmaceutically acceptable diluent or carrier. In one embodiment the anti-tumour substance is an anti-neoplastic agent.

In one embodiment there is provided a pharmaceutical composition comprising a compound of Formula (I) and at least one additional anti-tumour substance, for use in the treatment of cancer. In one embodiment the pharmaceutical composition also comprises at least one pharmaceutically acceptable diluent or carrier. In one embodiment the anti-tumour substance is an anti-neoplastic agent.

According to a further embodiment there is provided a kit comprising:

a) A compound of formula (I), or a pharmaceutically acceptable salt thereof, in a first unit dosage form;

b) A further additional anti-tumour substance in a further unit dosage form;

c) Container means for containing said first and further unit dosage forms; and optionally d) Instructions for use. In one embodiment the anti-tumour substance comprises an anti-neoplastic agent.

In any embodiment where an anti-neoplastic agent is mentioned, the anti-neoplastic agent is one or more of the agents listed under point (i) above.

The compounds of Formula (I), and pharmaceutically acceptable salts thereof, may be administered as pharmaceutical compositions, comprising one or more pharmaceutically acceptable diluents or carriers.

Therefore, in one embodiment there is provided a pharmaceutical composition comprising a compound of Formula (I), or a pharmaceutically acceptable salt thereof, and at least one pharmaceutically acceptable diluent or carrier.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing), or as a suppository for rectal dosing. The compositions may be obtained by conventional procedures using conventional pharmaceutical excipients, well known in the art. Thus, compositions intended for oral use may contain, for example, one or more colouring, sweetening, flavouring and % or preservative agents.

In one embodiment there is provided a pharmaceutical composition comprising a compound of Formula (I), or a pharmaceutically acceptable salt thereof, and at least one pharmaceutically acceptable diluent or carrier, for use in therapy.

In one embodiment there is provided a pharmaceutical composition comprising a compound of Formula (I), or a pharmaceutically acceptable salt thereof, and at least one pharmaceutically acceptable diluent or carrier, for use in the treatment of cancer. In one embodiment, said cancer is selected from the group consisting of colorectal cancer, glioblastoma, gastric cancer, ovarian cancer, diffuse large B-cell lymphoma, chronic lymphocytic leukaemia, acute myeloid leukaemia, head and neck squamous cell carcinoma, breast cancer, hepatocellular carcinoma, small cell lung cancer and non-small cell lung cancer. In one embodiment, said cancer is selected from the group consisting of colorectal cancer, glioblastoma, gastric cancer, ovarian cancer, diffuse large B-cell lymphoma, chronic lymphocytic leukaemia, head and neck squamous cell carcinoma and lung cancer. In one embodiment, said cancer is colorectal cancer.

The compound of Formula (I) will normally be administered to a warm-blooded animal at a unit dose within the range 2.5-5000 mg/m$^2$ body area of the animal, or approximately 0.05-100 mg/kg, and this normally provides a therapeutically-effective dose. A unit dose form such as a tablet or capsule will usually contain, for example 0.1-250 mg of active ingredient. The daily dose will necessarily be varied depending upon the host treated, the particular route of administration, any therapies being co-administered, and the severity of the illness being treated. Accordingly the practitioner who is treating any particular patient may determine the optimum dosage.

EXAMPLES

The various embodiments are illustrated by the following Examples. The invention is not to be interpreted as being limited to the Examples. During the preparation of the Examples, generally:
i. Operations were carried out at ambient temperature/room temperature. i.e. in the range of about 17° C. to 30° C. and under atmospheric conditions unless otherwise stated;
ii. Evaporations were carried out by rotary evaporation or utilising Genevac equipment in vacuo and work-up procedures were carried out after removal of residual solids by filtration;
iii. Flash chromatography purifications were performed on an automated Armen Glider Flash: Spot II Ultimate (Armen Instrument, Saint-Ave, France) or automated Presearch combiflash companions using prepacked Merck normal phase Si60 silica cartridges (granulometry: 15-40 or 40-63 μm) obtained from Merck, Darmstad, Germany, silicycle silica cartridges or graceresolv silica cartridges;
iv. Preparative chromatography was performed on a Waters instrument (600/2700 or 2525) fitted with a ZMD or ZQ ESCi mass spectrometers and a Waters X-Terra or a Waters X-Bridge or a Waters SunFire reverse-phase column (C-18, 5 microns silica, 19 mm or 50 mm diameter, 100 mm length, flow rate of 40 mL/minute) using decreasingly polar mixtures of water (containing 1% ammonia) and acetonitrile or decreasingly polar mixtures of water (containing 0.1% formic acid) and acetonitrile as eluents. Examples 2, 6-8, 13, 16, 18, 19-22, 27, 29, 34, 39, 59, 60, 70 and 71 were isolated directly from preparative HPLC solutions containing formic acid. The material isolated therefore comprises a certain amount of formic acid;
v. Yields, where present, are not necessarily the maximum attainable;
vi. Structures of end-products of Formula (I) were confirmed by nuclear magnetic resonance (NMR) spectroscopy, with NMR chemical shift values measured on the delta scale. Proton magnetic resonance spectra were determined using a Bruker advance 700 (700 MHz), Bruker Avance 500 (500 MHz), Bruker 400 (400 MHz) or Bruker 300 (300 MHz) instrument; 19F NMR were determined at 282 MHz or 376 MHz; 13C NMR were determined at 75 MHz or 100 MHz; measurements were taken at around 20-30° C. unless otherwise specified; the following abbreviations have been used: s=singlet: d=doublet; t=triplet, q=quartet; p=pentet/quintet; m=multiplet; dd=doublet of doublets; ddd=doublet of doublet of doublet; dt=doublet of triplets; td=triplet of doublets; qd=quartet of doublets; bs=broad signal;
vii. End-products of Formula (I) were also characterised by mass spectroscopy following liquid chromatography (LCMS); LCMS was carried out using an Waters Alliance HT (2790 & 2795) fitted with a Waters ZQ ESCi or ZMD ESCi mass spectrometer and an X Bridge 5 μm C-18 column (2.1×50 mm) at a flow rate of 2.4 mL/min. using a solvent system of 95% A+5% C to 95% B+5% C over 4 minutes, where A=water, B=methanol, C=1:1 methanol:water (containing 0.2% ammonium carbonate); or by using a Shimadzu UFLC or UHPLC coupled with DAD detector, ELSD detector and 2020 EV mass spectrometer (or equivalent) fitted with a Phenomenex Gemini-NX C18 3.0×50 mm, 3.0 μm column or equivalent (basic conditions) or a Shim pack XR-ODS 3.0×50 mm, 2.2 μm column or Waters BEH C18 2.1×50 mm, 1.7 μm column or equivalent using a solvent system of 95% D+5% E to 95% E+5% D over 4 minutes, where D=water (containing 0.05% TFA), E=Acetonitrile (containing 0.05% TFA) (acidic conditions) or a solvent system of 90% F+10% G to 95% G+5% F over 4 minutes, where F=water (containing 6.5 mM ammonium hydrogen carbonate and adjusted to pH 10 by addition of ammonia), G=Acetonitrile (basic conditions);
viii. Intermediates were not generally fully characterised and purity was assessed by thin layer chromatographic, mass spectral, HPLC and/or NMR analysis;

ix. X-ray powder diffraction spectra were determined (using a Bruker D4 Analytical Instrument) by mounting a sample of the crystalline material on a Bruker single silicon crystal (SSC) wafer mount and spreading out the sample into a thin layer with the aid of a microscope slide. The sample was spun at 30 revolutions per minute (to improve counting statistics) and irradiated with X-rays generated by a copper long-fine focus tube operated at 40 kV and 40 mA with a wavelength of 1.5418 angstroms. The collimated X-ray source was passed through an automatic variable divergence slit set at V20 and the reflected radiation directed through a 5.89 mm antiscatter slit and a 9.55 mm detector slit. The sample was exposed for 0.03 seconds per 0.00570° 2-theta increment (continuous scan mode) over the range 2 degrees to 40 degrees 2-theta in theta-theta mode. The running time was 3 minutes and 36 seconds. The instrument was equipped with a Position sensitive detector (Lynxeye). Control and data capture was by means of a Dell Optiplex 686 NT 4.0 Workstation operating with Diffrac+ software;

x. Differential Scanning Calorimetry was performed on a TA Instruments Q1000 DSC. Typically, less than 5 mg of material contained in a standard aluminium pan fitted with a lid was heated over the temperature range 25° C. to 300° C. at a constant heating rate of 10° C. per minute. A purge gas using nitrogen was used at a flow rate 50 ml per minute xi. The following abbreviations have been used: h=hour(s); r.t.=room temperature (~17-30° C.); conc.=concentrated; FCC=flash column chromatography using silica; DCM=dichloromethane; DIPEA=diisopropylethylamine; DMA=N,N-dimethylacetamide; DMF=N,N-dimethylformamide; DMSO=dimethylsulfoxide; Et$_2$O=diethyl ether; EtOAc=ethyl acetate; EtOH=ethanol; K$_2$CO$_3$=potassium carbonate; MeOH=methanol; MeCN=acetonitrile; MTBE=Methyltertbutylether; MgSO$_4$=anhydrous magnesium sulphate; Na$_2$SO$_4$=anhydrous sodium sulphate; THF=tetrahydrofuran; sat.=saturated aqueous solution; and xii. IUPAC names were generated using 'SmiToSd', a proprietary program built around the OpenEye Lexichem toolkit (http:/www.eyesopen.com/lexichem-tk), or Canvas, a different proprietary program. 'SmiToSd' was used to name Examples 1 to 22 and 25 to 42, and Canvas was used to name Examples 23, 24 and 43 to 71. 'SmiToSd' did not automatically recognise stereochemistry of the 3-substituted cyclobut-1-yl group present in certain of the Examples, so the names of these Examples were manually edited to include the correct cyclobutyl stereochemistry. Furthermore, as stated in the introduction, the compounds comprise an imidazo[4,5-c]quinolin-2-one core. However, in certain Examples the IUPAC name describes the core as an imidazo[5,4-c]quinolin-2-one. The imidazo[4,5-c]quinolin-2-one and imidazo[5,4-c]quinolin-2-one cores are nevertheless the same, with the naming convention slightly different because of the peripheral groups.

Example 1

8-[6-(3-Dimethylaminoprop oxy)pyridin-3-yl]-3-methyl-1-(oxan-4-yl)imidazo[5,4-c]quinolin-2-one

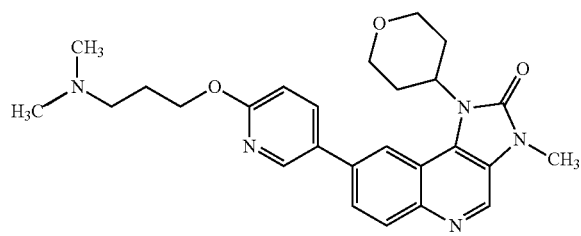

Sodium hydride (60% dispersion in mineral oil) (21.14 g, 528.56 mmol) was added portion-wise to 3-(dimethylamino) propan-1-ol (27.3 g, 264.27 mmol) in DMF (500 mL) at 10° C. over a period of 20 minutes under nitrogen. The resulting mixture was stirred at r.t. for 1 h. 8-(6-Fluoropyridin-3-yl)-3-methyl-1-(oxan-4-yl)imidazo[5,4-c]quinolin-2-one (50.0 g, 132.14 mmol) was added portion-wise to the reaction mixture at 10° C. over a period of 20 minutes under nitrogen. The resulting mixture was stirred at r.t. for 16 h. The reaction mixture was diluted with water and the precipitate collected by filtration, washed with water (300 mL) and dried under vacuum. The dried solid was triturated with EtOAc (2 L) and filtered. The crude product was purified by crystallisation from MeCN to afford the desired product (50.0 g, 82%) as a white solid. NMR Spectrum: $^1$H NMR (400 MHz, CDCl$_3$) δ 1.90-2.04 (4H, m), 2.29 (6H, s), 2.49 (2H, t), 2.93-3.07 (2H, m), 3.56-3.67 (5H, m), 4.10-4.30 (2H, m), 4.43 (2H, t), 5.10 (1H, t), 6.89 (1H, d), 7.80 (1H, d), 7.92 (1H, dd), 8.21 (1H, d), 8.40 (1H, s), 8.51 (1H, d), 8.71 (1H, s). Mass Spectrum: m/z (ES+) [M+H]+=462.3.

The title material (49.5 g, 107.25 mmol) was suspended in MeCN (300 mL) to give a freely stirring thick solution. This solution was allowed to stir at r.t. overnight giving a thinner solution. The material was filtered, washed with cold (0° C.) MeCN (200 mL) and dried overnight in vacuo at 30° C. to give the title material in crystalline form A (48 g, 97%) as a white solid. NMR Spectrum: $^1$H NMR (400 MHz, DMSO-d6) δ 1.81-1.99 (4H, m), 2.16 (6H, s), 2.37 (2H, t), 2.73 (2H, qd), 3.51 (3H, s), 3.59 (2H, t), 4.07 (2H, dd), 4.37 (2H, t), 5.14 (1H, ddd), 6.94-7.01 (1H, m), 7.95 (1H, dd), 8.14 (1H, d), 8.18 (1H, dd), 8.43 (1H, s), 8.66 (1H, d), 8.89 (1H, s). Mass Spectrum: m/z (ES+) [M+H]+=462.6.

The slurry filtrate and washings were combined and evaporated to recover additional title material (580 mg, 1.172%) as a pale cream solid. The material obtained by the above procedure was determined to be crystalline form A and was analysed by XRPD to give an X-Ray diffractogram with the following characteristic peaks.

TABLE 1

Characteristic X-Ray powder diffraction peaks for Form A of 8-[6-(3-dimethylaminopropoxy)pyridin-3-yl]-3-methyl-1-(oxan-4-yl)imidazo[5,4-c]quinolin-2-one

| Angle 2-Theta (2θ) | Intensity (%) |
|---|---|
| 3.9 | 100 |
| 11.6 | 78 |
| 21.3 | 32 |
| 22.2 | 28 |

TABLE 1-continued

Characteristic X-Ray powder diffraction peaks for Form A of 8-[6-(3-dimethylaminopropoxy)pyridin-3-yl]-3-methyl-1-(oxan-4-yl)imidazo[5,4-c]quinolin-2-one

| Angle 2-Theta (2θ) | Intensity (%) |
|---|---|
| 10.7 | 25 |
| 7.7 | 21 |
| 15.4 | 20 |
| 16.9 | 18 |
| 17.4 | 15 |
| 18.4 | 14 |

8-(6-Fluoropyridin-3-yl)-3-methyl-1-(oxan-4-yl)imidazo[5,4-c]quinolin-2-one can be prepared according to the following procedure.

Intermediate A1: 8-(6-Fluoropyridin-3-yl)-3-methyl-1-(oxan-4-yl)imidazo[5,4-c]quinolin-2-one

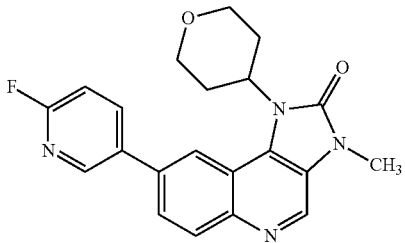 [SMILES: Cn1c(=O)n(C2CCOCC2)c2c3cc(-c4ccc(F)nc4)ccc3ncc21]

Monopalladium(IV) disodium tetrachloride (0.975 g, 3.31 mmol) was added to 8-bromo-3-methyl-1-(oxan-4-yl)imidazo[5,4-c]quinolin-2-one (60.0 g, 165.64 mmol), (6-fluoropyridin-3-yl)boronic acid (25.7 g, 182.21 mmol), K$_2$CO$_3$ (68.7 g, 496.93 mmol) and 3-(di-tert-butylphosphino)propane-1-sulfonic acid (0.445 g, 1.66 mmol) in 1,4-dioxane (400 mL) and water (100 mL) at r.t. under air. The resulting mixture was stirred at 80° C. for 16 h. The reaction mixture was diluted with water and the precipitate collected by filtration, washed with water (200 mL) and dried under vacuum. The resulting solid was dissolved with DCM (18 L) and the mixture filtered through celite to remove Palladium residues. The solvent was removed under reduced pressure to afford the desired material (60.0 g, 96%) as a white solid, which was used without further purification. NMR Spectrum: $^1$H NMR (400 MHz, CDCl$_3$) δ 1.85-2.01 (2H, m), 2.86-3.02 (2H, m), 3.57-3.68 (5H, m), 4.16-4.31 (2H, m), 5.11 (1H, t), 6.98-7.19 (1H, m), 7.83 (1H, dd), 8.16 (1H, td), 8.30 (1H, dd), 8.50 (1H, s), 8.60 (1H, s), 8.77 (1H, s). Mass Spectrum: m/z (ES+) [M+H]+=379.2.

Intermediate A2: 8-Bromo-3-methyl-1-(oxan-4-yl)imidazo[5,4-c]quinolin-2-one

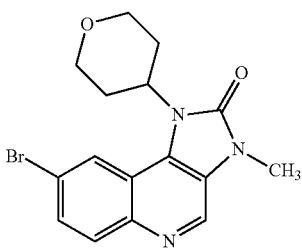 [SMILES: Cn1c(=O)n(C2CCOCC2)c2c3cc(Br)ccc3ncc21]

A solution of sodium hydroxide (10.34 g, 258.48 mmol) in water (900 mL) was added to a stirred mixture of 8-bromo-1-(oxan-4-yl)-3H-imidazo[4,5-c]quinolin-2-one (60.0 g, 172.32 mmol), iodomethane (48.9 g, 344.63 mmol) and tetrabutylammonium bromide (5.55 g, 17.23 mmol) in DCM (1500 mL) at r.t. under air. The resulting mixture was stirred for 16 h then the DCM removed under reduced pressure. The precipitate was collected by filtration, washed with water (200 mL) and dried under vacuum to afford the desired material (58.0 g, 93%) as a brown solid, which was used without further purification. NMR Spectrum: $^1$H NMR (400 MHz, CDCl$_3$) δ 1.81-1.98 (2H, m), 2.82-3.00 (2H, m), 3.60 (3H, s), 3.63 (2H, td), 4.05-4.35 (2H, m), 4.93 (1H, t), 7.69 (1H, dd), 8.03 (1H, d), 8.36 (1H, s), 8.71 (1H, s). Mass Spectrum: m/z (ES+) [M+H]+=364.

On a larger scale, 8-bromo-1-(oxan-4-yl)-3H-imidazo[4,5-c]quinolin-2-one (1300 g, 3.73 mol) was charged to the vessel along with tetrabutylammonium bromide (130 g, 0.40 mol) and 2-MeTHF (20.8 L). A solution of NaOH (240 g, 6.00 mol) in water (20.8 L) was then added over 5 minutes with an observed exotherm from 18-24° C. The biphasic mixture was heated to 42-48° C. before the addition of methyl iodide (465 mL, 7.47 mol) as a solution in 2-MeTHF (930 mL). The reaction was stirred at 45° C. for 17 h at which point HPLC analysis showed 2.9% starting material and 97.1% product. The reaction mixture was combined with that of the other large scale batches for concentration in vacuo. The resulting aqueous suspension was then returned to the vessel and slurried for 1 h with the product material obtained from the development batches combined at this point. The product was then isolated by filtration, washing with water (2×12 L) before oven drying under vacuum at 40° C. In total 3479 g of 8-bromo-3-methyl-1-(oxan-4-yl)imidazo[5,4-c]quinolin-2-one was isolated. Analytical data was consistent with that obtained from previous batches.

Intermediate A3: 8-Bromo-1-(oxan-4-yl)-3H-imidazo[4,5-c]quinolin-2-one

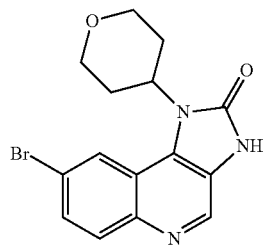

Triethylamine (143 mL, 1025.07 mmol) was added to 6-bromo-4-(oxan-4-ylamino)quinoline-3-carboxylic acid (120 g, 341.69 mmol) in DMF (600 mL) at r.t. under air. The resulting mixture was stirred for 30 minutes then diphenyl phosphorazidate (113 g, 410.03 mmol) was added. The resulting mixture was stirred for 30 minutes at r.t, then at 60° C. for 2 h. The solvent was removed under reduced pressure and the reaction mixture diluted with water. The precipitate was collected by filtration, washed with water (250 mL) and dried under vacuum to afford the desired material (120 g, 101%) as a brown solid, which was used without further purification. NMR Spectrum: $^1$H NMR (400 MHz, DMSO-d6) δ 1.72-1.95 (2H, m), 2.59-2.80 (2H, m), 3.58 (2H, td), 3.98-4.11 (2H, m), 4.75-5.04 (1H, m), 7.75 (1H, dd), 7.97

(1H, d), 8.43 (1H, s), 8.71 (1H, s), 11.71 (1H, s). Mass Spectrum: m/z (ES+) M+H+=348.

On a larger scale, 6-bromo-4-(oxan-4-ylamino)quinoline-3-carboxylic acid (2011 g, (2005 g active), 5.71 mol) was added to the vessel with DMF (18.2 L). Triethylamine (4.7 L, 33.72 mol) was added with an endotherm observed from 21-18° C. Diphenyl phosphorazidate (1600 mL, 7.42 mol) was added over 10 minutes with an observed exotherm from 21° C. to 23° C. over the addition. The exotherm continued with the batch reaching 55° C. after 1 h (jacket held at 30° C.) with gas evolution. The reaction initially went into solution with a precipitate then forming after ~30 minutes. Once the temperature had stabilised the batch was analysed by HPLC showing consumption of starting material and 99% product. The batch was heated to 60° C. for h with HPLC again indicating consumption of starting material and 98% product. The batch was concentrated in vacuo to a minimum volume (~3 volumes) and the residue added to water (17 L) rinsing in with a further portion of water (10 L). The mixture was slurried for 1 h and filtered, washing with water (2×17 L). The solid was then returned to the vessel and slurried in sat. NaHCO$_3$ solution (10 L) and MeOH (495 mL) for 1 h. The solid was collected by filtration, washing with water (2×3.5 L) and then oven dried in vacuo at 40° C. for 116 h to obtain 2023 g of desired material. Analytical data was consistent with that obtained from previous batches.

Intermediate A4:
6-Bromo-4-(oxan-4-ylamino)quinoline-3-carboxylic acid

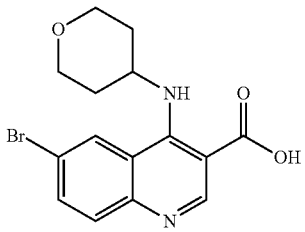 [SMILES: O=C(O)c1cnc2ccc(Br)cc2c1NC1CCOCC1]

A solution of sodium hydroxide (79 g, 1977.60 mmol) in water (1500 mL) was added to a stirred mixture of ethyl 6-bromo-4-(oxan-4-ylamino)quinoline-3-carboxylate (150 g, 395.52 mmol) in MeOH (1500 mL) at r.t. under air. The resulting mixture was stirred at 70° C. for 2 h then the solvent removed under reduced pressure. The reaction mixture was adjusted to pH=3 with 2M hydrochloric acid. The precipitate was collected by filtration, washed with water (500 mL) and dried under vacuum to afford the desired material (120 g, 86%) as a white solid, which was used without further purification. NMR Spectrum: $^1$H NMR (400 MHz, DMSO-d6) δ 1.75-1.82 (2H, m), 2.05-2.09 (2H, m), 3.85-3.94 (51H, m), 7.95 (1H, d), 8.18 (1H, d), 8.65 (1H, s), 9.01 (1H, s). Mass Spectrum: m/z (ES+) [M+H]+=351.1.

On a larger scale, ethyl 6-bromo-4-(oxan-4-ylamino)quinoline-3-carboxylate (1925 g, 5.08 as mol) was charged to the vessel with EtOH (12.5 L), 2M NaOH (12.5 L, 25.03 mol) was then added with an exotherm from 22-35° C. over the 20 minute addition. The batch was heated to 70-80° C. for 17 h at which point HPLC indicated 98.3% product and <1% starting material. The batch was concentrated in vacuo to remove EtOH and returned to the vessel. A 2M HCl solution (13 L) was then added until pH 5-6 was obtained maintaining a batch temperature below 50° C. An exotherm from 20-32° C. was observed over the 40 minute addition. A precipitate formed which was slurried at 20-25° C. for 1.5 h before filtration, washing with water until pH neutral (3×7 L). The collected solid was dried under vacuum at 70° C. to give 1794 g of desired material. Analytical data was consistent with that obtained from previous batches.

Intermediate A5: Ethyl 6-bromo-4-(oxan-4-ylamino)quinoline-3-carboxylate

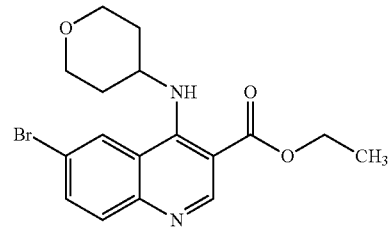 [SMILES: CCOC(=O)c1cnc2ccc(Br)cc2c1NC1CCOCC1]

DIPEA (139 mL, 794.75 mmol) was added to ethyl 6-bromo-4-chloroquinoline-3-carboxylate (100 g, 317.90 mmol) and tetrahydro-2H-pyran-4-amine (35.4 g, 349.69 mmol) in DMA (1000 mL) at r.t. under air. The resulting mixture was stirred at 60° C. for 16 h then the solvent removed under reduced pressure. The mixture was azeotroped twice with toluene to afford the desired material (150 g, 124%) as a brown solid, which was used without further purification. NMR Spectrum: $^1$H NMR (400 MHz, DMSO-d6) δ 1.36 (3H, t), 1.58-1.75 (2H, m), 1.90-2.02 (2H, m), 3.40 (2H, t), 3.81-3.98 (2H, m), 3.98-4.19 (1H, m), 4.37 (2H, q), 7.82 (1H, d), 7.92 (1H, dd), 8.56 (1H, s), 8.86 (1H, s). Mass Spectrum: m/z (ES-) [M-H]-=378, 380.

On a larger scale, ethyl 6-bromo-4-chloroquinoline-3-carboxylate (2196 g, (1976 g active), 6.28 mol) was charged to the vessel with DMA (16 L). Tetrahydro-2H-pyran-4-amine (1224 g, 12.10 mol) was added over 10 minutes with an observed exotherm of 21-27° C. DIPEA (3.5 L, 20.09 mol) was added with no observed exotherm. The mixture was heated to 75-85° C. and the resulting solution stirred for 18.5 h at 80° C. HPLC indicated consumption of starting material and 99.2% product. The reaction was cooled to 50° C. and then poured into water (50 L). The resulting suspension was stirred for 2 h at r.t. and the solids isolated by filtration, washing with water (8 L then 2×4 L). The solid was dried under vacuum at 40° C. for 55 h to give 2307 g of desired material. Analytical data was consistent with that obtained from previous batches.

Intermediate A6: Ethyl 6-bromo-4-chloroquinoline-3-carboxylate

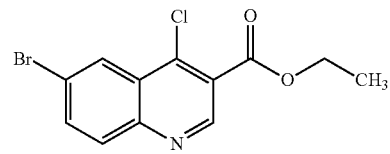 [SMILES: CCOC(=O)c1cnc2ccc(Br)cc2c1Cl]

DMF (0.119 mL, 1.54 mmol) was added to ethyl 6-bromo-1-[(4-methoxyphenyl)methyl]-4-oxoquinoline-3-carboxylate (160 g, 384.37 mmol) in thionyl chloride (800 mL) at r.t. under air. The resulting mixture was stirred at 75° C. for 16 h then the solvent removed under reduced pressure. The resulting mixture was azeotroped twice with toluene then n-hexane (500 mL) added. The precipitate was collected by filtration, washed with n-hexane (200 mL) and dried under vacuum to afford the desired material (100 g, 83%) as a brown solid. NMR Spectrum: $^1$H NMR (400 MHz, CDCl$_3$) δ 1.47 (3H, t), 4.51 (2H, q), 7.95 (1H, dd), 8.11 (1H, d), 8.60 (1H, d), 9.24 (1H, s). Mass Spectrum: m/z (ES+) [M+H]+=314, 316.

On a larger scale, ethyl 6-bromo-1-[(4-methoxyphenyl) methyl]-4-oxoquinoline-3-carboxylate (5765 g, 13.85 mol) was charged to the vessel with thionyl chloride (28.8 L). An exotherm from 20-26° C. was observed. DMF (4.4 mL) was added with no observed exotherm and the batch heated to 75° C. and stirred for 17 h. HPLC showed 1.3% starting material remained with 98.0% product. The reaction was concentrated in vacuo and the residue azeotroped with toluene (25 L). The resulting solid was then slurried in heptane (18.5 L) for 2.5 h, filtered and washed with heptane (3×4 L). The solid was dried under vacuum at 35° C. to give 4077 g of the desired material (93% crude yield) which contained ~5% of ethyl 6-bromo-1-[(4-methoxyphenyl) methyl]-4-oxoquinoline-3-carboxylate in addition to ~4% hydrolysis product by HPLC (90% pure). The crude material (4077 g) was returned to the vessel and reprocessed with thionyl chloride (14.5 L) and DMF (2.2 mL). The mixture was heated to 75° C. for 40 h. The thionyl chloride was removed in vacuo and the residue azeotroped with toluene (10 L). The residue was slurried in heptane (18 L) for ~16 h at 20° C. The solid was collected by filtration, one portion being filtered under nitrogen and washed with heptane (3 L) to yield 2196 g of desired material (90', NMR assay, 99% by HPLC). The remainder of the batch was filtered under air and washed with heptane (3 L) to yield 1905 g of the desired material (88% NMR assay, 99% by HPLC). The yellow solids were combined for further processing (4101 g, 3653 g active, 83% yield, 99% by HPLC).

Intermediate A7: Ethyl 6-bromo-1-[(4-methoxyphenyl)methyl]-4-oxoquinoline-3-carboxylate

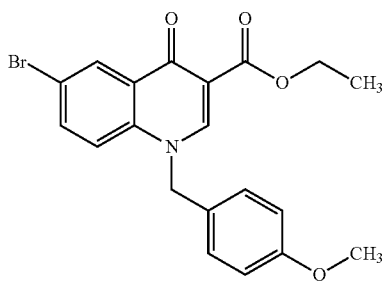 [SMILES: CCOC(=O)c1cn(Cc2ccc(OC)cc2)c2ccc(Br)cc2c1=O]

DBU (102 mL, 679.62 mmol) was added drop-wise to ethyl 2-(5-bromo-2-fluorobenzoyl)-3-[(4-melhoxyphenyl) methylamino]prop-2-enoate (296.5 g, 679.62 mmol), in acetone (1.2 L) at r.t. over a period of 2 minutes. The resulting solution was stirred for 16 h then the solid removed by filtration and washed with MTBE to afford the desired material (180 g, 64%) as light yellow solid. NMR Spectrum: $^1$H NMR (400 MHz, DMSO-d6) δ 1.30 (3H, t), 3.71 (3H, s), 4.25 (2H, q), 5.60 (2H, s), 6.90-6.95 (2H, m), 7.12-7.25 (2H, m), 7.67 (1H, d), 7.80-7.90 (1H, m), 8.30 (1H, d), 8.92 (1H, s). Mass Spectrum: m/z (ES+) [M+H]+=418.

On a larger scale, ethyl 2-(5-bromo-2-fluorobenzoyl)-3-[(4-methoxyphenyl)methylamino]prop-2-enoate (8434 g, (7730 g assumed active), 17.71 mol) was charged to the vessel with acetone (23.2 L) at 15° C. DBU (2.8 L, 18.72 mol) was added over 25 minutes with an observed exotherm from 18-23° C. over the addition. A precipitate formed after ~25 minutes and the batch continued to exotherm reaching a maximum of 37° C. after 1 h. The reaction was stirred at 20° C. for 16.5 h at which point HPLC indicated consumption of starting material and 96.5% product. The resulting precipitate was collected by filtration washing with TBME (4×3.4 L). The solid was then dried under vacuum at 40° C. to give 6033 g of the desired material as a white solid (81.6% yield over 3 steps, 99.8% purity by HPLC). Analytical data was consistent with that obtained on previous batches.

Intermediate A5: Ethyl 2-(S-bromo-2-fluorobenzoyl)-3-[(4-methoxyphenyl)methylamino]prop-2-enoate

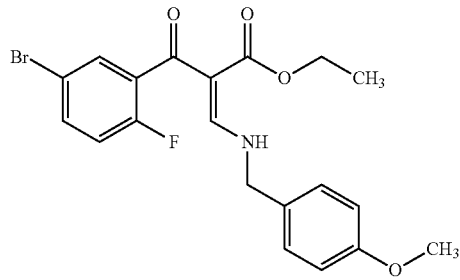 [SMILES: CCOC(=O)/C(=C\NCc1ccc(OC)cc1)C(=O)c1cc(Br)ccc1F]

(E)-Ethyl 3-(dimethylamino)acrylate (98 g, 685.00 mmol) was added portion-wise to 5-bromo-2-fluorobenzoyl chloride (163 g, 685 mmol) and DIPEA (120 mL, 685.00 mmol) in toluene (800 mL) at 10° C. over a period of 10 minutes. The resulting solution was stirred at 70° C. for 16 h then allowed to cool. (4-Methoxyphenyl)methanamine (94 g, 685 mmol) was added to the mixture over a period of 20 minutes at r.t. The resulting solution was stirred for 3 h then the reaction mixture diluted with DCM (4 L), and washed with water (3×11). The organic phase was dried over Na$_2$SO$_4$, filtered and evaporated to give the desired material (300 g, 100%) as brown oil, which was used immediately in the subsequent reaction without further purification. Mass Spectrum: m/z (ES+) [M+H]+=436.

On a larger scale, 5-bromo-2-fluorobenzoyl chloride (4318 g, 4205 g active, 17.71 mol) was charged to the vessel as a solution in toluene (7.5 L). DIPEA (3150 mL, 18.08 mol) was added with no observed exotherm. Ethyl-3-(dimethylamino)acrylate (2532 g, 17.71 mol) was added portion-wise over 30 minutes maintaining a batch temperature <40° C. An exotherm from 21-24° C. was noted over the 30 minute addition with a further slow rise to 38° C. over 1 h. The reaction was stirred at 20-30° C. for 16.5 h. 4-Methoxybenzylamine (2439 g, 17.78 mol) was added portionwise over 30 mins maintaining a batch temperature <40° C. An exotherm of 25-30° C. was observed over the addition with cooling provided by a reduced jacket temperature of 15° C. The reaction was stirred for 4 h at 20-30° C. after which HPLC indicated 93.2% of desired material. The batch was split for workup with each half of the mixture diluted with DCM (28.6 L) and washed with water (3×7.8 L). The organics were dried over MgSO$_4$ (~550 g) and filtered, washing with DCM (4 L). The combined organics were then concentrated to give 8444 g of the desired material as an oil (8434 g, 106% yield, 94.7% purity by HPLC). Analytical data was consistent with that obtained from previous batches.

Intermediate A9: 5-Bromo-2-fluorobenzoyl chloride

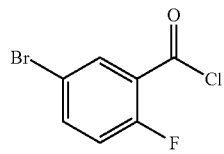 [SMILES: O=C(Cl)c1cc(Br)ccc1F]

Thionyl chloride (75.0 mL, 1027.36 mmol) was added drop-wise to 5-bromo-2-fluorobenzoic acid (150 g, 684.91 mmol), in toluene (1.2 L) and DMF (12 mL) at r.t. over a period of 1 h. The resulting mixture was stirred at 70° C. for 16 h then the mixture allowed to cool and concentrated in vacuo to afford the desired material (160 g, 98%) as light yellow oil, which was used without further purification. NMR Spectrum: $^1$H NMR (400 MHz, DMSO-d6) δ 7.26-7.31 (1H, m), 7.83 (1H, dd), 8.02 (1H, d).

On a larger scale, 3-bromo-6-fluorobenzoic acid (3888 g, 17.75 mol) was charged to the vessel at 20° C. followed by toluene (29.2 L). Thionyl chloride (1950 ml, 26.88 mol) was added, followed by DMF (310 mL) with no observed exotherm. The mixture was heated to 65-75° C. (solution obtained above ~45° C.) with no observed exotherm and slight gas evolution. The reaction was stirred for 40 h at this temperature at which point HPLC analysis showed 87.6% product, 3.4% starting material. The reaction was concentrated in vacuo and azeotroped with toluene (18 L) to give 4328 g of the desired material (103% yield, 87.3% by HPLC).

8-[6-(3-Dimethylaminopropoxy)pyridin-3-yl]-3-methyl-1-(oxan-4-yl)imidazo[5,4-c]quinolin-2-one can also be prepared directly from 8-bromo-3-methyl-1-(oxan-4-yl)imidazo[5,4-c]quinolin-2-one in the following manner:

8-[6-(3-Dimethylaminopropoxy)pyridin-3-yl]-3-methyl-1-(oxan-4-yl)imidazo[5,4-c]quinolin-2-one

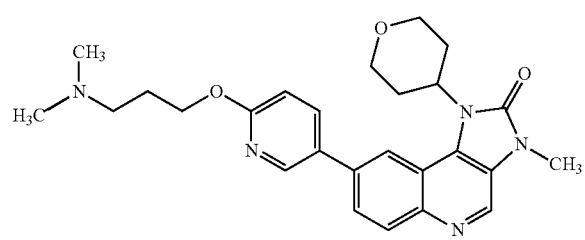

Chloro(2-dicyclohexylphosphino-2',4',6'-triisopropyl-1,1'-biphenyl)[2-(2'-amino-1,1'-biphenyl)]palladium(II) (0.070 g, 0.09 mmol) was added to 8-bromo-3-methyl-1-(oxan-4-yl)imidazo[5,4-c]quinolin-2-one (3.2 g, 8.83 mmol), K$_2$CO$_3$ (3.66 g, 26.50 mmol) and N,N-dimethyl-3-[5-(4,4,5,5-tetramethyl-1,3,2-dioxaborolan-2-yl)pyridin-2-yl]oxypropan-1-amine (3.25 g, 10.60 mmol) in 1,4-dioxane (80 mL) and water (15 mL) under nitrogen. The resulting mixture was stirred at 90° C. for 2 h. The reaction mixture was concentrated and diluted with EtOAc (500 mL) and washed sequentially with water (2×100 mL), and sat. brine (100 mL). The organic layer was dried over Na$_2$SO$_4$, filtered and the volume reduced to approximately 80 mL in vacuo. The precipitate was collected by filtration, washed with Et$_2$O (10 mL) and dried under vacuum to afford the desired material (2.80 g, 68.7%) as a white solid. Analytical data consistent with material synthesised by alternate route.

On a larger scale, 8-bromo-3-methyl-1-(oxan-4-yl)imidazo[5,4-c]quinolin-2-one (1700.1 g) was suspended in EtOH (20.4 L) in a 50 L vessel then K$_2$CO$_3$ (1948.7 g) and N,N-dimethyl-3-[5-(4,4,5,5-tetramethyl-1,3,2-dioxaborolan-2-yl)pyridin-2-yl]oxypropan-1-amine (1731.4 g) added. EtOH (6.8 L) and purified water (5.1 L) were added to the mixture followed by the addition chloro(2-dicyclohexylphosphino-2',4',6'-triisopropyl-1,1'-biphenyl)(2-(2'-amino-1,1'-biphenyl)palladium(II) (37.3 g). The mixture was heated to reflux (77-80° C.) and stirred for 30 mins at reflux then cooled to 20° C. prior to being distilled under reduced pressure to a volume of 12.6 L. The batch was then cooled to 15-25° C. and purified water (19.9 L) added. The batch was stirred for 1 h 5 mins, filtered and the filter cake washed with purified water (3×3.7 L) then dried under vacuum at 40° C. to afford crude desired material (1978 g, 91.3%). The reaction was repeated on a similar scale to deliver a further 2084 g of crude material. The purification of the crude 8-[6-(3-dimethylaminopropoxy)pyridin-3-yl]-3-methyl-1-(oxan-4-yl)imidazo[5,4-c]quinolin-2-one (2066.9 g) was carried out in 6 portions of 350 g or less. Crude 8-[6-(3-dimethylaminopropoxy)pyridin-3-yl]-3-methyl-1-(oxan-4-yl)imidazo[5,4-c]quinolin-2-one (350.1 g) was charged to a 10 L flask with EtOH (7.7 L) and heated until a solution was formed (68-73° C.). Activated charcoal (35 g) was added and the solution stirred at 70-75° C. for 1 h. The hot solution was filtered using a porosity 3 sinter funnel through a celite pad (~40 g) in small portions to ensure the product stayed in solution. The celite pad was washed with hot EtOH (2 L) to remove any residual product on the celite and the initial filtrate charged to the vessel and the wash filtrate was stored in a carboy. This process was repeated with the remaining portions of crude material. After completion of the 6 hot filtrations carried out over 2 days the filtrate in the vessel was distilled under reduced pressure until the remaining filtrate (held in a carboy) could be added. The batch was then heated until a solution was formed (69° C.) and the distillation was then continued until the volume in the vessel was equal to 5 volumes of the input material (maximum distillation batch temperature=55° C.). The distillation was stopped and the batch cooled to 5-15° C., filtered, washed with EtOH (2.3 L) and dried to give the pure desired product (1926 g, 93.2% yield).

Analytical data consistent with material synthesised by alternate routes/different scales.

Intermediate A3, 8-Bromo-1-(oxan-4-yl)-3H-imidazo[4,5-c]quinolin-2-one can also be prepared in the following manner:

Intermediate A3: 8-Bromo-1-(oxan-4-yl)-H-imidazo[4,5-c]quinolin-2-one

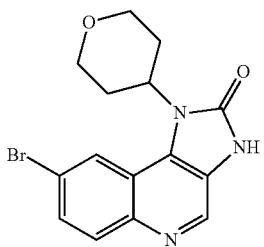 [SMILES: O=c1[nH]c2cnc3ccc(Br)cc3c2n1C1CCOCC1]

1,3,5-Trichloro-1,3,5-triazinane-2,4,6-trione (18.9 g, 81.9 mmol) was added portionwise to a mixture of 6-bromo-4-(oxan-4-ylamino)quinoline-3-carboxamide (57.3 g, 163.7 mmol) and DBU (54.7 g, 360.1 mmol) in MeOH (500 mL) at 0° C. The resulting mixture was allowed to warm and stirred at r.t. for 30 minutes. The resulting mixture was evaporated to dryness and the residue triturated with a mixture of petroleum ether/EtOAc (5:1, 1000 mL) to afford the desired material (46.0 g, 81%) as a yellow solid. NMR Spectrum: $^1$H NMR (400 MHz, DMSO-d6) δ 1.55-1.64 (2H, m), 1.87-1.98 (2H, m), 3.28-3.42 (2H, m), 3.79-3.89 (2H, m), 3.95-3.98 (1H, m), 7.62 (1H, bs), 7.70-7.85 (2H, m), 7.89 (1H, d), 8.12 (1H, bs), 8.60 (1H, s), 8.71 (1H, s).

Intermediate A10: 6-bromo-4-(oxan-4-ylamino)quinoline-3-carboxamide

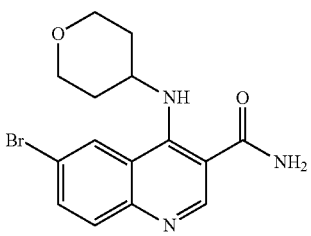 [SMILES: NC(=O)c1cnc2ccc(Br)cc2c1NC1CCOCC1]

A mixture of 6-bromo-4-chloroquinoline-3-carboxamide (50 g, 175.4 mmol), tetrahydro-2H-pyran-4-amine (26.2 g, 193 mmol) and DIPEA (56.13 mL, 438.5 mmol) in DMA (500 mL) was stirred at 90° C. overnight. The mixture was allowed to cool and poured into water (1500 mL). The precipitate was filtered, washed with water (2×200 mL) and dried under reduced pressure to afford the desired material (57.3 g, 93%) as a white solid. NMR Spectrum: $^1$H NMR (400 MHz, DMSO-d6) δ 2.88-1.92 (2H, m), 2.59-2.78 (2H, m), 3.50-3.62 (3H, m), 3.96-4.08 (2H, m), 4.92-4.98 (1H, m), 7.80 (1H, m), 7.99 (1H, dd), 8.46 (1H, d), 8.74 (1H, s).

Intermediate A1: 6-Bromo-4-chloroquinoline-3-carboxamide

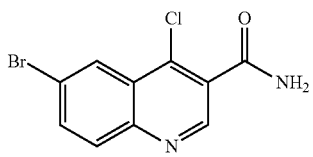 [SMILES: NC(=O)c1cnc2ccc(Br)cc2c1Cl]

DMF (1.506 mL, 19.37 mmol) was added to 6-bromo-4-oxo-1H-quinoline-3-carboxylic acid (51.93 g, 193.72 mmol) and thionyl chloride (353 mL, 4843.07 mmol) at r.t. and the resulting solution stirred at 70° C. for 2 h under an inert atmosphere. The resulting solution was evaporated to dryness and the residue azeotroped with toluene to afford 6-bromo-4-chloroquinoline-3-carbonyl chloride (62.13 g). The 6-bromo-4-chloroquinoline-3-carbonyl chloride was dissolved in DCM (420 mL) and added portionwise to ammonium hydroxide (251 mL, 1937.23 mmol) at 0° C. over 15 minutes. The organic solvent was removed under reduced pressure and the solid collected by filtration, washed with water, Et$_2$O and then dried to afford the desired material (52.8 g, 95%) as a white solid. NMR Spectrum: $^1$H NMR (500 MHz, DMSO-d6) δ 8.00-8.11 (3H, m), 8.24 (1H, s), 8.45 (1H, s), 8.92 (1H, s). Mass Spectrum: m/z (ES+) [M+H]+=287.

Intermediate A12: 6-Bromo-4-oxo-1H-quinoline-3-carboxylic acid

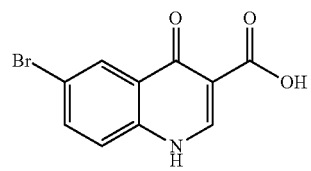 [SMILES: O=C(O)c1c[nH]c2ccc(Br)cc2c1=O]

2N Sodium hydroxide (506 mL, 1011.43 mmol) was added to a stirred suspension of ethyl 6-bromo-4-oxo-1H-quinoline-3-carboxylate (59.9 g, 202.29 mmol) in EtOH (590 mL) and the resulting solution stirred at 75° C. for 1.5 h. Water was added and the mixture cooled to 0° C. The pH of the solution was adjusted to 3 using hydrochloric acid and the precipitate collected by filtration. The solid was washed with water, EtOH/water (1:1) then Et$_2$O before being dried to afford the desired material (51.9 g, 96%) as a beige solid. NMR Spectrum: $^1$H NMR (500 MHz, DMSO-d6) δ 7.80 (1H, d), 8.05 (1H, d), 8.37 (1H, s), 8.93 (1H, s). Mass Spectrum: m/z (ES+) [M+H]+=270.

Intermediate A13: Ethyl 6-bromo-4-oxo-1H-quinoline-3-carboxylate

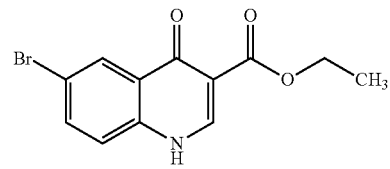 [SMILES: CCOC(=O)c1c[nH]c2ccc(Br)cc2c1=O]

Diphenyl ether (870 mL) was heated to 240° C., then diethyl 2-[[(4-bromophenyl)amino]methylidene]propanedioate (75 g, 219.18 mmol) added portionwise. The mixture was stirred at 240° C. for 60 minutes in a flask fitted with dean-stark apparatus. After cooling (25° C.) a crystallized solid was formed. The mixture was diluted with Et$_2$O and the solid was collected by filtration, washed with Et$_2$O and dried to afford the desired material (59.9 g) as a beige crystallized solid, which was used without purification or characterisation.

Intermediate A14: Diethyl 2-[[(4-bromophenyl)amino]methylidene]propanedioate

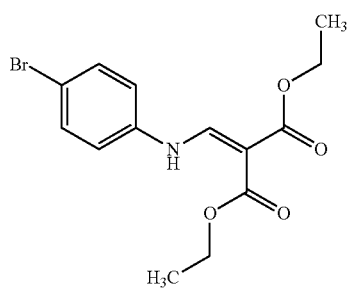 [SMILES: CCOC(=O)C(=CNc1ccc(Br)cc1)C(=O)OCC]

Diethyl 2-(ethoxymethylene)malonate (71.5 mL, 354.02 mmol) was added to 4-bromoaniline (42 g, 244.15 mmol) in EtOH (420 mL) and the resulting mixture stirred at 78° C. overnight. After cooling to 10° C., the white solid was collected by filtration, washed with heptane and dried to afford the desired material (75 g, 90%) as a white crystallized solid. NMR Spectrum: $^1$H NMR (500 MHz, DMSO-d6) δ 1.25 (6H, s), 4.10-4.27 (4H, m), 7.38 (2H, d), 7.57 (2H, d), 8.37 (1H, bs). Mass Spectrum: m/z (ES+) [M+H]+=344.

The preparation of N,N-dimethyl-3-[5-(4,4,5,5-tetramethyl-1,3,2-dioxaborolan-2-yl)pyridin-2-yl]oxypropan-1-amine is described below.

N,N-Dimethyl-3-[5-(4,4,5,5-tetramethyl-1,3,2-dioxaborolan-2-yl)pyridin-2-yl]oxypropan-1-amine

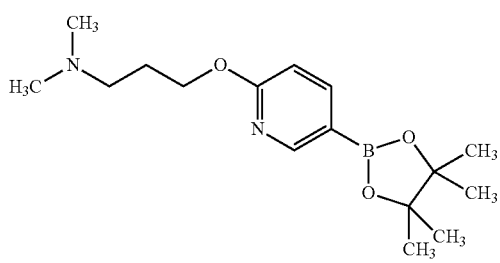

Butyllithium (2.5N, 4.8 mL, 50.96 mmol) was added to a solution of 3-(5-bromopyridin-2-yl)oxy-N,N-dimethylpropan-1-amine (2.07 g, 7.99 mmol) and 4,4,5,5-tetramethyl-2-(propan-2-yloxy)-1,3,2-dioxaborolane (2.79 g, 15.00 mmol) in THF (20 mL) at −78° C. over 10 minutes under an inert atmosphere. The resulting solution was stirred for 4 h at 18° C. The reaction was then quenched by the addition of a sat. aqueous solution of ammonium chloride then partitioned between EtOAc (100 mL) and water (100 mL). The organic layer was concentrated in vacuo and the residue purified by FCC, eluting with EtOAc/petroleum ether (1:3) to afford the desired material (270 mg, 11%) as a yellow solid. Mass Spectrum: m/z (ES+) [M+H]+=225.

3-(5-Bromopyridin-2-yl)oxy-N,N-dimethylpropan-1-amine

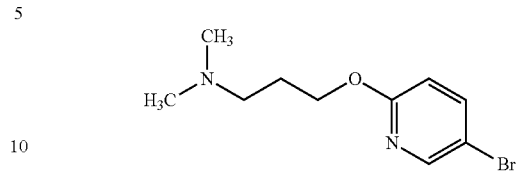

3-(Dimethylamino)propan-1-ol (3.09 g, 29.95 mmol) was added to a mixture of sodium hydride (2.4 g, 60.00 mmol) in DMF (50 mL) over a period of 20 min at r.t. 5-Bromo-2-fluoropyridine (5.81 g, 33.01 mmol) was added and the resulting solution stirred for 4 h at 30° C. The reaction was then quenched by the addition of a sat. aqueous solution of ammonium chloride and the resulting mixture concentrated under vacuum. The residue was purified by FCC, eluting with DCM/MeOH in Et$_2$O (10:1) to afford the desired material (5.2 g, 67%) as yellow oil. Mass Spectrum: m/z (ES+) [M+H]+=259.

Example 2

8-[6-(3-Dimethylaminopropoxy)pyridin-3-yl]-1-(cis-3-methoxycyclobutyl)-3-methylimidazo[4,5-c]quinolin-2-one

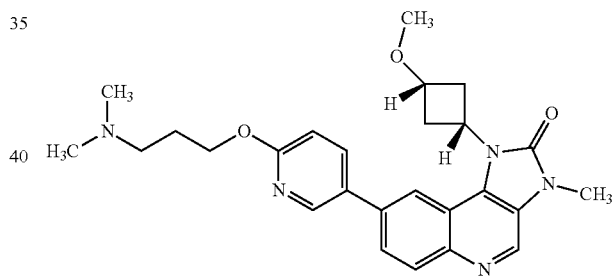

Pd(Ph$_3$P)$_4$ (2.074 g, 1.79 mmol) was added to a mixture of 8-bromo-1-(cis-3-methoxycyclobutyl)-3-methylimidazo[4,5-c]quinolin-2-one (13 g, 35.89 mmol), N,N-dimethyl-3-[5-(4,4,5,5-tetramethyl-1,3,2-dioxaborolan-2-yl)pyridin-2-yl]oxypropan-1-amine (13.15 g, 43.07 mmol) and cesium carbonate (23.39 g, 71.78 mmol) in 1,4-dioxane (200 mL) and water (40 mL) under nitrogen. The resulting mixture was stirred at 90° C. for 3 h before being allowed to cool. The reaction mixture was concentrated and diluted with EtOAc (750 mL), and washed sequentially with water (2×150 mL), and sat. brine (150 mL). The organic layer was dried over Na$_2$SO$_4$, filtered and evaporated to afford crude product. The crude product was purified by FCC, elution gradient 0 to 10% MeOH in DCM, to afford the desired material (12.50 g, 75%) as a white solid. NMR Spectrum: $^1$H NMR (400 MHz, DMSO-d6) δ 1.90 (2H, q), 2.16 (6H, s), 2.37 (2H, t), 2.72-2.92 (2H, m), 3.01 (2H, d), 3.21 (3H, s), 3.50 (3H, s), 3.79-3.95 (1H, m), 4.37 (2H, t), 5.12 (1H, t), 6.97 (1H, d), 7.82-7.98 (1H, m), 8.11 (1H, d), 8.19 (2H, dd), 8.42 (1H, s), 8.67 (1H, d), 8.87 (1H, s). Mass Spectrum: m/z (ES+) [M+H]+=462.

Intermediate B1: 8-Bromo-1-(cis-3-methoxycyclobutyl)-3-methylimidazo[4,5-c]quinolin-2-one

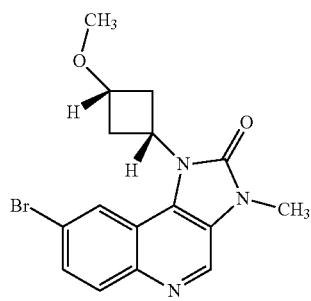 [SMILES: CO[C@H]1C[C@@H](n2c(=O)n(C)c3cnc4ccc(Br)cc4c32)C1]

Methyl iodide (11.49 mL, 183.81 mmol) was added to a mixture of 8-bromo-1-(cis-3-methoxycyclobutyl)-3H-imidazo[4,5-c]quinolin-2-one (32 g, 91.90 mmol), sodium hydroxide (5.51 g, 137.85 mmol) and tetrabutylammonium bromide (2.94 g, 9.19 mmol) in DCM (400 mL) and water (300 mL) and the resulting mixture stirred at r.t. for 12 h. The DCM was removed in vacuo and the precipitate collected by filtration, washed with water (200 mL) and dried under vacuum to afford the desired material (25.00 g, 75%) as a pale yellow solid. NMR Spectrum: $^1$H NMR (400 MHz, DMSO-d6) δ 2.72-2.86 (2H, m), 2.9-3.08 (2H, m), 3.22 (3H, s), 3.49 (3H, s), 3.85-3.89 (1H, m), 4.88-5.06 (1H, m), 7.74 (1H, dd), 7.98 (1H, d), 8.50 (1H, d), 8.92 (1H, s). Mass Spectrum: m/z (ES+) [M+H]+=362, 364.

Intermediate B2: 8-Bromo-1-(cis-3-methoxycyclobutyl)-3H-imidazo[4,5-c]quinolin-2-one

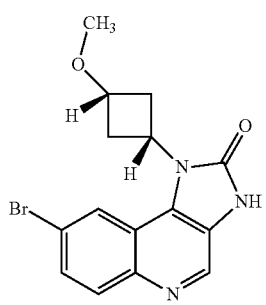 [SMILES: CO[C@H]1C[C@@H](n2c(=O)[nH]c3cnc4ccc(Br)cc4c32)C1]

Triethylamine (39.3 mL, 281.89 mmol) was added to 6-bromo-4-[(cis-3-methoxycyclobutyl)amino]quinoline-3-carboxylic acid (33 g, 93.96 mmol) in DMF (200 mL) at r.t. After stirring for 30 minutes diphenyl phosphorazidate (28.4 g, 103.36 mmol) was added and the resulting mixture stirred at 60° C. for 2 h. The reaction mixture was poured into water (500 mL), the precipitate collected by filtration, washed with water (200 mL) and dried under vacuum to afford the desired material (32.0 g, 98%) as a yellow solid, which was used without further purification. NMR Spectrum: $^1$H NMR (400 MHz, DMSO-d6) δ 2.75-2.82 (2H, m), 2.9-3.05 (2H, m), 3.22 (3H, s), 3.80-3.90 (1H, m), 4.85-4.99 (1H, m), 7.71 (1H, dd), 7.94 (1H, d), 8.48 (1H, d), 8.69 (1H, s), 10.42 (1H, s). Mass Spectrum: m/z (ES+) [M+H]+=348, 350.

Intermediate B3: 6-Bromo-4-[(cis-3-methoxycyclobutyl)amino]quinoline-3-carboxylic acid

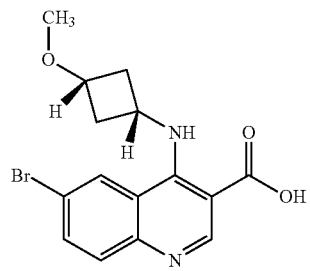 [SMILES: CO[C@H]1C[C@@H](Nc2c(C(=O)O)cnc3ccc(Br)cc23)C1]

Sodium hydroxide (190 mL, 379.70 mmol) was added to ethyl 6-bromo-4-[(cis-3-methoxycyclobutyl)amino]quinoline-3-carboxylate (36 g, 94.92 mmol) in a mixture of MeOH (120 mL) and THF (120 mL) and the resulting mixture stirred at 60° C. for 3 h. The solvent was removed under reduced pressure and the mixture adjusted to pH 3 with 2M hydrochloric acid. The precipitate was collected by filtration, washed with water (300 mL) and dried under vacuum to afford the desired material (33.0 g, 99%) as a pale yellow solid, which was used without further purification. Mass Spectrum: m/z (ES+) [M+H]+=351.

Intermediate B4: Ethyl 6-bromo-4-[(cis-3-methoxycyclobutyl)amino]quinoline-3-carboxylate

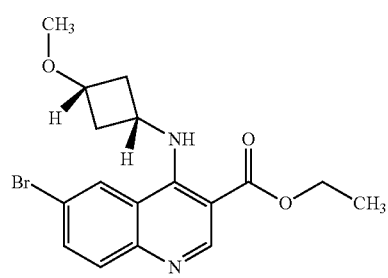 [SMILES: CCOC(=O)c1cnc2ccc(Br)cc2c1N[C@H]1C[C@@H](OC)C1]

DIPEA (41.6 mL, 238.43 mmol) was added to ethyl 6-bromo-4-chloroquinoline-3-carboxylate (30 g, 95.37 mmol) and 3-methoxycyclobutan-1-amine hydrochloride (15.75 g, 114.44 mmol) in DMA (100 mL) and the resulting mixture stirred at 75° C. for 5 h. The solvent was removed under reduced pressure to afford the desired material (36.0 g, 100%) as a yellow solid, which was used without further purification. NMR Spectrum: $^1$H NMR (300 MHz, DMSO-d6) δ 1.38 (3H, t), 1.85-1.98 (2H, m), 2.75-7.89 (2H, m), 3.17 (3H, s), 3.65-3.78 (1H, m), 3.98-4.05 (1H, m), 4.35 (2H, q), 7.60 (1H, d), 7.70 (1H, dd), 8.40 (1H, d), 8.84-8.85 (1H, m). Mass Spectrum: m/z (ES+) [M+H]+=379.

Intermediate B2: 8-Bromo-2-(cis-3-methoxycyclobutyl)-3H-imidazo[4,5-c]quinolin-2-one can also be prepared in the following manner.

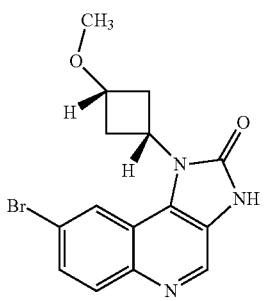 [SMILES: CO[C@H]1C[C@@H](n2c(=O)[nH]c3cnc4ccc(Br)cc4c32)C1]

DBU (5.36 mL, 35.86 mmol) was added in one portion to a mixture of 6-bromo-4-[(cis-3-methoxycyclobutyl)amino]quinoline-3-carboxamide (6.28 g, 17.93 mmol) and 1,3,5-trichloro-1,3,5-triazinane-2,4,6-trione (1.667 g, 7.17 mmol) in MeOH (65 mL). The resulting mixture was stirred at r.t. for 18 h. The resulting mixture was evaporated to dryness and the residue was purified by FCC, elution gradient 0 to 10% MeOH in DCM, to afford the desired material (6.48 g, 104%). Data consistent with material produced from alternate synthesis described earlier.

Intermediate B5: 6-Bromo-4-[(cis-3-methoxycyclobutyl)amino]quinoline-3-carboxamide

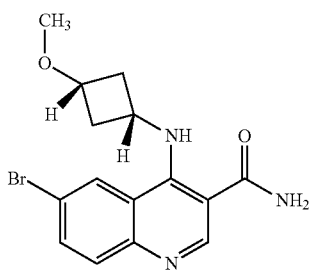 [SMILES: CO[C@H]1C[C@@H](Nc2c(C(N)=O)cnc3ccc(Br)cc23)C1]

DIPEA (13.76 mL, 78.80 mmol) was added to a mixture of 6-bromo-4-chloroquinoline-3-carboxamide (7.58 g, 26.27 mmol) and 3-methoxycyclobutan-1-amine hydrochloride (3.98 g, 28.89 mmol) in DMA (35 mL) and the resulting mixture stirred at 100° C. for 18 h. The reaction mixture was diluted with water (250 mL) and the precipitate was collected by filtration, washed with water (50 mL) and dried under vacuum to afford the desired material (6.28 g, 68.3%) as a tan solid, which was used without further purification. NMR Spectrum: $^1$H NMR (400 MHz, DMSO-d6) δ 2.45-2.55 (2H, m), 2.76-2.88 (2H, m), 3.17 (3H, s), 3.66 (1H, q), 4-4.16 (1H, m), 7.67 (1H, s), 7.80 (1H, dd), 7.93 (1H, dd), 8.15 (1H, s), 8.59 (1H, s), 8.69 (1H, s), 9.34 (1H, s). Mass Spectrum: m/z (ES+) [M+H]+=350, 352.

Example 3

8-[6-(3-Dimethylaminopropropoxy)pyridin-3-yl-7-fluoro-3-methyl-1-(4-methyloxan-4-yl)imidazo[5,4-c]quinolin-2-one

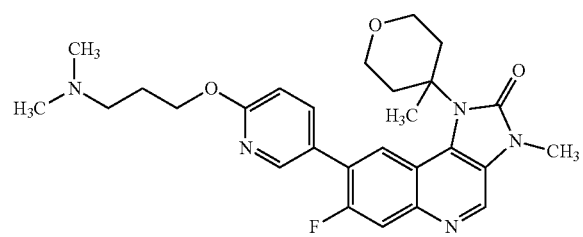

8-Bromo-7-fluoro-3-methyl-1-(4-methyloxan-4-yl)imidazo[5,4-c]quinolin-2-one (0.13 g, 0.33 mmol) was added to N,N-dimethyl-3-[5-(4,4,5,5-tetramethyl-1,3,2-dioxaborolan-2-yl)pyridin-2-yl]oxypropan-1-amine (0.121 g, 0.40 mmol), cesium carbonate (0.322 g, 0.99 mmol) and Pd(Ph$_3$P)$_4$ (0.038 g, 0.03 mmol) in 1,4-dioxane (5 mL) and water (1 mL) under nitrogen. The resulting mixture was stirred at 80° C. for 2 h. The crude product was purified by preparative HPLC (Waters XBridge Prep C18 OBD column, 5 μm silica, 19 mm diameter, 100 mm length), using decreasingly polar mixtures of water (containing 0.1% NH3) and MeCN as eluents. Fractions containing the desired compound were evaporated to dryness to afford the desired material (0.050 g, 30.8%) as a white solid. NMR Spectrum: $^1$H NMR (400 MHz, DMSO-d6) δ 1.82-2.10 (7H, m), 2.18 (6H, s), 2.35-2.50 (2H, m), 3.0-3.1 (2H, m), 3.31-3.39 (2H, m), 3.35 (3H, s), 3.61-3.74 (2H, m), 4.36 (2H, t), 6.99 (1H, d), 7.97 (1H, d), 8.01 (1H, dt), 8.39 (1H, d), 8.45 (1H, d), 8.97 (1H, s). Mass Spectrum: m/z (ES+) [M+H]+=494.

The following compounds were synthesised in an analogous fashion using the appropriate boronic ester and the appropriate bromide:

| Example | Structure | Name |
|---|---|---|
| 4* | 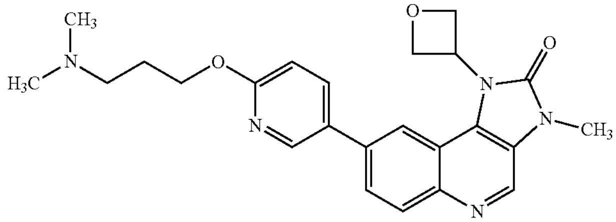 | 8-[6-(3-dimethylaminopropoxy)pyridin-3-yl]-3-methyl-1-(oxetan-3-yl)imidazo[5,4-c]quinolin-2-one methanesulfonic acid salt |

-continued

| Example | Structure | Name |
|---|---|---|
| 5** | 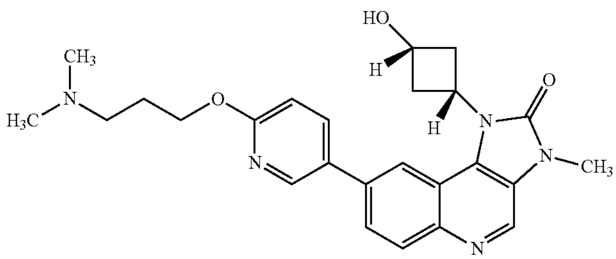 | 8-[6-(3-dimethylaminopropoxy)pyridin-3-yl]-1-(cis-3-hydroxycyclobutyl)-3-methylimidazo[4,5-c]quinolin-2-one |
| 6 | 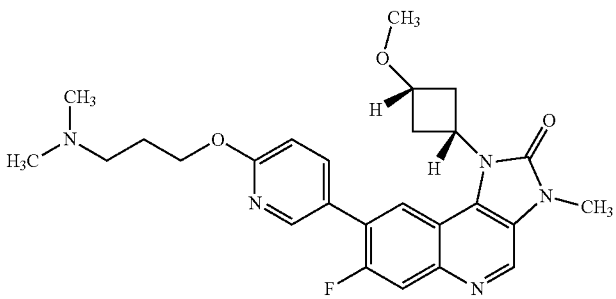 | 8-[6-(3-dimethylaminopropoxy)pyridin-3-yl]-7-fluoro-1-(cis-3-methoxycyclobutyl)-3-methylimidazo[4,5-c]quinolin-2-one |
| 7 | 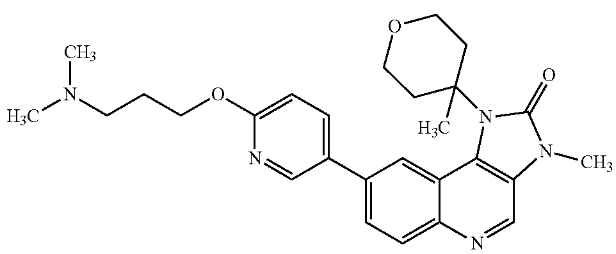 | 8-[6-(3-dimethylaminopropoxy)pyridin-3-yl]-3-methyl-1-(4-methyloxan-4-yl)imidazo[5,4-c]quinolin-2-one |
| 8** | 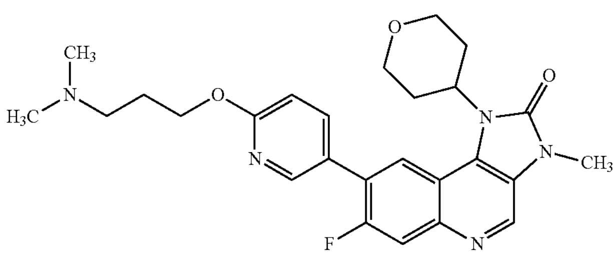 | 8-[6-(3-dimethylaminopropoxy)pyridin-3-yl]-7-fluoro-3-methyl-1-(oxan-4-yl)imidazo[5,4-c]quinolin-2-one |
| 9** | 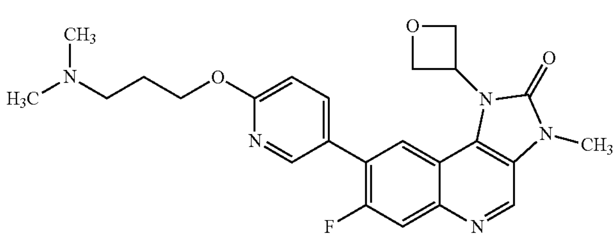 | 8-[6-(3-dimethylaminopropoxy)pyridin-3-yl]-7-fluoro-3-methyl-1-(oxetan-3-yl)imidazo[5,4-c]quinolin-2-one |
| 10*** | 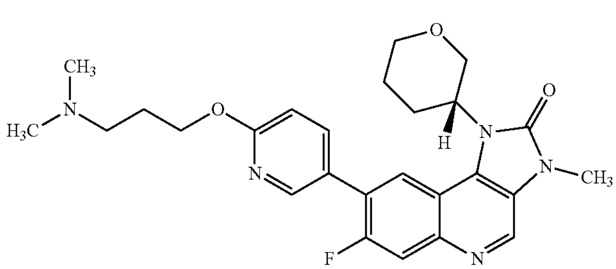 | 8-[6-(3-dimethylaminopropoxy)pyridin-3-yl]-7-fluoro-3-methyl-1-[(3R)-oxan-3-yl]imidazo[5,4-c]quinolin-2-one |

-continued

| Example | Structure | Name |
|---|---|---|
| 11*** | 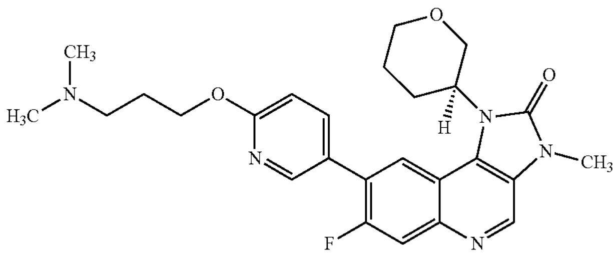 | 8-[6-(3-dimethylaminopropoxy)pyridin-3-yl]-7-fluoro-3-methyl-1-[(3S)-oxan-3-yl]imidazo[5,4-c]quinolin-2-one |
| 12** | 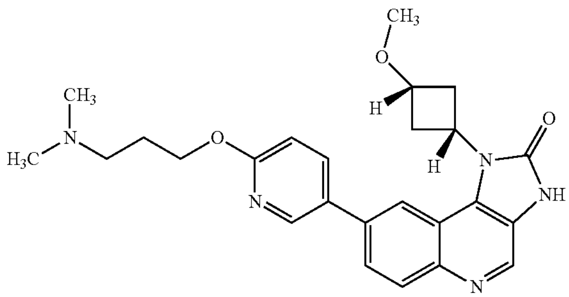 [SMILES: CO[C@H]1C[C@@H](n2c(=O)[nH]c3cnc4ccc(-c5ccc(OCCCN(C)C)nc5)cc4c32)C1] | 8-[6-(3-dimethylaminopropoxy)pyridin-3-yl]-1-(cis-3-methoxycyclobutyl)-3H-imidazo[4,5-c]quinolin-2-one |
| 13**** | 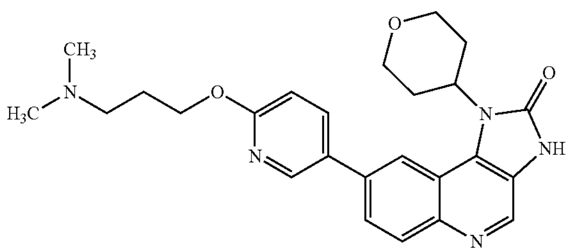 [SMILES: CN(C)CCCOc1ccc(-c2ccc3ncc4[nH]c(=O)n(C5CCOCC5)c4c3c2)cn1] | 8-[6-(3-dimethylaminopropoxy)pyridin-3-yl]-1-(oxan-4-yl)-3H-imidazo[4,5-c]quinolin-2-one |
| 14** | 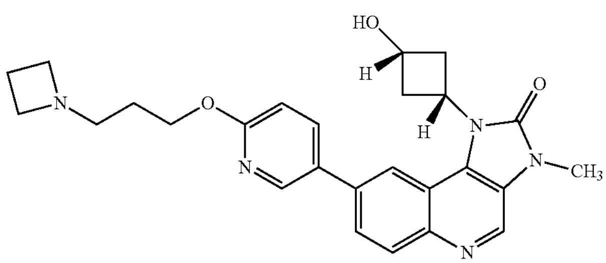 [SMILES: Cn1c(=O)n([C@H]2C[C@@H](O)C2)c2c3cc(-c4ccc(OCCCN5CCC5)nc4)ccc3ncc21] | 8-[6-[3-(azetidin-1-yl)propoxy]pyridin-3-yl]-1-(cis-3-hydroxycyclobutyl)-3-methylimidazo[4,5-c]quinolin-2-one |
| 15** | 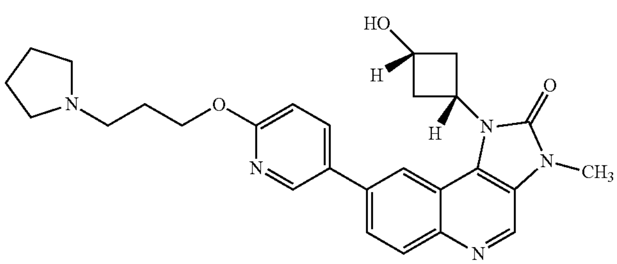 [SMILES: Cn1c(=O)n([C@H]2C[C@@H](O)C2)c2c3cc(-c4ccc(OCCCN5CCCC5)nc4)ccc3ncc21] | 1-(cis-3-hydroxycyclobutyl)-3-methyl-8-[6-(3-pyrrolidin-1-ylpropoxy)pyridin-3-yl]imidazo[4,5-c]quinolin-2-one |
| 16***** | 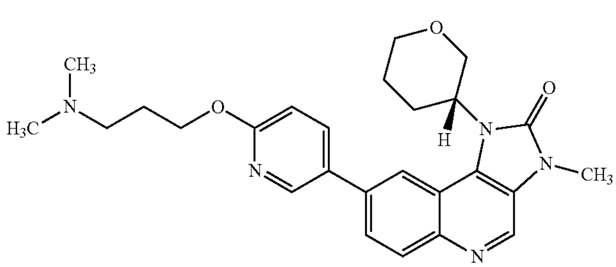 | 8-[6-(3-dimethylaminopropoxy)pyridin-3-yl]-3-methyl-1-[(3R)-oxan-3-yl]imidazo[5,4-c]quinolin-2-one |

| Example | Structure | Name |
|---|---|---|
| 17***** | 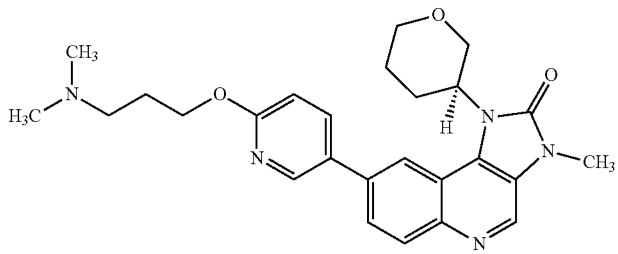 | 8-[6-(3-dimethylaminopropoxy)pyridin-3-yl]-3-methyl-1-[(3S)-oxan-3-yl]imidazo[5,4-c]quinolin-2-one |
| 18 | 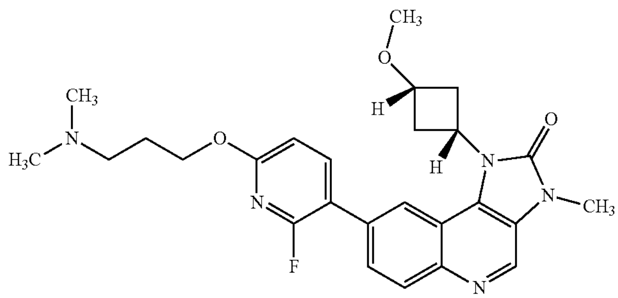 | 8-[6-(3-dimethylaminopropoxy)-2-fluoropyridin-3-yl]-1-(cis-3-methoxycyclobutyl)-3-methylimidazo[4,5-c]quinolin-2-one |
| 19 | 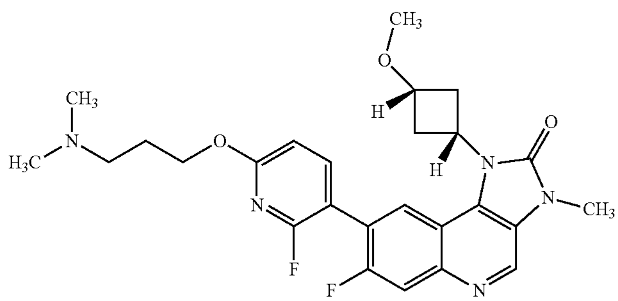 | 8-[6-(3-dimethylaminopropoxy)-2-fluoropyridin-3-yl]-7-fluoro-1-(cis-3-methoxycyclobutyl)-3-methylimidazo[4,5-c]quinolin-2-one |
| 20 | 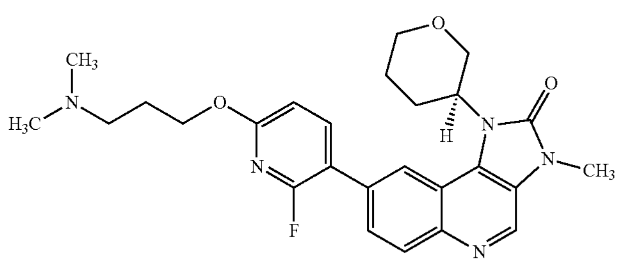 | 8-[6-(3-dimethylaminopropoxy)-2-fluoropyridin-3-yl]-3-methyl-1-[(3S)-oxan-3-yl]imidazo[5,4-c]quinolin-2-one |
| 21 | 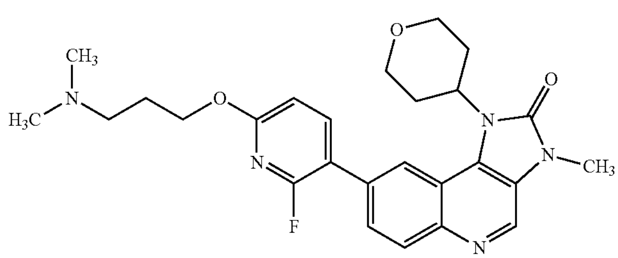 | 8-[6-(3-dimethylaminopropoxy)-2-fluoropyridin-3-yl]-3-methyl-1-(oxan-4-yl)imidazo[5,4-c]quinolin-2-one |

| Example | Structure | Name |
|---|---|---|
| 22 | 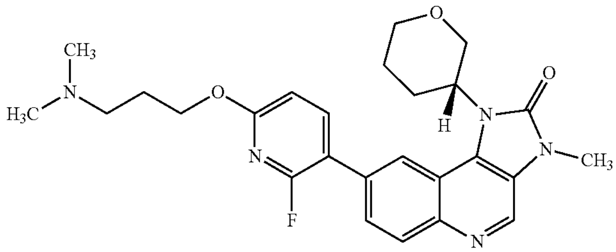 | 8-[6-(3-dimethylaminopropoxy)-2-fluoropyridin-3-yl]-3-methyl-1-[(3R)-oxan-3-yl]imidazo[5,4-c]quinolin-2-one |
| 23****** | 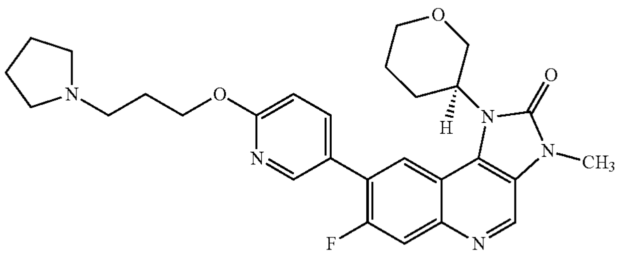 [SMILES: Cn1c(=O)n([C@H]2CCCOC2)c2c3cc(-c4ccc(OCCCN5CCCC5)nc4)c(F)cc3ncc21] | 7-fluoro-3-methyl-8-[6-(3-pyrrolidin-1-ylpropoxy)-3-pyridyl]-1-[(3S)-tetrahydropyran-3-yl]imidazo[4,5-c]quinolin-2-one |
| 24****** | 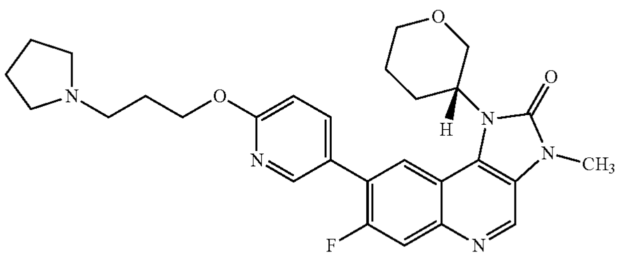 [SMILES: Cn1c(=O)n([C@@H]2CCCOC2)c2c3cc(-c4ccc(OCCCN5CCCC5)nc4)c(F)cc3ncc21] | 7-fluoro-3-methyl-8-[6-(3-pyrrolidin-1-ylpropoxy)-3-pyridyl]-1-[(3R)-tetrahydropyran-3-yl]imidazo[4,5-c]quinolin-2-one |

*Reaction stirred for 18 h at 80° C. This compound can also be isolated as the methanesulfonic acid salt by dissolving the free base in DCM, treating with methanesulfonic acid (~1.1 equiv), concentrating in vacuo and triturating the residue with Et₂O.
**Reaction stirred for 2 h at 90° C.
***Reaction stirred for 75 mins at 120° C.
****The reaction used starting material tert-butyl 8-bromo-1-(oxan-4-yl)-2-oxoimidazo[5,4-c]quinoline-3-carboxylate and was stirred at 90° C. for 2 h. The crude material was purified by prep HPLC using decreasingly polar mixtures of water (containing 0.3% formic acid) and MeCN as eluents. No additional deprotection step was required.
*****Reaction performed using chloro(2-dicyclohexylphosphino-2',4',6'-triisopropyl-1,1'-biphenyl)[2-(2'-amino-1,1'-biphenyl)]palladium(II) as the catalyst and stirred at 100° C. for 3 h.
******Reaction stirred for 1 h at 100° C.

Example 4

NMR Spectrum (free base): $^1$H NMR (500 MHz, DMSO-d6) δ 1.90 (2H, p), 2.18 (6H, s), 2.35-2.43 (2H, m), 3.55 (3H, s), 4.37 (2H, t), 5.07 (2H, dd), 5.28 (2H, t), 6.13-6.24 (1H, m), 6.97 (1H, d), 7.98 (1H, dd), 8.15 (1H, d), 8.17-8.27 (1H, m), 8.50 (1H, d), 8.69 (1H, d), 8.94 (1H, s). NMR Spectrum (methanesulfonic acid salt); $^1$H NMR (500 MHz, DMSO-d6) δ 2.06 (2H, dt), 2.31 (3H, s), 2.59 (6H, s), 2.79-3.05 (2H, m), 3.55 (3H, s), 4.40 (2H, t), 5.07 (2H, dd), 5.27 (2H, t), 6.14-6.24 (1H, m), 6.99 (1H, dd), 7.99 (1H, dd), 8.15 (1H, d), 8.25 (1H, dd), 8.53 (1H, d), 8.70 (1H, dd), 8.94 (1H, s), 9.35 (1H, s). Mass Spectrum: m/z (ES+) [M+H]+=433.6.

Example 5

NMR Spectrum: $^1$H NMR (400 MHz, DMSO-d6) δ 1.87-1.92 (2H, m), 2.15 (6H, s), 2.38 (2H, t), 2.78-2.98 (4H, m), 3.50 (3H, s), 4.01-4.19 (1H, m), 4.40 (2H, t), 4.92 (1H, p), 5.26 (1H, d), 6.97 (1H, d), 7.92 (1H, dd), 8.11 (1H, d), 8.20 (1H, dd), 8.41 (1H, s), 8.67 (1H, d), 8.85 (1H, s). Mass Spectrum: m/z (ES+) [M+H]+=462.3.

Example 6

NMR Spectrum: $^1$H NMR (300 MHz, DMSO-d6) δ 1.93 (2H, t), 2.22 (6H, s), 2.48 (2H, t), 2.77-2.79 (2H, m), 2.93-3.02 (2H, m), 3.10 (3H, s), 3.49 (3H, s), 3.69-3.9 (1H, m), 4.37 (2H, 1), 5.06 (1H, p), 6.98 (1H, d), 7.90 (1H, d), 8.04 (1H, dd), 8.37 (1H, d), 8.50 (1H, d), 8.91 (1H, s). Mass Spectrum: m/z (ES+) [M+H]+=480.

Example 7

NMR Spectrum: $^1$H NMR (400 MHz, DMSO-d6) δ 1.92-1.98 (2H, m), 2.00 (3H, s), 2.01-2.07 (2H, m), 2.28 (6H, s), 2.50-2.54 (2H, m), 3.11 (2H, d), 3.36 (2H, t), 4.35-4.38 (2H, m), 3.51 (3H, s), 4.36 (2H, t), 6.97 (1H, d), 7.90 (1H, dd), 8.11-8.15 (2H, m), 8.47 (1H, s), 8.57 (1H, d), 8.95 (1H, s). Mass Spectrum: m/z (ES+) [M+H]+=476.

Example 8

NMR Spectrum: $^1$H NMR (400 MHz, DMSO-d6) δ 1.92-1.96 (4H, m), 2.23 (6H, s), 2.49-2.51 (2H, m), 2.62-2.75 (2H, m), 3.33-3.57 (5H, m), 4.05 (2H, dd), 4.37 (2H, 1), 5.03-5.11 (1H, m), 6.98 (1H, d), 7.94 (1H, d), 8.08 (1H, dd), 8.34 (1H, d), 8.54 (1H, s), 8.93 (1H, s). Mass Spectrum: m/z (ES+) [M+H]+=480.

Example 9

NMR Spectrum: $^1$H NMR (400 MHz, DMSO-d6) δ 1.85-1.91 (2H, m), 2.16 (6H, s), 2.37 (2H, t), 3.53 (3H, s), 4.36 (2H, t), 5.01 (2H, t), 5.24 (2H, t), 6.13 (1H, p), 6.98 (1H, d), 7.93 (1H, d), 8.05 (1H, dd), 8.43 (1H, d), 8.50 (1H, s), 8.97 (1H, s). Mass Spectrum: m/z (ES+) [M+H]+452.

Example 10

NMR Spectrum: $^1$H NMR (500 MHz, DMSO-d6) δ 1.78 (2H, dd), 1.90 (2H, p), 2.17 (7H, s), 2.38 (2H, t), 2.66 (1H, qd), 3.38 (1H, td), 3.49 (3H, s), 3.91 (1H, d), 4.12 (1H, dd), 4.21 (1H, t), 4.38 (2H, t), 4.91 (1H, ddd), 7.01 (1H, d), 7.93 (1H, d), 8.06 (1H, dt), 8.26 (1H, d), 8.51 (1H, s), 8.92 (1H, s). Mass Spectrum: m/z (ES+) [M+H]+=479.

Example 11

NMR Spectrum: $^1$H NMR (500 MHz, DMSO-d6) δ 1.80 (2H, d), 1.90 (2H, p), 2.17 (7H, s), 2.38 (2H, t), 2.61-2.73 (1H, m), 3.38 (1H, td), 3.50 (3H, s), 3.91 (1H, d), 4.12 (1H, dd), 4.21 (1H, t), 4.38 (2H, t), 4.86-4.98 (1H, m), 7.01 (1H, d), 7.94 (1H, d), 8.06 (1H, dt), 8.27 (1H, d), 8.52 (1H, s), 8.92 (1H, s). Mass Spectrum: m/z (ES+) [M+H]+=479

Example 12

NMR Spectrum: $^1$H NMR (400 MHz, DMSO-d6) δ 1.89-1.91 (2H, m), 2.15 (6H, s), 2.35 (2H, t), 2.78-2.83 (2H, m), 2.96-3.303 (2H, m), 3.19 (3H, s), 3.83 (1H, p), 4.36 (2H, t), 5.09 (1H, p), 6.97 (1H, d), 7.91 (1H, dd), 8.08 (1H, d), 8.20 (1H, dd), 8.43 (1H, d), 8.65 (1H, d), 8.87 (1H, s), 11.54 (1H, bs). Mass Spectrum: m/z (ES+) [M+H]+=448.

Example 13

NMR Spectrum: $^1$H NMR (300 MHz, DMSO-d6) δ 1.85-1.92 (4H, m), 2.19 (6H, s), 2.40 (2H, t), 2.69-2.75 (2H, m), 3.57 (2H, t), 4.04-4.09 (2H, m), 4.36 (2H, t), 5.08 (1H, p), 6.98 (1H, d), 7.94 (1H, dd), 8.10-8.21 (2H, m), 8.42 (1H, s), 8.65 (1H, s), 8.66 (1H, s), 11.57 (1H, s). Mass Spectrum: m/z (ES+) [M+H]+=448.

Example 14

NMR Spectrum: $^1$H NMR (300 MHz, DMSO-d6) δ 1.77-1.90 (2H, m), 1.90-1.99 (2H, m), 2.47-2.51 (2H, m), 2.72-2.91 (4H, m), 3.09 (4H, t), 3.50 (3H, s), 4.04-4.08 (1H, m), 4.33 (2H, t), 4.94 (1H, p), 5.24 (1H, d), 6.95 (1H, d), 7.92 (1H, dd), 8.11 (1H, d), 8.20 (1H, dd), 8.41 (1H, d), 8.66 (1H, d), 8.87 (1H, s). Mass Spectrum: m/z (ES+) [M+H]+= 460.

Example 15

NMR Spectrum: $^1$H NMR (300 MHz, DMSO-d6) δ 1.67-1.70 (4H, m), 1.88-1.97 (2H, m), 2.44-2.51 (4H, m), 2.54-2.56 (2H, m), 2.79-2.95 (4H, m), 3.49 (3H, s), 4.05-4.11 (1H, m), 4.37 (2H, t), 4.93 (1H, p), 5.24 (1H, d), 6.96 (1H, d), 7.92 (1H, dd), 8.11 (1H, d), 8.20 (1H, dd), 8.40 (1H, d), 8.66 (1H, d), 8.87 (1H, s). Mass Spectrum: m/z (ES+) [M+H]+=474.

Example 16

NMR Spectrum: NMR (300 MHz, DMSO-d6) δ 1.75-1.97 (4H, m), 2.10-2.22 (1H, d), 2.24 (6H, s), 2.42-2.55 (2H, m), 2.62-2.77 (1H, m), 3.34-3.45 (1H, m), 3.50 (3H, s), 3.92 (1H, d), 4.10-4.26 (2H, m), 4.35 (2H, t), 4.89-5.02 (1H, m), 6.98 (1H, d), 7.92 (1H, dd), 8.12-8.19 (2H, m), 8.33 (1H, s), 8.62 (1H, d), 8.89 (1H, s). Mass Spectrum: m/z (ES+) [M+H]+=462.25.

Example 17

NMR Spectrum: $^1$H NMR (300 MHz, DMSO-d6) δ 1.75-1.97 (4l, m), 2.10-2.28 (7H, m), 2.40 (2H, t), 2.62-2.77 (1H, m), 3.33-3.47 (1H, m), 3.50 (3H, s), 3.93 (1H, d), 4.10-4.26 (2H, m), 4.35 (2H, t), 4.91-5.05 (1H, m), 6.98 (1H, d), 7.95 (1H, dd), 8.12-8.19 (1H, m), 8.35 (1H, s), 8.62 (1H, d), 8.89 (1H, s). Mass Spectrum: m/z (ES+) [M+H]+= 462.25.

Example 18

NMR Spectrum: $^1$H NMR (300 MHz, DMSO-d6) δ 1.85-2.00 (2H, m), 2.21 (6H, s), 2.46 (2H, t), 2.74-2.87 (2H, m), 2.91-3.07 (2H, m), 3.18 (3H, s), 3.50 (3H, s), 3.75-3.89 (1H, m), 4.32 (2H, t), 4.91-5.08 (1H, m), 6.94 (1H, d), 7.78 (1H, dd), 8.10 (1H, d), 8.16-8.27 (1H, m), 8.45 (1H, s), 8.90 (1H, s); $^{19}$F NMR (300 MHz, DMSO-d6) δ 73.62. Mass Spectrum: m/z (ES+) [M+H]+=480.

Example 19

NMR Spectrum: $^1$H NMR (300 MHz, DMSO-d6) δ 1.88-2.00 (2H, m), 2.23 (6H, s), 2.41-2.50 (2H, m), 2.71-2.83 (2H, m), 2.89-3.03 (1H, m), 3.15 (3H, s), 3.49 (3H, s), 3.71-3.86 (1H, m), 4.33 (2H, t), 4.91-5.08 (1H, m), 6.97 (1H, d), 7.90 (1H, d), 8.12 (1H, dt), 8.43 (1H, dd), 8.92 (1H, s). $^{19}$F NMR (300 MHz, DMSO-d6) δ 71.56 ppm, 116.913 ppm. Mass Spectrum: m/z (ES+) [M+H]+=498.

Example 20

NMR Spectrum: $^1$H NMR (300 MHz, DMSO-d6) δ 1.79-1.90 (2H, m), 2.10-2.25 (3H, m), 2.60-2.72 (1H, m), 2.73 (6H, s), 3.10-3.20 (2H, m), 3.30-3.47 (4H, m), 3.91 (1H, d), 4.10 (1H, d), 4.28 (1H, t), 4.39 (2H, t), 4.81-4.96 (1H, m), 6.99 (1H, d), 7.85 (1H, d), 8.14 (1H, d), 8.30 (1H, dd), 8.41 (1H, s), 8.91 (1H, s). Mass Spectrum: m/z (ES+) [M+H]+=480.

Example 21

NMR Spectrum: $^1$H NMR (300 MHz, MeOD) δ 1.94-204 (2H, m), 2.20-2.30 (2H, m), 2.82 (6H, s), 2.82-3.00 (2H, m), 3.18-3.35 (2H, m), 3.62 (3H, s), 3.62-3.71 (2H, m), 4.20 (2H, dd), 4.50 (2H, t), 5.12-5.25 (1H, m), 6.95 (1H, d), 7.91 (1H, d), 8.19 (2H, m), 8.64 (1H, d), 8.87 (1H, s). Mass Spectrum: m/z (ES+) [M+H]+=480.

Example 22

NMR Spectrum: $^1$H NMR (300 MHz, DMSO-d6) δ 1.75-1.99 (4H, m), 2.10-2.24 (7H, m), 2.35-2.47 (2H, m), 2.55-2.69 (1H, m), 3.34-3.46 (1H, m), 3.92 (1H, d), 4.03 (1H, d), 4.24-4.97 (3H, m), 4.81-4.99 (1H, m), 6.97 (1H, d), 7.84 (1H, d), 8.13 (1H, d), 8.24 (1H, dd), 8.40 (1H, s), 8.90 (1H, s). Mass Spectrum: m/z (ES+) [M+H]+=480.

Example 23

NMR Spectrum: $^1$H NMR (400 MHz, DMSO-d6) 1.71 (4H, p), 1.78 (2H, d), 1.95 (2H, p), 2.14 (1H, d), 2.53-2.74 (6H, m), 3.38 (2H, td), 3.49 (3H, s), 3.91 (1H, d), 4.12 (1H, dd), 4.21 (1H, t), 4.40 (2H, t), 4.91 (1H, t), 7.01 (1H, d), 7.94 (1H, d), 8.06 (1H, dt), 8.26 (1H, d), 8.51 (1H, s), 8.92 (1H, s). Mass Spectrum: m/z (ES+) [M+H]+=506.

Example 24

NMR Spectrum: $^1$H NMR (400 MHz, DMSO-d6) δ 1.64-1.74 (4H, m), 1.78 (2H, d), 1.94 (2H, p), 2.14 (1H, d), 2.46 (4H, d), 2.54-2.6 (1H, m), 2.61-2.73 (1H, m), 3.34-3.43 (2H, m), 3.49 (3H, s), 3.91 (1H, d), 4.07-4.17 (1H, m), 4.21 (1H, t), 4.40 (2H, t), 4.84-4.98 (1H, m), 6.98-7.04 (1H, m), 7.93 (1H, d), 8.06 (1H, dt), 8.26 (1H, d), 8.51 (1H, s), 8.92 (1H, s); Mass Spectrum: m/z (ES+) [M+H]+=506.

The preparations for the bromo intermediates required for the synthesis of Examples 3-24 have either already been described or were carried out in the following manner by methylation of the corresponding 31H-imidazo[4,5-c]quinolin-2-one intermediates.

Intermediate C1: 8-Bromo-7-fluoro-1-(cis-3-methoxycyclobutyl)-3-methylimidazo[4,5-c]quinolin-2-one

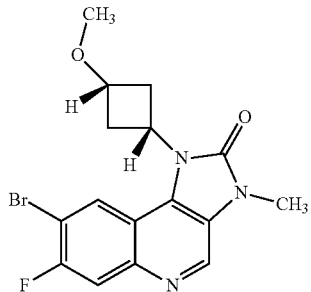 [SMILES: CO[C@H]1C[C@@H](n2c(=O)n(C)c3cnc4cc(F)c(Br)cc4c32)C1]

A solution of sodium hydroxide (4 g, 100 mmol) in water (240 mL) was added to a solution of 8-bromo-7-fluoro-1-(cis-3-methoxycyclobutyl)-3H-imidazo[4,5-c]quinolin-2-one (23 g, 62.81 mmol), methyl iodide (13.41 g, 94.48 mmol) and tetrabutylammonium bromide (2 g, 6.21 mmol) in DCM (400 mL) and the resulting solution stirred at r.t. overnight. The mixture was concentrated under vacuum and the solids collected by filtration. The crude product was re-crystallized from DCM:EtOAc in the ratio of 1:2 and the solid dried in an oven under reduced pressure to afford the desired material (18 g, 75%) as an off-white solid. NMR Spectrum: $^1$H NMR (300 MHz, DMSO-d6) δ 2.70-2.85 (2H, m), 2.93-3.07 (2H, m), 3.22 (3H, s), 3.48 (3H, s), 3.73-4.00 (1H, m), 4.86-5.15 (1H, m), 7.75-8.07 (1H, d), 8.52-8.73 (1H, d), 8.93 (1H, s). Mass Spectrum: m/z (ES+) [M+H]+= 380.

The following intermediates were prepared in an analogous fashion from the appropriate 3H-imidazo[4,5-c]quinolin-2-one intermediate:

| Intermediate | Structure | Name |
|---|---|---|
| Intermediate D1 | 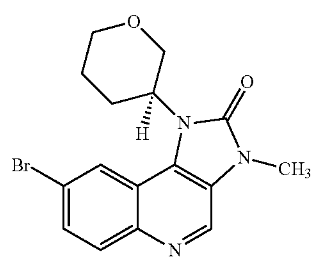 [SMILES: Cn1c(=O)n([C@H]2CCCOC2)c2c3cc(Br)ccc3ncc21] | 8-bromo-3-methyl-1-[(3S)-oxan-3-yl]imidazo[5,4-c]quinolin-2-one |
| Intermediate E1 * | 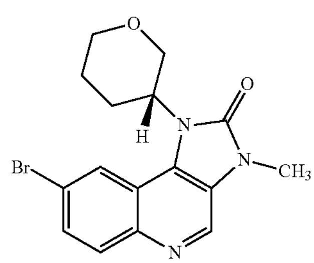 [SMILES: Cn1c(=O)n([C@@H]2CCCOC2)c2c3cc(Br)ccc3ncc21] | 8-bromo-3-methyl-1-[(3R)-oxan-3-yl]imidazo[5,4-c]quinolin-2-one |

-continued

| Intermediate | Structure | Name |
|---|---|---|
| Intermediate F1 | 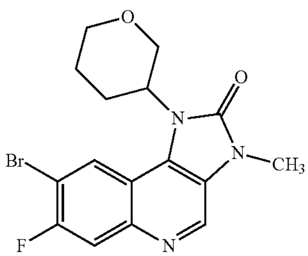 [SMILES: Cn1c(=O)n(C2CCCOC2)c2c3cc(Br)c(F)cc3ncc21] | 8-bromo-7-fluoro-3-methyl-1-(oxan-4-yl)imidazo[5,4-c]quinolin-2-one |
| Intermediate G1 | 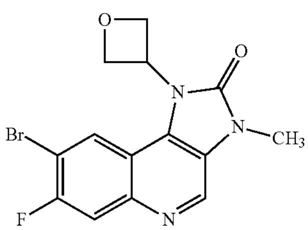 [SMILES: Cn1c(=O)n(C2COC2)c2c3cc(Br)c(F)cc3ncc21] | 8-bromo-7-fluoro-3-methyl-1-(oxetan-3-yl)imidazo[5,4-c]quinolin-2-one |
| Intermediate H1 * | 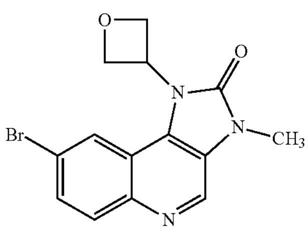 [SMILES: Cn1c(=O)n(C2COC2)c2c3cc(Br)ccc3ncc21] | 8-bromo-3-methyl-1-(oxetan-3-yl)imidazo[5,4-c]quinolin-2-one |
| Intermediate I1 | 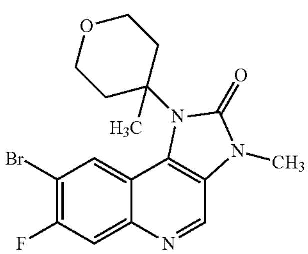 [SMILES: Cn1c(=O)n(C2(C)CCOCC2)c2c3cc(Br)c(F)cc3ncc21] | 8-bromo-7-fluoro-3-methyl-1-(4-methyloxan-4-yl)imidazo[5-4-c]quinolin-2-one |
| Intermediate J1 | 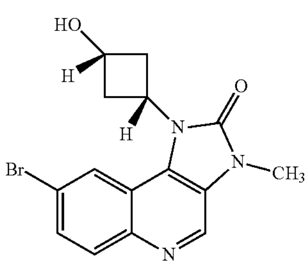 [SMILES: Cn1c(=O)n([C@H]2C[C@@H](O)C2)c2c3cc(Br)ccc3ncc21] | 8-bromo-1-(cis-3-hydroxycyclobutyl)-3-methylimidazo[4,5-c]quinolin-2-one |
| Intermediate K1 ** | 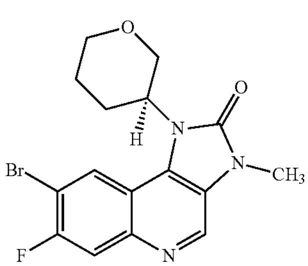 [SMILES: Cn1c(=O)n([C@H]2CCCOC2)c2c3cc(Br)c(F)cc3ncc21] | 8-bromo-7-fluoro-3-methyl-1-[(3S)-oxan-3-yl]imidazo[5,4-c]quinolin-2-one |

-continued

| Intermediate | Structure | Name |
|---|---|---|
| Intermediate L1 | 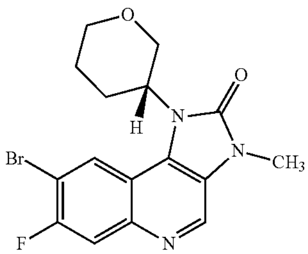 [SMILES: Cn1c(=O)n([C@@H]2CCCOC2)c2c3cc(Br)c(F)cc3ncc21] | 8-bromo-7-fluoro-3-methyl-1-[(3R)-oxan-3-yl]imidazo[5,4-c]quinolin-2-one |

\* The reaction had not proceeded to completion so additional methyl iodide, sodium hydroxide and tetrabutylammonium bromide were added and the reaction stirred a further 16-18 h.
\*\* The reaction was stirred for 72 h at ambient temperature.

Intermediate D1

NMR Spectrum: $^1$H NMR (300 MHz, DMSO-d6) δ 1.82-1.88 (2H, m), 2.09-2.15 (1H, m), 2.55-2.78 (1H, m), 3.30-3.47 (1H, m) 3.48 (3H, s), 3.92 (1H, d), 4.02-4.22 (2H, m), 4.68-4.88 (1H, m), 7.75 (1H, d), 7.99 (1H, d), 8.35 (1H, s), 8.92 (1H, s). Mass Spectrum: m/z (ES+) [M+H]+=362.2.

Intermediate E1

NMR Spectrum: $^1$H NMR (300 MHz, DMSO-d6) δ 1.80-1.86 (2H, m), 2.07-2.12 (1H, m), 2.61-2.75 (1H, m), 3.32-3.46 (1H, m), 3.47 (3H, s), 3.92-3.98 (1H, m), 4.01-4.20 (2H, m), 4.72-4.83 (1H, m), 7.76 (1H, dd), 8.00 (1H, d), 8.34 (1H, d), 8.92 (1H, s). Mass Spectrum: m/z (ES+) [M+H]+=362, 364.

Intermediate F1

NMR Spectrum: $^1$H NMR (400 MHz, DMSO-d6, 100° C.) δ 1.88 (2H, d), 2.59-2.84 (2H, m), 3.50 (3H, s), 3.60 (2H, t), 4.06 (2H, d), 4.95 (1H, s), 7.90 (1H, d), 8.56 (1H, d), 8.89 (1H, s). Mass Spectrum: m/z (ES+) [M+H]+=381.96.

Intermediate G1

Mass Spectrum: m/z (ES+) [M+H]+=352.

Intermediate H1

NMR Spectrum: $^1$H NMR (400 MHz, DMSO-d6) δ 3.53 (3H, s), 5.01 (2H, dd), 5.22 (2H, t), 6-6.18 (1H, m), 7.77 (1H, dd), 8.00 (1H, d), 8.51 (1H, d), 8.97 (1H, s). Mass Spectrum: m/z (ES+) [M+H]+=334, 336.

Intermediate H

NMR Spectrum: $^1$H NMR (400 MHz, DMSO-d6, 100° C.) δ 1.99 (3H, s), 2.00-2.04 (2H, m), 2.98 (1H, d), 3.13-3.16 (1H, m), 3.32-3.38 (2H, m), 3.53 (3H, s), 3.66-3.70 (2H, m), 7.99 (1H, d), 8.63 (1H, d), 9.00 (1H, s) Mass Spectrum: m/z (ES+) [M+H]+=394, 396.

Intermediate J1

NMR Spectrum: $^1$H NMR (400 MHz, DMSO-d6) δ 2.65-2.72 (2H, m), 2.85-2.93 (2H, m), 3.51 (3H, s), 4.02-4.09 (1H, m), 4.78 (1H, m), 5.26 (1H, d), 7.73 (1H, dd), 7.97 (1H, d), 8.45 (1H, d), 8.92 (1H, s). Mass Spectrum: m/z (ES+) [M+H]+=348.

Intermediate K1

NMR Spectrum: $^1$H NMR (400 MHz, DMSO-d6) δ 1.88-190 (2H, m), 2.09 (1H, d), 2.70 (1H, ddd), 3.36-3.44 (1H, m), 3.47 (3H, s), 3.94 (1H, d), 4.07 (1H, dd), 4.15 (1H, t), 4.79 (1H, ddd), 7.97 (1H, d), 8.48 (1H, d), 8.93 (1H, s). Mass Spectrum: m/z (ES+) [M+H]+=380, 382.

Intermediate L1

NMR Spectrum: $^1$H NMR (400 MHz, DMSO-d6) δ 1.86 (2H, dd), 2.11 (1H, d), 2.69 (1H, ddd), 3.37-3.45 (1H, m), 3.48 (3H, s), 3.95 (1H, d), 4.08 (1H, dd), 4.18 (1H, t), 4.80 (1H, ddd), 7.98 (1H, d), 8.50 (1H, d), 8.94 (1H, s). Mass Spectrum: m/z (ES+) [M+H]+=380, 382.

Intermediate M1, 8-bromo-3-methyl-1-(4-methyl-oxan-4-yl)imidazo[5,4-c]quinolin-2-one was prepared in the following manner:

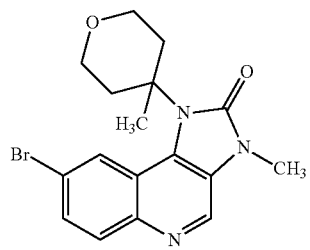 [SMILES: Cn1c(=O)n(C2(C)CCOCC2)c2c3cc(Br)ccc3ncc21]

1,1-Dimethoxy-N,N-dimethylmethanamine (1.663 mL, 12.42 mmol) was added to a stirred suspension of 8-bromo-1-(4-methyloxan-4-yl)-3H-imidazo[4,5-c]quinolin-2-one (0.9 g, 2.48 mmol) in DMF (8.2 mL) under an inert atmosphere and the reaction heated at 80° C. overnight. The reaction mixture was evaporated to dryness and the crude product was dry-loaded onto silica and purified by FCC, elution gradient 2 to 10% MeOH in DCM, to afford the desired material (0.591 g, 63.2%) as a yellow solid. NMR Spectrum: $^1$H NMR (400 MHz, DMSO-d6) δ 1.92 (3H, s), 2.02 (2H, ddd), 2.95-3.03 (2H, m), 3.36 (2H, td), 3.50 (3H, s), 3.68 (2H, dt), 7.72 (1H, dd), 8.00 (1H, d), 8.49 (1H, d), 8.98 (1H, s). Mass Spectrum: m/z (ES+) [M+H]+=376.4.

The required 3H-imidazo[4,5-c]quinolin-2-one intermediates were prepared by cyclisation of the appropriate acid intermediate as follows:

Intermediate C2: 8-Bromo-7-fluoro-1-(cis-3-methoxycyclobutyl)-3H-imidazo[4,5-c]quinolin-2-one

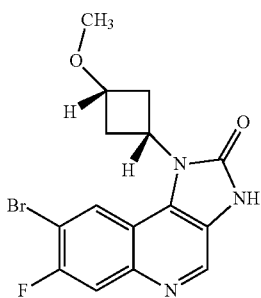 [SMILES: CO[C@H]1C[C@@H](n2c(=O)[nH]c3cnc4cc(F)c(Br)cc4c32)C1]

A solution of 6-bromo-7-fluoro-4-[(cis-3-methoxycyclobutyl)amino]quinoline-3-carboxylic acid (5.90 g, 15.98 mmol), and triethylamine (9.72 g, 96.06 mmol) in DMF (100 mL) was stirred at ambient temperature for 2 h then diphenyl phosphorazidate (11.02 g, 40.04 mmol) added The resulting solution was stirred at 60° C. for 2 h before being concentrated in vacuo. The residue was diluted with water (80 mL) and the solids collected by filtration and dried in an oven under reduced pressure to afford the desired material (4.5 g, 77%) as a white solid. NMR Spectrum: $^1$H NMR (300 MHz, CDCl$_3$) δ 2.75 (2H, m), 2.95 (2H, m), 3.25 (3H, s), 3.85 (1H, m), 4.75 (1H, m), 8.00 (1H, d), 8.62-8.58 (2H, t). Mass Spectrum: m/z (ES+) [M+H]+=366.

The following 3H-imidazo[4,5-c]quinolin-2-one intermediates were prepared in a similar fashion from the appropriate carboxylic acid intermediates:

| Intermediate | Structure | Name |
| --- | --- | --- |
| Intermediate D2 * | 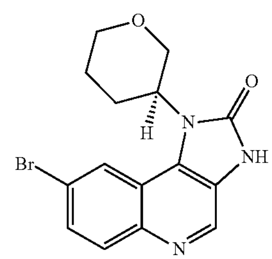 [SMILES: O=c1[nH]c2cnc3ccc(Br)cc3c2n1[C@H]1CCCOC1] | 8-bromo-1-[(3S)-oxan-3-yl]-3H-imidazo[4,5-c]quinolin-2-one |
| Intermediate E2 * | 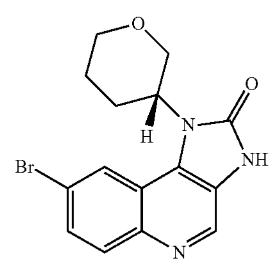 [SMILES: O=c1[nH]c2cnc3ccc(Br)cc3c2n1[C@@H]1CCCOC1] | 8-bromo-1-[(3R)-oxan-3-yl]-3H-imidazo[4,5-c]quinolin-2-one |
| Intermediate F2 | 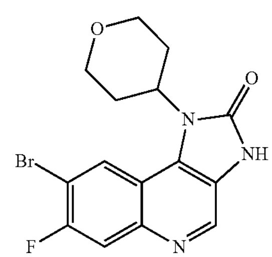 [SMILES: O=c1[nH]c2cnc3cc(F)c(Br)cc3c2n1C1CCOCC1] | 8-bromo-7-fluoro-1-(oxetan-4-yl)-3H-imidazo[4,5-c]quinolin-2-one |
| Intermediate G2 * | 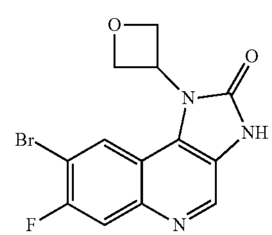 [SMILES: O=c1[nH]c2cnc3cc(F)c(Br)cc3c2n1C1COC1] | 8-bromo-7-fluoro-1-(oxetan-3-yl)-3H-imidazo[4,5-c]quinolin-2-one |

-continued

| Intermediate | Structure | Name |
|---|---|---|
| Intermediate J2 * | 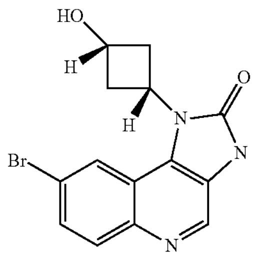 [SMILES: O=c1[nH]c2cnc3ccc(Br)cc3c2n1[C@H]1C[C@@H](O)C1] | 8-bromo-1-(cis-3-hydroxycyclobutyl)-3H-imidazo[4,5-c]quinolin-2-one |

* The reaction was stirred at 60° C. for 1 h.

Intermediate D2

NMR Spectrum: ¹H NMR (300 MHz, DMSO-d6) δ 1.84-2.11 (3H, m), 2.62-2.76 (1H, m), 3.35-3.44 (1H, m), 3.92-4.22 (3H, m), 4.71-4.80 (1H, m), 7.76 (1H, dd), 7.98 (2H, d), 8.32 (1H, dd), 8.71 (1H, s), 11.85 (1H, bs). Mass Spectrum: m/z (ES+) [M+H]+=350.

Intermediate E2

NMR Spectrum: ¹H NMR (300 MHz, DMSO-d6) δ 1.82-2.11 (3H, m), 2.61-2.75 (1H, m), 3.34-3.43 (1H, m), 3.91-4.21 (3H, m), 4.69-4.78 (1H, m), 7.75 (1H, dd), 7.99 (2H, d), 8.33 (1H, dd), 8.69 (1H, s), 11.70 (1H, bs). Mass Spectrum: m/z (ES+) [M+H]+=350.

Intermediate F2

NMR Spectrum: ¹H NMR (400 MHz, DMSO-d6, 100° C.) δ 1.88 (2H, dd), 2.71 (2H, qd), 3.59 (2H, td), 4.06 (2H, dd), 4.92 (1H, tt), 7.92 (1H, d), 8.57 (1H, d), 8.72 (1H, s), 11.43 (1H, s). Mass Spectrum: m/z (ES+) [M+H]+=367.92.

Intermediate G2

NMR Spectrum: ¹H NMR (300 MHz, DMSO-d6) δ 5.01 (2H, t), 5.20 (2H, t), 6.08 (1H, m), 7.96 (1H, d) 8.70-8.73 (1H, m), 8.74 (1H, s), 11.80 (1H, bs). Mass Spectrum: m/z (ES+) [M+H]+338.

Intermediate J2

NMR Spectrum: ¹H NMR (400 MHz, DMSO-d6) δ 2.70-2.76 (2H, m), 2.81-2.90 (2H, m), 4.04-4.08 (1H, m), 4.75 (1H, p), 7.74 (1H, dd), 7.95 (1H, d), 8.45 (1H, d), 8.68 (1H, s), 11.62 (1H, bs). Mass Spectrum: m/z (ES+) [M+H]+= 334, 336.

The above acid intermediates were prepared from the corresponding ester intermediate as follows:

Intermediate C3: 6-Bromo-7-fluoro-4-[(cis-3-methoxycyclobutyl)amino]quinoline-3-carboxylic acid

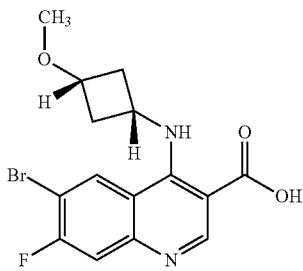 [SMILES: CO[C@H]1C[C@@H](Nc2c(C(=O)O)cnc3cc(F)c(Br)cc23)C1]

A solution of sodium hydroxide (8 g, 200 mmol) in water (100 mL) was added to a solution of ethyl 6-bromo-7-fluoro-4-[(cis-3-methoxycyclobutyl)amino]quinoline-3-carboxylate (6.0 g, 15.10 mmol) in MeOH (300 mL) and the resulting solution stirred overnight at ambient temperature. The temperature was increased to 40° C. for a further 2 h. The pH value of the solution was adjusted to 5 with 1.5 hydrochloric acid and the solids collected by filtration and dried in an oven under reduced pressure to afford the desired material (5.6 g) as a white solid which was used without further purification. NMR Spectrum: ¹H NMR (400 MHz, DMSO-d6) δ 1.98-1.91 (2H, m), 2.8-2.84 (2H, m), 3.17 (1H, s), 3.77-3.70 (1H, t), 4.22-4.19) (1H, t), 7.73 (1H, d), 8.44 (1H, d), 8.88 (1H, s), 13.27 (1H, s). Mass Spectrum: m/z (ES+) [M+H]+=369.

The following carboxylic acid intermediates were prepared in a similar fashion from the appropriate ester precursor:

| Intermediate | Structure | Name |
|---|---|---|
| Intermediate D3 * | 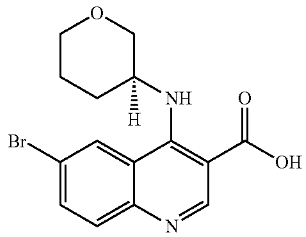 [SMILES: O=C(O)c1cnc2ccc(Br)cc2c1N[C@H]1CCCOC1] | 6-bromo-4-[[(3S)oxan-3-yl]amino]quinoline-3-carboxylic acid |
| Intermediate E3 * | 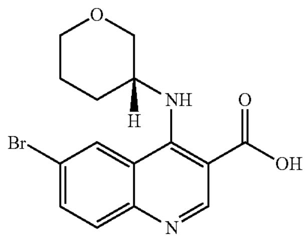 [SMILES: O=C(O)c1cnc2ccc(Br)cc2c1N[C@@H]1CCCOC1] | 6-bromo-4-[[(3R)oxan-3-yl]amino]quinoline-3-carboxylic acid |
| Intermediate F3 ** | 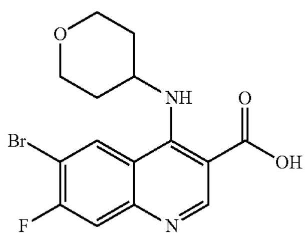 [SMILES: O=C(O)c1cnc2cc(F)c(Br)cc2c1NC1CCOCC1] | 6-bromo-7-fluoro-4-(oxan-4-ylamino)quinoline-3-carboxylic acid |
| Intermediate G3 *** | 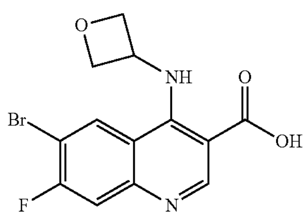 [SMILES: O=C(O)c1cnc2cc(F)c(Br)cc2c1NC1COC1] | 6-bromo-7-fluoro-4-(oxetan-3-ylamino)quinoline-3-carboxylic acid |
| Intermediate J3 * | 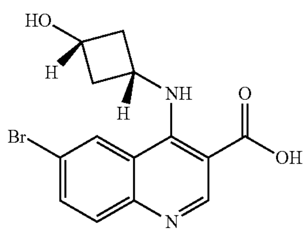 [SMILES: O=C(O)c1cnc2ccc(Br)cc2c1N[C@H]1C[C@@H](O)C1] | 6-bromo-4-[(cis-3-hydroxycyclobutyl)amino]quinoline-3-carboxylic acid |

\* The reaction was stirred between 60-70° C. for 1-3 h.
\*\* The reaction was stirred at ambient temperature overnight.
\*\*\*The reaction was performed using a mixture of THF and water as the solvent and was heated at 65° C. for 3 h.

Intermediate D3

NMR Spectrum: $^1$H NMR (300 MHz, DMSO-d6) δ 1.50-1.57 (1H, m), 1.61-1.82 (2H, m), 1.98-2.13 (1H, m), 3.48-3.72 (3H, m), 3.89 (1H, d), 4.15-4.26 (1H, m), 7.77 (1H, dd), 7.95 (1H, d), 8.31 (1H, d), 8.90 (1H, s), 13.38 (1H, bs). Mass Spectrum: m/z (ES+) [M+H]+=351.

Intermediate E3

NMR Spectrum: $^1$H NMR (300 MHz, DMSO-d6) δ 1.50-1.56 (1H, m), 1.62-1.83 (2H, m), 1.99-2.12 (1H, m), 3.50-3.71 (3H, m), 3.89 (1H, d), 4.16-4.28 (1H, m), 7.78 (1H, dd), 7.94 (1H, d), 8.30 (1H, d), 8.94 (1H, s), 13.50 (1H, bs). Mass Spectrum: m/z (ES+) [M+H]+=351.

Intermediate F3

Mass Spectrum: m/z (ES+) [M+H]+=369.

Intermediate G3

Mass Spectrum: m/z (ES+) [M+H]+=341.

Intermediate J3

NMR Spectrum: $^1$H NMR (300 MHz, DMSO-d6) δ 2.03-2.07 (2H, m), 2.85-2.93 (2H, m), 4.00-4.04 (1H, t), 4.21-4.35 (2H, m), 7.95 (1H, d), 8.16 (1H, dd), 8.58 (1H, s), 8.99 (1H, s), 11.02 (1H, bs). Mass Spectrum: m/z (ES+) [M+H]+=337, 339.

The above ester intermediates were prepared from the appropriate ethyl 4-chloroquinoline-3-carboxylate intermediates as follows:

Intermediate C4: Ethyl 6-bromo-7-fluoro-4-[(cis-3-methoxycyclobutyl)amino]quinoline-3-carboxylate

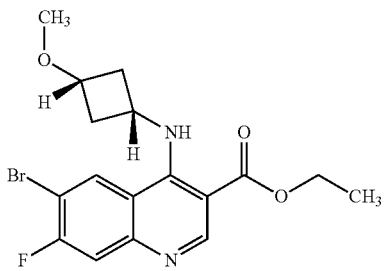 [SMILES: CCOC(=O)c1cnc2cc(F)c(Br)cc2c1N[C@H]1C[C@@H](OC)C1]

A solution of ethyl 6-bromo-4-chloro-7-fluoroquinoline-3-carboxylate (7.5 g, 22.55 mmol), 3-methoxycyclobutan-1-aminehydrochloride (3.41 g, 24.78 mmol) and DIPEA (14.61 g, 113.04 mmol) in DMA (25 mL) was stirred at 85° C. for 3 h. The reaction mixture was cooled and the solids collected by filtration, washed with water (3×20 mL) and dried in an oven under reduced pressure to afford the desired material (6.9 g, 77%) as a white solid which was used without further purification. NMR Spectrum: $^1$H NMR (400 MHz, CDCl$_3$) δ 1.44-1.41 (3H, t), 2.21-2.14 (2H, m), 3.05-2.98 (2H, m), 3.30 (3H, s), 3.94-3.75 (1H, m), 4.11-4.06 (1H, m), 4.43-4.37 (2H, d), 7.70 (1H, d), 8.29 (1H, d), 9.07 (1H, d), 9.69 (1H, s). Mass Spectrum: m/z (ES+) [M+H]+=397.

The following ester intermediates were prepared in an analogous fashion from the appropriate amine and either ethyl 6-bromo-4-chloro-7-fluoroquinoline-3-carboxylate or ethyl 6-bromo-4-chloroquinoline-3-carboxylate:

| Intermediate | Structure | Name |
| --- | --- | --- |
| Intermediate D4 * | 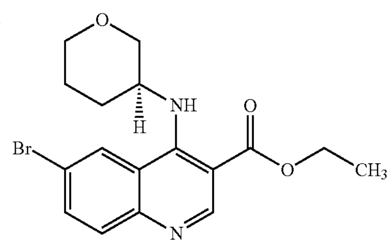 [SMILES: CCOC(=O)c1cnc2ccc(Br)cc2c1N[C@H]1CCCOC1] | ethyl 6-bromo-4-[[(3S)-oxan-3-yl]amino]quinoline-3-carboxylate |
| Intermediate E4 * | 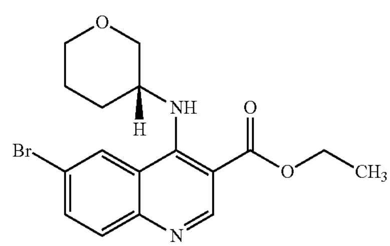 [SMILES: CCOC(=O)c1cnc2ccc(Br)cc2c1N[C@@H]1CCCOC1] | ethyl 6-bromo-4-[[(3R)-oxan-3-yl]amino]quinoline-3-carboxylate |
| Intermediate F4 ** | 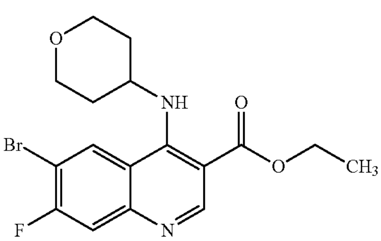 [SMILES: CCOC(=O)c1cnc2cc(F)c(Br)cc2c1NC1CCOCC1] | ethyl 6-bromo-7-fluoro-4-(oxan-4-ylamino)quinoline-3-carboxylate |
| Intermediate G4 ** | 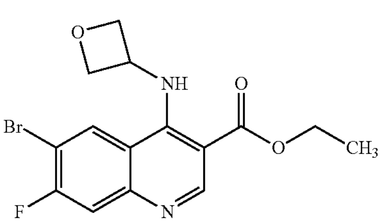 [SMILES: CCOC(=O)c1cnc2cc(F)c(Br)cc2c1NC1COC1] | ethyl 6-bromo-7-fluoro-4-(oxetan-3-ylamino)quinoline-3-carboxylate |

| Intermediate | Structure | Name |
|---|---|---|
| Intermediate J4 ** | 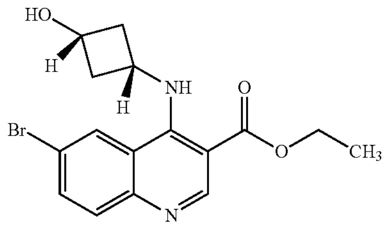 [SMILES: CCOC(=O)c1cnc2ccc(Br)cc2c1N[C@H]1C[C@@H](O)C1] | ethyl 6-bromo-4-[(cis-3-hydroxycyclobutyl)amino]quinoline-3-carboxylate |

\* The reaction was stirred at 80° C. for 16 h.
\*\* The reaction was stirred at 90° C. for 1-3 h.

Intermediate D4

NMR Spectrum: ¹H NMR (300 MHz, DMSO-d6) δ 1.36 (3H, t), 1.70-1.74 (1H, m), 1.75-1.77 (2H, m), 2.03-2.05 (1H, m), 3.58-3.61 (3H, m), 3.80-3.85 (1H, m), 4.01-4.03 (1H, m), 4.35 (2H, q), 7.80 (1H, d), 7.89 (1H, dd), 8.58 (1H, s), 8.67 (1H, d), 8.93 (1H, s). Mass Spectrum: m/z (ES+) [M+H]+=380.8.

Intermediate E4

NMR Spectrum: ¹H NMR (400 MHz, DMSO-d6) δ 1.50-1.56 (1H, m), 1.62-1.84 (2H, m), 1.99-2.13 (1H, m), 3.51-3.73 (3H, m), 3.89 (1H, d), 4.12-4.22 (1H, m), 7.77 (1H, d), 7.90 (1H, d), 8.31 (1H, s), 8.94 (1H, s), 13.41 (1H, bs). Mass Spectrum: m/z (ES+) [M+H]+=379.

Intermediate F4

Mass Spectrum: m/z (ES+) [M+H]+=397.

Intermediate G4

Mass Spectrum: m/z (ES) [M+H]+=369.

Intermediate J4

NMR Spectrum: ¹H NMR (300 MHz, DMSO-d6) δ 1.35 (3H, t), 1.91-1.95 (2H, m), 2.77-2.81 (2H, m), 3.91-3.95 (2H, m), 4.35 (2H, q), 5.28 (1H, d), 7.78 (1H, d), 7.85 (1H, dd), 8.37 (1H, d), 8.85 (1H, s), 8.89 (1H, d). Mass Spectrum: m/z (ES+) [M+H]+=365, 367.

The preparation of ethyl 6-bromo-4-chloroquinoline-3-carboxylate has been described earlier. The preparation of ethyl 6-bromo-4-chloro-7-fluoroquinoline-3-carboxylate is described below:

Intermediate C5: Ethyl 6-bromo-4-chloro-7-fluoroquinoline-3-carboxylate

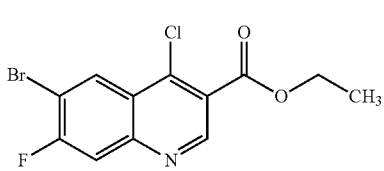 [SMILES: CCOC(=O)c1cnc2cc(F)c(Br)cc2c1Cl]

Thionyl chloride (150 mL, 2.08 mol) was added to a solution of ethyl 6-bromo-7-fluoro-4-oxo-1H-quinoline-3-carboxylate (25 g, 79.59 mmol) in DMF (50 mL) and the solution stirred at 80° C. for 4 h. The mixture was concentrated under vacuum and quenched by the addition of ice/water. The reaction mixture was extracted with DCM (8×100 mL), the organic extracts combined and the mixture adjusted to pH=7 by the addition of 1.5M ammonium hydrogen carbonate. The resulting mixture was washed with water (3×100 mL), the organics dried over Na₂SO₄ and concentrated in vacuo to afford the desired material (20 g, 76%) as a light yellow solid which was used without further purification. NMR Spectrum: ¹H NMR (400 MHz, CDCl₃) δ 1.49-1.42 (3H, m), 4.54-4.82 (2H, q), 7.86 (1H, d), 8.69 (1H, d), 9.23 (1H, s). Mass Spectrum: m/z (ES+) [M+H]+=334.

Intermediate C6: Ethyl 6-bromo-7-fluoro-4-oxo-1H-quinoline-3-carboxylate

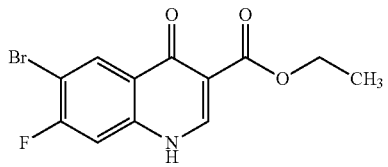 [SMILES: CCOC(=O)c1c[nH]c2cc(F)c(Br)cc2c1=O]

A solution of diethyl 2-[[(4-bromo-3-fluorophenyl)amino]methylidene]propanedioate (90 g, 249.88 mmol) in diphenyl ether (600 mL, 3.79 mol) was stirred at 240° C. for 2.5 h. The mixture was allowed to cool to 70° C., the solids collected by filtration and dried in a vacuum oven to afford the desired material (50 g, 64%) as a white solid which was used without further purification. NMR Spectrum: ¹H NMR (500 MHz, DMSO-d6, (100° C.)) δ 1.26-1.33 (3H, m), 4.25 (2H, q), 7.52 (1H, d), 8.37 (1H, d), 8.48 (1H, s), 12.05 (1H, s). Mass Spectrum: m/z (ES+) [M+H]+=314.

Intermediate C7: Diethyl 2-[[(4-bromo-3-fluorophenyl)amino]methylidene]propanedioate

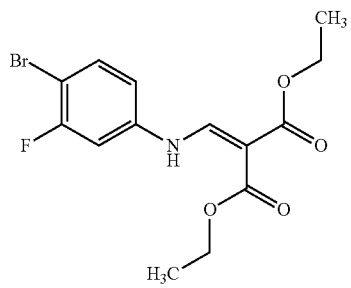 [SMILES: CCOC(=O)C(=CNc1ccc(Br)c(F)c1)C(=O)OCC]

A solution of 4-bromo-3-fluoroaniline (56.6 g, 297.87 mmol) and 1,3-diethyl 2-(ethoxymethylidene)propanedioate (72.45 g, 335.06 mmol) in EtOH (560 mL) was stirred at 80° C. for 4 h. The reaction mixture was allowed to cool, the solids collected by filtration and dried in an oven to afford the desired material (90 g, 84%) as an off-white solid which was used without further purification. NMR Spectrum: $^1$H NMR (400 MHz, DMSO-d6) δ 1.26 (6H, q), 4.14 (2H, q), 4.22 (2H, q), 7.18-7.25 (1H, m), 7.57 (1H, dd), 7.64-7.7 (1H, m), 8.33 (1H, d), 10.62 (1H, d). Mass Spectrum: m/z (ES+) [M+H]+=360.

The required 3H-imidazo[4,5-c]quinolin-2-one intermediates were prepared by cyclisation of the appropriate carboxamide intermediates as follows:

Intermediate H2: 8-Bromo-1-(oxetan-3-yl)-3H-imidazo[4,5-c]quinolin-2-one

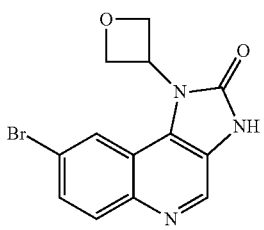 [SMILES: O=c1[nH]c2cnc3ccc(Br)cc3c2n1C1COC1]

DBU (2.34 mL, 15.64 mmol) was added to 6-bromo-4-(oxetan-3-ylamino)quinoline-3-carboxamide (2.52 g, 7.82 mmol) and 1,3,5-trichloro-1,3,5-triazinane-2,4,6-trione (0.727 g, 3.13 mmol) in MeOH (35 mL) and the resulting mixture stirred at ambient temperature overnight. The mixture was evaporated to dryness and the residue purified by FCC, elution gradient 0 to 20% MeOH in DCM, to afford the desired material (0.485 g, 19.37%) as a cream solid. NMR Spectrum: $^1$H NMR (400 MHz, DMSO-d6) δ 5.00 (2H, dd), 5.21 (2H, t), 5.87-6.15 (1H, m), 7.75 (1H, dd), 7.97 (1H, d), 8.51 (1H, d), 8.72 (1H, s), 11.73 (1H, s). Mass Spectrum: m/z (ES+) [M+H]+=320, 322.

The following 3H-imidazo[4,5-c]quinolin-2-one intermediates were prepared in an analogous fashion:

| Intermediate | Structure | Name |
|---|---|---|
| Intermediate K2 * | 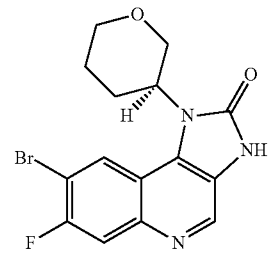 [SMILES: O=c1[nH]c2cnc3cc(F)c(Br)cc3c2n1[C@H]1CCCOC1] | 8-bromo-7-fluoro-1-[(3S)-oxan-3-yl]-3H-imidazo[4,5-c]quinolin-2-one |
| Intermediate L2 | 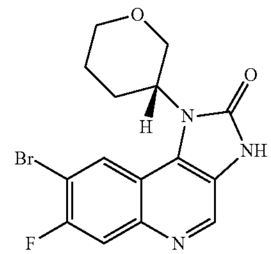 [SMILES: O=c1[nH]c2cnc3cc(F)c(Br)cc3c2n1[C@@H]1CCCOC1] | 8-bromo-7-fluoro-1-[(3R)-oxan-3-yl]-3H-imidazo[4,5-c]quinolin-2-one |

* The reaction was stirred at ambient temperature for 70 h but was still incomplete and so additional DBU and 1,3,5-trichloro-1,3,5-triazinane-2,4,6-trione and the mixture stirred at ambient temperature for a further 3 h.

Intermediate K2

NMR Spectrum: $^1$H NMR (400 MHz, DMSO-d6) δ 1.77-1.93 (2H, m), 2.10 (1H, d), 2.68 (1H, qd), 3.34-3.44 (1H, m), 3.94 (1H, d), 4.08 (1H, dd), 4.18 (1H, t), 4.75 (1H, ddd), 7.94 (1H, d), 8.48 (1H, d), 8.69 (1H, s), 11.63 (1H, s). Mass Spectrum: m/z (ES+) [M+H]+=366, 368.

Intermediate L2

NMR Spectrum: $^1$H NMR (400 MHz, DMSO-d6) δ 1.7-1.93 (2H, m), 2.10 (1H, d), 2.63-2.75 (1H, m), 3.49-3.61 (1H, m), 3.84-4.03 (1H, m), 4.08 (1H, dd), 4.19 (1H, t), 4.76 (1H, t), 7.95 (1H, d), 8.49 (1H, d), 8.70 (1H, s), 11.66 (1H, s). m/z: ES+[M+H]+366, 368 Mass Spectrum: m/z (ES+) [M+H]+=366, 368.

The appropriate carboxamide intermediates were prepared as follows:

Intermediate H3: 6-Bromo-4-(oxetan-3-ylamino)quinoline-3-carboxamide

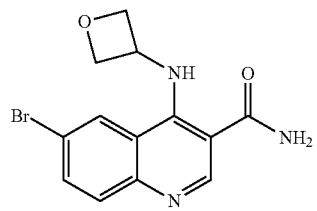 [SMILES: NC(=O)c1cnc2ccc(Br)cc2c1NC1COC1]

Oxetan-3-amine (0.614 g, 8.41 mmol) was added to 6-bromo-4-chloroquinoline-3-carboxamide (2 g, 7.00 mmol) and DIPEA (2.440 mL, 14.01 mmol) in DMA (24 mL) and the resulting mixture stirred at 100° C. for 18 h. The crude product was purified by ion exchange chromatography, using an SCX column and eluting with 7M NH$_3$/MeOH, to afford the desired material (2.52 g, 112%) as a dark brown solid which was used without further purification. NMR Spectrum: $^1$H NMR (400 MHz, DMSO-d6) δ 4.06-4.15 (2H, m), 4.16-4.20 (2H, m), 5.63-5.96 (1H, m), 7.16-7.2 (2H, m), 7.22-7.26 (2H, m), 7.32 (1H, d), 7.93 (1H, d). Mass Spectrum: m/z (ES+) [M+H]+=322, 324.

The following intermediates were prepared in an analogous fashion from 6-bromo-4-chloro-7-fluoroquinoline-3-carboxamide:

| Intermediate | Structure | Name |
|---|---|---|
| Intermediate K3 * | 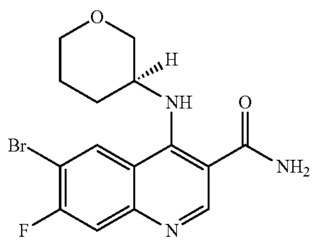 [SMILES: NC(=O)c1cnc2cc(F)c(Br)cc2c1N[C@H]1CCCOC1] | 6-bromo-7-fluoro-4-[[(3S)-oxan-3-yl]amino]quinoline-3-carboxamide |
| Intermediate L3 | 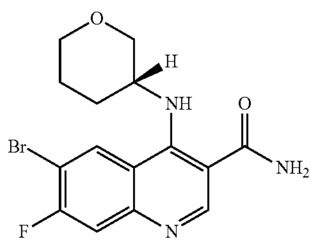 [SMILES: NC(=O)c1cnc2cc(F)c(Br)cc2c1N[C@@H]1CCCOC1] | 6-bromo-7-fluoro-4-[[(3R)-oxan-3-yl]amino]quinoline-3-carboxamide |

* The reaction was stirred at 80° C. overnight.

Intermediate K3

NMR Spectrum: $^1$H NMR (400 MHz, DMSO-d6) δ 1.52 (1H, td), 1.59-1.79 (2H, m), 2.02 (1H, d), 3.32-3.48 (2H, m), 3.68 (1H, dd), 3.87 (1H, dd), 3.9-4.01 (1H, m), 7.56 (1H, s), 7.71 (1H, d), 8.10 (1H, s), 8.20 (1H, d), 8.62 (2H, d). Mass Spectrum: m/z (ES−)(M−H)−=366.

Intermediate L3

NMR Spectrum: $^1$H NMR (400 MHz, DMSO-d6) δ 1.52 (1H, td), 1.67 (2H, ddd), 2.02 (1H, d), 3.32-3.5 (2H, m), 3.68 (1H, dd), 3.87 (1H, dd), 3.91-4.02 (1H, m), 7.56 (1H, s), 7.71 (1H, d), 8.10 (1H, s), 8.20 (1H, d), 8.62 (2H, d). Mass Spectrum: m/z (ES+) [M+H]+=368, 370.

The preparation of 6-bromo-4-chloroquinoline-3-carboxamide has been described earlier.

The preparation of 6-bromo-4-chloro-7-fluoroquinoline-3-carboxamide is described below.

Intermediate K4: 6-Bromo 4-chloro-7-fluoroquinoline-3-carboxamide

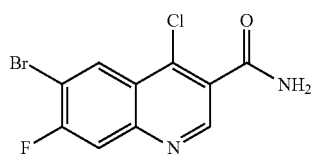 [SMILES: NC(=O)c1cnc2cc(F)c(Br)cc2c1Cl]

DMF (0.5 mL) was added to a stirred suspension of 6-bromo-7-fluoro-4-oxo-1H-quinoline-3-carboxylic acid (22.5 g, 78.66 mmol) in thionyl chloride (140 g, 1179.85 mmol) and the mixture heated to reflux for 2 h. The reaction was allowed to cool, concentrated in vacuo and the residue azeotroped twice with toluene to afford a yellow solid. This solid was added portionwise to a solution of ammonium hydroxide (147 mL, 1179.85 mmol) at 0° C. The white suspension was stirred for 15 minutes then the solid filtered, washed with water and dried under vacuum to afford the desired material (23.80 g, 100%) as a white powder. NMR Spectrum: $^1$H NMR (400 MHz, DMSO-d6) δ 8.92 (1H, s), 8.59 (1H, d), 8.21 (1H, s), 8.09 (1H, d), 7.98 (1H, s). Mass Spectrum: m/z (ES+) [M+H]+=304.8.

Intermediate K5: 6-Bromo-7-fluoro-4-oxo-1H-quinoline-3-carboxylic acid

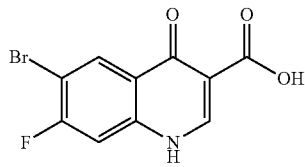 [SMILES: O=C(O)c1c[nH]c2cc(F)c(Br)cc2c1=O]

A solution of sodium hydroxide (18.34 g, 458.44 mmol) in water (100 mL) was added to a stirred suspension of ethyl 6-bromo-7-fluoro-4-oxo-1H-quinoline-3-carboxylate (28.8 g, 91.69 mmol) in EtOH (500 mL) at ambient temperature. The reaction mixture was then stirred at 75° C. for 2 h, allowed to cool and the pH adjusted to 4 using 2N hydrochloric acid. The precipitate was collected by filtration, washed with water and dried under vacuum to afford the desired material (23.30 g, 89%) as a white powder. NMR Spectrum: $^1$H NMR (400 MHz, DMSO-d6) δ 14.78 (1H, s), 13.45 (1H, s), 8.93 (1H, s), 8.46 (1H, d), 7.70 (1H, d). Mass Spectrum: m/z (ES+) [M+H]+=287.8.

The preparation of ethyl 6-bromo-7-fluoro-4-oxo-1H-quinoline-3-carboxylate has already been described.

The required 3H-imidazo[4,5-c]quinolin-2-one intermediates were prepared by cyclisation of the appropriate amino intermediates as follows:

Intermediate I2: 8-Bromo-7-fluoro-1-(4-methyloxan-4-yl)-3H-imidazo[4,5-c]quinolin-2-one

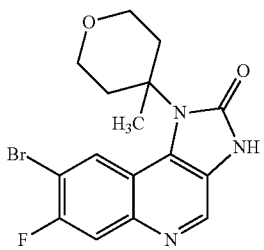 [SMILES: CC1(n2c(=O)[nH]c3cnc4cc(F)c(Br)cc4c32)CCOCC1]

6-Bromo-7-fluoro-N-(4-methyloxan-4-yl)quinoline-3,4-diamine (1.1 g, 3.11 mmol) was added to bis(trichloromethyl)carbonate (0.553 g, 1.86 mmol) in DCM (20 mL) and the resulting mixture stirred at 30° C. for 2 h. The crude product was purified by FCC, elution gradient 0 to 5% MeOH in DCM, to afford the desired material (0.950 g, 80%) as a brown solid which was used without further purification.

The following intermediate was prepared in an analogous fashion from the appropriate precursor:

| Intermediate | Structure | Name |
|---|---|---|
| Intermediate M2 * | 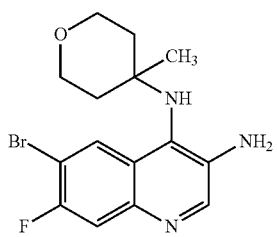 [SMILES: CC1(Nc2c(N)cnc3cc(F)c(Br)cc23)CCOCC1] | 8-bromo-1-(4-methyloxan-4-yl)-3H-imidazo[4,5-c]quinolin-2-one |

Intermediate M2

* Triethylamine (1.2 equivalents) was added to the reaction mixture and the reaction proceeded at ambient temperature over 2 h. The reaction mixture was purified using an SCX column with the desired material eluted with 7M ammonia in MeOH.

Mass Spectrum: m/z (ES−) [M−H]−=362.39.

The preparation of the appropriate amino intermediates is described below:

Intermediate I3: 6-Bromo-7-fluoro-N'-(4-methyloxan-4-yl)quinoline-3,4-diamine

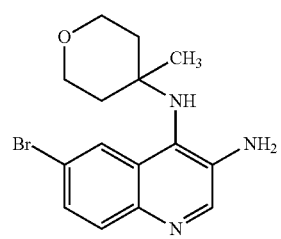

6-Bromo-7-fluoro-N-(4-methyloxan-4-yl)-3-nitroquinolin-4-amine (1.215 g, 3.16 mmol) was added to iron powder (1.8 g) in acetic acid (15 mL). The mixture was stirred and heated gently with a hot air gun (approximately 60° C.) to initiate reaction. The heat source was removed and the resulting mixture was stirred for 1 h. The reaction mixture was diluted with water and the solids removed by filtration and discarded. The filtrate was concentrated in vacuo, diluted with water and extracted with EtOAc. The organics were dried over $Na_2SO_4$ and concentrated in vacuo to afford the desired material (1.10 g, 98%) as a brown solid which was used without further purification.

Intermediate I4: 6-Bromo-7-fluoro-N-(4-methyloxan-4-yl)-3-nitroquinolin-4-amine

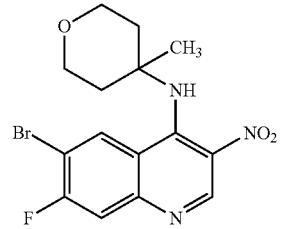 [SMILES: CC1(Nc2c([N+](=O)[O-])cnc3cc(F)c(Br)cc23)CCOCC1]

6-Bromo-4-chloro-7-fluoro-3-nitroquinoline (1 g, 3.27 mmol) was added to a solution of 4-methyltetrahydro-2H-pyran-4-amine hydrochloride (0.596 g, 3.93 mmol) and DIPEA (1.715 mL, 9.82 mmol) in DMA (10 mL) and the resulting mixture stirred at 100° C. for 4 h. The reaction mixture was diluted with water and the solid collected by filtration and dried to afford the desired material (1.215 g, 97%) as a brown solid which was used without further purification.

The synthesis of 6-bromo-4-chloro-7-fluoro-3-nitroquinoline has been reported in the literature (e.g. Garcia-Echeverria, C. et al., WO2006122806) and is available as a commercial reagent (e.g. Aces Pharma, Inc—order number 74244).

6-Bromo-N'-(4-methyloxan-4-yl)quinoline-3,4-diamine was prepared as follows:

Intermediate M3: 6-Bromo-N'-(4-methyloxan-4-yl)quinoline-3,4-diamine

Water (8.35 mL) was added to a stirred mixture of 6-bromo-N-(4-methyloxan-4-yl)-3-nitroquinolin-4-amine (1.07 g, 2.92 mmol), iron (0.979 g, 17.53 mmol) and ammonia hydrochloride (0.109 g, 2.05 mmol) in EtOH (50.1 mL) and the resulting slurry heated to 105° C. for 2 h. The reaction was filtered warm through a pad of celite, washing with MeOH, and the filtrate evaporated to dryness. The crude solid was dissolved in DCM (10 mL) and washed with a sat. aqueous solution of NaHCO₃ (10 mL) and sat. brine (10 mL). The organic layer was dried over MgSO₄, filtered and evaporated to afford the desired material (0.850 g, 87%) as a pale orange solid. This was used without further purification. NMR Spectrum: $^1$H NMR (400 MHz, DMSO-d6) δ 1.19 (3H, s), 1.51 (2H, d), 1.76 (2H, td), 3.43 (2H, td), 3.73 (2H, dt), 4.15 (1H, s), 5.45 (2H, s), 7.39 (1H, dd), 7.67 (1H, d), 8.22 (1H, d), 8.51 (1H, s). Mass Spectrum: m/z (ES+) [M+H]+=336, 338.

Intermediate M4: 6-Bromo-N-(4-methyloxan-4-yl)-3-nitroquinolin-4-amine

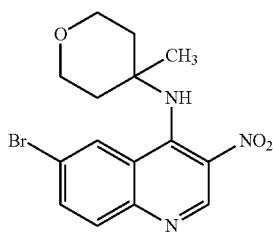 [SMILES: CC1(Nc2c([N+](=O)[O-])cnc3ccc(Br)cc23)CCOCC1]

A solution of 6-bromo-4-chloro-3-nitroquinoline (1 g, 3.48 mmol), 4-methyltetrahydro-2H-pyran-4-amine hydrochloride (1.055 g, 6.96 mmol) and triethylamine (1.939 mL, 13.91 mmol) in DMF (10 mL) was heated to 100° C. for 1 h in a sealed tube in the microwave reactor. The mixture was allowed to cool then poured into stirred water (50 mL) and the resulting yellow precipitate was collected by filtration and dried under vacuum to afford the desired material (1.070 g, 84%) as a yellow solid. This was used without further purification. NMR Spectrum: $^1$H NMR (400 MHz, DMSO-d6) δ 1.40 (3H, s), 1.78 (2H, dt), 1.89 (2H, ddd), 3.51-3.64 (4H, m), 7.80 (1H, s), 7.91 (1H, d), 8.01 (1H, dd), 8.48 (1H, d), 9.18 (1H, s). Mass Spectrum: m/z (ES+) [M+H]+=366, 368.

The synthesis of 6-bromo-4-chloro-3-nitroquinoline has been reported in the literature (e.g. Garcia-Echeverria, C. et al., WO2005054238) and is available as a commercial reagent (e.g. Aces Pharma, Inc—order number 74381).

Intermediate N1 tert-butyl 8-bromo-1-(oxan-4-yl)-2-oxoimidazo[5,4-c]quinoline-3-carboxylate, used for the preparation of example 13 was prepared as described below:

Intermediate N1: tert-Butyl 8-bromo-1-(oxan-4-yl)-2-oximidazo[5,4-c]quinoline-3-carboxylate

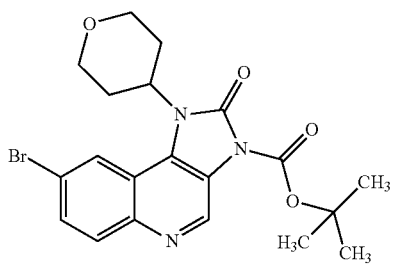 [SMILES: CC(C)(C)OC(=O)n1c(=O)n(C2CCOCC2)c2c3cc(Br)ccc3ncc21]

Di-tert-butyl dicarbonate (376 mg, 1.72 mmol) was added to a mixture of 8-bromo-1-(oxan-4-yl)-3H-imidazo[4,5-c]quinolin-2-one (300 mg, 0.86 mmol) and triethylamine (0.240 mL, 1.72 mmol) in DCM (20 mL). The resulting solution was stirred at ambient temperature for 4 h then concentrated in vacuo. The crude product was purified by FCC, elution gradient 0 to 60% MeOH in DCM, to afford the desired material (310 mg, 80%) as a white solid. NMR Spectrum: $^1$H NMR (300 MHz, CDCl₃) δ 1.72 (9H, s), 1.81-1.95 (2H, m), 2.92-3.03 (2H, m), 3.57-3.65 (2H, m), 4.26 (2H, dd), 4.89-4.94 (1H, m), 7.82 (1H, d), 8.32-8.35 (1H, m), 8.39 (1H, s), 9.49 (1H, m). Mass Spectrum: m/z (ES+) [M+H]+=448.

2-[3-(Azetidin-1-yl)propoxy]-5-(4,4,5,5-tetramethyl-1,3,2-dioxaborolan-2-yl)pyridine, 2-(3-pyrrolidin-1-yl-propoxy)-5-(4,4,5,5-tetramethyl-1,3,2-dioxaborolan-2-yl)pyridine and 3-[6-fluoro-5-(4,4,5,5-tetramethyl-1,3,2-dioxaborolan-2-yl)pyridin-2-yl]oxy-N,N-dimethylpropan-1-amine were prepared as follows:

2-[3-(Azetidin-1-yl)propoxy]-5-(4,4,5,5-tetramethyl-1,3,2-dioxaborolan-2-yl)pyridine

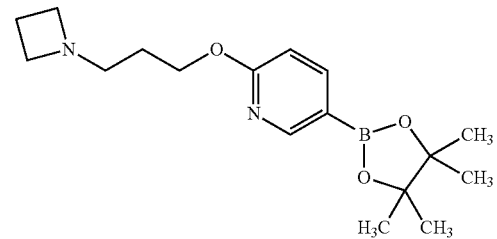 [SMILES: CC1(C)OB(c2ccc(OCCCN3CCC3)nc2)OC1(C)C]

n-Butyl lithium (4.65 mL, 11.62 mmol) was added to 2-[3-(azetidin-1-yl)propoxy]-5-bromopyridine (2.1 g, 7.74 mmol) and 2-isopropoxy-4,4,5,5-tetramethyl-1,3,2-dioxaborolane (2.161 g, 11.62 mmol) in THF (50 mL) at −78° C. over a period of 10 minutes and the resulting solution stirred at −78° C. for 1 h. The reaction was quenched with sat. Na₂SO₄ (10 mL) and the solvent removed in vacuo. The residue was dissolved in DCM (100 mL), dried over Na₂SO₄, filtered and evaporated to afford the desired material (2.00 g, 81%) as a white solid. Mass Spectrum: m/z (ES+) [M+H]+=319.

2-[3-(Azetidin-1-yl)propoxy]-5-bromopyridine

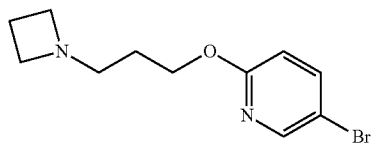 [SMILES: Brc1ccc(OCCCN2CCC2)nc1]

Sodium hydride (1.364 g, 56.82 mmol) was added to 3-(azetidin-1-yl)propan-1-ol (2.62 g, 22.73 mmol) in THF (20 mL) at ambient temperature under an inert atmosphere and the reaction stirred for 10 minutes. 5-Bromo-2-fluoropyridine (2.0 g, 11.36 mmol) was added and the resulting solution stirred for 1 h before being quenched with water (20 mL) and extracted with EtOAc (5×50 mL). The organics were combined, dried over Na₂SO₄, filtered and concentrated in vacuo to afford the desired material (3.75 g, 122%)

as a white solid. NMR Spectrum: ¹H NMR (300 MHz, CDCl₃) δ 1.80 (2H, m), 2.11 (2H, m), 2.55 (2H, t), 3.18 (4H, t), 4.328 (2H, t), 6.64 (1H, d), 7.62 (1H, dd), 8.16 (1H, d). Mass Spectrum: m/z (ES+) [M+H]+=271.

3-(Azetidin-1-yl)propan-1-ol

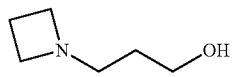

A solution of lithium aluminium hydride (2.0 M in THF) (8.38 mL, 16.76 mmol) diluted in further THF (20 mL) was added to a mixture of methyl 3-(azetidin-1-yl)propanoate (2 g, 13.97 mmol) in THF (5 mL) dropwise at 0° C. under an inert atmosphere. The resulting solution was stirred at 0° C. for 1 h then the reaction mixture treated with sodium sulphate decahydrate and stirred for 30 minutes. The solid was removed by filtration and discarded and the filtrate evaporated to afford the desired material (1.240 g, 77%) as a colourless oil. NMR Spectrum: ¹H NMR (400 MHz, CDCl₃) δ 1.51-1.57 (2H, m), 2-2.07 (2H, m), 2.6-2.66 (2H, m), 3.20 (4H, t), 3.7-3.76 (2H, m).

Methyl 3-(azetidin-1-yl)propanoate

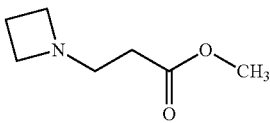

Methyl acrylate (2.082 mL, 23.12 mmol) was added to a solution of azetidine (1.2 g, 21.02 mmol) in DCM and the resulting solution stirred at ambient temperature, under an inert atmosphere for 16 h. The reaction mixture was evaporated and the crude product purified by FCC, eluted with 25% EtOAc in DCM, to afford the desired material (2.0 g, 66.5%) as a colourless oil. NMR Spectrum: ¹H NMR (400 MHz, CDCl₃) δ 1.97-2.1 (2H, m), 2.33 (2H, d), 2.67 (2H, d), 3.18 (4H, t), 3.67 (3H, s).

2-(3-Pyrrolidin-1-ylpropoxy)-5-(4,4,5,5-tetramethyl-1,3,2-dioxaborolan-2-yl)pyridine

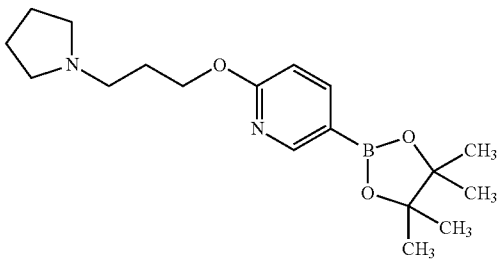 [SMILES: CC1(C)OB(c2ccc(OCCCN3CCCC3)nc2)OC1(C)C]

n-Butyllithium (5.68 mL, 14.20 mmol) was added dropwise to a mixture of 5-bromo-2-(3-pyrrolidin-1-ylpropoxy)pyridine (2.7 g, 9.47 mmol) and 2-isopropoxy-4,4,5,5-tetramethyl-1,3,2-dioxaborolane (2.64 g, 14.20 mmol) in THF (20 mL) at −78° C. over a period of 10 minutes under an inert atmosphere. The resulting mixture was allowed to warm to ambient temperature and stirred for 12 h. The reaction mixture was quenched by the addition of a sat. aqueous solution of ammonium chloride, extracted with EtOAc (2×50 mL) and the organic layer dried over Na₂SO₄, filtered and evaporated to afford the desired material (3.10 g, 99%) as a yellow oil. The product was used in the next step directly without further purification. NMR Spectrum: ¹H NMR (400 MHz, CDCl₃) δ 1.26-1.41 (12H, m), 1.77-1.80 (4H, m), 1.95-2.04 (2H, m), 2.50-2.58 (4H, m), 2.62 (2H, t), 4.37 (2H, t), 6.69 (1H, d), 7.91 (1H, d), 8.52 (1H, s). Mass Spectrum: m/z (ES+) [M+H]+=251.

5-bromo-2-(3-pyrrolidin-1-ylpropoxy)pyridine

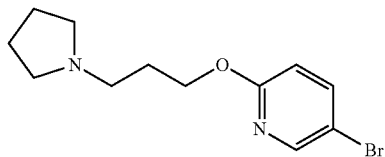 [SMILES: Brc1ccc(OCCCN2CCCC2)nc1]

Sodium hydride (0.591 g, 14.77 mmol) was added portionwise to a solution of 3-(pyrrolidin-1-yl)propan-1-ol (1.615 g, 12.50 mmol) in THF (20 mL) at to 0° C., then stirred at ambient temperature for 30 minutes. 5-Bromo-2-fluoropyridine (2 g, 11.36 mmol) was added and the resulting mixture stirred at ambient temperature for 2 h before being quenched by the addition of a sat. aqueous solution of ammonium chloride. The moisture was extracted with EtOAc (2×100 mL), the organic layer dried over Na₂SO₄, filtered and evaporated to afford pale yellow solid. The crude product was purified by FCC, elution gradient 0 to 10% MeOH in DCM, to afford the desired material (2.70 g, 83%) as a yellow solid. Mass Spectrum: m/z (ES+) [M+H]+=285.

3-[6-Fluoro-5-(4,4,5,5-tetramethyl-1,3,2-dioxaborolan-2-yl)pyridin-2-yl]oxy-N,N-dimethylpropen-1-amine

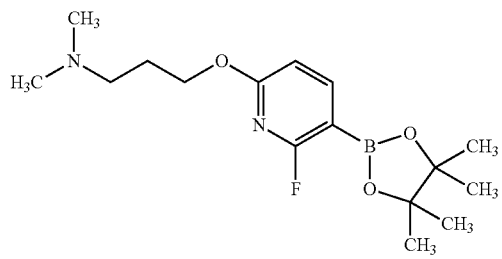

A solution of n-butyllithium (0.693 g, 10.83 mmol) in n-hexane (4.33 mL) was added to a stirred mixture of 3-(5-bromo-6-fluoropyridin-2-yl)oxy-N,N-dimethylpropan-1-amine (2 g, 7.22 mmol) and 2-isopropoxy-4,4,5,5-tetramethyl-1,3,2-dioxaborolane (2.014 g, 10.83 mmol) in THF (20 mL) at −78° C. over a period of 20 minutes under an inert atmosphere. The resulting mixture was allowed to warm to ambient temperature and stirred for 2 h. The reaction mixture was quenched with sat. NaHCO₃ solution and concentrated in vacuo. The crude product was purified by FCC, elution gradient 0 to 10% MeOH in DCM, to afford the desired material (2.50 g, 107%). Mass Spectrum: m/z (ES+) [M+H]+=325.

3-(5-Bromo-6-fluoropyridin-2-yl)oxy-N,N-dimethyl-propan-1-amine

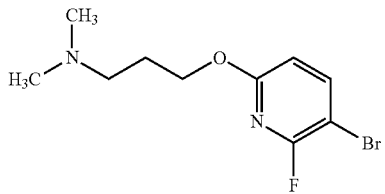

(E)-Diisopropyl diazene-1,2-dicarboxylate (15.80 g, 78.13 mmol) was added dropwise to 3-(dimethylamino) propan-1-ol (8.06 g, 78.13 mmol), 5-bromo-6-fluoropyridin-2-ol (10 g, 52.09 mmol) and triphenylphosphine (20.49 g, 78.13 mmol) in DCM (150 mL) cooled to 0-5° C. under an inert atmosphere. The resulting solution was stirred at ambient temperature for 16 h then the solvent removed under reduced pressure. The residue was diluted with EtOAc (50 mL) and the solid removed by filtration and discarded. The filtrate was acidified with hydrogen chloride in dioxane. The solid was collected by filtration then dissolved in a sat. aqueous solution of $Na_2CO_3$ (200 mL) and extracted with EtOAc (3×100 mL). The combined organic layers were washed with water, brine, dried over $Na_2SO_4$ and concentrated in vacuo to afford the desired material (9.00 g, 62.3%). NMR Spectrum: $^1$H NMR (300 MHz, CDCl$_3$) δ 1.89-1.98 (2H, m), 2.26 (6H, s), 2.34 (2H, t), 4.30 (2H, t), 6.53 (1H, d), 7.74 (1H, t). Mass Spectrum: m/z (ES+) [M+H]+=277.

5-Bromo-6-fluoropyridin-2-ol

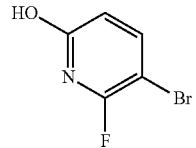

A solution of sodium nitrite (21.67 g, 314.13 mmol) in water (150 mL) was added dropwise to a stirred mixture of 5-bromo-6-fluoropyridin-2-amine (50 g, 261.78 mmol) and sulphuric acid (1.2 mL, 22.51 mmol) in water (750 mL) at 0-5° C. The resulting suspension was stirred for 48 h at ambient temperature then the precipitate collected by filtration, washed with water (200 mL) and dried under vacuum to afford the desired material (40.0 g, 80%) as a pale yellow solid, which was used without further purification. NMR Spectrum: $^1$H NMR (300 MHz, DMSO-d6) δ 6.55 (1H, d), 8.00 (1H, t), 11.71 (1H, bs). Mass Spectrum: m/z (ES+) [M+H]++=192.

5-bromo-6-fluoropyridin-2-amine

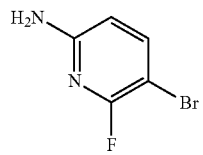

NBS (50.0 g, 280.99 mmol) was added slowly to 6-fluoropyridin-2-amine (30 g, 267.61 mmol) in MeCN (300 mL) cooled to 10-20° C. over a period of 30 minutes. The resulting solution was stirred at ambient temperature for 60 minutes then the solvent removed under reduced pressure. The residue was diluted with water, the precipitate collected by filtration, washed with water (200 mL) and dried under vacuum to afford the desired material (50.0 g, 98%) as a white solid, which was used without further purification. NMR Spectrum: $^1$H NMR (300 MHz, DMSO-d6) δ 6.29 (1H, d), 6.57 (2H, bs), 7.65 (1H, t). Mass Spectrum: m/z (ES+) [M+H]+=191.

Examples 25 & 26

8-[6-(3-Dimethylaminoproropoxy)pyridin-3-yl]-1-[(1R,3R)-3-methoxycyclopentyl]-3-methylimidazo[4,5-c]quinolin-2-one and 8-[6-(3-Dimethylaminopropoxy)pyridin-3-yl]-[(1S,3S)-3-methoxycyclopentyl]-3-methylimidazo[4,5-c]quinolin-2-one

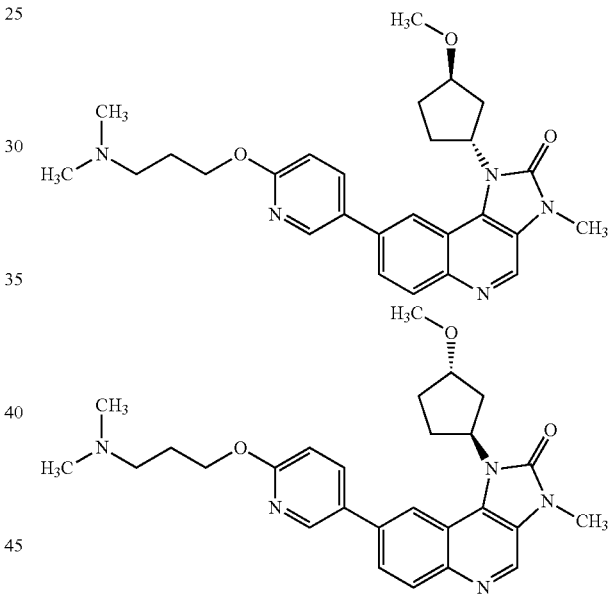

Chloro(2-dicyclohexylphosphino-2',4',6'-triisopropyl-1,1'-biphenyl)[2-(2'-amino-1,1'-biphenyl)]palladium(II) (26.1 mg, 0.03 mmol) was added to 8-bromo-1-[(1R,3R)-3-methoxycyclopentyl]-3-methylimidazo[4,5-c]quinolin-2-one:8-bromo-1-[(1S,3S)-3-methoxycyclopentyl]-3-methylimidazo[4,5-c]quinolin-2-one (1:1 mixture) (250 mg, 0.66 mmol). N,N-dimethyl-3-[5-(4,4,4,5,5-tetramethyl-1,3,2-dioxaborolan-2-yl)pyridin-2-yl]oxypropan-1-amine (244 mg, 0.80 mmol) and $Cs_2CO_3$ (433 mg, 1.33 mmol) in 1,4-dioxane (20 mL) and water (5 mL) and the resulting mixture stirred at 100° C. for 2 h. The reaction mixture was poured into water (25 mL), extracted with DCM (2×50 mL), the organic layer dried over $Na_2SO_4$, filtered and evaporated to afford yellow residue. The crude product was purified by preparative HPLC (XSelect CSH Prep C18 OBD column, 5µ silica, 19 mm diameter, 150 mm length), using decreasingly polar mixtures of water (containing 0.1% Formic acid) and MeCN as eluents. Fractions containing the desired compound were evaporated to dryness to afford the desired material as a racemic mixture (175 mg, 53.3%) as a white solid. Optimisation on the Agilent 1100, AD column, (20 micron μm silica, 4.6 mm diameter, 250 mm length) showed that MeCN/MeOH/TEA, 95/05/0.1 would give the best separation. This method was used for the preparative HPLC purification. The racemic mixture (130 mg, 0.27 mmol) was dissolved in EtOH (10 mL) and separated using preparative HPLC on AD column (20 μm silica, 50 mm diameter, 250 mm length), two injections were required in order to prep the entire sample. Mixed fractions were subjected to a second separation using the above method and fractions containing the desired pure enantiomers were evaporated to afford the desired materials. This method gave mixed fractions which were repurified using the same conditions. Fractions containing the separated isomers were evaporated to dryness:

Example 25

Isomer 1 (58 mg)

NMR Spectrum: $^1$H NMR (400 MHz, CDCl$_3$) δ 1.87-1.98 (1H, m), 2.04 (3H, dt), 2.33 (8H, s), 2.47-2.64 (3H, m), 2.72 (1H, ddd), 3.36 (3H, s), 3.59 (3H, s), 4.019-4.21 (1H, m), 4.43 (2H, t), 5.59 (1H, q), 6.88 (1H, d), 7.80 (1H, dd), 7.92 (1H, dd), 8.22 (1H, d), 8.33 (1H, d), 8.50 (1H, d), 8.70 (1H, s). Mass Spectrum: m/z (ES+) [M+H]+=476.

Example 26

Isomer 2 (58 mg)

NMR Spectrum: $^1$H NMR (400 MHz, CDCl$_3$) δ 1.94 (1H, m), 1.99-2.11 (3H, m), 2.32 (8H, s), 2.46-2.64 (3H, m), 2.66-2.83 (2H, m), 3.36 (3H, s), 3.59 (3H, s), 4.17 (1H, m), 4.43 (2H, t), 5.44-5.72 (1H, m), 6.88 (1H, d), 7.80 (1H, dd), 7.91 (1H, dd), 8.22 (1H, d), 8.33 (1H, d), 8.50 (1H, d), 8.70 (1H, s). Mass Spectrum: m/z (ES+) [M+H]+=476.

The preparation of 8-bromo-1-[(1R,3R)-3-methoxycyclopentyl]-3-methylimidazo[4,5-c]quinolin-2-one:8-bromo-1-[(1S,3S)-3-methoxycyclopentyl]-3-methylimidazo[4,5-c]quinolin-2-one (1:1 mixture) is described below:

Intermediate O1: 8-bromo-1-[(1R,3R)-3-methoxycyclopentyl]-3-methylimidazo[4,5-c]quinolin-2-one:
8-bromo-1-[(1S,3S)-3-methoxycyclopentyl]-3-methylimidazo[4,5-c]quinolin-2-one (1:1 mixture)

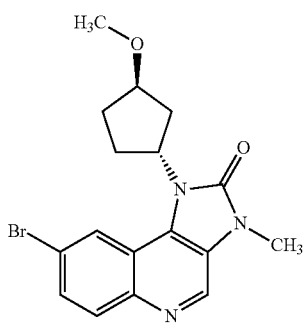

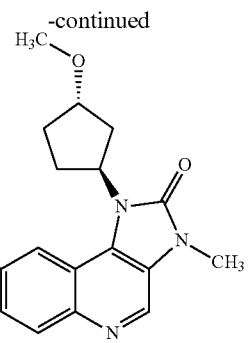

A mixture of 6-bromo-4-[[(1R,3R)-3-methoxycyclopentyl]amino]quinoline-3-carboxylic acid: 6-bromo-4-[[(1S,3S)-3-methoxycyclopentyl]amino]quinoline-3-carboxylic acid (1:1 mixture) (13 g, 35.8 mmol), tetrabutylammonium bromide (1.16 g, 3.60 mmol), iodomethane (7.645 g, 53.86 mmol) and sodium hydroxide (2.15 g, 53.75 mmol) in DCM (600 mL) and water (380 mL) was stirred at ambient temperature overnight. The resulting solution was concentrated under vacuum to remove the organics and the solids collected by filtration, washed with water (5×10 mL) and dried in a vacuum oven to afford the desired material (racemic mixture) (9.8 g, 73%) as a off-white solid. NMR Spectrum: $^1$H NMR (400 MHz, DMSO-d6) δ 1.81-1.87 (1H, m), 2.33-2.51 (4H, m), 2.45-2.51 (1H, m), 3.28 (3H, s), 3.49 (3H, s), 4.02-4.21 (1H, m), 5.40 (1H, p), 7.73 (1H, dd), 7.98 (1H, d), 8.35 (1H, d), 8.91 (1H, s). Mass Spectrum: m/z (ES+) [M+H]+=375.9.

Intermediate O2: 8-bromo-1-[(1R,3R)-3-methoxycyclopentyl]-3H-imidazo[4,5-c]quinolin-2-one:8-bromo-1-[(1S,3S)-3-methoxycyclopentyl]-3H-imidazo[4,5-c]quinolin-2-one (1:1 mixture)

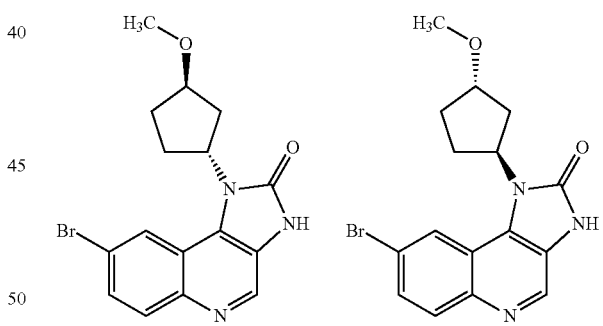

A mixture of 6-bromo-4-[[(1R,3R)-3-methoxycyclopentyl]amino]quinoline-3-carboxylic acid: 6-bromo-4-[[(1S,3S)-3-methoxycyclopentyl]amino]quinoline-3-carboxylic acid (1:1 mixture) (17 g, 46.54 mmol), triethylamine (14.1 g, 139.34 mmol) in DMF (270 mL) was stirred at ambient temperature for 1 h. Diphenyl phosphorazidate (25.6 g, 93.02 mmol) was added dropwise with stirring and the solution stirred at ambient temperature for a further 20 minutes before being heated to 60° C. for 1 h. The reaction was allowed to cool and concentrated under vacuum. The residue was diluted with water (300 mL), the solids collected by filtration and dried in an oven under reduced pressure to afford the desired material (as a racemic mixture) (13 g, 77%) as a off-white solid. Mass Spectrum: m/z (ES+) [M+H]+=362.2.

Intermediate O3: 6-bromo-4-[[(1R,3R)-3-methoxy-cyclopentyl]amino]quinoline-3-carboxylic acid: 6-bromo-4-[[(1S,3S)-3-methoxycyclopentyl]amino]quinoline-3-carboxylic acid (1:1 mixture)

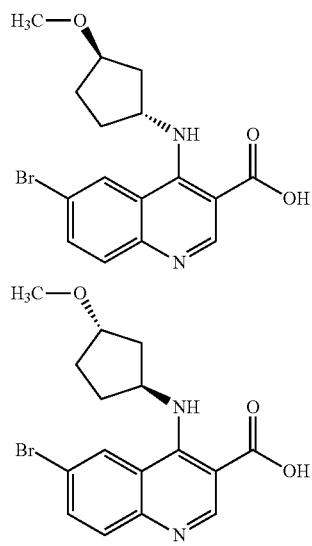

2N Sodium hydroxide (50 mL) was added to a mixture of ethyl 6-bromo-4-[[(1R,3R)-3-methoxycyclopentyl]amino]quinoline-3-carboxylate:ethyl 6-bromo-4-[[(1S,3S)-3-methoxycyclopentyl]amino]quinoline-3-carboxylate (1:1 mixture) (18.6 g, 47.2 mmol) in MeOH (500 mL) and water (100 mL) and the resulting solution stirred for 15 h at ambient temperature. The mixture was concentrated under vacuum and the residue diluted with water (300 mL). The pH value of the solution was adjusted to 5 with 2N hydrochloric acid, the solids collected by filtration and dried in an oven under reduced pressure to afford the desired material (as a racemic mixture) (17.1 g) as a off-white solid. NMR Spectrum: $^1$H NMR (400 MHz, DMSO-d6) δ 1.60-1.71 (2H, m), 1.81-1.88 (1H, m), 1.96-2.02 (1H, m), 2.03-2.10 (2H, m), 3.21 (3H, s), 3.91-3.96 (1H, m), 4.51-4.72 (1H, m), 7.77 (1H, d), 7.93 (1H, d), 8.45 (1H, d), 8.85 (1H, s), 13.30 (1H, bs). Mass Spectrum: m/z (ES+) [M+H]+=365.2.

Intermediate O4: Ethyl 6-bromo-4-[[(1R,3R)-3-methoxycyclopentyl]amino]quinoline-3-carboxylate: ethyl 6-bromo-4-[[(1S,3S)-methoxycyclopentyl]amino]quinoline-3-carboxylate (1:1 mixture)

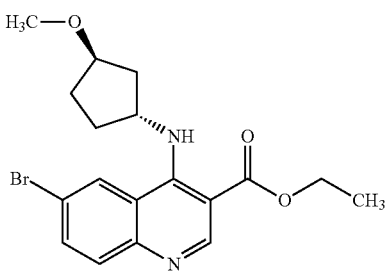

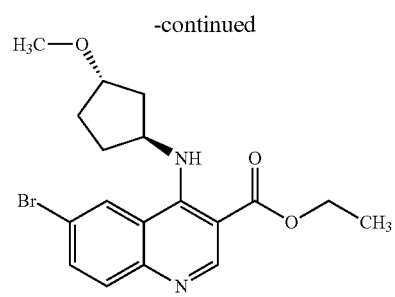

A mixture of ethyl 6-bromo-4-chloroquinoline-3-carboxylate (15 g, 47.69 mmol), (trans)-3-methoxycyclopentan-1-amine (racemic mixture) (8.09 g, 26.68 mmol) and DIPEA (19.68 g, 152.27 mmol) in DMA (100 mL) was stirred at 80° C. for 4 h under an inert atmosphere. The reaction was quenched by the addition of water (500 mL), the solids collected by filtration and dried in an oven under reduced pressure to afford the desired material (as a racemic mixture) (18.6 g) as a light brown solid. Mass Spectrum: m/z (ES+) [M+H]+=393, 395.

The preparation of ethyl 6-bromo-4-chloroquinoline-3-carboxylate has been described earlier.

Example 27

7-Fluoro-1-(cis-3-methoxycyclobutyl)-3-methyl-8-[6-[3-pyrrolidin-1-ylpropoxy)pyridin-3-yl]imidazo[4,5-c]quinolin-2-one

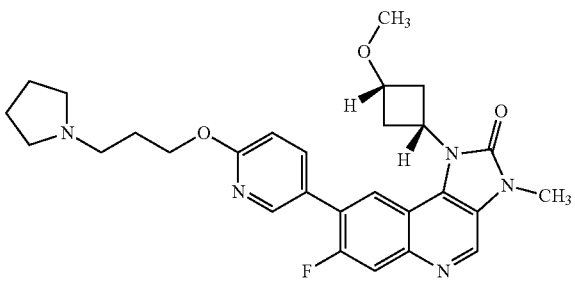 [SMILES: CO[C@H]1C[C@@H](n2c(=O)n(C)c3cnc4cc(F)c(-c5ccc(OCCCN6CCCC6)nc5)cc4c32)C1]

3-(Pyrrolidin-1-yl)propan-1-ol (46.9 mg, 0.36 mmol) was added to sodium hydride (29.1 mg, 1.21 mmol) in THF (4 mL) at ambient temperature over a period of 20 minutes. 7-Fluoro-8-(6-fluoropyridin-3-yl)-1-(cis-3-methoxycyclobutyl)-3-methylimidazo[4,5-c]quinolin-2-one (120 mg, 0.30 mmol) was added. The resulting mixture was stirred at ambient temperature for 2 h. The reaction mixture was quenched with water and the crude product purified by FCC, elution gradient 0 to 5% MeOH in DCM. The crude product was purified by preparative HPLC (Waters XBridge Prep C18 OBD column, 5μ silica, 19 mm diameter, 100 mm length), using decreasingly polar mixtures of water (containing 0.1% formic acid) and MeCN as eluents. Fractions containing the desired compound were evaporated to dryness to afford the desired material (60.0 mg, 38.7%) as a off-white solid. NMR Spectrum: $^1$H NMR (300 MHz, MeOD) δ 1.90-2.00 (4H, m), 2.10-2.20 (2H, m), 2.81-3.00 (8H, m), 3.04-3.17 (2H, m), 3.28 (3H, s), 3.6 (3H, s), 3.85-3.96 (1H, m), 4.48 (2H, t), 5.00)-5.13 (1H, m), 6.88 (1H, d), 7.82 (1H, d), 8.05 (1H, d), 8.43-8.50 (2H, m), 8.83 (1H, s) Mass Spectrum: m/z (ES+) [M+H]+=506.

The following compounds were prepared in an analogous fashion using the appropriate alcohol and the appropriate pyridyl fluoro intermediate.

| Example | Structure | Name |
|---|---|---|
| 28* | 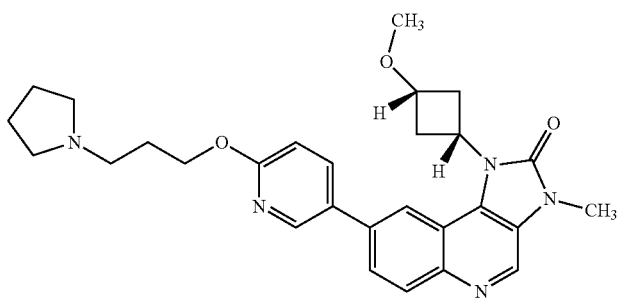 [SMILES: CO[C@H]1C[C@@H](n2c(=O)n(C)c3cnc4ccc(-c5ccc(OCCCN6CCCC6)nc5)cc4c32)C1] | 1-(cis-3-methoxycyclobutyl)-3-methyl-8-[6-(3-pyrrolidin-1-ylpropoxy)pyridin-3-yl]imidazo[4,5-c]quinolin-2-one |
| 29 | 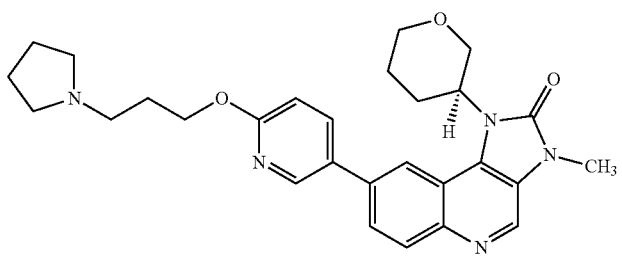 [SMILES: Cn1c(=O)n([C@H]2CCCOC2)c2c3cc(-c4ccc(OCCCN5CCCC5)nc4)ccc3ncc21] | 3-methyl-1-[(3S)-oxan-3-yl]-8-[6-(3-pyrrolidin-1-ylpropoxy)pyridin-3-yl]imidazo[5,4-c]quinolin-2-one |
| 30 | 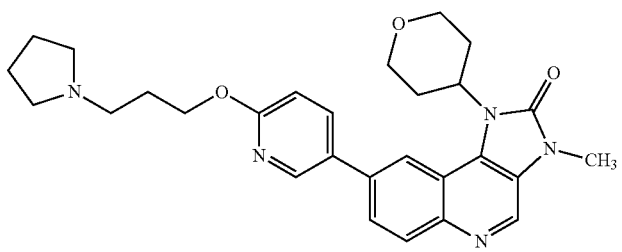 [SMILES: Cn1c(=O)n(C2CCOCC2)c2c3cc(-c4ccc(OCCCN5CCCC5)nc4)ccc3ncc21] | 3-methyl-1-(oxan-4-yl)-8-[6-(3-pyrrolidin-1-ylpropoxy)pyridin-3-yl]imidazo[5,4-c]quinolin-2-one |
| 31 | 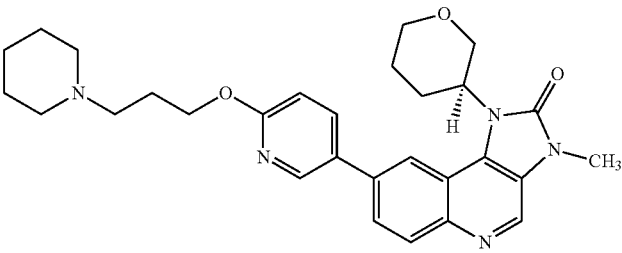 [SMILES: Cn1c(=O)n([C@H]2CCCOC2)c2c3cc(-c4ccc(OCCCN5CCCCC5)nc4)ccc3ncc21] | 3-methyl-1-[(3S)-oxan-3-yl]-8-[6-(3-piperidin-1-ylpropoxy)pyridin-3-yl]imidazo[5,4-c]quinolin-2-one |
| 32 | 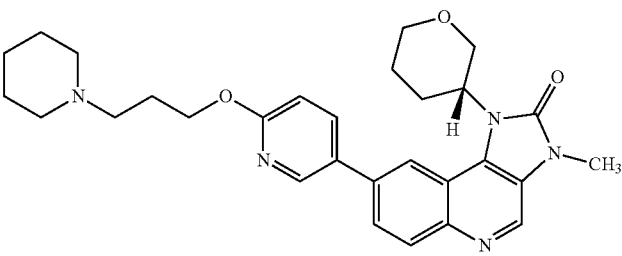 [SMILES: Cn1c(=O)n([C@@H]2CCCOC2)c2c3cc(-c4ccc(OCCCN5CCCCC5)nc4)ccc3ncc21] | 3-methyl-1-[(3R)-oxan-3-yl]-8-[6-(3-piperidin-1-ylpropoxy)pyridin-3-yl]imidazo[5,4-c]quinolin-2-one |

-continued

| Example | Structure | Name |
|---|---|---|
| 33* | 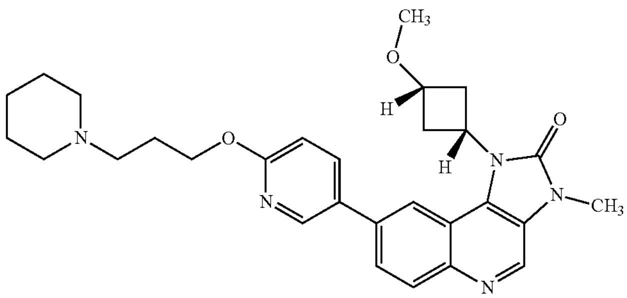 [SMILES: CO[C@H]1C[C@@H](n2c(=O)n(C)c3cnc4ccc(-c5ccc(OCCCN6CCCCC6)nc5)cc4c32)C1] | 1-(cis-3-methoxycyclobutyl)-3-methyl-8-[6-(3-piperidin-1-ylpropoxy)pyridin-3-yl]imidazo[4,5-c]quinolin-2-one |
| 34 | 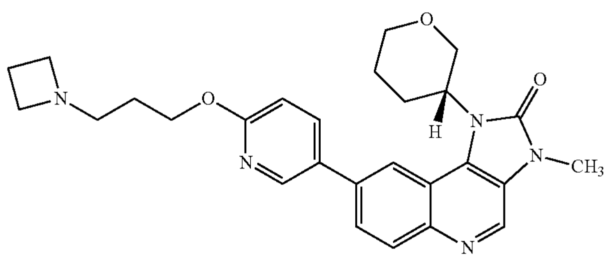 [SMILES: Cn1c(=O)n([C@@H]2CCCOC2)c2c3cc(-c4ccc(OCCCN5CCC5)nc4)ccc3ncc21] | 8-[6-[3-(azetidin-1-yl)propoxy]pyridin-3-yl]-3-methyl-1-[(3R)-oxan-3-yl]imidazo[5,4-c]quinolin-2-one |
| 35** | 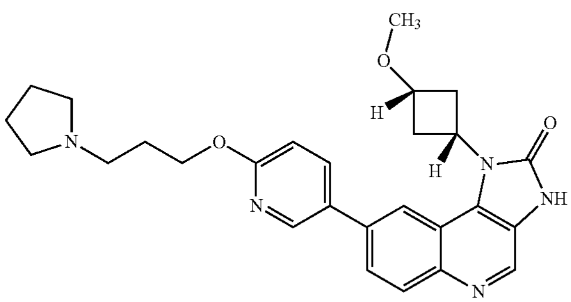 [SMILES: CO[C@H]1C[C@@H](n2c(=O)[nH]c3cnc4ccc(-c5ccc(OCCCN6CCCC6)nc5)cc4c32)C1] | 1-(cis-3-methoxycyclobutyl)-8-[6-(3-pyrrolidin-1-ylpropoxy)pyridin-3-yl]-3H-imidazo[4,5-c]quinolin-2-one |
| 36* | 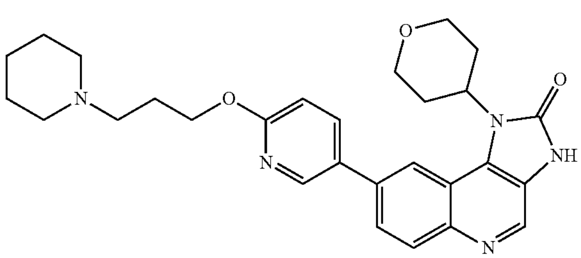 [SMILES: O=c1[nH]c2cnc3ccc(-c4ccc(OCCCN5CCCCC5)nc4)cc3c2n1C1CCOCC1] | 1-(oxan-4-yl)-8-[6-(3-piperidin-1-ylpropoxy)pyridin-3-yl]-3H-imidazo[4,5-c]quinolin-2-one |
| 37** | 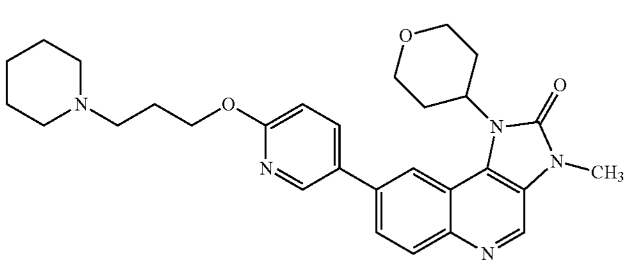 [SMILES: Cn1c(=O)n(C2CCOCC2)c2c3cc(-c4ccc(OCCCN5CCCCC5)nc4)ccc3ncc21] | 3-methyl-1-(oxan-4-yl)-8-[6-(3-piperidin-1-ylpropoxy)pyridin-3-yl]imidazo[5,4-c]quinolin-2-one |

| Example | Structure | Name |
|---|---|---|
| 38** | 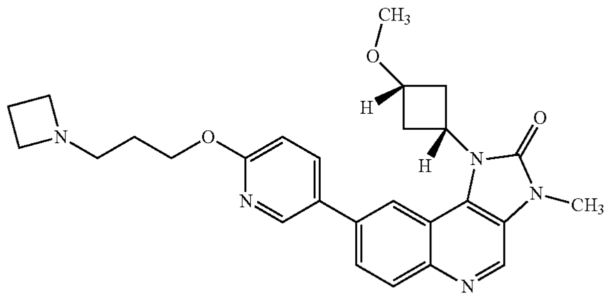 [SMILES: CO[C@H]1C[C@@H](n2c(=O)n(C)c3cnc4ccc(-c5ccc(OCCCN6CCC6)nc5)cc4c32)C1] | 8-[6-[3-(azetidin-1-yl)propoxy]pyridin-3-yl]-1-(cis-3-methoxycyclobutyl)-3-methylimidazo[4,5-c]quinolin-2-one |
| 39* | 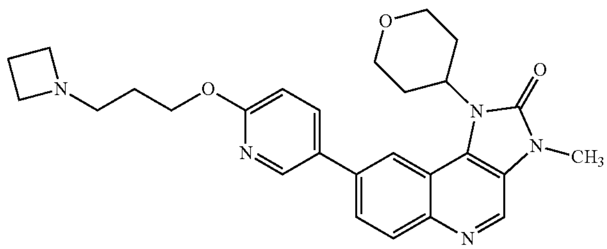 [SMILES: Cn1c(=O)n(C2CCOCC2)c2c3cc(-c4ccc(OCCCN5CCC5)nc4)ccc3ncc21] | 8-[6-[3-(azetidin-1-yl)propoxy]pyridin-3-yl]-3-methyl-1-(oxan-4-yl)imidazo[5,4-c]quinolin-2-one |

*The reaction was performed in DMF between 0° C. and ambient temperature.
**The reaction was performed in DMA at 50° C.

Example 28

NMR Spectrum: $^1$H NMR (400 MHz, DMSO-d6) δ 1.67-1.96 (6H, m), 2.44-2.55 (6H, m), 2.78-3.03 (4H, m), 3.19 (3H, s), 3.50 (3H, s), 3.84-3.88 (1H, m), 4.38 (2H, t), 5.13 (1H, p), 6.97 (1H, d), 7.92 (1H, dd), 8.12 (1H, dd), 8.20 (1H, dd), 8.43 (1H, s), 8.67 (1H, d), 8.88 (1H, s). Mass Spectrum: m/z (ES+) [M+H]+=488.

Example 29

NMR Spectrum: $^1$H NMR (300 MHz, DMSO-d6) δ 1.68-1.86 (6H, m), 1.95 (2H, p), 2.10-2.19 (1H, d), 2.51-2.75 (7H, m), 3.35-3.49 (1H, m), 3.50 (3H, s), 3.92 (1H, d), 4.08-4.18 (1H, m), 4.22 (1H, t), 4.38 (2H, t), 4.90-5.03 (1H, m), 6.98 (1H, d), 7.92 (1H, dd), 8.15-8.20 (1H, m), 8.25 (1H, s), 8.32 (1H, s), 8.66 (1H, d), 8.90 (1H, s). Mass Spectrum: m/z (ES+) [M+H]+=488.

Example 30

NMR Spectrum: $^1$H NMR (400 MHz, DMSO-d6) δ 1.67-1.73 (4H, m), 1.90-1.98 (4H, m), 2.39-2.46 (4H, m), 2.54-2.61 (2H, m), 2.72 (2H, ddd), 3.52 (3H, s), 3.59 (2H, t), 4.06 (2H, dd), 4.38 (2H, t), 5.13-5.16 (1H, m), 6.98 (1H, d), 7.96 (1H, dd), 8.14 (1H, d), 8.20 (1H, dd), 8.45 (1H, s), 8.67 (1H, d), 8.91 (1H, s). Mass Spectrum: m/z (ES+) [M+H]+=488.

Example 31

NMR Spectrum: $^1$H NMR (300 MHz, DMSO-d6) δ 1.38-1.50 (6H, m), 1.83-1.95 (4H, m), 2.13-2.18 (1H, m), 2.35-2.43 (6H, m), 2.62-2.75 (1H, m), 3.38-3.44 (1H, m), 3.49 (3H, s), 3.94 (1H, d), 4.13-4.27 (2H, m), 4.35 (2H, t), 4.90-5.02 (1H, m), 6.99 (1H, d), 7.94 (1H, d), 8.13-8.18 (2H, m), 8.34 (1H, s), 8.48 (1H, d), 8.90 (1H, s). Mass Spectrum: m/z (ES+) [M+H]+=502.

Example 32

NMR Spectrum: $^1$H NMR (300 MHz, DMSO-d6) δ 1.35-1.58 (6H, m), 1.85-1.98 (4H, m), 2.12-2.21 (1H, m), 2.21-2.50 (6H, m), 2.60-2.80 (1H, m), 3.33-3.48 (1H, m), 3.48 (3H, s), 3.89-3.97 (1H, m), 4.10-4.28 (2H, m), 4.30-4.38 (2H, m), 4.90-5.08 (1H, m), 6.98 (1H, d), 7.93-8.0 (1H, m), 8.13-8.22 (2H, m), 8.35 (1H, s), 8.63 (1H, s), 8.94 (1H, s). Mass Spectrum: m/z (ES+) [M+H]+=502.3.

Example 33

NMR Spectrum: $^1$H NMR (300 MHz, DMSO-d6) δ 1.32-1.45 (2H, m), 1.45-1.51 (4H, m), 1.88-1.98 (2H, m), 2.31-2.51 (6H, m), 2.81-2.83 (2H, m), 2.97-3.11 (2H, m), 3.19 (3H, s), 3.50 (3H, s), 3.84-3.91 (1H, m), 4.36 (2H, t), 5.10-5.17 (1H, m), 6.97 (1H, d), 7.93 (1H, d), 8.12 (1H, d), 8.21 (1H, dd), 8.43 (1H, s), 8.68 (1H, d), 8.89 (1H, s). Mass Spectrum: m/z (ES+) [M+H]+=502.

Example 34

NMR Spectrum: $^1$H NMR (300 MHz, DMSO-d6) δ 1.78-1.85 (4H, m), 2.05-2.18 (3H, m), 2.66-2.80 (3H, m), 3.36-3.49 (8H, m), 3.94 (1H, d), 4.12-4.35 (2H, m), 4.38 (2H, t), 4.94-4.98 (1H, m), 7.00 (1H, d), 7.92 (1H, d), 8.13-8.20 (2H, m), 8.33 (1H, s), 8.63 (1H, s), 8.90 (1H, s). Mass Spectrum: m/z (ES+) [M+H]+=474.3.

Example 35

NMR Spectrum: $^1$H NMR (400 MHz, DMSO-d6) δ 1.64-1.75 (4H, m), 1.94 (2H, p), 2.45 (3H, d), 2.53-2.58 (3H, m), 2.75-2.88 (2H, m), 2.94-3.08 (2H, m), 3.21 (3H, s), 3.87 (1H, p), 4.39 (2H, t), 5.08 (1H, p), 6.97 (1H, d), 7.90 (1H, dd), 8.09 (1H, d), 8.19 (1H, dd), 8.43 (1H, d), 8.65 (1H, s), 8.67 (1H, d), 11.50 (1H, s). m/z: ES+ [M+H]+474. Mass Spectrum: m/z (ES+) [M+H]+=474.

Example 36

NMR Spectrum: ¹H NMR (300 MHz, DMSO-d6) δ 1.38 (2H, d), 1.46-1.53 (4H, m), 1.85-1.92 (4H, m), 2.27-2.42 (6H, m), 2.67-2.80 (2H, m), 3.52 (2H, t), 4.08 (2H, dd), 4.33 (2H, t), 5.10 (1H, p), 6.97 (1H, d), 7.93 (1H, d), 8.09 (1H, d), 8.12 (1H, d), 8.20 (1H, dd), 8.42 (1H, s), 8.65 (1H, s). Mass Spectrum: m/z (ES+) [M+H]+=488.

Example 37

NMR Spectrum: ¹H NMR (400 MHz, DMSO-d6) δ 1.40 (2H, d), 1.50 (4H, q), 1.92 (4H, dq), 2.3-2.45 (6H, m), 2.66-2.8 (2H, m), 3.52 (3H, s), 3.59 (2H, t), 4.07 (2H, dd), 4.37 (2H, t), 5.09-5.2 (1H, m), 6.96-6.99 (1H, d), 7.96 (1H, dd), 8.15 (1H, d), 8.18-8.21 (1H, m), 8.44 (1H, s), 8.66 (1H, d), 8.90 (1H, s). Mass Spectrum: m/z (ES+) [M+H]+=502.46.

Example 38

NMR Spectrum: ¹H NMR (400 MHz, DMSO-d6) δ 1.74 (2H, p), 1.96 (2H, p), 2.47 (2H, t), 2.78-2.87 (2H, m), 3.01 (2H, qd), 3.10 (4H, t), 3.21 (3H, s), 3.51 (3H, s), 3.87 (1H, p), 4.35 (2H, t), 5.08-5.18 (1H, m), 6.93-6.97 (1H, d), 7.92 (1H, dd), 8.12 (1H, d), 8.18-8.21 (1H, d), 8.43 (1H, d), 8.65-8.68 (1H, m), 8.88 (1H, s). Mass Spectrum: m/z (ES+) [M+H]+=474.43.

Example 39

NMR Spectrum: ¹H NMR (300 MHz, DMSO-d6) δ 1.74-1.78 (2H, m), 1.81-1.93 (2H, m), 2.00-2.09 (2H, m), 2.65-2.77 (4H, m), 3.31-3.36 (4H, m), 3.51 (3H, s), 3.58 (2H, t), 4.04-4.09 (2H, m), 4.34 (2H, t), 5.14 (1H, p), 6.97 (11H, d), 7.94 (1H, dd), 8.13 (1H, d), 8.20 (1H, dd), 8.22 (1H, s), 8.66 (1H, d), 8.90 (1H, s). Mass Spectrum: m/z (ES+) [M+H]+=474.

The required fluoro intermediates for Examples 27-39 have either already been described or were prepared from the appropriate bromo intermediates as described below:

Intermediate P: 8-(6-fluoropyridin-3-yl)-3-methyl-1-[(3S)-oxan-3-yl]imidazo[5,4-c]quinolin-2-one

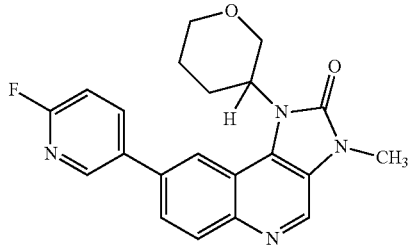 [SMILES: Cn1c(=O)n(C2CCCOC2)c2c3cc(-c4ccc(F)nc4)ccc3ncc21]

Pd(Ph₃P)₄ (0.160 g, 0.14 mmol) was added to 8-bromo-3-methyl-1-[(3S)-oxan-3-yl]imidazo[5,4-c]quinolin-2-one (1 g, 2.76 mmol), (6-fluoropyridin-3-yl)boronic acid (0.506 g, 3.59 mmol) and Cs₂CO₃ (1.799 g, 5.52 mmol) in 1,4-dioxane (23 mL) and water (3 mL) under nitrogen. The resulting mixture was stirred at 100° C. for 3 h then allowed to cool and the solvent removed under reduced pressure. The crude product was purified by FCC, elution gradient 0 to 7% MeOH in DCM to give the desired material (0.905 g, 87%) as a yellow solid. NMR Spectrum: ¹H NMR (300 MHz, DMSO-d6) δ 1.83-1.86 (2H, m), 2.15-2.19 (1H, m), 2.49-2.64 (1H, m), 3.38-3.41 (1H, m), 3.49 (3H, s), 3.93 (1H, d), 4.15-4.26 (2H, m), 4.91-5.10 (1H, m), 7.42 (1H, dd), 7.96 (1H, dd), 8.13 (1H, d), 8.38 (1H, s), 8.44 (1H, td), 8.72 (1H, d), 8.96 (1H, s). Mass Spectrum: m/z (ES+) [M+H]+=379.1.

The following fluoro intermediates were prepared in an analogous fashion from (6-fluoropyridin-3-yl)boronic acid and the appropriate bromo intermediates, the synthesis of which has already been described:

| Intermediate | Structure | Name |
|---|---|---|
| Intermediate Q | 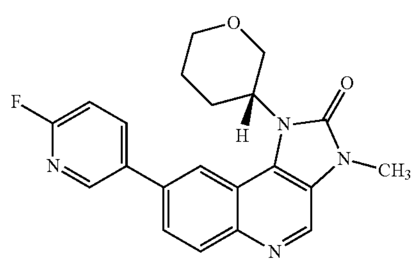 [SMILES: Cn1c(=O)n([C@@H]2CCCOC2)c2c3cc(-c4ccc(F)nc4)ccc3ncc21] | 8-(6-fluoropyridin-3-yl)-3-methyl-1-[(3R)-oxan-3-yl]imidazo[5,4-c]quinolin-2-one |
| Intermediate R * | 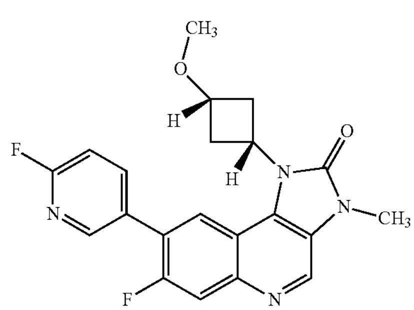 [SMILES: CO[C@H]1C[C@@H](n2c(=O)n(C)c3cnc4cc(F)c(-c5ccc(F)nc5)cc4c32)C1] | 7-fluoro-8-(6-fluoropyridin-3-yl)-1-(cis-3-methoxycyclobutyl)-3-methylimidazo[4,5-c]quinolin-2-one |

| Intermediate | Structure | Name |
|---|---|---|
| Intermediate S ** | 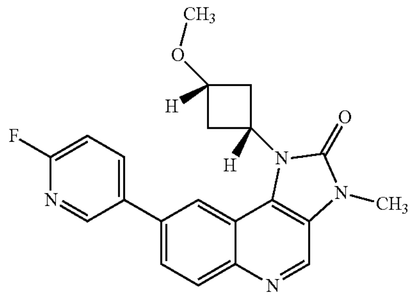 [SMILES: CO[C@H]1C[C@@H](n2c(=O)n(C)c3cnc4ccc(-c5ccc(F)nc5)cc4c32)C1] | 8-(6-fluoropyridin-3-yl)-1-(cis-3-methoxycyclobutyl)-3-methylimidazo[4,5-c]quinolin-2-one |
| Intermediate T ** | 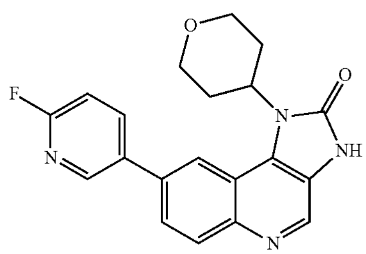 [SMILES: O=c1[nH]c2cnc3ccc(-c4ccc(F)nc4)cc3c2n1C1CCOCC1] | 8-(6-fluoropyridin-3-yl)-1-(oxan-4-yl)-3H-imidazo[4,5-c]quinolin-2-one |
| Intermediate U *** | 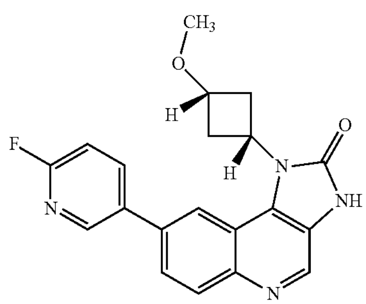 [SMILES: CO[C@H]1C[C@@H](n2c(=O)[nH]c3cnc4ccc(-c5ccc(F)nc5)cc4c32)C1] | 8-(6-fluoropyridin-3-yl)-1-(cis-3-methoxycyclobutyl)-3H-imidazo[4,5-c]quinolin-2-one |

\* The reaction was stirred at 80° C. for 2 h.
\*\* The reaction was performed using chloro(2-dicyclohexylphosphino-2',4',6'-triisopropyl-1,1'-biphenyl)[2-(2'-amino-1,1'-biphenyl)]palladium(II) as the catalyst and was stirred at 90° C. for 2 h.
\*\*\* The reaction was performed with a 1:2 mixture of sodium tetrachloropalladate and 3-(di-tert-butylphosphino)propane-1-sulfonic acid (0.05 M in water) as the catalyst and ligand and $K_2CO_3$ as the base. The reaction was stirred at 80° C. for 3 h.

Intermediate Q

NMR Spectrum: $^1$H NMR (300 MHz, DMSO-d6) δ 1.80-1.83 (2H, m), 2.15-2.18 (1H, m), 2.49-2.73 (1H, m), 3.37-3.41 (1H, m), 3.49 (3H, s), 3.93 (1H, d), 4.16-4.26 (2H, m), 4.90-5.10 (1H, m), 7.42 (1H, dd), 7.97 (1H, dd), 8.14 (1H, d), 8.38 (1H, s), 8.45 (1H, td), 8.71 (1H, d), 8.95 (1H, s). Mass Spectrum: m/z (ES+) [M+H]+=379.

Intermediate R

NMR Spectrum: $^1$H NMR (300 MHz, DMSO-d6) δ 2.76-2.81 (2H, m), 2.91-3.05 (2H, m), 3.13 (3H, s), 3.49 (3H, s), 3.78-3.82 (1H, m), 5.07-5.10 (1H, m), 7.40 (1H, dd), 7.94 (1H, d), 8.32 (1H, td), 8.45 (d) 8.59 (1H, s), 8.95 (1H, s). Mass Spectrum: m/z (ES+) [M+H]+=397.

Intermediate S

NMR Spectrum: $^1$H NMR (400 MHz, DMSO-d6) δ 2.83 (2H, s), 3.01 (2H, d), 3.20 (3H, s), 3.51 (3H, s), 3.86 (1H, s), 5.07-5.18 (1H, m), 7.37 (1H, d), 7.96 (1H, d), 8.16 (1H, d), 8.49 (2H, d), 8.75 (1H, s), 8.92 (1H, s). Mass Spectrum: m/z (ES+) [M+H]+=379.

Intermediate T

NMR Spectrum: $^1$H NMR (34 MHz, DMSO-d6) δ 1.90-1.96 (2H, m), 2.65-2.79 (2H, s), 3.65 (2H, t), 4.01-4.11 (2H, m), 5.06-5.14 (1H, m), 7.40 (1H, dd), 8.02 (1H, dd), 8.15 (1H, d), 8.44-8.50 (2H, m), 8.71 (1H, s), 8.75 (1H, dd), 11.75 (1H, bs). Mass Spectrum: m/z (ES+) [M+H]+=365.

Intermediate U

NMR Spectrum: $^1$H NMR (400 MHz, DMSO-d6) δ 2.71-2.84 (3H, m), 2.97-3.09 (2H, m), 3.20 (3H, s), 3.86 (1H, p), 5.09 (1H, ddd), 7.35 (1H, dd), 7.83 (1H, dd), 8.07 (1H, d), 8.42-8.5 (2H, m), 8.63 (1H, s), 8.73 (1H, d). Mass Spectrum: m/z (ES+) [M+H]+=365, 367.

Example 40

3-Methyl-8-[6-(3-methylaminopropoxy)pyridin-3-yl]-1-(oxan-4-yl)imidazo[5,4-c]quinolin-2-one

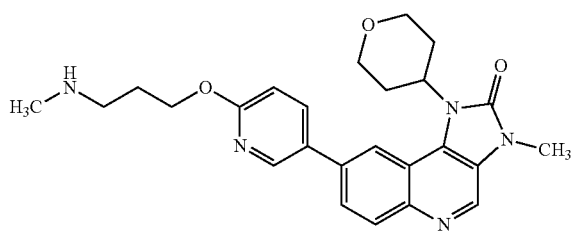

Sodium hydride (50.7 mg, 2.11 mmol) was added to tert-butyl (3-hydroxypropyl)(methyl)carbamate (200 mg, 1.06 mmol) in DMF (5 mL) at ambient temperature under air. The resulting solution was stirred for 1 h then 8-(6-fluoropyridin-3-yl)-3-methyl-1-(oxan-4-yl)imidazo[5,4-c]quinolin-2-one (200 mg, 0.53 mmol) was added and the resulting solution stirred at ambient temperature overnight. The reaction mixture was quenched with water (20 mL), extracted with EtOAc (5×20 mL), the organic layers combined and washed with water (3×50 mL). The organic layer was dried over Na₂SO₄, filtered and evaporated to afford a white solid (262 mg, 91%). This material was dissolved in DCM (10 mL) and TFA (5 mL, 64.90 mmol) added. The reaction was stirred at ambient temperature for 1 h then the solvent removed in vacuo. The crude product was purified by preparative HPLC (XSelect CSH Prep C18 OBD column, 5 m silica, 19 mm diameter, 150 mm length), using decreasingly polar mixtures of water (containing 0.1% NH₄HCO₃) and MeCN as eluents. Fractions containing the desired compound were evaporated to dryness to afford the desired material (60.0 mg, 27.7%) as a white solid. NMR Spectrum: ¹H NMR (300 MHz, DMSO-d6) δ 1.86-1.94 (4H, m), 2.30 (3H, s), 3.08 (2H, t), 2.71 (2H, dd), 3.52 (3H, s), 3.58 (2H, t), 4.05 (2H, dd), 4.36 (2H, t), 5.15 (1H, p), 6.98 (1H, d), 7.94 (1H, dd), 8.12 (1H, d), 8.20 (1H, dd), 8.42 (1H, s), 8.65 (1H, d), 8.90 (1H, s). Mass Spectrum: m/z (ES+) [M+H]+= 448.

The following compounds were prepared in an analogous fashion from tert-butyl (3-hydroxypropyl)(methyl)carbamate and the appropriate fluoro intermediate.

| Example | Structure | Name |
|---|---|---|
| 41 | 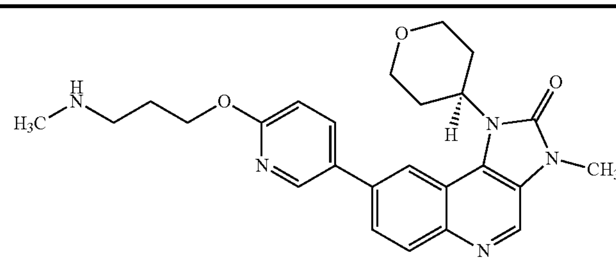 | 3-methyl-8-[6-(3-methylaminopropoxy)pyridin-3-yl]-1-[(3S)-oxan-3-yl]imidazo[5,4-c]quinolin-2-one |
| 42 | 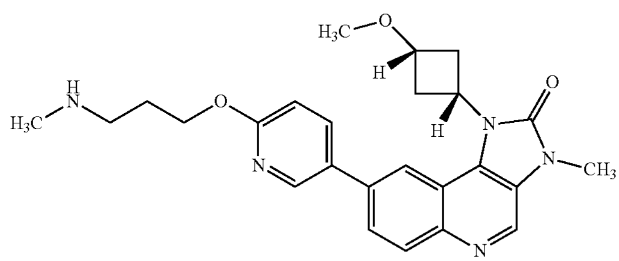 | 1-(cis-3-methoxycyclobutyl)-3-methyl-8-[6-(3-methylaminopropoxy)pyridin-3-yl]imidazo[4,5-c]quinolin-2-one |
| 43* | 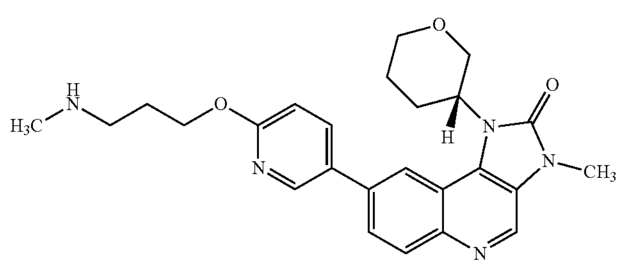 | 3-methyl-8-[6-[3-(methylamino)propoxy]-3-pyridyl]-1-[(3R)-tetrahydropyran-3-yl]imidazo[4,5-c]quinolin-2-one |

*The initial deprotonation and displacement reaction was performed in THF.

Example 41

NMR Spectrum: ¹H NMR (300 MHz, DMSO-d6) δ 1.79-1.84 (2H, m), 2.06-2.21 (3H, m), 2.67 (3H, s), 2.68-2.80 (1H, m), 3.10 (2H, t), 3.40-3.60 (5H, m), 3.94 (1H, d), 4.12-4.25 (2H, m), 4.43 (2H, t), 5.20 (1H, p), 7.08 (1H, d), 8.10 (1H, d), 8.19-8.28 (1H, m), 8.40 (1H, s), 8.68 (1H, s), 9.06 (1H, s). Mass Spectrum: m/z (ES+) [M+H]+=448.2.

Example 42

NMR Spectrum: ¹H NMR (300 MHz, DMSO-d6) δ 1.82-1.92 (2H, m), 2.29 (3H, s), 2.62 (2H, t), 2.77-2.88 (2H, m), 3.00 (2H, q), 3.21 (3H, s), 3.50 (3H, s), 3.87 (1H, p), 4.38 (2H, t), 5.10 (1H, p), 6.98 (1H, d), 7.91 (1H, d), 8.10 (1H, d), 8.21 (1H, dd), 8.42 (1H, s), 8.67 (1H, s), 8.89 (1H, s). Mass Spectrum: m/z (ES+) [M+H]+=448.

Example 43

NMR Spectrum: $^1$H NMR (300 MHz, DMSO-d6) δ 1.84 (2H, m), 2.10 (3H, m), 2.70 (4H, m), 3.10 (2H, m), 3.40 (1H, m), 3.50 (3H, s), 3.92 (1H, d), 4.18 (2H, m), 4.43 (2H, t), 5.02 (1H, bs), 7.03 (1H, d), 8.03-9.01 (6H, m). Mass Spectrum: m/z (ES+) [M+H]+=448.2.

The preparation of the required fluoro intermediates for examples 40-43 have already been described.

Example 44

8-[6-[3-(Dimethylamino)propoxy]-3-pyridyl]-3-methyl-1-[(3R)-tetrahydrofuran-3-yl]imidazo[4,5-c]quinolin-2-one methanesulfonic acid salt

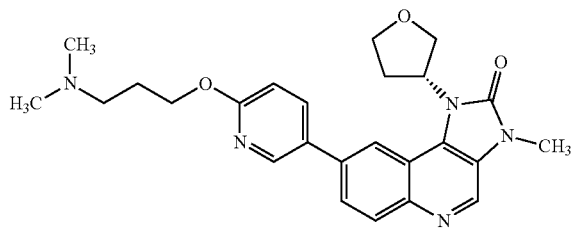

N,N-Dimethyl-3-[5-(4,4,5,5-tetramethyl-1,3,2-dioxaborolan-2-yl)pyridin-2-yl]oxypropan-1-amine (106 mg, 0.34 mmol), 2M K$_2$CO$_3$ (0.718 mL, 1.44 mmol) and 8-bromo-3-methyl-1-[(3R)-tetrahydrofuran-3-yl]imidazo[4,5-c]quinolin-2-one (100 mg, 0.29 mmol) were suspended in dioxane (3 mL) and then degassed with nitrogen. To this suspension was added dichloro[1,1'-bis(di-tert-butylphosphino)ferrocene]palladium(II) (18.72 mg, 0.03 mmol) and the resulting suspension heated in a sealed microwave vial at 80° C. for 1 h. The reaction was partitioned between water and DCM and the organic layer concentrated under reduced pressure. The crude product was purified by FCC, elution gradient 0 to 10% methanolic ammonia in DCM, to afford the desired compound (90 mg). The desired material can be isolated as a methanesulfonic acid salt by dissolving the isolated material in DCM (10 mL) then adding 1 M methanesulfonic acid in DCM (0.201 mL, 0.20 mmol) and stirring the mixture at room temperature for 1 h. The solvent was removed in vacuo and the solid was triturated in Et$_2$O to afford the methanesulfonic acid salt as a beige solid (64.0 mg). NMR Spectrum (methanesulfonic acid salt): $^1$H NMR (500 MHz, DMSO-d$_6$) δ 2.08-2.24 (2H, m), 2.31 (3H, s), 2.33-2.46 (1H, m), 2.54 (1H, s), 2.83 (6H, s), 3.18-3.29 (2H, m), 3.55 (3H, s), 3.91 (1H, td), 4.09-4.23 (2H, m), 4.27 (1H, td), 4.42 (2H, t), 5.79-5.9 (1H, m), 7.00 (1H, dd), 7.98 (1H, dd), 8.16 (1H, d), 8.26 (1H, dd), 8.61 (1H, d), 8.71 (1H, dd), 8.94 (1H, s), 9.34 (1H, s). Mass Spectrum: m/z (ES+) [M+H]+=448.

The following compounds were prepared in an analogous fashion from the appropriate bromo intermediate.

| Example | Structure | Name |
|---|---|---|
| 45 | 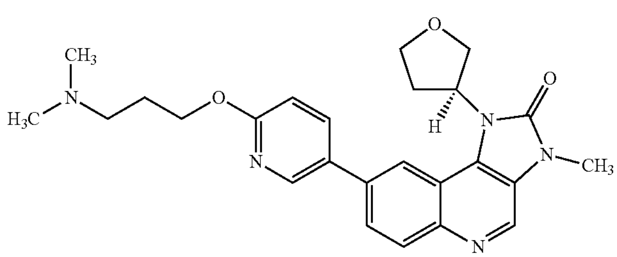 | 8-[6-[3-(dimethylamino)propoxy]-3-pyridyl]-3-methyl-1-[(3S)-tetrahydrofuran-3-yl]imidazo[4,5-c]quinolin-2-one methanesulfonic acid salt |
| 46 | 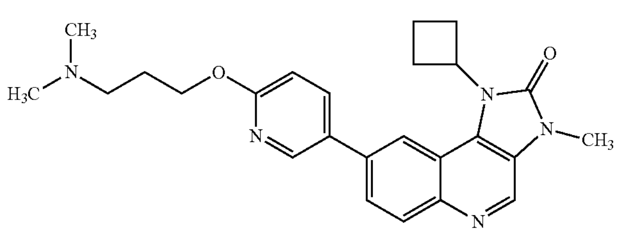 | 1-cyclobutyl-8-[6-[3-(dimethylamino)propoxy]-3-pyridyl]-3-methyl-imidazo[4,5-c]quinolin-2-one methanesulfonic acid salt |

Example 45

NMR Spectrum (methanesulfonic acid salt): ¹H NMR (500 MHz, DMSO-$d_6$) δ 2.11-2.21 (2H, m), 2.29-2.33 (3H, m), 2.32-2.46 (1H, m), 2.52-2.6 (1H, m), 2.83 (6H, s), 3.21-3.28 (2H, m), 3.55 (3H, s), 3.91 (1H, td), 4.12-4.23 (2H, m), 4.27 (1H, td), 4.42 (2H, t), 5.79-5.9 (1H, m), 7.00 (1H, dd), 7.98 (1H, dd), 8.16 (1H, d), 8.27 (1H, dd), 8.61 (1H, d), 8.71 (1H, d), 8.94 (1H, s), 9.33 (1H, s). Mass Spectrum: m/z (ES+) [M+H]+=448.

Example 46

NMR Spectrum (free base): ¹H NMR (500 MHz, DMSO-$d_6$) 1.39 (3H, d), 1.92-2.01 (1H, m), 2.01-2.11 (1H, m), 2.34 (6H, s), 2.43 (1H, dd), 2.51-2.61 (2H, m), 2.73 (1H, dd), 3.24 (2H, pd), 3.58 (3H, s), 5.31-5.41 (1H, m), 5.43-5.53 (1H, m), 6.89 (1H, dd), 7.78 (1H, dd), 7.89 (1H, dd), 8.18-8.22 (1H, m), 8.32 (1H, d), 8.51 (1H, dd), 8.69 (1H s). NMR Spectrum (methanesulfonic acid salt): ¹H NMR (500 MHz, DMSO-d4) δ 1.76-2.01 (2H, m), 2.08-2.22 (2H, m), 2.31 (3H, s), 2.41-2.49 (2H, m), 2.83 (6H, s), 3.09 (2H, pd), 3.18-3.28 (2H, m), 3.51 (3H, s), 4.42 (2H, t), 5.51 (1H, p), 7.01 (1H, dd), 7.93 (1H, dd), 8.13 (1H, d), 8.24 (1H, dd), 8.42 (1H, d), 8.69 (1H, dd), 8.89 (1H, s), 9.34 (1H, s). Mass Spectrum: m/z (ES+) [M+H]+=432.

The bromo intermediates required for the preparation of examples 44-46 were prepared as described below:

Intermediate V1: 8-Bromo-3-methyl-1-[(3R)-tetrahydrofuran-3-yl]imidazo[4,5-c]quinolin-2-one

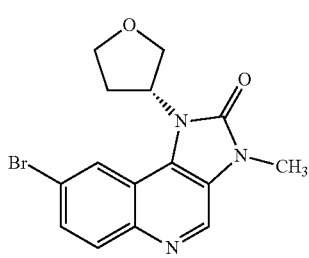 [SMILES: Cn1c(=O)n([C@@H]2CCOC2)c2c3cc(Br)ccc3ncc21]

Tetrabutylammonium bromide (0.222 g, 0.69 mmol) was added to 8-bromo-1-[(3R)-tetrahydrofuran-3-yl]-3H-imidazo[4,5-c]quinolin-2-one (2.3 g, 6.88 mmol), methyl iodide (1.291 mL, 20.65 mmol) and NaOH (0.551 g, 13.77 mmol) in DCM (65 mL) and water (39 mL) and the resulting mixture stirred at ambient temperature overnight. The solvent was removed under reduced pressure and the crude product purified by FCC, elution gradient 2 to 5% MeOH in DCM, to afford the desired material as a yellow solid (1.80 g, 75%). NMR Spectrum: ¹H NMR (400 MHz, CDCl₃) δ 2.41-2.49 (1H, m), 2.59-2.65 (1H, m), 3.62 (3H, s), 4.00-4.06 (1H, m), 4.21-4.48 (2H, m), 4.49-4.52 (1H, m), 5.69-5.77 (1H, m), 7.69 (1H, d), 8.02 (1H, d), 8.64 (1H, s), 8.74 (1H, s). Mass Spectrum: m/z (ES+) [M+H]+=350.

The following compounds were prepared in an analogous fashion from the appropriate intermediate:

| Intermediate | Structure | Name |
|---|---|---|
| Intermediate W1 | 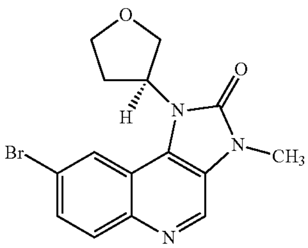 [SMILES: Cn1c(=O)n([C@H]2CCOC2)c2c3cc(Br)ccc3ncc21] | 8-bromo-3-methyl-1-[(3S)-tetrahydrofuran-3-yl]imidazo[4,5-c]quinolin-2-one |
| Intermediate X1 | 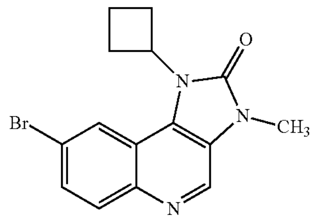 [SMILES: Cn1c(=O)n(C2CCC2)c2c3cc(Br)ccc3ncc21] | 8-bromo-1-cyclobutyl-3-methyl-imidazo[4,5-c]quinolin-2-one |

Intermediate W1

NMR Spectrum: ¹H NMR (400 MHz, DMSO-$d_6$) δ 2.40-2.48 (1H, m), 2.58-2.67 (1H, m), 3.63 (3H, s), 3.98-4.05 (1H, m), 4.19-4.28 (2H, m), 4.46-4.51 (1H, td), 5.68-5.76 (1H, m), 7.72 (1H, d), 8.07 (1H, d), 8.67 (1H, d), 8.76 (1H, s). Mass Spectrum: m/z (ES+) [M+H]+=348.

Intermediate X1

NMR Spectrum: ¹H NMR (40 MHz, CDCl₃) δ 1.95-2.12 (2H, m), 2.52-2.59 (2H, m), 3.17-3.28 (2H, m), 3.59 (3H, s), 5.18-5.27 (1H, m), 7.8 (1H, d), 8.02 (1H, d), 8.37 (1H, d), 8.70 (1H, s). Mass Spectrum: m/z (ES+) [M+H]+=332.

Intermediate V2: 8-Bromo-1-[(3R)-tetrahydrofuran-3-yl]-3H-imidazo[4,5-c]quinolin-2-one Triethylamine (2.60 mL, 18.69 mmol) was added to 6-bromo-4-[[(3R)-tetrahydrofuran-3-yl]amino]quinoline-3-carboxylic acid (2.1 g, 6.23 mmol) in DMF (30 mL) and the resulting mixture stirred at ambient temperature for 1 h. Diphenyl phosphorazidate (3.43 g, 12.46 mmol) was added and the resulting mixture stirred at 60% C overnight. The reaction mixture was diluted with water (300 mL) and the solids collected by filtration to afford the desired material as a yellow solid (2.0 g, 96%). NMR Spectrum: ¹H NMR (300 MHz, DMSO-$d_6$) δ 2.42-2.45 (2H, m), 3.85-3.90 (1H, m), 4.05-4.16 (2H, m), 4.16-4.25 (1H, m), 5.62-5.72 (1H, m), 7.16-7.18 (1H, m), 7.74 (1H, d), 7.97 (1H, d), 8.68 (1H, s), 8.73 (1H, s), 11.84 (1H, s). Mass Spectrum: m/z (ES+) [M+H]+=334.

The following compounds were prepared in an analogous fashion from the appropriate intermediate

| Intermediate | Structure | Name |
|---|---|---|
| Intermediate W2 | 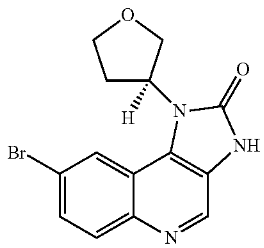 [SMILES: O=c1[nH]c2cnc3ccc(Br)cc3c2n1[C@H]1CCOC1] | 8-bromo-1-[(3S)-tetrahydrofuran-3-yl]-3H-imidazo[4,5-c]quinolin-2-one |
| Intermediate X2 | 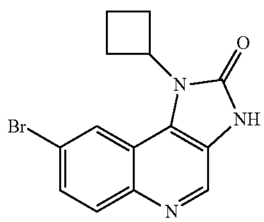 [SMILES: O=c1[nH]c2cnc3ccc(Br)cc3c2n1C1CCC1] | 8-bromo-1-cyclobutyl-3H-imidazo[4,5-c]quinolin-2-one |

Intermediate W2

Mass Spectrum: m/z (ES+) [M+H]+=334.

Intermediate X2

Mass Spectrum: m/z (ES+) [M+H]+=318.

Intermediate V3: 6-Bromo-4-[[(3R)-tetrahydrofuran-3-yl]amino]quinoline-3-carboxylic acid

Sodium hydroxide (0.657 g, 16.43 mmol) was added to ethyl 6-bromo-4-[[(3R)-tetrahydrofuran-3-yl]amino]quinoline-3-carboxylate (3 g, 8.21 mmol) in THF (60 mL) and water (30 mL) and the resulting mixture stirred at 60° C. overnight. The aqueous component was removed under reduced pressure and the remaining solution was adjusted to pH 6 with 2 M HCl. The solids were collected by filtration and dried in an oven to afford the desired material as a white solid (2.1 g, 76%). NMR Spectrum: $^1$H NMR (300 MHz, MeOH-d$_4$) δ 2.05-2.08 (1H, m), 2.38-2.48 (1H, m), 3.72-3.93 (4H, m), 4.83-5.01 (1H, m) 7.09 (1H, d), 8.04 (1H, d), 8.55 (1H, s), 8.95 (1H, s). Mass Spectrum: m/z (ES+) [M+H]+=339.

The following compounds were prepared in an analogous fashion from the appropriate intermediate

| Intermediate | Structure | Name |
|---|---|---|
| Intermediate W3 | 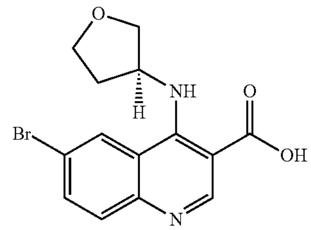 [SMILES: O=C(O)c1cnc2ccc(Br)cc2c1N[C@H]1CCOC1] | 6-bromo-4-[[(3S)-tetrahydrofuran-3-yl]amino]quinoline-3-carboxylic acid |
| Intermediate X3 | 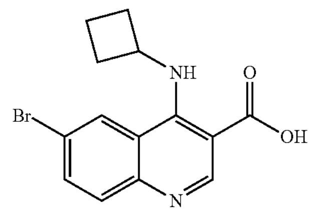 [SMILES: O=C(O)c1cnc2ccc(Br)cc2c1NC1CCC1] | 6-bromo-4-(cyclobutylamino)quinoline-3-carboxylic acid |

Intermediate W3

NMR Spectrum: $^1$H NMR (400 MHz, DMSO-d$_6$) 1.95-2.05 (1H, m), 2.31-2.41 (1H, m), 3.79-3.87 (2H, m), 3.89-3.95 (2H, m), 4.82-4.92 (1H, m), 7.78 (1H, d), 7.92-7.94 (1H, m), 8.44 (1H, d), 8.90 (1H, s), 13.3 (1H, s). Mass Spectrum: m/z (ES+) [M+H]+=337.

Intermediate X3

NMR Spectrum: $^1$H NMR (400 MHz, DMSO-d$_6$) δ 1.81-1.95 (3H, m), 2.01-2.15 (3H, m), 4.53-4.55 (1H, m), 7.74 (1H, d), 7.88 (1H, d), 8.25 (1H, s), 8.89 (1H, s), 13.27 (1H, s). Mass Spectrum: m/z (ES+) [M+H]+=321.

Intermediate V4: Ethyl 6-bromo-4-[[(3R)-tetrahydrofuran-3-yl]amino]quinoline-3-carboxylate

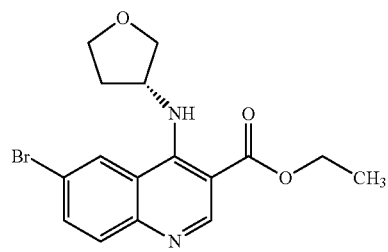 [SMILES: CCOC(=O)c1cnc2ccc(Br)cc2c1N[C@@H]1CCOC1]

DIPEA (7.77 mL, 44.51 mmol) was added to ethyl 6-bromo-4-chloroquinoline-3-carboxylate (3.5 g, 11.13 mmol) and (R)-tetrahydrofuran-3-amine (1.939 g, 22.25 mmol) in DMF (40 mL) and the resulting mixture stirred at 100° C. overnight. The reaction mixture was cooled, filtered and the solid dried in an oven to afford the desired material as a white solid (3.00 g, 73.8%). NMR Spectrum: $^1$H NMR (300 MHz, MeOH-d$_4$) δ 1.35 (3H, t), 1.96-2.01 (1H, m), 2.33-2.38 (1H, m), 3.73 (2H, m), 3.94 (2H, m), 4.67 (1H, m), 7.77-7.89 (2H, m), 8.50 (1H, s), 8.75 (1H, d), 8.87 (1H, s). Mass Spectrum: m/z (ES+) [M+H]+=365.

The following compounds were prepared in an analogous fashion from the appropriate intermediate.

| Intermediate | Structure | Name |
|---|---|---|
| Intermediate W4 | 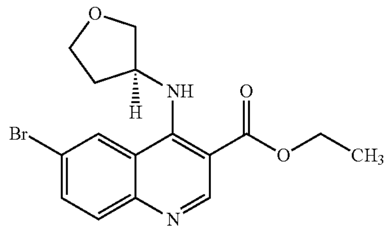 [SMILES: CCOC(=O)c1cnc2ccc(Br)cc2c1N[C@H]1CCOC1] | ethyl 6-bromo-4-[[(3S)-tetrahydrofuran-3-yl]amino]quinoline-3-carboxylate |
| Intermediate X4 * | 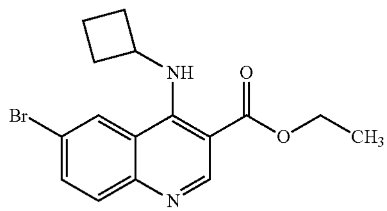 [SMILES: CCOC(=O)c1cnc2ccc(Br)cc2c1NC1CCC1] | ethyl 6-bromo-4-(cyclobutylamino)quinoline-3-carboxylate |

* The reaction was stirred at 60° C. for 16 h.

Intermediate W4

NMR Spectrum: $^1$H NMR (400 MHz, CDCl$_3$) δ 1.45 (3H, t), 2.12-2.19 (1H, m), 2.48-2.55 (1H, m), 3.87-4.04 (2H, m), 4.12 (2H, td), 4.43 (2H, q), 4.76-4.86 (1H, m), 7.80 (1H, dd), 7.95 (1H, d), 8.34 (1H, d), 9.14 (1H, s), 9.64 (1H, s). Mass Spectrum: m/z (ES+) [M+H]+=365.

Intermediate X4

NMR Spectrum: $^1$H NMR (400 MHz, CDCl$_3$) δ 1.45 (3H, t), 1.77-2.01 (2H, m), 2.16-2.31 (2H, m), 2.58-2.71 (2H, m), 4.45 (3H, m), 7.74 (1H, dd), 7.82 (1H, d), 8.23 (1H, d), 9.09 (1H, s), 9.57 (1H, d) Mass Spectrum: m/z (ES+) [M+H]+= 349.

The preparation of ethyl 6-bromo-4-chloroquinoline-3-carboxylate has been described earlier.

Example 47

7-Fluoro-3-methyl-8-[6-[3-(1-piperidyl)propoxy]-3-pyridyl]-1-[(3S)-tetrahydropyran-3-yl]imidazo[4,5-c]quinolin-2-one methanesulfonic acid salt

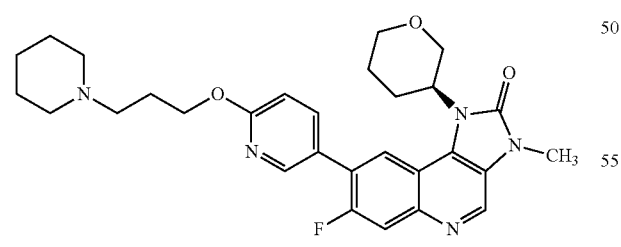

3-(Piperidin-1-yl)propan-1-ol (43.4 mg, 0.30 mmol) in THF (0.5 mL) was added dropwise to a stirred suspension of sodium hydride (24.22 mg, 0.61 mmol) in THF (0.5 mL) at room temperature. The resulting suspension was stirred for 10 minutes under nitrogen then 7-fluoro-8-[6-fluoro-3-pyridyl]-3-methyl-1-[(3S)-tetrahydropyran-3-yl]imidazo[4,5-c]quinolin-2-one (100 mg, 0.25 mmol) in DMF (1.5 mL) added and the reaction mixture stirred at room temperature overnight. The reaction mixture was diluted with EtOAc (40 mL), washed twice with water (20 mL), the organic layer dried over MgSO$_4$, filtered and evaporated to afford crude product. The crude product was purified by FCC, elution gradient 0 to 4% 2N methanolic ammonia in DCM, to afford the desired material as a white solid (80 mg, 61.0%). The isolated material (79 mg) was dissolved in DCM (2 mL) and methanesulfonic acid (16.07 mg, 0.17 mmol) in DCM added. The solution was evaporated to dryness to afford the methanesulfonic acid salt of the desired material as a pale yellow solid (97 mg). NMR Spectrum (methanesulfonic acid salt): $^1$H NMR (500 MHz, DMSO-d6) δ 1.40 (1H, dd), 1.55-1.92 (6H, m), 2.06-2.26 (3H, m), 2.31 (3H, s), 2.59-2.77 (1H, m), 2.82-3.03 (2H, m), 3.19-3.29 (2H, m), 3.38 (2H, td), 3.49 (51-1, s), 3.84-3.95 (1H, m), 4.12 (1H, dd), 4.19 (1H, t), 4.44 (2H, t), 4.76-5.07 (1H, m), 7.04 (1H, dd), 7.96 (1H, d), 8.11 (1H, dt), 8.26 (1H, d), 8.54 (1H, s), 8.95 (1H, s), 9.01 (1H, s). Mass Spectrum: m/z (ES+) [M+H]+= 520.2

7-Fluoro-8-[6-fluoro-3-pyridyl]-3-methyl-1-[(3S)-tetrahydropyran-3-yl imidazo[4,5-c]quinolin-2-one was prepared as described below:

Intermediate K4: 7-Fluoro-8-[6-fluoro-3-pyridyl]-3-methyl-1-[(3S)-tetrahydropyran-3-yl]imidazo[4,5-c]quinolin-2-one 8-Bromo-7-fluoro-3-methyl-1-[(3S)-oxan-3-yl]imidazo[5,4-c]quinolin-2-one (250 mg, 0.66 mmol), (6-fluoropyridin-3-yl]boronic acid (120 mg, 0.85 mmol) and 2M K$_2$CO$_3$ (1 mL, 2.00 mmol) were suspended in 1,4-dioxane (3 mL), degassed, then [Pd-118] (22 mg, 0.03 mmol) added. The reaction was heated to 80° C. for 1 h under nitrogen then allowed to cool. The reaction mixture was diluted with EtOAc (50 mL) then washed with water (2×25 mL), brine, the organic phase dried over MgSO$_4$, filtered and concentrated in vacuo. The crude product was purified by FCC, elution gradient 0 to 4% 2N methanolic ammonia in DCM, to afford the desired material as an off-white solid (205 ing, 79%). NMR Spectrum: $^1$H NMR (00 MHz, DMSO-d6) δ 1.71-1.87 (2H, m), 2.14 (1H, d), 2.57-2.76 (1H, m), 3.32-3.42 (1H, m), 3.49 (3H, s), 3.90 (1H, d), 4.06-4.16 (1H, m), 4.21 (1H, t), 4.79-5.1 (1H, m), 7.36-7.54 (1H, m), 7.97 (1H, d), 8.32 (1H, d), 8.37 (1H, t), 8.62 (1H, s), 8.95 (1H, s). Mass Spectrum: m/z (ES+) [M+H]+=397.

The preparation of 8-bromo-7-fluoro-3-methyl-1-[(3S)-oxan-3-yl]imidazo[5,4-c]quinolin-2-one has been described earlier.

Example 48

8-[6-[3-(Dimethylamino)propoxy]-2-fluoro-3-pyridyl-7-fluoro-3-methyl-1-[(3S)-tetrahydropyran-3-yl]imidazo[4,5-c]quinolin-2-one methanesulfonic acid salt

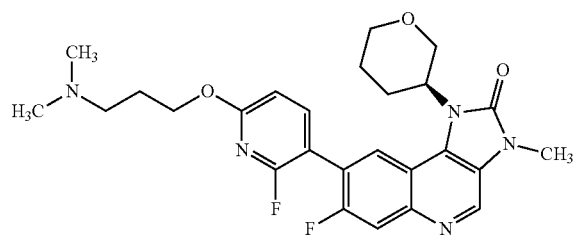

Chloro(2-dicyclohexylphosphino-2',4',6'-triisopropyl-1,1'-biphenyl) 2-(2'-amino-1,1'-biphenyl)]palladium(II) (103 mg, 0.13 mmol) was added to a 3-[6-fluoro-5-(4,4,5,5-tetramethyl-1,3,2-dioxaborolan-2-yl)pyridin-2-yl]oxy-N,N-dimethylpropan-1-amine (468 mg, 1.44 mmol), 8-bromo-7-fluoro-3-methyl-1-[(3S)-oxan-3-yl]imidazo[5,4-c]quinolin-2-one (500 mg, 1.32 mmol) and cesium carbonate (1285 mg, 3.95 mmol) in 1,4-dioxane (5 mL) and water (2.5 mL). The resulting mixture was stirred at 80° C. for three h then allowed to cool. The reaction mixture was diluted with EtOAc (100 mL), washed twice with water (50 mL), the organic layer dried over MgSO$_4$, filtered and evaporated to afford crude product. The crude product was purified by FCC, elution gradient 0 to 4% 2N methanolic ammonia in DCM, to afford the desired material as a white solid (130 mg, 19.87%). The material can also be isolated as the methanesulfonic acid salt by dissolving in DCM and treating with 1-1.1 equivalents of methanesulfonic acid then concentrating the mixture in vacuo and triturating the residue with Et$_2$O. NMR Spectrum (free base): $^1$H NMR (500 MHz, DMSO-d6) δ 1.77 (2H, t), 1.89 (2H, p), 2.11 (1H, d), 2.16 (6H, s), 2.37 (2H, t), 2.54-2.72 (1H, m), 3.33-3.42 (1H, m), 3.49 (3H, s), 3.89 (1H, d), 4.08 (1H, dd), 4.23 (1H, t), 4.33 (2H, t), 4.85 (1H, s), 6.98 (1H, dd), 7.93 (1H, d), 8.11-8.24 (1H, m), 8.30 (1H, d), 8.93 (1H, s). NMR Spectrum (methanesulfonic acid salt): $^1$H NMR (500 MHz, DMSO-d6) δ 1.66-1.89 (2H, m), 2.04-2.26 (3H, m), 2.31 (3H, s), 2.59-2.7 (1H, m), 2.84 (6H, d), 3.22-3.43 (31H, m), 3.50 (3H, s), 3.88 (1H, d), 4.03-4.15 (1H, m), 4.22 (1H, t), 4.39 (2H, t), 4.85 (1H, t), 7.01 (1H, d), 7.96 (1H, d), 8.17-8.26 (1H, m), 8.30 (1H, d), 8.96 (1H, s), 9.35 (1H, s). Mass Spectrum: m/z (ES+) [M+H]+498.

The following compounds were prepared in an analogous fashion from the appropriate intermediates.

| Example | Structure | Name |
|---|---|---|
| 49 | 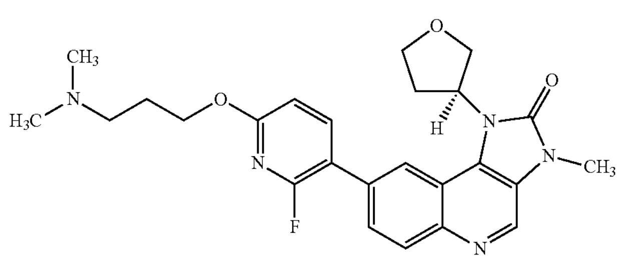 | 8-[6-[3-(dimethylamino)propoxy]-2-fluoro-3-pyridyl]-3-methyl-1-[(3S)-tetrahydrofuran-3-yl]imidazo[4,5-c]quinolin-2-one methanesulfonic acid salt |
| 50 | 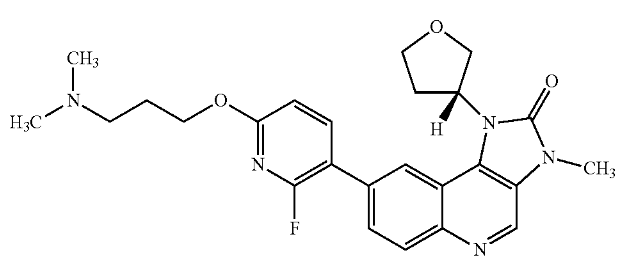 | 8-[6-[3-(dimethylamino)propoxy]-2-fluoro-3-pyridyl]-3-methyl-1-[(3R)-tetrahydrofuran-3-yl]imidazo[4,5-c]quinolin-2-one methanesulfonic acid salt |

| Example | Structure | Name |
|---|---|---|
| 51 | 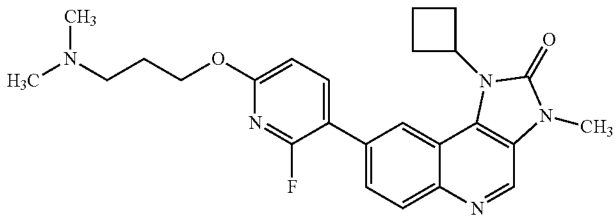 | 1-cyclobutyl-8-[6-[3-(dimethylamino)propoxy]-2-fluoro-3-pyridyl]-3-methyl-imidazo[4,5-c]quinolin-2-one methanesulfonic acid salt |
| 52 | 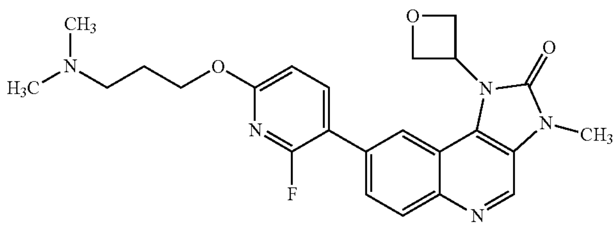 | 8-[6-[3-(dimethylamino)propoxy]-2-fluoro-3-pyridyl]-3-methyl-1-(oxetan-3-yl)imidazo[4,5-c]quinolin-2-one methanesulfonic acid salt |

Example 49

NMR Spectrum (free base): $^1$H NMR (500 MHz, DMSO-$d_6$) δ 1.82-0.95 (2H, m), 2.16 (6H, s), 2.36 (3H, t), 2.52-2.59 (1H, m), 3.54 (3H, s), 3.87 (1H, d), 4.11 (2H, dd), 4.21 (1H, d), 4.31 (2H, t), 5.76 (1H, s), 6.94 (1H, dd), 7.81 (1H, dt), 8.13 (1H, d), 8.20 (1H dd), 8.57 (1H, d), 8.94 (1H, s). NMR Spectrum (methanesulfonic acid salt): $^1$H NMR (500 MHz, DMSO-$d_6$) δ 2.08-2.25 (2H, m), 2.31 (3H, s), 2.32-2.42 (1H, m), 2.52-2.59 (1H, m), 2.84 (6H, s), 3.2-3.28 (2H, m), 3.54 (3H, s), 3.8-3.97 (1H, m) 4.03-4.17 (2H, m), 4.22 (1H, td), 4.38 (2H, t), 5.64-5.97 (1H, m), 6.97 (1H, d), 7.82 (1H, d), 8.15 (1H, d), 8.25 (1H, dd), 8.59 (1H, s), 8.96 (1H, s), 9.35 (1H, s). Mass Spectrum: m/z (ES+) [M+H]+=466.

Example 50

NMR Spectrum (free base): $^1$H NMR (500 MHz, DMSO-$d_6$) δ 1.89 (2H, p), 2.16 (6H, s), 2.36 (3H, t), 2.52-2.6 (1H, m), 3.54 (3H, s), 3.79-3.98 (1H, m), 4.04-4.18 (2H, m), 4.21 (1H, td), 4.31 (2H, t), 5.76 (1H, d), 6.94 (1H, dd), 7.81 (1H, dt), 8.13 (1H, d), 8.20 (1H, dd), 8.57 (1H, d), 8.94 (1H, s). NMR Spectrum (methanesulfonic acid salt): $^1$H NMR (500 MHz, DMSO-$d_6$) δ 2.1-2.25 (2H, m), 2.33 (3H, s), 2.35-2.44 (1H, m), 2.53-2.61 (1H, m), 2.85 (6H, d), 3.26 (2H, s), 3.57 (3H, s), 3.81-3.98 (1H, m), 4.07-4.17 (2H, m), 4.19-4.29 (1H, m), 4.39 (2H, t), 5.71-5.9 (1H, m), 6.99 (1H, d), 7.91 (1H, d), 8.20 (1H, d), 8.27 (1H, dd), 8.65 (1H, s), 9.06 (1H, s), 9.40 (1H, s). Mass Spectrum: m/z (ES+) [M+H]+=466.

Example 51

NMR Spectrum (free base): $^1$H NMR (500 MHz, DMSO-$d_6$) δ 1.79-1.95 (4H, m), 2.16 (6H, s), 2.37 (2H, t), 2.4-2.49 (2H, m), 3.07 (2H, td), 3.50 (3H, s), 4.32 (2H, t), 5.40 (1H, p), 6.95 (1H, d), 7.80 (1H, d), 8.11 (1H, d), 8.22 (1H, dd), 8.44 (1H, s), 8.90 (1H, s). NMR Spectrum (methanesulfonic acid salt): $^1$H NMR (500 MHz, DMSO-$d_6$) δ 1.78-1.99 (2H, m), 2.08-2.23 (2H, m), 2.31 (3H, s), 2.38-2.48 (2H, m), 2.84 (6H, s), 3.01-3.14 (2H, m), 3.2-3.29 (2H, m), 3.51 (3H, s), 4.38 (2H, t), 5.28-5.58 (1H, m), 6.98 (1H, m, 2 d), 7.83 (1H, d), 8.15 (1H, d), 8.23-8.39 (1H, m), 8.46 (1H, s), 8.94 (1H, s), 9.38 (1H, s). Mass Spectrum: m/z (ES+) [M+H]+=450.

Example 52

NMR Spectrum (free base): $^1$H NMR (500 MHz, DMSO-$d_6$) δ 1.83-1.96 (2H, m), 2.16 (6H, s), 2.36 (2H, t), 3.53 (3H, s), 4.32 (2H, t), 5.01 (2H, dd), 5.25 (2H, t), 5.95-6.24 (1H, m), 6.94 (1H, dd), 7.82 (1H, dt), 8.13 (1H, d), 8.19 (1H, dd), 8.39 (1H, s), 8.95 (1H, s). NMR Spectrum (methanesulfonic acid salt): $^1$H NMR (500 MHz, DMSO-$d_6$) δ 2.09-2.25 (2H, m), 2.32 (3H, s), 2.85 (6H, s), 3.22-3.29 (2H, m), 3.55 (3H, s), 4.39 (2H, t), 4.95-5.14 (2H, m), 5.26 (2H, t), 6.10 (1H, p), 6.98 (1H, d), 7.85 (1H, d), 8.17 (1H, d), 8.25 (1H, dd), 8.45 (1H, s), 9.01 (1H, s), 9.36 (1H, s) Mass Spectrum: m/z (ES+) [M+H]+=452.

The 3-[6-fluoro-5-(4,4,5,5-tetramethyl-1,3,2-dioxaborolan-2-yl)pyridin-2-yl]oxy-N,N-dimethylpropan-1-amine used for these examples was prepared directly before use by treating 3-(5-bromo-6-fluoropyridin-2-yl)oxy-N,N-dimethylpropan-1-amine (1 equiv) with 4,4,4',4'-5,5,5',5'-octamethyl-2,2'-bi(1,3,2-dioxaborolane) (2 equiv), potassium acetate (3 equiv) and [1,1-bis(diphenylphosphino)ferrocene]dichloropalladium (II) complex with DCM (1:1) (0.1 equiv) in 1,4-dioxane at 100° C. for 6 h. This mixture was allowed to cool then used directly in the subsequent reaction.

The preparation of 3-(5-bromo-6-fluoropyridin-2-yl)oxy-N,N-dimethylpropan-1-amine and the required bromo intermediates have been described previously.

Example 53

7-Fluoro-3-methyl-8-[6-[3-(1-piperidyl)propoxy]-3-pyridyl]-1-tetrahydropyran-4-yl-imidazo[4,5-c]quinolin-2-one

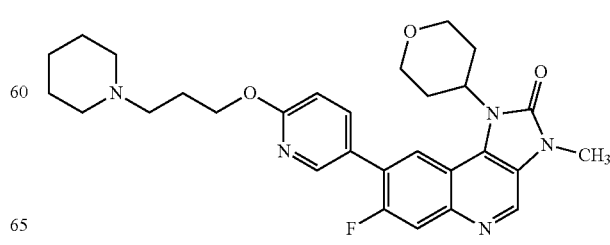

3-(Piperidin-1-yl)propan-1-ol (0.053 mL, 0.35 mmol) was added slowly to a slurry of sodium hydride (31.5 mg, 0.79 mmol) in THF (7 mL) and the solution stirred at ambient temperature for 30 minutes. 7-Fluoro-8-[6-fluoro-3-pyridyl]-3-methyl-1-tetrahydropyran-4-yl-imidazo[4,5-c]quinolin-2-one (125 mg, 0.32 mmol) in THF (3 mL) was added to the reaction mixture via syringe over a period of 1 minute and the reaction stirred for 24 h. The reaction was quenched with water then extracted into DCM, the organic phase separated and concentrated in vacuo. The crude product was purified by FCC, elution gradient 0 to 10% 1 M methanolic ammonia in DCM, and the resultant oil triturated with Et$_2$O to afford the desired material as a white solid (92 mg, 56%). NMR Spectrum: $^1$H NMR (500 MHz, CDCl$_3$) δ 1.38-1.52 (2H, m), 1.61 (4H, p), 1.92 (2H, dd), 2.03 (2H, dt), 2.43 (4H, s), 2.47-2.58 (2H, m), 2.94 (2H, d), 3.53-3.63 (5H, m), 4.22 (2H, dd), 4.42 (2H, t), 5.01 (1H, s), 6.89 (1H, dd), 7.85-7.96 (2H, m), 8.26 (1H, s), 8.44 (1H, s), 8.71 (1H, s). Mass Spectrum: m/z (ES+) [M+H]+=520.

The following compounds were prepared in an analogous fashion from the appropriate intermediates.

| Example | Structure | Name |
|---|---|---|
| 54* | 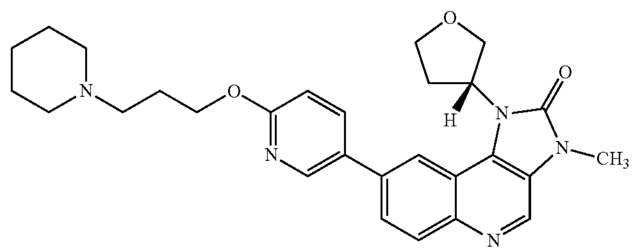 [SMILES: Cn1c(=O)n([C@@H]2CCOC2)c2c3cc(-c4ccc(OCCCN5CCCCC5)nc4)ccc3ncc21] | 3-methyl-8-[6-[3-(1-piperidyl)propoxy]-3-pyridyl]-1-[(3R)-tetrahydrofuran-3-yl]imidazo[4,5-c]quinolin-2-one methane sulfonic acid salt |
| 55** | 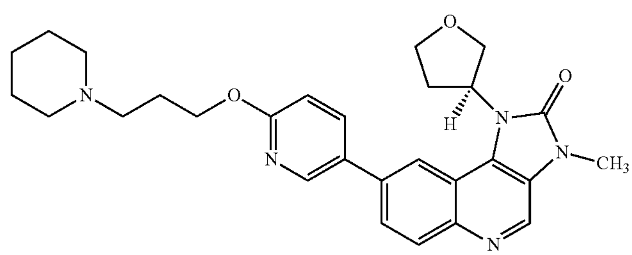 [SMILES: Cn1c(=O)n([C@H]2CCOC2)c2c3cc(-c4ccc(OCCCN5CCCCC5)nc4)ccc3ncc21] | 3-methyl-8-[6-[3-(1-piperidyl)propoxy]-3-pyridyl]-1-[(3S)-tetrahydrofuran-3-yl]imidazo[4,5-c]quinolin-2-one |
| 56*** | 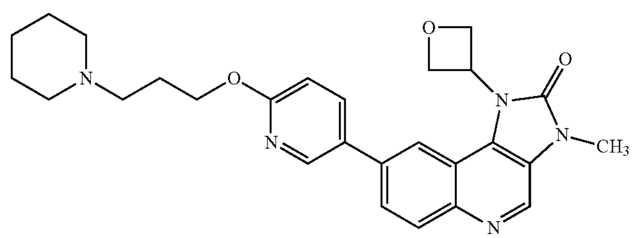 [SMILES: Cn1c(=O)n(C2COC2)c2c3cc(-c4ccc(OCCCN5CCCCC5)nc4)ccc3ncc21] | 3-methyl-1-(oxetan-3-yl)-8-[6-[3-(1-piperidyl)propoxy]-3-pyridyl]imidazo[4,5-c]quinolin-2-one trifluoroacetic acid salt |
| 57*** | 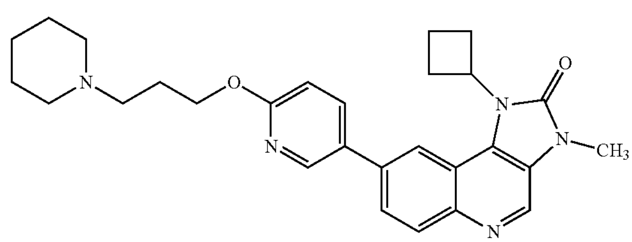 [SMILES: Cn1c(=O)n(C2CCC2)c2c3cc(-c4ccc(OCCCN5CCCCC5)nc4)ccc3ncc21] | 1-cyclobutyl-3-methyl-8-[6-[3-(1-piperidyl)propoxy]-3-pyridyl]imidazo[4,5-c]quinolin-2-one trifluoroacetic acid salt |
| 58**** | 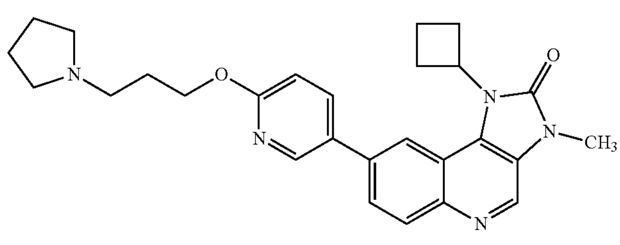 [SMILES: Cn1c(=O)n(C2CCC2)c2c3cc(-c4ccc(OCCCN5CCCC5)nc4)ccc3ncc21] | 1-cyclobutyl-3-methyl-8-[6-(3-pyrrolidin-1-ylpropoxy)-3-pyridyl]imidazo[4,5-c]quinolin-2-one |

| Example | Structure | Name |
|---|---|---|
| 59***** | 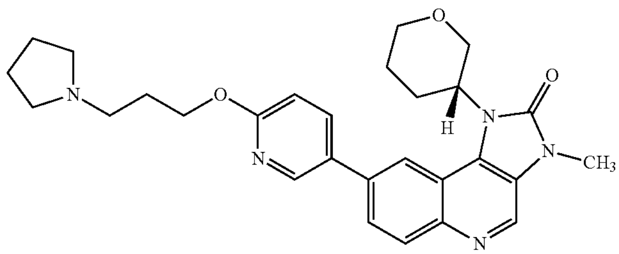 [SMILES: Cn1c(=O)n([C@@H]2CCCOC2)c2c3cc(-c4ccc(OCCCN5CCCC5)nc4)ccc3ncc21] | 3-methyl-8-[6-(3-pyrrolidin-1-ylpropoxy)-3-pyridyl]-1-[(3R)-tetrahydropyran-3-yl]imidazo[4,5-c]quinolin-2-one |
| 60****** | 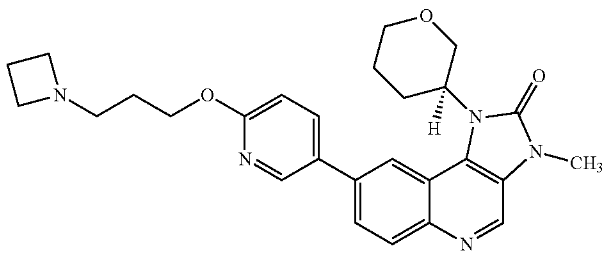 [SMILES: Cn1c(=O)n([C@H]2CCCOC2)c2c3cc(-c4ccc(OCCCN5CCC5)nc4)ccc3ncc21] | 8-[6-[3-(azetidin-1-yl)propoxy]-3-pyridyl]-3-methyl-1-[(3S)-tetrahydropyran-3-yl]imidazo[4,5-c]quinolin-2-one |

*The reaction was stirred at ambient temperature for 4 h then at 45° C. for 2 h. The material could also be isolated as a methanesulfonic acid salt by dissolving in DCM, treating with methanesulfonic acid (~1 equiv) and concentrating in vacuo then triturating the residue with Et$_2$O.
**The reaction was stirred at ambient temperature for 4 h then at 45° C. for 2 h.
***The reaction was stirred at r.t. for 4 h then at 45° C. for 2 h. The material could also be isolated as a trifluoroacetic acid salt by dissolving in DCM, treating with trifluoroacetic acid (~1 equiv) and concentrating in vacuo then triturating the residue with Et$_2$O.
****The reaction was stirred at 50° C. for overnight. The material could also be isolated as a methanesulfonic acid salt by dissolving in DCM, treating with methanesulfonic acid (~1 equiv) and concentrating in vacuo.
*****The reaction was stirred at r.t. for 3 days.
******The reaction was stirred at r.t. for 2 h.

Example 54

NMR Spectrum (methanesulfonic acid salt): $^1$H NMR (500 MHz, CDCl$_3$) δ 1.5-1.63 (2H, m), 1.7-1.98 (7H, m), 2.2-2.3 (2H, m), 2.45 (2H, dtd), 2.59-2.72 (2H, m), 2.82 (3H, s), 3.63 (3H, s), 3.79-3.87 (1H, m), 3.97 (1H, td), 4.19-4.33 (2H, m), 4.37-4.45 (1H, m), 4.46 (2H, t), 5.81-5.93 (1H, m), 6.87 (1H, dd), 7.84 (1H, dd), 8.05 (1H, dd), 8.23 (1H, d), 8.56 (1H, dd), 8.58 (1H, d), 8.74 (1H, s). Mass Spectrum: m/z (ES+) [M+H]+=488.

Example 55

NMR Spectrum: $^1$H NMR (500 MHz, CDCl$_3$) δ 1.36-1.51 (2H, m), 1.61 (4H, p), 2.02 (2H, dt), 2.44 (5H, did), 2.48-2.55 (2H, m), 2.59-2.71 (1H, m), 3.63 (3H, s), 3.98 (1H, td), 4.21-4.33 (2H, m), 4.41 (3H, t), 5.86 (1H, qd), 6.87 (1H, dd), 7.85 (1H, dd), 8.03 (1H, dd), 8.17-8.25 (1H, m), 8.5-8.59 (2H, m), 8.73 (1H, s). Mass Spectrum: m/z (ES+) [M+H]+=488.

Example 56

NMR Spectrum (free base): $^1$H NMR (500 MHz. CDCl$_3$) δ 0.07 (1H, s), 1.45 (2H, s), 1.57-1.64 (3H, m), 1.99-2.06 (2H, m), 2.42 (4H, s), 2.47-2.54 (2H, m), 3.62 (3H, s), 4.41 (2H, t), 5.18-5.25 (2H, m), 5.37 (2H, t), 6.08-6.18 (1H, m), 6.87 (1H, dd), 7.87 (1H, dd), 7.97 (1H, dd), 8.24 (1H, d), 8.52-8.58 (2H, m), 8.75 (1H, s). NMR Spectrum (trifluoroacetic acid salt): $^1$H NMR (500 MHz, DMSO-d6) δ 1.6-1.78 (4H, m), 1.85 (2H, d), 2.14-2.23 (2H, m), 2.94 (1H, s), 3.2-3.28 (2H, m), 3.51 (2H, d), 3.58 (3H, s), 4.44 (2H, t), 5.05-5.12 (2H, m), 5.28 (2H, t), 6.23-6.31 (1H, m), 7.02 (1H, d), 8.05-8.37 (4H, m), 8.60 (1H, s), 8.74 (1H, d), 9.17 (1H, s). Mass Spectrum: m/z (ES+) [M+H]+=474.

Example 57

NMR Spectrum (free base): $^1$H NMR (500 MHz, CDCl$_3$) δ 1.45 (2H, 4), 1.60 (4H, p), 1.86-2.12 (4H, m), 2.43 (4H, s), 2.47-2.63 (4H, m), 3.24 (2H, pd), 3.58 (3H, s), 4.42 (2H, t), 5.36 (1H, p), 6.89 (1H, dd), 7.77 (1H, dd), 7.90 (1H, dd), 8.21 (1H, d), 8.32 (1H, d), 8.51 (1H, dd), 8.69 (1H, s). NMR Spectrum (trifluoroacteic acid salt): $^1$H NMR (500 MHz, DMSO-d6) δ 1.42 (2H, s), 1.58-1.76 (4H, m), 1.82-1.97 (4H, m), 2.14-2.28 (2H, m), 2.93 (2H, d), 3.06-3.14 (2H, m), 3.21-3.29 (2H, m), 3.53 (3H, s), 4.44 (2H, t), 5.51-5.58 (1H, m), 6.99-7.05 (1H, m), 8.00 (1H, d), 8.17 (1H, d), 8.26 (1H, d), 8.27 (1H, d), 8.46 (1H, s), 8.71 (1H, d), 8.97 (2H, s). Mass Spectrum: m/z (ES+) [M+H]+=472.

Example 58

NMR Spectrum (free base): $^1$H NMR (500 MHz, DMSO-d$_4$) δ 1.67-1.73 (4H, m), 1.86-1.99 (4H, m), 2.45-2.5 (6H, m), 2.57 (2H, t), 3.09 (2H, pd), 3.51 (3H, s), 4.39 (2H, t), 5.52 (1H, p), 6.99 (1H, dd), 7.92 (1H, dd), 8.12 (1H, d), 8.20 (1H, dd), 8.41 (1H, d), 8.67 (1H, dd), 8.88 (1H, s). NMR Spectrum (methanesufonic acid salt): $^1$H NMR (500 MHz, DMSO-d$_6$) δ 1.84-1.98 (4H, m), 2.01-2.1 (2H, m), 2.13-2.23 (2H, m), 2.32 (3H, s), 3.03-3.14 (4H, m), 3.28-3.36 (4H, m), 3.54 (3H, s), 3.58-3.67 (2H, m), 4.45 (2H, t), 5.52-5.63 (1H, m), 7.04 (1H, dd), 8.06 (1H, d), 8.19 (1H, d), 8.27 (1H, dd), 8.49 (1H, s), 8.71-8.74 (1H, m), 9.03 (1H, s), 9.50 (1H, s). Mass Spectrum: m/z (ES+) [M+H]+=458.

Example 59

NMR Spectrum: $^1$H NMR (300 MHz, DMSO-d6) δ 1.68-1.86 (6H, m), 1.95 (2H, m), 2.15 (1H, m), 2.51-2.75 (7H, m), 3.40 (1H, m), 3.49 (3H, s), 3.92 (1H, m), 4.15 (2H, m), 4.38 (2H, m), 4.97 (1H, m), 6.98 (1H, m), 7.91-8.89 (6.82H, m). Mass Spectrum: m/z (ES+) [M+H]+=488.3.

Example 60

NMR Spectrum: ¹H NMR (300 MHz, DMSO-d6) δ 1.80 (4H, m), 2.10 (3H, m), 2.68 (3H, m), 3.35 (5H, m), 3.49 (3H, m), 3.92 (1H, m), 4.15 (2H, m), 4.33 (2H, m), 4.93 (1H, m), 6.98 (1H, m), 7.91-8.89 (6.92H, m). Mass Spectrum: m/z (ES+) [M+H]+=474.2.

The required fluoro intermediates for Examples 53-60 have either been described previously or were prepared from the appropriate bromo intermediates as described below:

Intermediate F5: 7-Fluoro-8-[6-fluoro-3-pyridyl]-3-methyl-1-tetrahydropyran-4-yl-imidazo[4,5-c]quinolin-2-one

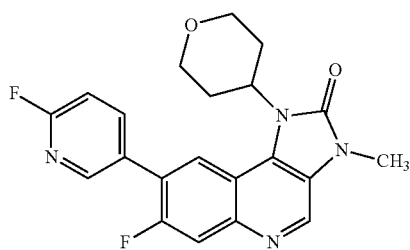 [SMILES: Cn1c(=O)n(C2CCOCC2)c2c3cc(-c4ccc(F)nc4)c(F)cc3ncc21]

(6-Fluoropyridin-3-yl)boronic acid (0.445 g, 3.16 mmol), 8-bromo-7-fluoro-3-methyl-1-(oxan-4-yl)imidazo[5,4-c]quinolin-2-one (1 g, 2.63 mmol) and 2M $K_2CO_3$ (3.95 mL, 7.89 mmol) were suspended in dioxane (3 mL) and water (0.75 mL). The reaction was degassed with nitrogen and then dichloro[1,1'-bis(di-tert-butylphosphino)ferrocene]palladium(II) (0.086 g, 0.13 mmol) was added and the reaction heated to 80° C. for 1 h in the microwave reactor. The mixture was allowed to cool, diluted with water then extracted with DCM (2×100 mL). The combined organic phases were separated and concentrated in vacuo. The crude product was purified by FCC, elution gradient 0 to 10% methanolic ammonia in DCM, to afford the desired material as a beige solid (0.92 g, 88%). NMR Spectrum: ¹H NMR (500 MHz, DMSO-d6) δ 1.90 (2H, dd), 2.69 (2H, qt), 3.49-3.59 (5H, m), 3.97-4.06 (2H, m), 5.08 (1H, tt), 7.38-7.45 (1H, m), 7.96 (1H, d), 8.34-8.42 (2H, m), 8.61-8.65 (1H, m), 8.95 (1H, s). Mass Spectrum: m/z (ES+) [M+H]+= 397

The following fluoro intermediates were prepared in an analogous fashion:

| Intermediate | Structure | Name |
|---|---|---|
| Intermediate V5 | 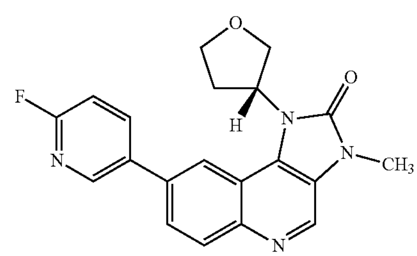 [SMILES: Cn1c(=O)n([C@@H]2CCOC2)c2c3cc(-c4ccc(F)nc4)ccc3ncc21] | 8-(6-fluoro-3-pyridyl)-3-methyl-1-[(3R)-tetrahydrofuran-3-yl]imidazo[4,5-c]quinolin-2-one |
| Intermediate W5 | 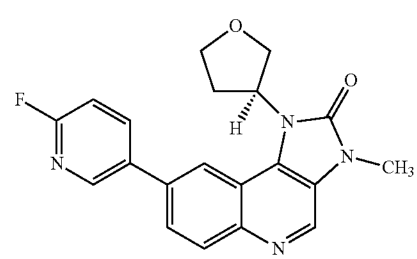 [SMILES: Cn1c(=O)n([C@H]2CCOC2)c2c3cc(-c4ccc(F)nc4)ccc3ncc21] | 8-(6-fluoro-3-pyridyl)-3-methyl-1-[(3S)-tetrahydrofuran-3-yl]imidazo[4,5-c]quinolin-2-one |
| Intermediate G5 | 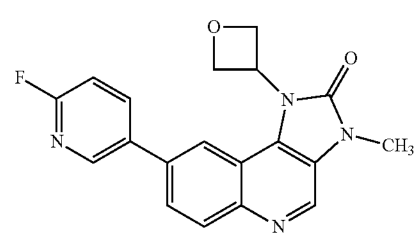 [SMILES: Cn1c(=O)n(C2COC2)c2c3cc(-c4ccc(F)nc4)ccc3ncc21] | 8-(6-fluoro-3-pyridyl)-3-methyl-1-(oxetan-3-yl)imidazo[4,5-c]quinolin-2-one |

| Intermediate | Structure | Name |
|---|---|---|
| Intermediate X5 | 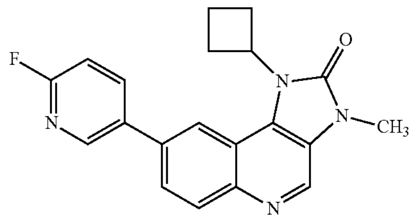 [SMILES: Cn1c(=O)n(C2CCC2)c2c3cc(-c4ccc(F)nc4)ccc3ncc21] | 1-cyclobutyl-8-(6-fluoro-3-pyridyl)-3-methyl-imidazo[4,5-c]quinolin-2-one |

Intermediate V5

NMR Spectrum: $^1$H NMR (500 MHz, DMSO-d$_6$) δ 2.34-2.45 (1H, m), 2.52-2.67 (1H, m), 3.55 (3H, s), 3.91 (1H, td), 4.13-4.23 (2H, m), 4.27 (1H, td), 5.76-5.92 (1H, m), 7.38 (1H, dd), 8.02 (1H, dd), 8.18 (1H, d), 8.49 (1H, ddd), 8.68 (1H, d), 8.77 (1H, d), 8.96 (1H, s). Mass Spectrum: m/z (ES+) [M+H]+=365.

Intermediate W5

NMR Spectrum: $^1$H NMR (500 MHz, DMSO-d$_6$) δ 2.33-2.44 (1H, m), 2.53-2.67 (1H, m), 3.55 (3H, s), 3.91 (1H, td), 4.13-4.22 (2H, m), 4.27 (1H, d), 5.79-5.9 (1H, m), 7.3-7.41 (1H, m), 8.02 (1H, d), 8.18 (1H, d), 8.49 (1H, ddd), 8.68 (1H, d), 8.77 (1H, d), 8.96 (1H, s). Mass Spectrum: m/z (ES+) [M+H]+=365.

Intermediate G5

NMR Spectrum: $^1$H NMR (500 MHz, DMSO-d$_6$) δ 3.55 (3H, s), 5.07 (2H, dd), 5.28 (2H, t), 6.09-6.31 (1H, m), 7.29-7.43 (1H, m), 8.02 (1H, dd), 8.18 (1H, d), 8.49 (1H, ddd), 8.56 (1H, d), 8.77 (1H, d), 8.97 (1H, s). Mass Spectrum: m/z (ES+) [M+H]+=351

Intermediate X5

NMR Spectrum: $^1$H NMR (300 MHz, DMSO-d$_6$) δ 1.77-2.01 (2H, m), 2.46 (2H, ddt), 3.09 (2H, pd), 3.51 (3H, s), 5.53 (1H, p), 7.32-7.44 (1H, m), 7.96 (1H, dd), 8.15 (1H, d), 8.43-8.54 (2H, m), 8.75 (1H, d), 8.91 (1H, s). Mass Spectrum: m/z (ES+) [M+H]+=349.

The preparation of the bromo intermediates required for the above reactions have been described previously.

Example 61

8-[2-Fluoro-6-(3-pyrrolidin-1-ylpropoxy)-3-pyridyl]-3-methyl-1-[(3S)-tetrahydropyran-3-yl]imidazo[4,5-c]quinolin-2-one

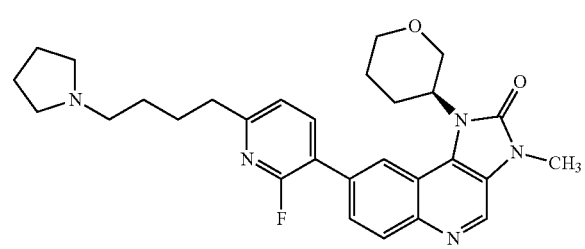 [SMILES: Cn1c(=O)n([C@H]2CCCOC2)c2c3cc(-c4ccc(CCCCN5CCCC5)nc4F)ccc3ncc21]

A solution of 3-(pyrrolidin-1-yl)propan-1-ol (0.047 g, 0.36 mmol) in THF (2 mL) was added slowly to a stirred suspension of sodium hydride (0.038 g, 0.96 mmol) in THF (2.0 mL) and the resulting suspension stirred at r.t. for 30 minutes. A solution of 8-(2,6-difluoro-3-pyridyl)-3-methyl-1-[(3S)-tetrahydropyran-3-yl]imidazo[4,5-c]quinolin-2-one (0.12 g, 0.34 mmol) in DMF (2 mL) was added slowly and the reaction stirred overnight. Water was added and the mixture stirred for 30 minutes before being extracted with EtOAc (50 mL). The organics were washed with sat. brine (25 mL), dried and evaporated to give crude product. The crude product was purified by FCC, elution gradient 0 to 10%((1% NH$_3$ in MeOH) in DCM, to afford the desired material as a white solid (0.005 g, 4%). NMR Spectrum: $^1$H NMR (500 MHz, CDCl$_3$) δ 0.8-0.92 (1H, m), 1.21-1.29 (1H, m), 1.88-1.97 (2H, m), 1.99-2.1 (4H, m), 2.23 (1H, d), 2.26-2.36 (2H, m), 2.77 (1H, qd), 2.9-3.16 (4H, m), 3.53-3.56 (1H, m), 3.57 (3H, s), 3.98-4.09 (1H, m), 4.12-4.21 (1H, m), 4.45 (2H, t), 4.53 (1H, t), 4.9-5.01 (1H, m), 6.80 (1H, dd), 7.75 (1H, d), 7.93 (1H, dd), 8.22 (1H, d), 8.42 (1H, s), 8.71 (1H, s). Mass Spectrum: m/z (ES+) [M+H]+=506.

The preparation of 8-(2,6-difluoro-3-pyridyl)-3-methyl-1-[(3S)-tetrahydropyran-3-yl]imidazo[4,5-c]quinolin-2-one is described below:

Intermediate D5: 8-(2,6-difluoro-3-pyridyl)-3-methyl-1-[(3S)-tetrahydropyran-3-yl]imidazo[4,5-c]quinolin-2-one

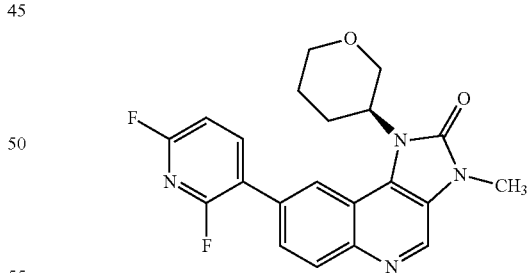

(2,6-Difluoropyridin-3-yl)boronic acid (158 mg, 0.99 mmol) and 8-bromo-3-methyl-1-[(3S)-oxan-3-yl]imidazo[5,4-c]quinolin-2-one (300 mg, 0.83 mmol) were suspended in dioxane (8 mL) and 2M K$_2$CO$_3$ (2.071 mL, 4.14 mmol). The mixture was degassed with nitrogen and dichloro[1,1'-bis(di-tert-butylphosphino)ferrocene]palladium(II) (27.0 mg, 0.04 mmol) added. The resulting suspension was heated at 80° C. for 1 h in a microwave reactor. The reaction mixture was diluted with EtOAc then washed with water (20 mL), brine and the organic phase dried over MgSO$_4$, filtered and concentrated in vacuo. The crude product was purified by FCC, elution gradient 0 to 10% MeOH in DCM, to afford the desired material as a brown solid (196 mg, 60%). NMR Spectrum: $^1$H NMR (500 MHz, DMSO-$d_6$) δ 1.82 (2H, hept), 2.15 (1H, d), 2.55-2.67 (1H, m), 3.36-3.44 (1H, m), 3.51 (3H, s), 3.92 (1H, d), 4.06-4.14 (1H, m), 4.29 (1H, t), 4.91 (1H, ddd), 7.42 (1H, dd), 7.85-7.91 (1H, m), 8.19 (1H, d), 8.47 (1H, s), 8.56 (1H, dt), 8.95 (1H, s). Mass Spectrum: m/z (ES+) [M+H]+=397.

The preparation of 8-bromo-3-methyl-1-[(3S)-oxan-3-yl]imidazo[5,4-c]quinolin-2-one has been described previously.

Examples 62 & 63

8-[6-[3-(Dimethylamino)propoxy]-3-pyridyl]-7-fluoro-1-[(1R,3R)-3-methoxycyclopentyl]-3-methyimidazo[4,5-c]quinolin-2-one and 8-[6-[3-(Dimethylamino)propoxy]-3-pyridyl]-7-fluoro-1-[(1S,3S)-3-methoxycyclopentyl]-3-methyl-imidazo[4,5-c]quinolin-2-one

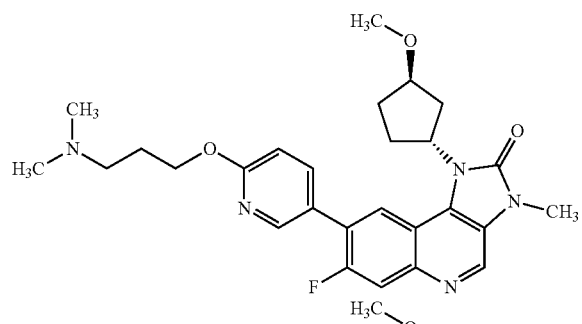

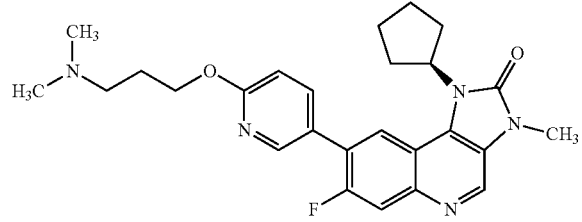

8-bromo-7-fluoro-1-[(1R,3R)-3-methoxycyclopentyl]-3-methyl-imidazo[4,5-c]quinolin-2-one: 8-bromo-7-fluoro-1-[(1S,3S)-3-methoxycyclopentyl]-3-methyl-imidazo[4,5-c]quinolin-2-one (1:1 mixture) (400 mg, 1.01 mmol). N,N-dimethyl-3-[5-(4,4,5,5-tetramethyl-1,3,2-dioxaborolan-2-yl)pyridin-2-yl]oxypropan-1-amine (227 mg, 1.01 mmol) and chloro(2-dicyclohexylphosphino-2',4',6'-triisopropyl-1,1'-biphenyl)[2-(2'-amino-1,1'-biphenyl)]palladium(II) (160 mg, 0.20 mmol) were suspended in a mixture of dioxane (5 mL) and water (0.5 mL) and Cs$_2$CO$_3$ (661 mg, 2.03 mmol) added. The reaction was heated to 120° C. for 1 h in the microwave reactor then allowed to cool. The reaction mixture was evaporated to dryness and redissolved in EtOAc (100 mL), washed sequentially with water (2×20 mL), the organic layer dried over Na$_2$SO$_4$, filtered and evaporated to afford crude product. The crude product was purified by preparative HPLC, using decreasingly polar mixtures of water (containing 0.03% NH$_3$) and MeCN as eluents, to afford the desired material as a racemic mixture. The mixture was purified by preparative chiral-HPLC on a Chiralpak IA column, eluting isocratically with 10% isopropyl alcohol in heptane (modified with 0.2% diethylamine) as eluent to deliver the two separated isomers.

Example 62

Isomer 1 (12 mg) NMR Spectrum: $^1$H NMR (400 MHz, DMSO-d6) δ 1.73-1.85 (1H, m), 1.84-1.96 (2H, m), 2.09-2.26 (9H, s), 2.35-2.50 (4H, m), 3.21-3.26 (3H, s), 3.45-3.58 (3H, s), 4.05-4.14 (1H, m), 4.33-4.42 (2H, m), 5.45-5.56 (1H, m), 6.97-7.04 (4 (1H, m), 7.90-7.98 (1H, m), 8.01-8.09 (1H, m), 8.26-8.33 (1H, m), 8.48-8.54 (1H, m), 8.91-8.96 (1H, s). Mass Spectrum: m/z (ES+) [M+H]+=494.

Example 63

Isomer 2 (12 mg) NMR Spectrum: $^1$H NMR (400 MHz, DMSO-d6) δ 1.75-1.82 (1H, m), 1.85-1.97 (2H, m), 2.11-2.26 (9H, s), 2.37-2.50 (4H, m), 3.21-3.26 (3H, s), 3.46-3.56 (3H, s), 4.07-4.13 (1H, m), 4.33-4.42 (2H, m), 5.47-5.58 (1H, m), 6.97-7.04 (1H, m), 7.90-7.98 (1H, m), 8.01-8.09 (1H, m), 8.27-8.34 (1H, m), 8.49-8.54 (1H, s), 8.91-8.96 (1H, s). Mass Spectrum: m/z (ES+) [M+H]+=494.

The preparation of 8-bromo-7-fluoro-1-[(1R,3R)-3-methoxycyclopentyl]-3-methyl-imidazo[4,5-c]quinolin-2-one:8-bromo-7-fluoro-1-[(1S,3S)-3-methoxycyclopentyl]-3-methyl-imidazo[4,5-c]quinolin-2-one (1:1 mixture) is described below:

Intermediate Y1: 8-bromo-7-fluoro-1-[(1R,3R)-3-methoxycyclopentyl]-3-methyl-imidazo[4,5-c]quinolin-2-one and 8-bromo-7-fluoro-1-[(1S,3S)-3-methoxycyclopentyl]-3-methyl-imidazo[4,5-c]quinolin-2-one (1:1 mixture)

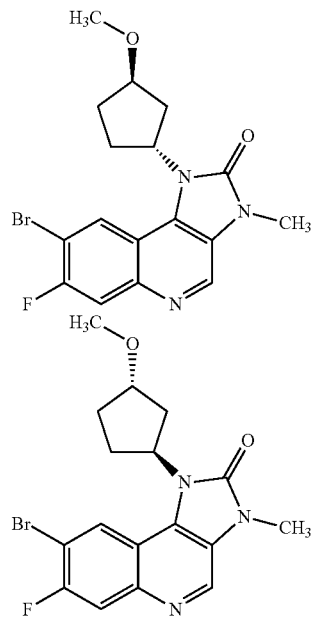

A mixture of 8-bromo-7-fluoro-1-[(1R,3R)-3-methoxycyclopentyl]-3H-imidazo[4,5-c]quinolin-2-one:8-bromo-7-fluoro-1-[(1S,3S)-3-methoxycyclopentyl]-3H-imidazo[4,5-c]quinolin-2-one (1:1 mixture) (2.8 g, 7.33 mmol), sodium hydroxide (440 mg, 11.00 mmol), tetrabutylammonium bromide (240 mg, 0.75 mmol) and methyl iodide (1.6 g, 11.27 mmol) in DCM (150 mL) and water (100 mL) was stirred for 12 h at r.t. The resulting mixture was concentrated in vacuo and the residue triturated with water. The solids were collected by filtration and dried to afford the desired material as a white solid (2.5 g, 86%). NMR Spectrum: $^1$H NMR (300 MHz, DMSO-d6) δ 1.76-1.86 (1H, m), 2.11-2.32 (4H, m), 2.41-2.44 (1H, m), 3.27 (3H, s), 3.30 (3H, s), 4.12-4.15 (1H, m), 5.38-5.45 (1H, m), 7.96 (1H, d), 8.53 (1H, d), 8.94 (1H, s). Mass Spectrum: m/z (ES+) [M+H]+=394.

Intermediate Y2: 8-bromo-7-fluoro-1-[(1R,3R)-3-methoxycyclopentyl]-3H-imidazo[4,5-c]quinolin-2-one and 8-bromo-7-fluoro-1-[(1S,3S)-3-methoxycyclopentyl]-3H-imidazo[4,5-c]quinolin-2-one (1:1 mixture)

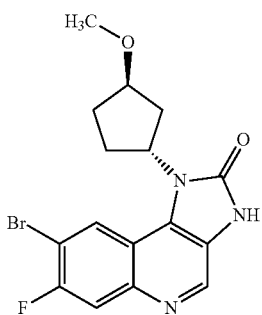

Intermediate Y3: 6-bromo-7-fluoro-4-[[(1R,3R)-3-methoxycyclopentyl]amino]quinoline-3-carboxylic acid and 6-bromo-7-fluoro-4-[[(1S,3S)-3-methoxycyclopentyl]amino]quinoline-3-carboxylic acid (1:1 mixture)

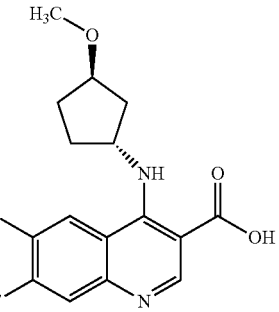

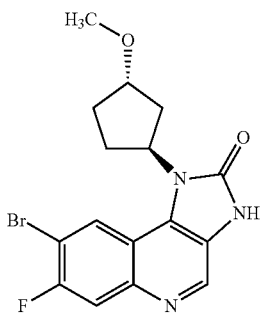

A mixture of 6-bromo-7-fluoro-4-[[(1R,3R)-3-methoxycyclopentyl]amino]quinoline-3-carboxylic acid:6-bromo-7-fluoro-4-[[(1S,3S)-3-methoxycyclopentyl]amino]quinoline-3-carboxylic acid (1:1 mixture) (2.9 g, 7.53 mmol) and triethylamine (2.3 g, 22.73 mmol) in DMA (20 mL) was stirred at r.t. for 30 mins. Diphenyl phosphorazidate (2.5 g, 9.09 mmol) was added and the resulting solution stirred for 2 h at 60° C. The reaction mixture was allowed to cool and the solids collected by filtration. The solid was dried in an oven under reduced pressure to afford the desired material as a white solid (2.8 g, 97%). NMR Spectrum: $^1$H NMR (300 MHz, DMSO-d6) δ 1.78-1.88 (1H, m), 2.11-2.31 (4H, m), 2.41-2.45 (1H, m), 3.27 (3H, s), 4.08-4.15 (1H, m), 5.34-5.39 (1H, m), 7.92 (1H, d), 8.51 (1H, d), 8.68 (1H, s). Mass Spectrum: m/z (ES+) [M+H]+=380.

A mixture of ethyl 6-bromo-7-fluoro-4-[[(1R,3R)-3-methoxycyclopentyl]amino]quinoline-3-carboxylate:ethyl 6-bromo-7-fluoro-4-[[(1S,3S)-3-methoxycyclopentyl]amino]quinoline-3-carboxylate (1:1 mixture) (3.4 g, 8.23 mmol) and 2N sodium hydroxide (12 mL) in MeOH (15 mL) and TI-IF (15 mL) was stirred for 12 h at r.t. The pH of the solution was adjusted to 3 with 1M HCl and the resultant solid collected by filtration and dried to afford the desired material as a white solid (2.9 g, 91%). NMR Spectrum: $^1$H NMR (300 MHz, DMSO-d6) δ 1.61-1.71 (2H, m), 1.76-1.86 (1H, m), 1.92-2.03 (1H, m), 2.11-2.26 (2H, m), 3.21 (3H, s), 3.86-3.96 (1H, m), 4.56-4.64 (1H, m), 7.70 (1H, d), 8.56 (1H, d), 8.88 (1H, s), 13.31 (1H, s). Mass Spectrum: m/z (ES+) [M+H]+=383.

Intermediate Y4: Ethyl 6-bromo-7-fluoro-4-[[(1R,3R)-3-methoxycyclopentyl]amino]quinoline-3-carboxylate and Ethyl 6-bromo-7-fluoro-4-[[(1S,3S)-3-methoxycyclopentyl]amino]quinoline-3-carboxylate (1:1 mixture)

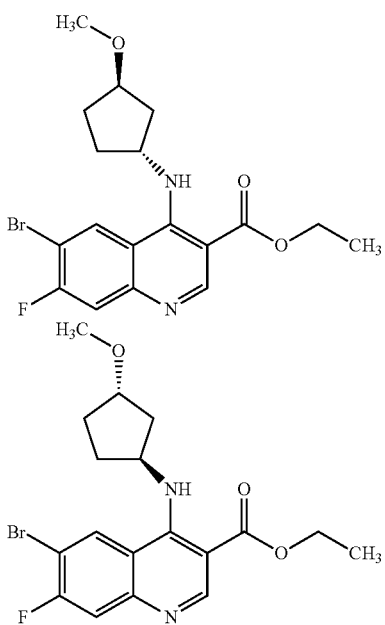

A mixture of ethyl 6-bromo-4-chloro-7-fluoroquinoline-3-carboxylate (2 g, 6.01 mmol), (1R,3R)-3-methoxycyclopentanamine hydrochloride and (1S,3S)-3-methoxycyclopentanamine hydrochloride (1:1 mixture) (1.4 g, 9.21 mmol) and DIPEA (1.6 g, 12.38 mmol) in DMA (10 mL) was stirred for 2 h at 80° C. The reaction mixture was allowed to cool and the residue triturated with water. The solids were collected by filtration and dried to afford the desired material as a white solid (2.4 g, 97%). Mass Spectrum: m/z (ES+) [M+H]+=411.

The preparation of ethyl 6-bromo-4-chloro-7-fluoroquinoline-3-carboxylate has been described previously.

Examples 64 & 65

1-[(1R,3R)-3-Methoxycyclopentyl]-3-methyl-8-[6-[3-(1-piperidyl)propoxy]-3-pyridyl]imidazo[4,5-c]quinolin-2-one and 1-[(1S,3S)-3-Methoxycyclopentyl]-3-methyl-8-[6-[3-(1-piperidyl)propoxy]-3-pyridyl]imidazo[4,5-c]quinolin-2-one

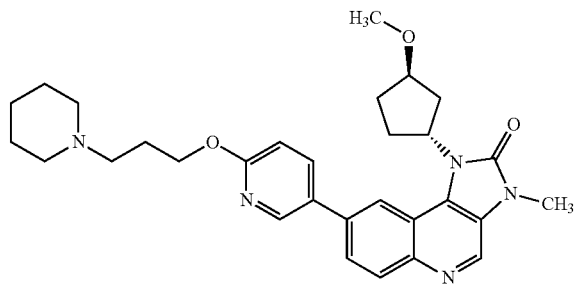

-continued

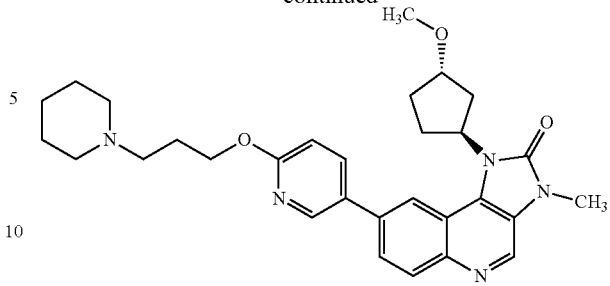

A mixture of 3-(piperidin-1-yl)propan-1-ol (175 mg, 1.22 mmol) and NaH (122 mg, 3.06 mmol) in THF (10 mL) was stirred under nitrogen at 0° C. for 30 min then 8-(6-fluoro-3-pyridyl)-1-[(1R,3R)-3-methoxycyclopentyl]-3-methyl-imidazo[4,5-c]quinolin-2-one:8-(6-fluoro-3-pyridyl)-1-[(1S,3S)-3-methoxycyclopentyl]-3-methyl-imidazo[4,5-c]quinolin-2-one (1:1 mixture) (400 mg, 1.02 mmol) added. The resulting mixture was stirred at r.t. for 1 h then was quenched with water (50 mL), extracted with EtOAc (3×50 mL), the organic layer was dried over Na₂SO₄, filtered and evaporated to afford yellow oil. The crude liquid was triturated with heptane to give the desired material as a mixture of isomers (350 mg, 66.6%) as a yellow solid. The racemic mixture was purified by preparative chiral-HPLC on an AD column, eluting with 10% isopropyl alcohol in hexane (modified with 0.1% diethylamine) as eluent, and fractions containing the separated isomers evaporated to dryness.

Example 64

Isomer 1 (120 mg) NMR Spectrum: ¹H NMR (300 MHz, MeOH-d4) δ 1.61-1.71 (2H, m), 1.76-1.86 (1H, m), 1.92-2.03 (1H, m), 2.11-2.26 (2H, m), 3.21 (3H, s), 3.86-3.9 (1H, m), 4.56-4.64 (1H, m), 7.70 (1H, d), 8.56 (1H, d), 8.88 (1H, s), 13.31 (1H, s). Mass Spectrum: m/z (ES+) [M+H]+=516.

Example 65

Isomer 2 (120 mg) NMR Spectrum: ¹H NMR (300 MHz, MeOH-d4) δ 1.53 (2H, q), 1.67 (4H, p), 1.89-2.14 (3H, m), 2.23-2.41 (3H, m), 2.47-2.71 (8H, m), 3.40 (3H, s), 3.58 (3H, s), 4.17-4.18 (1H, m), 4.41 (2H, t), 5.62 (1H, p), 6.94 (1H, d), 7.88 (1H, d), 8.02-8.17 (2H, m), 8.38 (1H, d), 8.51 (1H, d), 8.76 (1H, s). Mass Spectrum: m/z (ES+) [M+H]+=516.

The following compounds were prepared in an analogous fashion from 8-(6-fluoro-3-pyridyl)-1-[(1R,3R)-3-methoxy-cyclopentyl]-3-methyl-imidazo[4,5-c]quinolin-2-one:8-(6-fluoro-3-pyridyl)-1-[(1S,3 S)-3-methoxycyclopentyl]-3-methyl-imidazo[4,5-c]quinolin-2-one (1:1 mixture) and the appropriate alcohol.

| Example | Structure | Name |
|---|---|---|
| 66 & 67* | 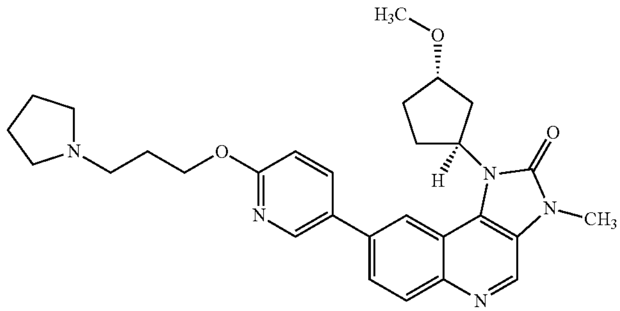 [SMILES: CO[C@H]1CC[C@H](n2c(=O)n(C)c3cnc4ccc(-c5ccc(OCCCN6CCCC6)nc5)cc4c32)C1] | 1-[(1S,3S)-3-methoxycyclopentyl]-3-methyl-8-[6-(3-pyrrolidin-1-ylpropoxy)-3-pyridyl]imidazo[4,5-c]quinolin-2-one and |
| | | 1-[(1R,3R)-3-methoxycyclopentyl]-3-methyl-8-[6-(3-pyrrolidin-1-ylpropoxy)-3-pyridyl]imidazo[4,5-c]quinolin-2-one |

*The reaction was stirred at r.t. for 5 h. The isomers were separated by preparative chiral-HPLC on an AD column, eluting with 10% isopropyl alcohol in hexane (modified with 0.1% diethylamine) as eluent.

Example 66

Isomer 1 (105 mg) NMR Spectrum: $^1$H NMR (300 MHz. CDCl$_3$) δ 1.91-2.05 (5H, m), 2.14-2.18 (2H, m), 2.22-2.46 (3H, m), 2.52-2.83 (8H, m), 3.39 (3H, s), 3.62 (3H, s), 4.20 (1H, p), 4.47 (2H, t), 5.62 (1H, q), 6.91 (1H, d), 7.83 (1H, d), 7.94 (1H, d), 8.24 (1H, d), 8.36 (1H, d), 8.53 (1H, d), 8.73 (1H, s). Mass Spectrum: m/z (ES+) [M+H]+502.

Example 67

Isomer 2 (105 mg) NMR Spectrum: $^1$H NMR (300 MHz, CDCl$_3$) δ 1.80-2.00 (5H, m), 2.12-2.18 (2H, m), 2.35-2.55 (3H, m), 2.63-2.83 (8H, m), 3.40 (3H, s), 3.62 (3H, s), 4.20 (1H, t), 4.47 (2H, t), 5.61 (1H, p), 6.91 (1H, d), 7.83 (1H, d), 7.94 (1H, d), 8.25 (1H, d), 8.36 (1H, d), 8.53 (1H, d), 8.73 (1H, s). Mass Spectrum: m/z (ES+) [M+H]+=502

The preparation of 8-(6-fluoro-3-pyridyl)-1-[(1R,3R)-3-methoxycyclopentyl]-3-methyl-imidazo[4,5-c]quinolin-2-one:8-(6-fluoro-3-pyridyl)-1-[(1S,3S)-3-methoxycyclopentyl]-3-methyl-imidazo[4,5-c]quinolin-2-one (1:1 mixture) is described below.

Intermediate O5: 8-(6-Fluoro-3-pyridyl)-1-[(1R, 3R)-3-methoxycyclopentyl]-3-methyl-imidazo[4,5-c]quinolin-2-one and 8-(6-fluoro-3-pyridyl)-1-[(1S, 3S)-3-methoxycyclopentyl]-3-methyl-imidazo[4,5-c] quinolin-2-one (1:1 mixture)

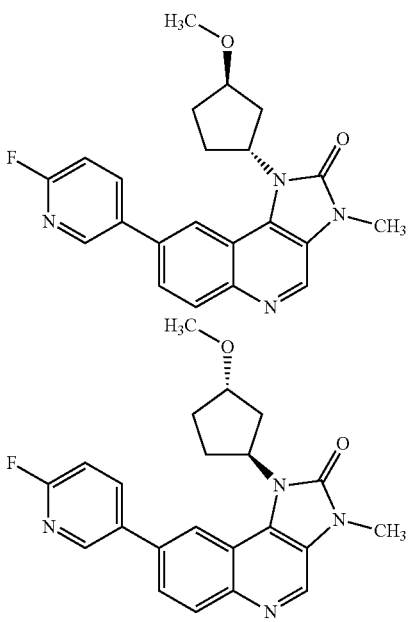

A mixture of 8-bromo-1-[(1R,3R)-3-methoxycyclopentyl]-3-methylimidazo[4,5-c]quinolin-2-one:8-bromo-1-[(1S,3S)-3-methoxycyclopentyl]-3-methylimidazo[4,5-c]quinolin-2-one (1:1 mixture) (1.5 g, 3.99 mmol), (6-fluoropyridin-3-yl)boronic acid (0.674 g, 4.78 mmol) and chloro(2-dicyclohexylphosphino-2',4',6'-triisopropyl-1,1'-biphenyl)[2-(2'-amino-1,1'-biphenyl)]palladium(II) (0.314 g, 0.40 mmol) in dioxane:water (10:1 mixture) (16.5 mL) was heated to 120° C. for 45 mins in the microwave reactor then allowed to cool and concentrated in vacuo. The crude product was purified by FCC, elution gradient 0 to 10% MeOH in DCM, to afford the desired material as a yellow solid (1.20 g, 77%). NMR Spectrum: $^1$H NMR (400 MHz, CDCl$_3$) δ 1.91-1.99 (1H, m), 2.21-2.36 (3H, m), 2.58-2.78 (2H, m), 3.38 (3H, s), 3.62 (3H, s), 4.15-4.17 (1H, m), 5.52-5.65 (1H, m), 7.12 (1H, dd), 7.83 (1H, dd), 8.13 (1H, td), 8.31 (1H, d), 8.40 (1H, d), 8.59 (1H, d), 8.76 (1H, s). Mass Spectrum: m/z (ES+) [M+H]+=393.

The preparation of 8-bromo-1-[(1R,3R)-3-methoxycyclopentyl]-3-methylimidazo[4,5-c]quinolin-2-one:8-bromo-1-[(1S,3S)-3-methoxycyclopentyl]-3-methylimidazo[4,5-c]quinolin-2-one (1:1 mixture) has been described previously.

Examples 68 & 69

8-[6-[3-(Dimethylamino)propoxy]-2-fluoro-3-pyridyl]-1-[(1R,3R)-3-methoxycyclopentyl]-3-methyl-imidazo[4,5-c]quinolin-2-one and 8-[6-[3-(dimethylamino)propoxy]-2-fluoro-3-pyridyl]-1-[(1S,3S)-3-methoxycyclopentyl]-3-methyl-imidazo[4,5-c]quinolin-2-one

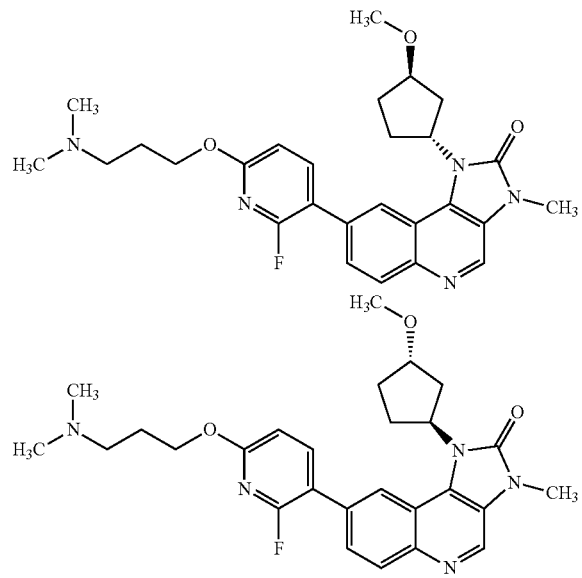

Chloro(2-dicyclohexylphosphino-2',4',6'-triisopropyl-1,1'-biphenyl)[2-(2'-amino-1,1'-biphenyl)]palladium(II) (107 mg, 0.13 mmol) was added to a 3-[6-fluoro-5-(4,4,5,5-tetramethyl-1,3,2-dioxaborolan-2-yl)pyridin-2-yl]oxy-N,N-dimethylpropan-1-amine (474 mg, 1.46 mmol), 8-bromo-1-[(1R,3R)-3-methoxycyclopentyl]-3-methylimidazo[4,5-c]quinolin-2-one:8-bromo-1-[(1S,3S)-3-methoxycyclopentyl]-3-methylimidazo[4,5-c]quinolin-2-one (1:1 mixture) (500 mg, 1.33 mmol) and cesium carbonate (1299 mg, 3.99 mmol) in 1,4-dioxane (10 mL) and water (2.5 mL). The resulting mixture was stirred at 80° C. for 5 h then allowed to cool. The crude product was purified by C18-FCC, elution gradient 5 to 50% MeOH in water, to afford the desired material as a mixture of isomers (350 mg, 53.4%). The racemic mixture was purified by preparative chiral HPLC on a Chiralcel IC column, eluting with isopropyl alcohol, and fractions containing the separated isomers evaporated to dryness.

Example 68

Isomer 1 (50 mg) NMR Spectrum: $^1$H NMR (300 MHz, MeOH-d$_4$) δ 1.90-1.96 (1H, m), 2.12-2.13 (2H, m), 2.20-2.31 (3H, m), 2.47-2.50 (1H, m), 2.54 (6H, s), 2.68-2.70 (1H, m), 2.78-2.90 (2H, m), 3.36 (3H, s), 3.60 (3H, s), 4.17-4.18 (1H, m), 4.43 (2H, t), 5.55-5.67 (1H, m), 6.89 (1H, d), 7.80-7.91 (1H, m), 8.07-8.20 (2H, m), 8.48 (1H, s), 8.82 (1H, s). Mass Spectrum: m/z (ES+) [M+H]+=494.

Example 69

Isomer 2 (45 mg) (contaminated with 0.38 equivalents of diethylamine) NMR Spectrum: $^1$H NMR (300 MHz, MeOH-d4) δ 1.93-1.95 (1H, m), 2.29-2.51 (6H, m), 2.60-2.77 (2H, m), 2.95 (6H, s), 3.36-3.38 (4H, s), 3.60 (3H, s), 4.17-4.18 (1H, m), 4.48 (2H, t), 5.62-5.63 (1H, m), 6.92 (1H, d), 7.85 (1H, d), 8.15-8.20 (2H, m), 8.48 (1H, s), 8.82 (1H, s). Mass Spectrum: m/z (ES+) [M+H]+=494.

The preparation of 8-bromo-1-[(1R,3R)-3-methoxycyclopentyl]-3-methylimidazo[4,5-c]quinolin-2-one:8-bromo-1-[(1S,3S)-3-methoxycyclopentyl]-3-methylimidazo[4,5-c]quinolin-2-one (1:1 mixture) has been described previously.

Examples 70 & 71

8-[6-[3-(dimethylamino)propoxy]-3-pyridyl]-7-fluoro-1-[(1R,3S)-3-methoxycyclopentyl]-3-methyl-imidazo[4,5-c]quinolin-2-one and 8-[6-[3-(dimethylamino)propoxy]-3-pyridyl]-7-fluoro-1-[(1S,3R)-3-methoxycyclopentyl]-3-methyl-imidazo[4,5-c]quinolin-2-one

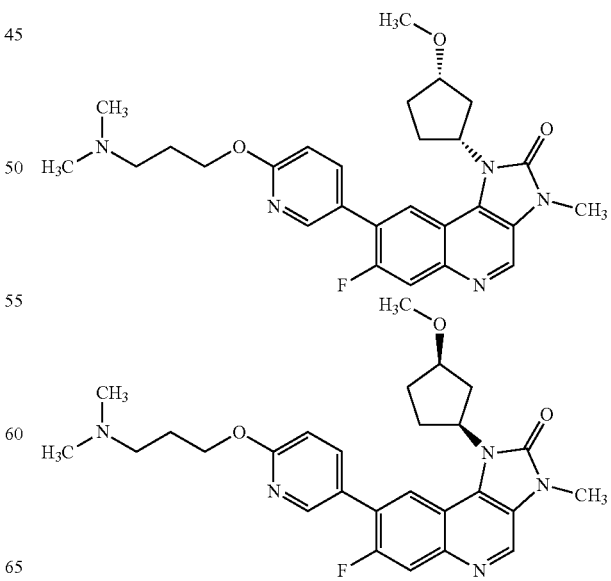

8-Bromo-7-fluoro-1-[(1R,3S)-3-methoxycyclopentyl]-3-methyl-imidazo[4,5-c]quinolin-2-one: 8-bromo-7-fluoro-1-[(1S,3R)-3-methoxycyclopentyl]-3-methyl-imidazo[4,5-c]quinolin-2-one (1:1 mixture) (500 mg, 1.27 mmol), N,N-dimethyl-3-[5-(4,4,5,5-tetramethyl-1,3,2-dioxaborolan-2-yl)pyridin-2-yl]oxypropan-1-amine (284 mg, 1.27 mmol) and chloro(2-dicyclohexylphosphino-2',4',6'-triisopropyl-1,1'-biphenyl)[2-(2'-amino-1,1'-biphenyl)]palladium(II) (200 mg, 0.25 mmol) were suspended in a mixture of dioxane:water (10:1 mixture, 20 mL) and Cs$_2$CO$_3$ (826 mg, 2.54 mmol) added. The reaction was heated to 120° C. for 1 h in the microwave reactor then allowed to cool. The reaction mixture was evaporated to dryness and redissolved in EtOAc (100 mL), washed sequentially with water (2×20 mL), the organic layer dried over Na$_2$SO$_4$, filtered and evaporated to afford crude product. The crude product was purified by preparative HPLC, using decreasingly polar mixtures of water (containing 0.03% NH$_3$) and MeCN as eluents, to afford the desired material as a racemic mixture. The mixture was purified by preparative chiral-HPLC on a Chiralpak IA column, eluting isocratically with 10% IPA in heptane (modified with 0.2% diethylamine) as eluent to deliver the two separated isomers.

Example 70

Isomer 1 (250 mg) NMR Spectrum: $^1$H NMR (400 MHz, DMSO-d$_6$) δ 1.83-2.06 (5H, m), 2.14-2.19 (6H, s), 2.26-2.51 (5H, m), 3.02-3.07 (3H, s), 3.47-3.64 (3H, s), 3.86-3.96 (1H, m), 4.33-4.41 (2H, m), 5.26-5.40 (1H, m), 6.94-7.01 (1H, d), 7.89-7.97 (1H, d), 7.98-8.06 (1H, m), 8.39-8.49 (2H, m), 8.92-8.97 (1H, s). Mass Spectrum: m/z (ES+) [M+H]+=494.

Example 71

Isomer 2 (250 mg) NMR Spectrum: $^1$H NMR (400 MHz, DMSO-d$_6$) δ 1.83-2.08 (5H, m), 2.13-2.18 (5H, s), 2.24-2.56 (4H, m), 3.02-3.07 (3H, s), 3.50-3.55 (3H, s), 3.85-3.96 (1H, m), 4.33-4.41 (2H, m), 5.25-5.39 (1H, m), 6.94-7.01 (1H, m), 7.87-7.95 (1H, m), 7.97-8.05 (1H, m), 8.35-8.50 (2H, m), 8.91-8.96 (1H, s). Mass Spectrum: m/z (ES+) [M+H]+= 494.

The preparation of 8-bromo-7-fluoro-1-[(1R,3S)-3-methoxycyclopentyl]-3-methyl-imidazo[4,5-c]quinolin-2-one and 8-bromo-7-fluoro-1-[(1S,3R)-3-methoxycyclopentyl]-3-methyl-imidazo[4,5-c]quinolin-2-one (1:1 mixture) is described below:

Intermediate Z1: 8-Bromo-7-fluoro-1-[(1R,3S)-3-methoxycyclopentyl]-3-methyl-imidazo[4,5-c]quinolin-2-one and 8-bromo-7-fluor-1-[(1S,3R)-3-methoxycyclopentyl]-3-methyl-imidazo[4,5-c]quinolin-2-one (1:1 mixture)

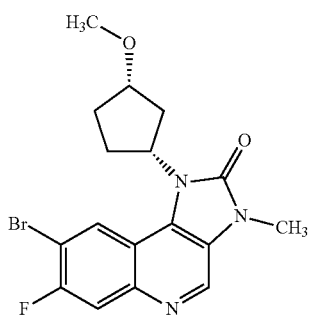

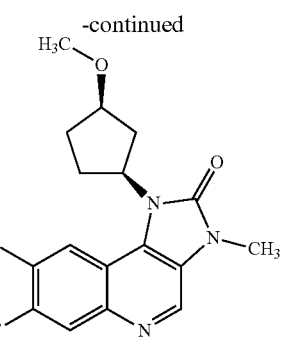

NaH (0.213 g, 8.88 mmol) was added portionwise to 8-bromo-7-fluoro-1-[(1R,3S)-3-hydroxycyclopentyl]-3H-imidazo[4,5-c]quinolin-2-one:8-bromo-7-fluoro-1-[(1S,3R)-3-hydroxycyclopentyl]-3H-imidazo[4,5-c]quinolin-2-one (1:1 mixture) (1.3 g, 3.55 mmol) in DMF (10 mL) at −20° C. under nitrogen and the resulting mixture stirred at 0° C. for 30 minutes. Methyl iodide (0.444 mL, 7.10 mmol) was added dropwise to the mixture at −20° C. under nitrogen and the resulting mixture was stirred at r.t. for 16 h. The reaction mixture was poured into water (20 mL), the solid filtered and dried to afford the desired material as a brown solid (1.30 g, 93%). NMR Spectrum: $^1$H NMR (400 MHz, DMSO-d$_6$) δ 1.96-2.02 (3H, t), 2.22-2.51 (3H, m), 3.30-3.32 (3H, s), 3.97 (1H, m), 5.26-5.31 (1H, m), 7.89-7.52 (1H, d), 8.74 (1H, d), 8.93 (1H, s). Mass Spectrum: m/z (ES+) [M+H]+ 396.

Intermediate Z2: 8-Bromo-7-fluoro-1-[(1R,3S)-3-hydroxycyclopentyl]-3H-imidazo[4,5-c]quinolin-2-one and 8-bromo-7-fluoro-1-[(1S,3R)-3-hydroxycyclopentyl]-3H-imidazo[4,5-c]quinolin-2-one (1:1 mixture)

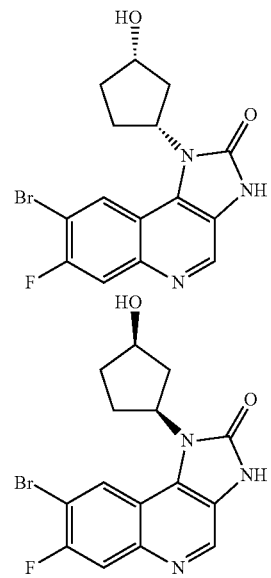

A mixture of triethylamine (2.105 mL, 15.10 mmol) and 6-bromo-7-fluoro-4-[[(1R,3S)-3-hydroxycyclopentyl]amino]quinoline-3-carboxylic acid: 6-bromo-7-fluoro-4-[[(1S,3R)-3-hydroxycyclopentyl]amino]quinoline-3-carboxylic acid (1:1 mixture) (2 g, 5.03 mmol) in DMF (10 mL)

was stirred for 1 h. Diphenyl phosphorazidate (1.663 g, 6.04 mmol) was added and the resulting solution stirred overnight at 60° C. The reaction mixture was poured into water, the solids collected by filtration and dried to afford the desired material as a yellow solid (1.3 g, 71%). NMR Spectrum: $^1$H NMR (400 MHz, DMSO-$d_6$) δ 1.88 (2H, dt), 1.97-2.10 (1H, m), 2.17 (1H, m), 2.38 (2H, m), 4.23-4.30 (1H, m), 5.27 (1H, m), 7.88 (1H, m), 8.69 (1H, s), 8.80 (1H, d), 11.77 (1H s). Mass Spectrum: m/z (ES+) [M+H]+=366.

Intermediate Z3: 6-bromo-7-fluoro-4-[[(1R,3S)-3-hydroxycyclopentyl]amino]quinoline-3-carboxylic acid and 6-bromo-7-fluoro-4-[[(1S,3R)-3-hydroxycyclopentyl]amino]quinoline-3-carboxylic acid (1:1 mixture)

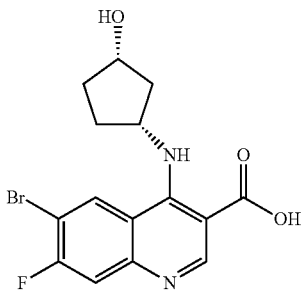

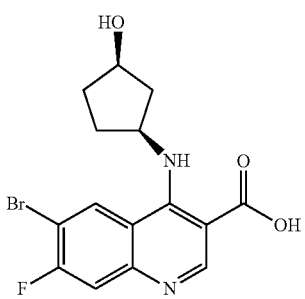

A mixture of ethyl 6-bromo-7-fluoro-4-[[(1R,3S)-3-hydroxycyclopentyl]amino]quinoline-3-carboxylate:ethyl 6-bromo-7-fluoro-4-[[(1S,3R)-3-hydroxycyclopentyl]amino]quinoline-3-carboxylate (1:1 mixture) (3 g, 7.55 mmol) and sodium hydroxide (0.604 g, 15.10 mmol) in THF (10 mL) and water (5 mL) was stirred for 16 h at 60° C. The organics were removed in vacuo and the pH of the resultant mixture adjusted to 6-7 with 2M HCl. The resultant solid collected by filtration and dried to afford the desired material as a grey solid (2.0 g, 72%). NMR Spectrum: $^1$H NMR (400 MHz, DMSO-$d_6$) δ 1.68-1.82 (3H, m), 1.90-1.98 (1H, m), 2.26 (2H, m), 2.51 (4H, s), 4.26 (1H, s), 4.68 (1H, s), 7.86 (1H, d), 8.62 (1H, d), 8.93 (1H, s), 10.95 (1H, s). Mass Spectrum: m/z (ES+) [M+H]+=369.

Intermediate Z4: Ethyl 6-bromo-7-fluoro-4-[[(1R,3S)-3-hydroxycyclopentyl]amino]quinoline-3-carboxylate and ethyl 6-bromo-7-fluoro-4-[[(1S,3R)-3-hydroxycyclopentyl]amino]quinoline-3-carboxylate (1:1 mixture)

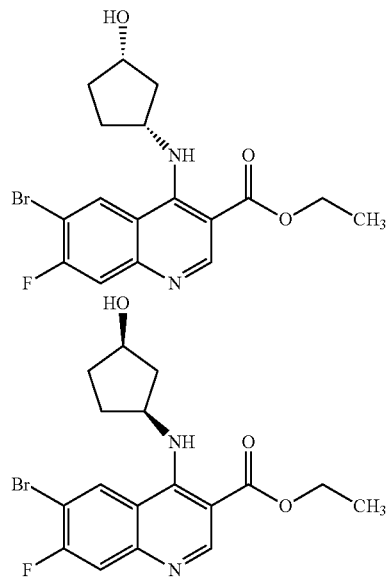

DIPEA (3.94 mL, 22.55 mmol) was added to a mixture of cis-3-aminocyclopentanol hydrochloride (1.49 g, 10.83 mmol) and ethyl 6-bromo-4-chloro-7-fluoroquinoline-3-carboxylate (3 g, 9.02 mmol) in DMA (20 mL) under nitrogen and the resulting mixture stirred at 100° C. for 6 h. The reaction mixture was poured into water (50 mL) and the solid filtered and dried to afford the desired material as brown oil (3.0 g, 84%). NMR Spectrum: $^1$H NMR (400 MHz, DMSO-$d_6$) δ 1.35 (3H, t), 1.67 (1H, d), 1.72-1.79 (2H, m), 1.81-1.92 (1H, m), 1.96 (3H, s), 2.19 (2H, ddt), 2.79 (3H, s), 2.95 (3H, s), 3.08 (1H, d), 4.23 (1H, s), 4.33 (2H, q), 4.45 (1H, s), 4.83 (1H, s), 7.69 (1H, dd), 8.52 (1H, d), 8.85 (1H, s), 9.25 (1H, d). Mass Spectrum: m/z (ES+) [M+H]+=397.

The preparation of ethyl 6-bromo-4-chloro-7-fluoroquinoline-3-carboxylate has been described previously.

Biological Assays

The following assays were used to measure the effects of the compounds of the present invention: a) ATM cellular potency assay; b) PI3K cellular potency assay; c) mTOR cellular potency assay; d) ATR cellular potency assay; e) mouse xenograft model. During the description of the assays, generally:
  i. The following abbreviations have been used: 4NQO=4-Nitroquinoline N-oxide; Ab=Antibody; BSA=Bovine Serum Albumin; $CO_2$=Carbon Dioxide; DMEM=Dulbecco's Modified Eagle Medium; DMSO=Dimethyl Sulphoxide; EDTA=Ethylenediaminetetraacetic Acid; EGTA=Ethylene Glycol Tetraacetic Acid; ELISA=Enzyme-linked Immunosorbent Assay; EMEM=Eagle's Minimal Essential Medium; FBS=Foetal Bovine Serum; h=Hour(s); HRP=Horseradish Peroxidase; i.p.=intraperitoneal;

PBS=Phosphate buffered saline; PBST=Phosphate buffered saline/Tween; TRIS=Tris(Hydroxymethyl) aminomethane; MTS reagent: [3-(4,5-dimethylthiazol-2-yl)-5-(3-carboxymethoxyphenyl)-2-(4-sulfophenyl)-2H-tetrazolium, inner salt, and an electron coupling reagent (phenazine methosulfate) PMS; s.c. sub-cutaneously.

ii. $IC_{50}$ values were calculated using a smart fitting model in Genedata. The $IC_{50}$ value was the concentration of test compound that inhibited 50% of biological activity.

Assay a): ATM Cellular Potency

Rationale:

Cellular irradiation induces DNA double strand breaks and rapid intermolecular autophosphorylation of serine 1981 that causes dimer dissociation and initiates cellular ATM kinase activity. Most ATM molecules in the cell are rapidly phosphorylated on this site after doses of radiation as low as 0.5 Gy, and binding of a phosphospecific antibody is detectable after the introduction of only a few DNA double-strand breaks in the cell.

The rationale of the pATM assay is to identify inhibitors of ATM in cells. HT29 cells are incubated with test compounds for 1 hr prior to X-ray-irradiation. 1 h later the cells are fixed and stained for pATM (Ser1981). The fluorescence is read on the arrayscan imaging platform.

Method Details:

HT29 cells (ECACC #85061109) were seeded into 384 well assay plates (Costar #3712) at a density of 3500 cells/well in 40 µl EMEM medium containing 1% L glutamine and 10% FBS and allowed to adhere overnight. The following morning compounds of Formula (I) in 100% DMSO were added to assay plates by acoustic dispensing. After 1 h incubation at 37° C. and 5% $CO_2$, plates (up to 6 at a time) were irradiated using the X-RAD 320 instrument (PXi) with equivalent to ~600 cGy. Plates were returned to the incubator for a further 1 h. Then cells were fixed by adding 20 µl of 3.7% formaldehyde in PBS solution and incubating for 20 minutes at r.t. before being washed with 50 µl/well PBS, using a Biotek EL405 plate washer. Then 20 µl of 0.1% Triton X100 in PBS was added and incubated for 20 minutes at r.t., to permeabalise cells. Then the plates were washed once with 50 µl/well PBS, using a Biotek EL405 plate washer.

Phospho-ATM Ser1981 antibody (Millipore #MAB3806) was diluted 10000 fold in PBS containing 0.05% polysorbate/Tween and 3% BSA and 20 µl was added to each well and incubated over night at r.t. The next morning plates were washed three times with 50 µl/well PBS, using a Biotek EL405 plate washer, and then 20 µl of secondary Ab solution, containing 500 fold diluted Alexa Fluor® 488 Goat anti-rabbit IgG (Life Technologies, A11001) and 0.002 mg/ml Hoechst dye (Life technologies #H-3570), in PBS containing 0.05% polysorbate/Tween and 3% BSA, was added. After 1 h incubation at r.t., the plates were washed three times with 50 µl/well PBS, using a Biotek EL405 plate washer, and plates were sealed and kept in PBS at 4° C. until read. Plates were read using an ArrayScan VTI instrument, using an XF53 filter with 10x objective. A two laser set up was used to analyse nuclear staining with Hoechst (405 nm) and secondary antibody staining of pSer1981 (488 nm).

Assay b): ATR Cellular Potency

Rationale:

ATR is a PI 3-kinase-related kinase which phosphorylates multiple substrates on serine or threonine residues in response to DNA damage or replication blocks. Chk1, a downstream protein kinase of ATR, plays a key role in DNA damage checkpoint control. Activation of Chk1 involves phosphorylation of Ser317 and Ser345 (the latter regarded as the preferential target for phosphorylation/activation by ATR). This was a cell based assay to measure inhibition of ATR kinase, by measuring a decrease in phosphorylation of Chk1 (Ser 345) in HT29 cells, following treatment with compound of Formula (I) and the UV mimetic 4NQO (Sigma #N8141).

Method Details:

HT29 cells (ECACC #85061109) were seeded into 384 well assay plates (Costar #3712) at a density of 6000 cells/well in 40 µl EMEM medium containing 1% L glutamine and 10% FBS and allowed to adhere overnight. The following morning compound of Formula (I) in 100% DMSO was added to assay plates by acoustic dispensing. After 1 h incubation at 37° C. and 5% $CO_2$, 40 µl of 3 mM 4NQO in 100% DMSO was added to all wells by acoustic dispensing, except minimum control wells which were left untreated with 4NQO to generate a null response control. Plates were returned to the incubator for a further 1 h. Then cells were fixed by adding 20 µl of 3.7% formaldehyde in PBS solution and incubating for 20 mins at r.t. Then 20 µl of 0.1% Triton X100 in PBS was added and incubated for 10 minutes at r.t., to permeabalise cells. Then the plates were washed once with 50 µl/well PBS, using a Biotek EL405 plate washer.

Phospho-Chk1 Ser 345 antibody (Cell Signalling Technology #2348) was diluted 150 fold in PBS containing 0.05% polysorbate/Tween and 15 µl was added to each well and incubated over night at r.t. The next morning plates were washed three times with 50 µl/well PBS, using a Biotek EL405 plate washer, and then 20 µl of secondary Ab solution, containing 500 fold diluted Alexa Fluor 488 Goat anti-rabbit IgG (Molecular Probes #A-11008) and 0.002 mg/ml Hoechst dye (Molecular Probes #H-3570), in PBST, was added. After 2 h incubation at r.t., the plates were washed three times with 50 µl/well PBS, using a Biotek EL405S plate washer, and plates were then sealed with black plate seals until read. Plates were read using an ArrayScan VTI instrument, using an XF53 filter with 10x objective. A two laser set up was used to analyse nuclear staining with Hoechst (405 nm) and secondary antibody staining of pChk1 (488 nm).

Assay c): PI3K Cellular Potency

Rationale:

This assay was used to measure PI3K-α inhibition in cells. PDK1 was identified as the upstream activation loop kinase of protein kinase B (Akt1), which is essential for the activation of PKB. Activation of the lipid kinase phosphoinositide 3 kinase (PI3K) is critical for the activation of PKB by PDK1.

Following ligand stimulation of receptor tyrosine kinases, PI3K is activated, which converts PIP2 to PIP3, which is bound by the PH domain of PDK1 resulting in recruitment of PDK1 to the plasma membrane where it phosphorylates AKT at Thr308 in the activation loop.

The aim of this cell-based mode of action assay is to identify compounds that inhibit PDK activity or recruitment of PDK1 to membrane by inhibiting PI3K activity. Phosphorylation of phospho-Akt (T308) in BT474c cells following treatment with compounds for 2 h is a direct measure of PDK1 and indirect measure of PI3K activity.

Method Details:

BT474 cells (human breast ductal carcinoma, ATCC HTB-20) were seeded into black 384 well plates (Costar, #3712) at a density of 5600 cells/well in DMEM containing 10% FBS and 1% glutamine and allowed to adhere overnight.

The following morning compounds in 100% DMSO were added to assay plates by acoustic dispensing. After a 2 h incubation at 37° C. and 5% $CO_2$, the medium was aspirated and the cells were lysed with a buffer containing 25 mM Tris, 3 mM EDTA, 3 mM EGTA, 50 mM sodium fluoride, 2 mM Sodium orthovanadate, 0.27M sucrose, 10 mM (3-glycerophosphate, 5 mM sodium pyrophosphate, 0.5% Triton X-100 and complete protease inhibitor cocktail tablets (Roche #04 693 116 001, used 1 tab per 50 ml lysis buffer).

After 20 minutes, the cell lysates were transferred into ELISA plates (Greiner #781077) which had been pre-coated with an anti total-AKT antibody in PBS buffer and non-specific binding was blocked with 1% BSA in PBS containing 0.05% Tween 20. Plates were incubated over night at 4° C. The next day the plates were washed with PBS buffer containing 0.05% Tween 20 and further incubated with a mouse monoclonal anti-phospho AKT T308 for 2 h. Plates were washed again as above before addition of a horse anti-mouse-HRP conjugated secondary antibody. Following a 2 h incubation at r.t., plates were washed and QuantaBlu substrate working solution (Thermo Scientific #15169, prepared according to provider's instructions) was added to each well. The developed fluorescent product was stopped after 60 minutes by addition of Stop solution to the wells. Plates were read using a Tecan Satire plate reader using 325 nm excitation and 420 nm emission wavelengths respectively. Except where specified, reagents contained in the Path Scan Phospho AKT (Thr308) sandwich ELISA kit from Cell Signalling (#7144) were used in this ELISA assay.

Assay d): mTOR Cellular Potency
Rationale:

This assay was used to measure mTOR inhibition in cells. The aim of the phospho-AKT cell based mechanism of action assay using the Acumen Explorer is to identify inhibitors of either PI3Kα or mTOR-Rictor (Rapamycin insensitive companion of mTOR). This is measured by any decrease in the phosphorylation of the Akt protein at Ser473 (AKT lies downstream of PI3Kα in the signal transduction pathway) in the MDA-MB-468 cells following treatment with compound.

Method Details:

MDA-MB-468 cells (human breast adenocarcinoma #ATCC HTB 132) were seeded at 1500 cells/well in 40 μl of DMEM containing 10% FBS and 1% glutamine into Greiner 384 well black flat-bottomed plates. Cell plates were incubated for 18 h in a 37° C. incubator before dosing with compounds of formula (I) in 100% DMSO using acoustic dispensing. Compounds were dosed in a 12 point concentration range into a randomised plate map. Control wells were generated either by dosing of 100% DMSO (max signal) or addition of a reference compound (a PI3K-β inhibitor) that completely eliminated the pAKT signal (min control). Plates were incubated at 37° C. for 2 h, cells were then fixed by the addition of 10 μl of a 3.7% formaldehyde solution. After 30 minutes the plates were washed with PBS using a Tecan PW384 plate washer. Wells were blocked and cells permeabilised with the addition of 40 μl of PBS containing 0.5% Tween20 and 1% Marvel™ (dried milk powder) and incubated for 60 minutes at r.t. The plates were washed with PBS containing 0.5% (v/v) Tween20 and 20 μl rabbit anti-phospho AKT Ser473 (Cell Signalling Technologies, #3787) in same PBS-Tween+1% Marvel™ was added and incubated overnight at 4° C.

Plates were washed 3 times with PBS+0.05% Tween 20 using a Tecan PW384, 20 μl of secondary antibody Alexa Fluor 488 anti-Rabbit (Molecular Probes, #A11008) diluted in PBS+0.05% Tween20 containing 1% Marvel™ was added to each well and incubated for 1 h at r.t. Plates were washed three times as before then 20 μl PBS added to each well and plates sealed with a black plate sealer.

The plates were read on an Acumen plate reader as soon as possible, measuring green fluorescence after excitation with 488 nm laser. Using this system $IC_{50}$ values were generated and quality of plates was determined by control wells. Reference compounds were run each time to monitor assay performance.

Assay e): Mouse Xenograft Model
Irinotecan Combination

Male nude mice were transplanted s.c. with SW620 cells (ATCC-CCL-227) to determine the in-vivo anti-tumour activity of ATM inhibitors. 1×10^6 cells in 50% matrigel (BD Bioscience) were injected s.c. on the left flank of the animals. Animals were randomised into groups of 10-15 when tumours reached a volume of ~200-300 mm³ and treatment commenced. Animals received 3 weekly cycles of treatment with compound. Animals were dosed once weekly with Irinotecan by i.p., and then 24 h post Irinotecan animals received a once daily dose on 3 consecutive days by peroral route with a compound of Formula (I). Tumours were measured twice weekly by caliper and volume of tumours calculated using elliptical formula (π/6×width×width×length). Irinotecan was formulated in a 7.5% DMSO 92.5% water for injection solution. Compounds of Formula (I) were formulated in a 10% DMSO/90% Captisol (30% w/v) solution. Captisol was sourced from Cydex Pharmaceuticals (Trademarked) f-cyclodextrin suitable for in vivo use and formulations.

Olaparib Combination

Female nude mice were transplanted s.c. with a HBCx-10 patient derived tumour fragment to determine the in-vivo anti-tumour activity of ATM inhibitors. Human tumour samples of various histological origins were obtained from patients and established as transplantable xenografts in immunodeficient mice.

Tumours of the same passage were transplanted subcutaneously onto 5-10 mice. When these tumours reached 1000 to 2000 mm³, donor mice were sacrificed by cervical dislocation, tumours were aseptically excised and dissected and cut into fragments measuring approximately 20 mm; and transferred in culture medium before grafting. Mice were anaesthetized and the skin incised at the level of the interscapular region, and a 20 mm³ tumour fragment was placed in the subcutaneous tissue Animals were randomised into groups of 10-12 when tumours reached a volume of 62.5-196 mm³ and treatment commenced. Animals received 8 weekly cycles of treatment with compound. Animals were dosed 7 days a week with Olaparib per orally, and then 1 h prior to Olaparib animals received a once daily dose on 3 consecutive days by per oral route with a compound of Formula (I). Tumours were measured twice weekly by caliper and volume of tumours calculated using formula [length×width²]/2 was used, where the length and the width are the longest and the shortest diameters of the tumour, respectively. Olaparib was formulated in a 10% (w/v) DMSO/10% (w/v) HP-b-CD (Kleptose), 80% water for injection solution. Compounds of Formula (I) were formulated in a 10% DMSO/90% Captisol (30% w/v) solution. Captisol was sourced from Cydex Pharmaceuticals (Trademarked) β-cyclodextrin suitable for in vivo use and formulations.

Figure 3:
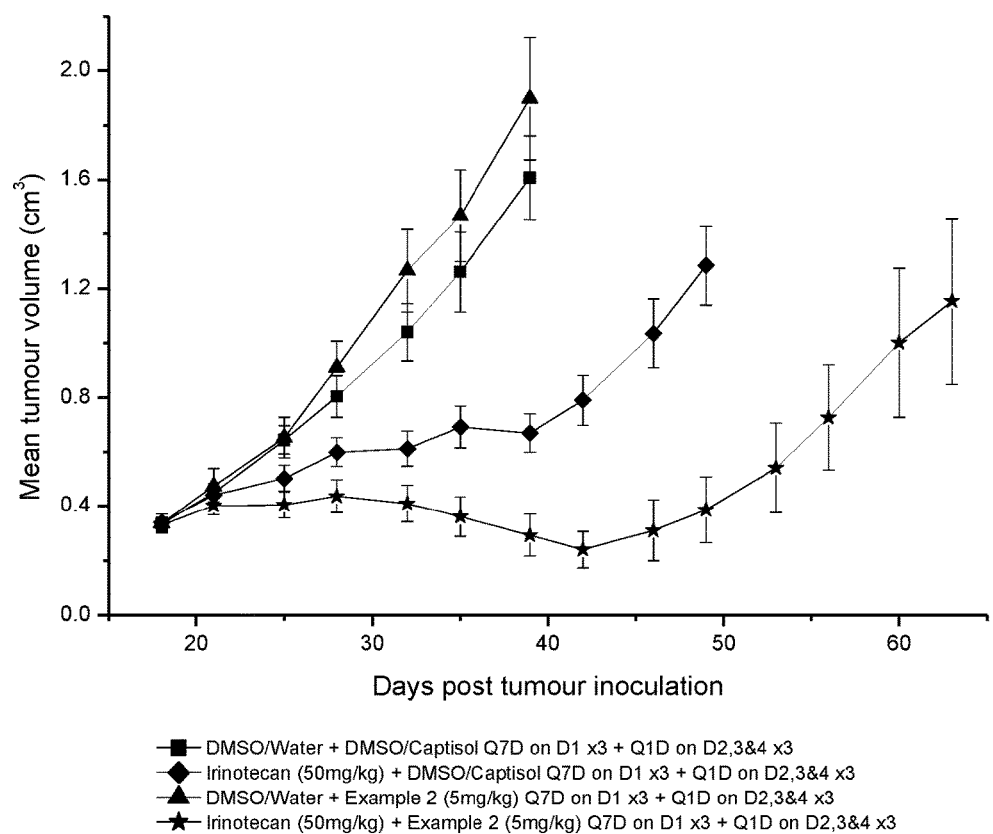
FIG. 3: Tumour Growth Inhibition in the Mouse Xenograft Model by 8-[6-(3-Dimethylaminopropoxy)pyridin-3-yl]-1-(cis-3-methoxycyclobutyl)-3-methylimidazo[4,5-c]quinolin-2-one (Example 2) in Combination with Irinotecan.
Figure 4:
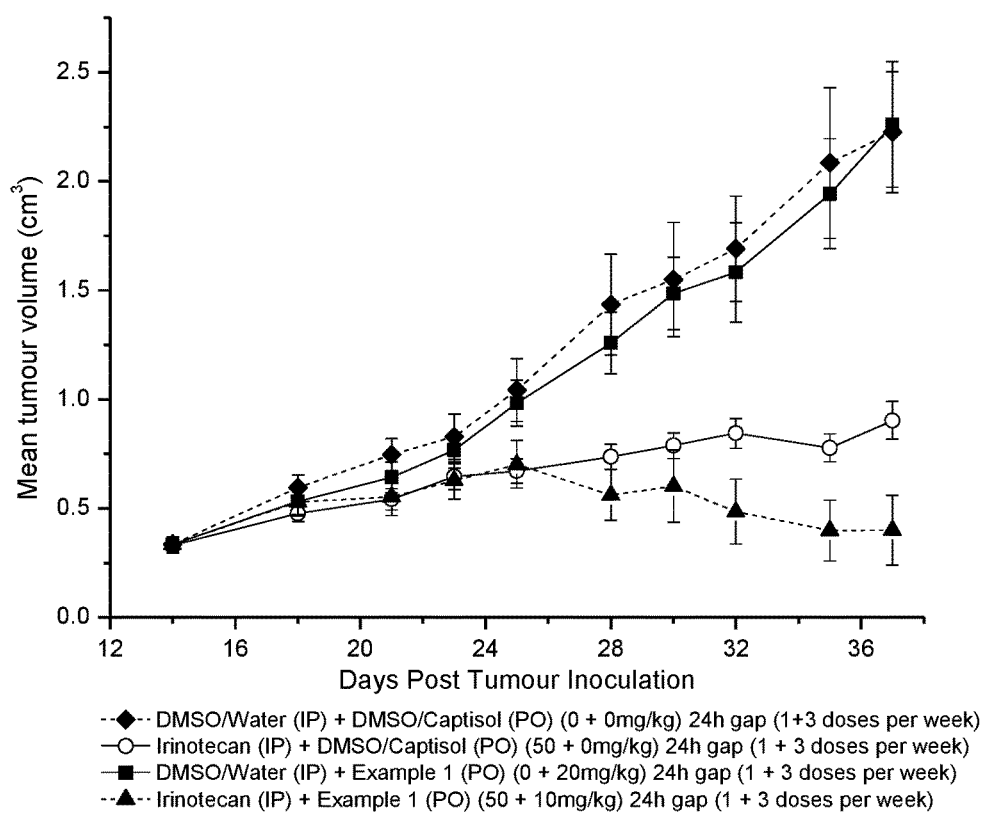
FIG. 4: Tumour Growth Inhibition in the Mouse Xenograft Model by 8-[6-(3-Dimethylaminopropoxy)pyridin-3-yl]-3-methyl-1-(oxan-4-yl)imidazo[5,4-c]quinolin-2-one (Example 1) in Combination with Irinotecan.
Figure 5:
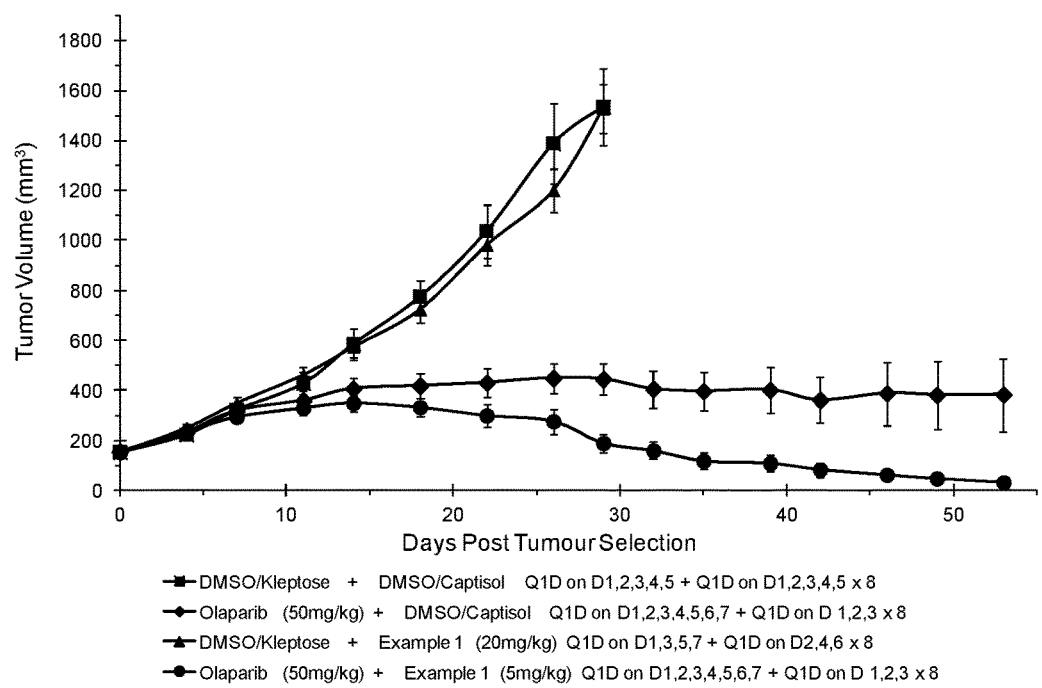
FIG. 5: Tumour Growth Inhibition in the Mouse Xenograft Model by 8-[6-(3-Dimethylaminopropoxy)pyridin-3-yl]-3-methyl-1-(oxan-4-yl)imidazo[5,4-c]quinolin-2-one (Example 1) in Combination with Olaparib.

The results of testing Examples 1 and 2 in assay e) are shown in FIGS. 3, 4 and 5. "Q7D" Means a once weekly dose. "Q1 D" is a once daily dose.

Table 2 shows the results of testing the Examples in assays a) b) c) and d). Where multiple repeat tests were carried out on a given Example, the result reported is the geometric mean.

TABLE 2

Potency Data for Examples 1-71 in Assays a)-d)

| Example | Assay a) ATM Cell IC$_{50}$ (µM) | Assay b) ATR Cell IC$_{50}$ (µM) | Assay c) PI3Kα Cell IC$_{50}$ (µM) | Assay d) mTOR Cell IC$_{50}$ (µM) |
|---|---|---|---|---|
| 1 | 0.000575 | 6.16 | 1.41 | 0.61 |
| 2 | 0.000249 | >29 | 1.77 | 1.17 |
| 3 | 0.00203 | >30 | 22.4 | 4.93 |
| 4 | 0.00146 | >30 | 6.84 | 3.46 |
| 5 | 0.00024 | >30 | 1.08 | 1.36 |
| 6 | 0.00105 | >30 | >30 | >16.9 |
| 7 | 0.00096 | 10.8 | 0.541 | 0.266 |
| 8 | 0.000782 | >30 | 18.1 | 14 |
| 9 | 0.0038 | >30 | >29.1 | >21.3 |
| 10 | 0.001 | >30 | 10 | 5.9 |
| 11 | 0.00114 | >29.6 | >20.2 | 9.29 |
| 12 | 0.00103 | >25.2 | 0.769 | 0.54 |
| 13 | 0.00322 | >30 | 1.52 | 0.248 |
| 14 | 0.00105 | >30 | 0.616 | 1.04 |
| 15 | 0.000447 | >30 | 2.39 | 2.58 |
| 16 | 0.000935 | >22.8 | 0.311 | 0.714 |
| 17 | 0.000329 | >30 | 0.968 | 1.47 |
| 18 | 0.000765 | >30 | 2.73 | 3.78 |
| 19 | 0.00262 | >30 | >28 | 13.7 |
| 20 | 0.000365 | >30 | 1.03 | 0.529 |
| 21 | 0.000301 | >30 | 0.68 | 0.797 |
| 22 | 0.000552 | >30 | 0.849 | 1.37 |
| 23 | 0.000563 | >30 | >30 | 18.2 |
| 24 | 0.00069 | >18.8 | 7.29 | >9.43 |
| 25 | 0.000315 | >20.7 | 1.05 | 1.19 |
| 26 | 0.000152 | >21.8 | 0.331 | 0.36 |
| 27 | 0.000418 | >23.3 | >29.8 | >17.5 |
| 28 | 0.000176 | >22.8 | 2.03 | 2.77 |
| 29 | 0.000238 | 19 | 1.65 | 0.605 |
| 30 | 0.00112 | 19 | 2.33 | 1.57 |
| 31 | 0.00109 | >30 | >10.9 | 19.5 |
| 32 | 0.00178 | >30 | 2.94 | 6.1 |
| 33 | 0.0002 | >24.7 | 12.4 | 2.87 |
| 34 | 0.00084 | >16.9 | 0.402 | 0.505 |
| 35 | 0.000589 | 17.8 | 3 | 0.579 |
| 36 | 0.00301 | >30 | >25 | 10.6 |
| 37 | 0.0012 | >29.4 | 20.7 | 12.4 |
| 38 | 0.000292 | >24.4 | 0.729 | 2.24 |
| 39 | 0.00133 | 10.7 | 0.828 | 1.27 |
| 40 | 0.000567 | 1.33 | 0.184 | 0.191 |
| 41 | 0.000555 | 3.94 | 0.267 | 0.395 |
| 42 | 0.000249 | 4.37 | 0.321 | 0.214 |
| 43 | 0.000592 | 2.69 | 0.167 | 0.262 |
| 44 | 0.00107 | >19.2 | 0.56 | 2.37 |
| 45 | <0.000534 | 9.6 | 0.26 | 1.19 |
| 46 | 0.00315 | >26 | 0.794 | |
| 47 | 0.000799 | >30 | >23.5 | >30 |
| 48 | 0.00102 | >30 | >9.4 | 23 |
| 49 | 0.00134 | >30 | 2.03 | 3.76 |
| 50 | 0.00144 | >30 | 1.1 | 4.48 |
| 51 | 0.000722 | >30 | 3.2 | 5.38 |
| 52 | 0.00476 | >30 | 7.2 | 12.1 |
| 54 | 0.0011 | >27.1 | >16.7 | >29.3 |
| 54 | 0.000715 | >22.4 | 3.47 | 8.12 |
| 55 | 0.000493 | >16.1 | >9.13 | 3.38 |
| 56 | 0.00302 | >30 | >26.3 | 12.4 |
| 57 | 0.000434 | >30 | >14.3 | 5.77 |
| 58 | 0.00031 | >28.1 | >9.56 | 7.29 |
| 59 | 0.000233 | >19.1 | 0.264 | 0.61 |
| 60 | 0.000765 | >24 | 0.499 | 1.36 |
| 61 | 0.000554 | >30 | >16.2 | |
| 62 | 0.000507 | | | >30 |
| 63 | 0.00031 | >30 | 3.28 | 10.8 |
| 64 | 0.000741 | >24.1 | >30 | 12 |
| 65 | 0.000022 | >26.6 | 1.84 | 6.34 |
| 66 | 0.000334 | 7.85 | 1.49 | 3.32 |
| 67 | <0.0000525 | 15.2 | >2.85 | 0.996 |
| 68 | 0.000208 | >29 | 0.644 | 3.18 |

TABLE 2-continued

Potency Data for Examples 1-71 in Assays a)-d)

| Example | Assay a) ATM Cell IC$_{50}$ (µM) | Assay b) ATR Cell IC$_{50}$ (µM) | Assay c) PI3Kα Cell IC$_{50}$ (µM) | Assay d) mTOR Cell IC$_{50}$ (µM) |
|---|---|---|---|---|
| 69 | 0.000324 | >30 | >2.77 | |
| 70 | 0.00243 | >24.9 | >30 | >30 |
| 71 | 0.00145 | >30 | >11.4 | 15.2 |

Table 3 shows comparative data for certain Compounds of CN102399218A and CN102372711A in tests a) b) c) and d). Where multiple repeat tests were carried out on a given Compound, the result reported is the geometric mean.

TABLE 3

Potency Data for Certain Compounds of CN102399218A and CN102372711A in Assays a)-d)

| Reference Compound | Assay a) ATM Cell IC$_{50}$ (µM) | Assay b) ATR Cell IC$_{50}$ (µM) | Assay c) PI3Ka Cell IC$_{50}$ (µM) | Assay d) mTOR Cell IC$_{50}$ (µM) |
|---|---|---|---|---|
| CN102372711A Compound 1 | 0.125 | 0.281 | 0.188 | 0.237 |
| CN102372711A Compound 4 | 0.0112 | 0.0686 | 0.102 | 0.0729 |
| CN102372711A Compound 5 | 0.0265 | 0.0644 | 0.153 | 0.113 |
| CN102399218A Compound 60 | 1.76 | 0.418 | 4.67 | 2.31 |
| CN102399218A Compound 61 | 3.46 | 1.48 | 1.73 | 0.177 |
| CN102399218A Compound 62 | 0.135 | 0.0553 | 0.149 | 0.0155 |
| CN102399218A Compound 64 | 0.216 | 0.162 | 0.247 | 0.287 |
| CN102399218A Compound 94 | 0.494 | 0.0129 | 0.0804 | 0.0414 |
| CN102399218A Compound 114 | 0.0741 | 0.0686 | 0.0131 | 0.0469 |

The invention claimed is:

1. A compound, or a pharmaceutically acceptable salt thereof, wherein the compound is selected from the group consisting of:

8-[6-(3-Dimethylaminopropoxy)pyridin-3-yl]-1-(cis-3-methoxycyclobutyl)-3-methylimidazo[4,5-c]quinolin-2-one;

8-[6-(3-Dimethylaminopropoxy)pyridin-3-yl]-7-fluoro-3-methyl-1-(4-methyloxan-4-yl)imidazo[5,4-c]quinolin-2-one;

8-[6-(3-Dimethylaminopropoxy)pyridin-3-yl]-3-methyl-1-(oxetan-3-yl)imidazo[5,4-c]quinolin-2-one;

8-[6-(3-Dimethylaminopropoxy)pyridin-3-yl]-1-(cis-3-hydroxycyclobutyl)-3-methylimidazo[4,5-c]quinolin-2-one;

8-[6-(3-Dimethylaminopropoxy)pyridin-3-yl]-7-fluoro-1-(cis-3-methoxycyclobutyl)-3-methylimidazo[4,5-c]quinolin-2-one;

8-[6-(3-Dimethylaminopropoxy)pyridin-3-yl]-3-methyl-1-(4-methyloxan-4-yl)imidazo[5,4-c]quinolin-2-one;

8-[6-(3-Dimethylaminopropoxy)pyridin-3-yl]-7-fluoro-3-methyl-1-(oxan-4-yl)imidazo[5,4-c]quinolin-2-one;

8-[6-(3-Dimethylaminopropoxy)pyridin-3-yl]-7-fluoro-3-methyl-1-(oxetan-3-yl)imidazo[5,4-c]quinolin-2-one;

8-[6-(3-Dimethylaminopropoxy)pyridin-3-yl]-7-fluoro-3-methyl-1-[(3R)-oxan-3-yl]imidazo[5,4-c]quinolin-2-one;

8-[6-(3-Dimethylaminopropoxy)pyridin-3-yl]-7-fluoro-3-methyl-1-[(3S)-oxan-3-yl]imidazo[5,4-c]quinolin-2-one;

8-[6-(3-Dimethylaminopropoxy)pyridin-3-yl]-1-(cis-3-methoxycyclobutyl)-3H-imidazo[4,5-c]quinolin-2-one;

8-[6-(3-Dimethylaminopropoxy)pyridin-3-yl]-1-(oxan-4-yl)-3H-imidazo[4,5-c]quinolin-2-one;

8-[6-[3-(Azetidin-1-yl)propoxy]pyridin-3-yl]-1-(cis-3-hydroxycyclobutyl)-3-methylimidazo[4,5-c]quinolin-2-one;

1-(3-cis-Hydroxycyclobutyl)-3-methyl-8-[6-(3-pyrrolidin-1-ylpropoxy)pyridin-3-yl]imidazo[4,5-c]quinolin-2-one;

8-[6-(3-Dimethylaminopropoxy)pyridin-3-yl]-3-methyl-1-[(3R)-oxan-3-yl]imidazo[5,4-c]quinolin-2-one;

8-[6-(3-Dimethylaminopropoxy)pyridin-3-yl]-3-methyl-1-[(3S)-oxan-3-yl]imidazo[5,4-c]quinolin-2-one;

8-[6-(3-Dimethylaminopropoxy)-2-fluoropyridin-3-yl]-1-(cis-3-methoxycyclobutyl)-3-methylimidazo[4,5-c]quinolin-2-one;

8-[6-(3-Dimethylaminopropoxy)-2-fluoropyridin-3-yl]-7-fluoro-1-(cis-3-methoxycyclobutyl)-3-methylimidazo[4,5-c]quinolin-2-one;

8-[6-(3-Dimethylaminopropoxy)-2-fluoropyridin-3-yl]-3-methyl-1-[(3S)-oxan-3-yl]imidazo[5,4-c]quinolin-2-one;

8-[6-(3-Dimethylaminopropoxy)-2-fluoropyridin-3-yl]-3-methyl-1-(oxan-4-yl)imidazo[5,4-c]quinolin-2-one;

8-[6-(3-Dimethylaminopropoxy)-2-fluoropyridin-3-yl]-3-methyl-1-[(3R)-oxan-3-yl]imidazo[5,4-c]quinolin-2-one;

7-Fluoro-3-methyl-8-[6-(3-pyrrolidin-1-ylpropoxy)-3-pyridyl]-1-[(3S)-tetrahydropyran-3-yl]imidazo[4,5-c]quinolin-2-one;

7-Fluoro-3-methyl-8-[6-(3-pyrrolidin-1-ylpropoxy)-3-pyridyl]-1-[(3S)-tetrahydropyran-3-yl]imidazo[4,5-c]quinolin-2-one;

8-[6-(3-Dimethylaminopropoxy)pyridin-3-yl]-1-[(1R,3R)-3-methoxycyclopentyl]-3-methylimidazo[4,5-c]quinolin-2-one;

8-[6-(3-Dimethylaminopropoxy)pyridin-3-yl]-1-[(1S,3S)-3-methoxycyclopentyl]-3-methylimidazo[4,5-c]quinolin-2-one;

7-Fluoro-1-(cis-3-methoxycyclobutyl)-3-methyl-8-[6-(3-pyrrolidin-1-ylpropoxy)pyridin-3-yl]imidazo[4,5-c]quinolin-2-one;

1-(cis-3-Methoxycyclobutyl)-3-methyl-8-[6-(3-pyrrolidin-1-ylpropoxy)pyridin-3-yl]imidazo[4,5-c]quinolin-2-one;

3-Methyl-1-[(3S)-oxan-3-yl]-8-[6-(3-pyrrolidin-1-ylpropoxy)pyridin-3-yl]imidazo[5,4-c]quinolin-2-one;

3-Methyl-1-(oxan-4-yl)-8-[6-(3-pyrrolidin-1-ylpropoxy)pyridin-3-yl]imidazo[5,4-c]quinolin-2-one;

3-Methyl-1-[(3S)-oxan-3-yl]-8-[6-(3-piperidin-1-ylpropoxy)pyridin-3-yl]imidazo[5,4-c]quinolin-2-one;

3-Methyl-1-[(3R)-oxan-3-yl]-8-[6-(3-piperidin-1-ylpropoxy)pyridin-3-yl]imidazo[5,4-c]quinolin-2-one;

1-(cis-3-Methoxycyclobutyl)-3-methyl-8-[6-(3-piperidin-1-ylpropoxy)pyridin-3-yl]imidazo[4,5-c]quinolin-2-one;

8-[6-[3-(Azetidin-1-yl)propoxy]pyridin-3-yl]-3-methyl-1-[(3R)-oxan-3-yl]imidazo[5,4-c]quinolin-2-one;

1-(cis-3-Methoxycyclobutyl)-8-[6-(3-pyrrolidin-1-ylpropoxy)pyridin-3-yl]-3H-imidazo[4,5-c]quinolin-2-one;

1-(Oxan-4-yl)-8-[6-(3-piperidin-1-ylpropoxy)pyridin-3-yl]-3H-imidazo[4,5-c]quinolin-2-one;

3-Methyl-1-(oxan-4-yl)-8-[6-(3-piperidin-1-ylpropoxy)pyridin-3-yl]imidazo[5,4-c]quinolin-2-one;

8-[6-[3-(Azetidin-1-yl)propoxy]pyridin-3-yl]-1-(cis-3-methoxycyclobutyl)-3-methylimidazo[4,5-c]quinolin-2-one;

8-[6-[3-(Azetidin-1-yl)propoxy]pyridin-3-yl]-3-methyl-1-(oxan-4-yl)imidazo[5,4-c]quinolin-2-one;

3-Methyl-8-[6-(3-methylaminopropoxy)pyridin-3-yl]-1-(oxan-4-yl)imidazo[5,4-c]quinolin-2-one;

3-Methyl-8-[6-(3-methylaminopropoxy)pyridin-3-yl]-1-[(3 S)-oxan-3-yl]imidazo[5,4-c]quinolin-2-one; and 1-(cis-3-Methoxycyclobutyl)-3-methyl-8-[6-(3-methylaminopropoxy)pyridin-3-yl]imidazo[4,5-c]quinolin-2-one;

3-Methyl-8-[6-[3-(methylamino)propoxy]-3-pyridyl]-1-[(3R)-tetrahydropyran-3-yl]imidazo[4,5-c]quinolin-2-one;

8-[6-[3-(Dimethylamino)propoxy]-3-pyridyl]-3-methyl-1-[(3R)-tetrahydrofuran-3-yl]imidazo[4,5-c]quinolin-2-one;

8-[6-[3-(Dimethylamino)propoxy]-3-pyridyl]-3-methyl-1-[(3S)-tetrahydrofuran-3-yl]imidazo[4,5-c]quinolin-2-one;

1-Cyclobutyl-8-[6-[3-(dimethylamino)propoxy]-3-pyridyl]-3-methyl-imidazo[4,5-c]quinolin-2-one;

7-Fluoro-3-methyl-8-[6-[3-(1-piperidyl)propoxy]-3-pyridyl]-1-[(3S)-tetrahydropyran-3-yl]imidazo[4,5-c]quinolin-2-one;

8-[6-[3-(Dimethylamino)propoxy]-2-fluoro-3-pyridyl]-7-fluoro-3-methyl-1-[(3S)-tetrahydropyran-3-yl]imidazo[4,5-c]quinolin-2-one;

8-[6-[3-(Dimethylamino)propoxy]-2-fluoro-3-pyridyl]-3-methyl-1-[(3S)-tetrahydrofuran-3-yl]imidazo[4,5-c]quinolin-2-one;

8-[6-[3-(Dimethylamino)propoxy]-2-fluoro-3-pyridyl]-3-methyl-1-[(3R)-tetrahydrofuran-3-yl]imidazo[4,5-c]quinolin-2-one;

1-Cyclobutyl-8-[6-[3-(dimethylamino)propoxy]-2-fluoro-3-pyridyl]-3-methyl-imidazo[4,5-c]quinolin-2-one;

8-[6-[3-(Dimethylamino)propoxy]-2-fluoro-3-pyridyl]-3-methyl-1-(oxetan-3-yl)imidazo[4,5-c]quinolin-2-one;

7-Fluoro-3-methyl-8-[6-[3-(1-piperidyl)propoxy]-3-pyridyl]-1-tetrahydropyran-4-yl-imidazo[4,5-c]quinolin-2-one 3-Methyl-8-[6-[3-(1-piperidyl)propoxy]-3-pyridyl]-1-[(3R)-tetrahydrofuran-3-yl]imidazo[4,5-c]quinolin-2-one;

3-Methyl-8-[6-[3-(1-piperidyl)propoxy]-3-pyridyl]-1-[(3S)-tetrahydrofuran-3-yl]imidazo[4,5-c]quinolin-2-one;

3-Methyl-1-(oxetan-3-yl)-8-[6-[3-(1-piperidyl)propoxy]-3-pyridyl]imidazo[4,5-c]quinolin-2-one;

1-Cyclobutyl-3-methyl-8-[6-[3-(1-piperidyl)propoxy]-3-pyridyl]imidazo[4,5-c]quinolin-2-one;

1-Cyclobutyl-3-methyl-8-[6-(3-pyrrolidin-1-ylpropoxy)-3-pyridyl]imidazo[4,5-c]quinolin-2-one;

3-Methyl-8-[6-(3-pyrrolidin-1-ylpropoxy)-3-pyridyl]-1-[(3R)-tetrahydropyran-3-yl]imidazo[4,5-c]quinolin-2-one;

8-[6-[3-(Azetidin-1-yl)propoxy]-3-pyridyl]-3-methyl-1-[(3S)-tetrahydropyran-3-yl]imidazo[4,5-c]quinolin-2-one;

8-[2-Fluoro-6-(3-pyrrolidin-1-ylpropoxy)-3-pyridyl]-3-methyl-1-[(3S)-tetrahydropyran-3-yl]imidazo[4,5-c]quinolin-2-one;

8-[6-[3-(Dimethylamino)propoxy]-3-pyridyl]-7-fluoro-1-[(1R,3R)-3-methoxycyclopentyl]-3-methyl-imidazo[4,5-c]quinolin-2-one;

8-[6-[3-(Dimethylamino)propoxy]-3-pyridyl]-7-fluoro-1-[(1S,3S)-3-methoxycyclopentyl]-3-methyl-imidazo[4,5-c]quinolin-2-one;

1-[(1R,3R)-3-Methoxycyclopentyl]-3-methyl-8-[6-[3-(1-piperidyl)propoxy]-3-pyridyl]imidazo[4,5-c]quinolin-2-one;

1-[(1S,3S)-3-Methoxycyclopentyl]-3-methyl-8-[6-[3-(1-piperidyl)propoxy]-3-pyridyl]imidazo[4,5-c]quinolin-2-one;

1-[(1S,3S)-3-Methoxycyclopentyl]-3-methyl-8-[6-(3-pyrrolidin-1-ylpropoxy)-3-pyridyl]imidazo[4,5-c]quinolin-2-one;

1-[(1R,3R)-3-Methoxycyclopentyl]-3-methyl-8-[6-(3-pyrrolidin-1-ylpropoxy)-3-pyridyl]imidazo[4,5-c]quinolin-2-one;

8-[6-[3-(Dimethylamino)propoxy]-2-fluoro-3-pyridyl]-1-[(1R,3R)-3-methoxycyclopentyl]-3-methyl-imidazo[4,5-c]quinolin-2-one;

8-[6-[3-(Dimethylamino)propoxy]-2-fluoro-3-pyridyl]-1-[(1S,3S)-3-methoxycyclopentyl]-3-methyl-imidazo[4,5-c]quinolin-2-one;

8-[6-[3-(Dimethylamino)propoxy]-3-pyridyl]-7-fluoro-1-[(1R,3S)-3-methoxycyclopentyl]-3-methyl-imidazo[4,5-c]quinolin-2-one; and 8-[6-[3-(Dimethylamino)propoxy]-3-pyridyl]-7-fluoro-1-[(1S,3R)-3-methoxycyclopentyl]-3-methyl-imidazo[4,5-c]quinolin-2-one.

2. A pharmaceutical composition which comprises a compound of claim 1,
or a pharmaceutically acceptable salt thereof, and at least one pharmaceutically acceptable diluent or carrier.

* * * * *